(12) United States Patent
Olejnik et al.

(10) Patent No.: US 9,926,595 B2
(45) Date of Patent: *Mar. 27, 2018

(54) METHODS AND SOLUTIONS FOR INHIBITING UNDESIRED CLEAVING OF LABELS

(71) Applicant: Intelligent BioSystems, Inc., Waltham, MA (US)

(72) Inventors: Jerzy Olejnik, Brookline, MA (US); Evan Guggenheim, Brookline, MA (US); Visalakshi Meyyappan, Ashland, MA (US)

(73) Assignee: INTELLIGENT BIO-SYSTEMS, INC., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/466,237

(22) Filed: Mar. 22, 2017

(65) Prior Publication Data

US 2017/0275671 A1    Sep. 28, 2017

Related U.S. Application Data

(63) Continuation of application No. 14/456,321, filed on Aug. 11, 2014, now Pat. No. 9,605,301, which is a continuation of application No. 12/405,925, filed on Mar. 17, 2009, now Pat. No. 8,883,999.

(60) Provisional application No. 61/037,845, filed on Mar. 19, 2008.

(51) Int. Cl.
*C12Q 1/68* (2006.01)
*G06F 19/20* (2011.01)

(52) U.S. Cl.
CPC .......... *C12Q 1/6869* (2013.01); *C12Q 1/6806* (2013.01); *C12Q 1/6825* (2013.01); *G06F 19/20* (2013.01)

(58) Field of Classification Search
CPC .................................................... C12Q 1/6869
USPC .................................................... 435/6.1
See application file for complete search history.

(56) References Cited

U.S. PATENT DOCUMENTS

| | | | | |
|---|---|---|---|---|
| 6,664,079 B2 * | 12/2003 | Ju | ............. | C12Q 1/686 435/6.1 |
| 8,623,598 B2 * | 1/2014 | Olejnik | ............. | C12Q 1/6825 435/6.1 |
| 8,883,999 B2 * | 11/2014 | Olejnik | ............. | C12Q 1/6825 435/6.1 |
| 9,605,301 B2 * | 3/2017 | Olejnik | ............. | C12Q 1/6825 |
| 2007/0117104 A1 * | 5/2007 | Buzby | ............. | C07H 21/00 435/6.11 |

* cited by examiner

*Primary Examiner* — Jezia Riley
(74) *Attorney, Agent, or Firm* — Medlen & Carroll, LLP

(57) ABSTRACT

The invention provides methods and compositions, including, without limitation, algorithms, computer readable media, computer programs, apparatus, and systems for determining the identity of nucleic acids in nucleotide sequences using, for example, data obtained from sequencing by synthesis methods. The methods of the invention include correcting one or more phenomena that are encountered during nucleotide sequencing, such as using sequencing by synthesis methods. These phenomena include, without limitation, sequence lead, sequence lag, spectral crosstalk, and noise resulting from variations in illumination and/or filter responses.

10 Claims, 63 Drawing Sheets

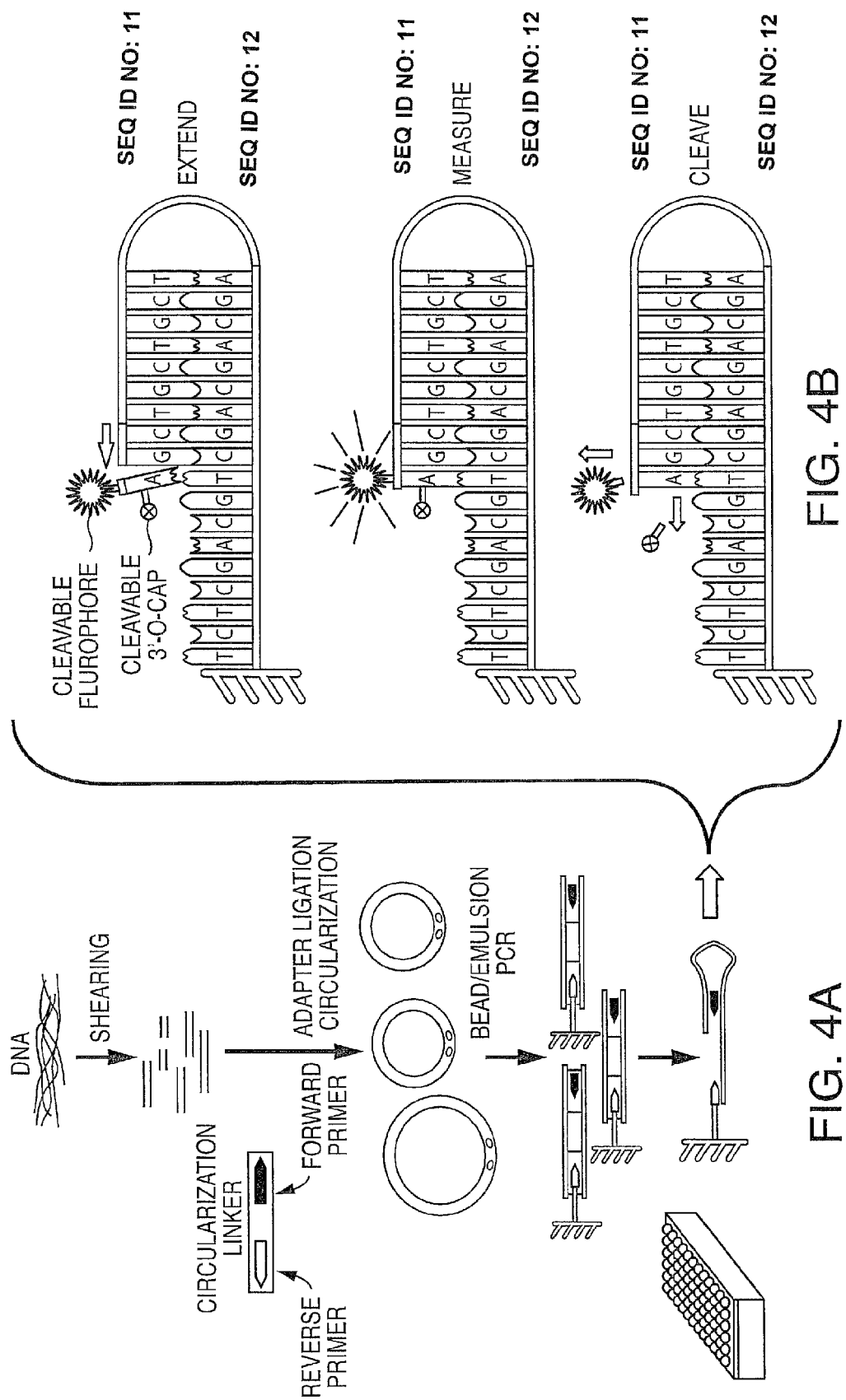

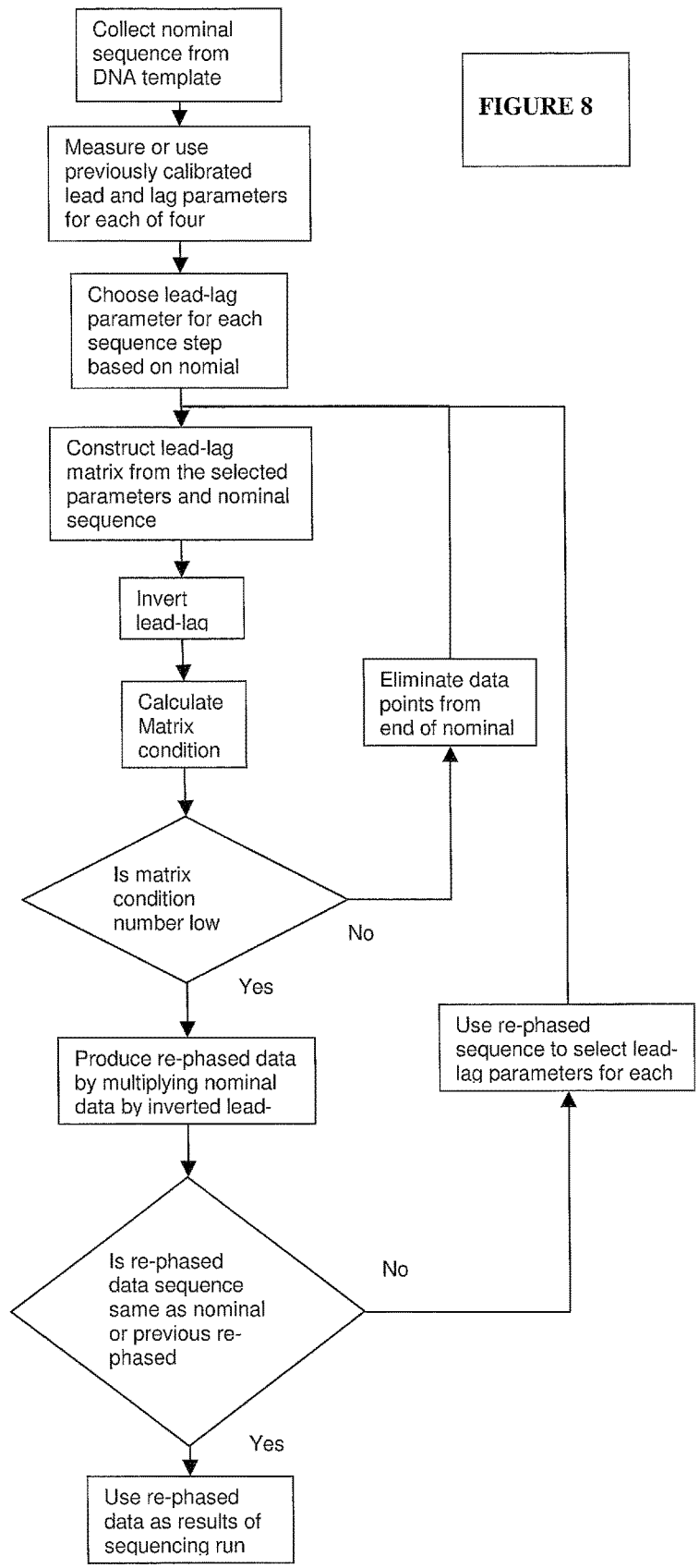

Synthetic DNA templates used in the sequencing experiment.

SEQ ID NO: 1

5'-NH2-CAT CAC TCT CAC ATG TCA GAC TCG AGC TGA ATT CCG CGT TCG CGG AAT TCA GC-3'

SEQ ID NO: 2

5'-NH2-GCG AAA AAG AAG AGA TGG GGT GAA GGC TGA ATT CCG CGT TCG CGG AAT TCT GC-3'

SEQ ID NO: 3

5'-NH2-TGA TTT CGC TTT TAC CCT ACA CTC TGC TGA ATT CCG CGT TCG CGG AAT TCA GC-3'

SEQ ID NO: 4

5'-NH2-ATC GCC CTA TAT TCT AAC TTG ACT CGC TGA ATT CCG CGT TCG CGG AAT TCA GC-3'

FIGURE 27
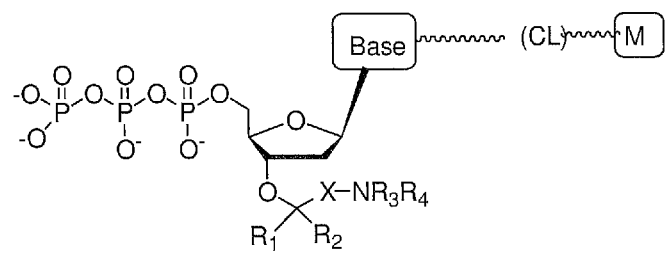
X = O, NH; $R_1, R_2, R_3, R_4$ = H, alkyl group
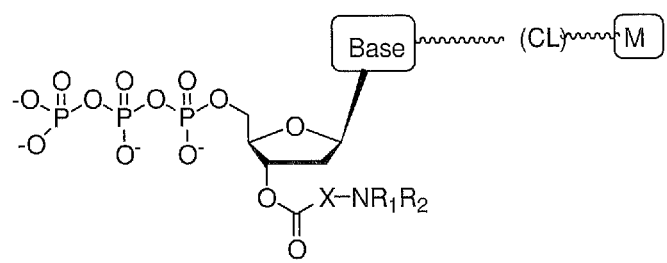
X = O, NH; $R_1, R_2$ = H, alkyl group B = nucleobase, or properly protected nucleobase CONDITIONS: HONO/OTHER NO+ SOURCES, H2O2/HORSE RADISH PEROXIDASE, OTHER MILD OXIDIZING AGENTS THAT GENERATE REACTIVE OXYGEN SPECIES.

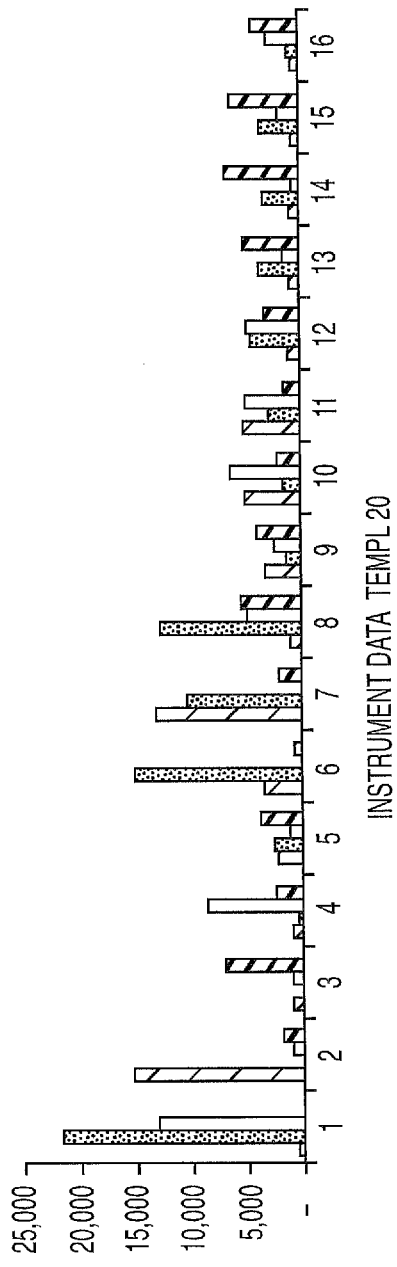
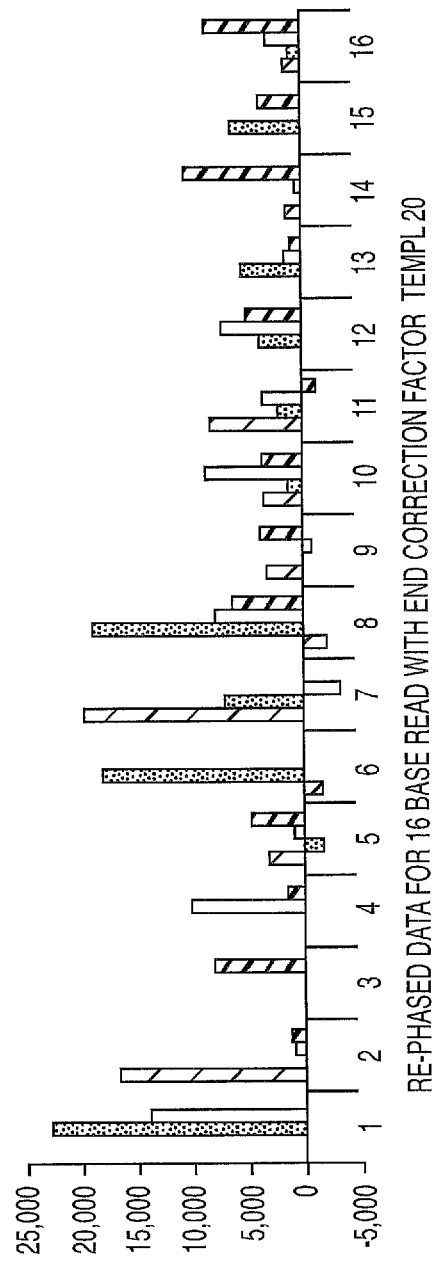
FIG. 33A
FIG. 33B

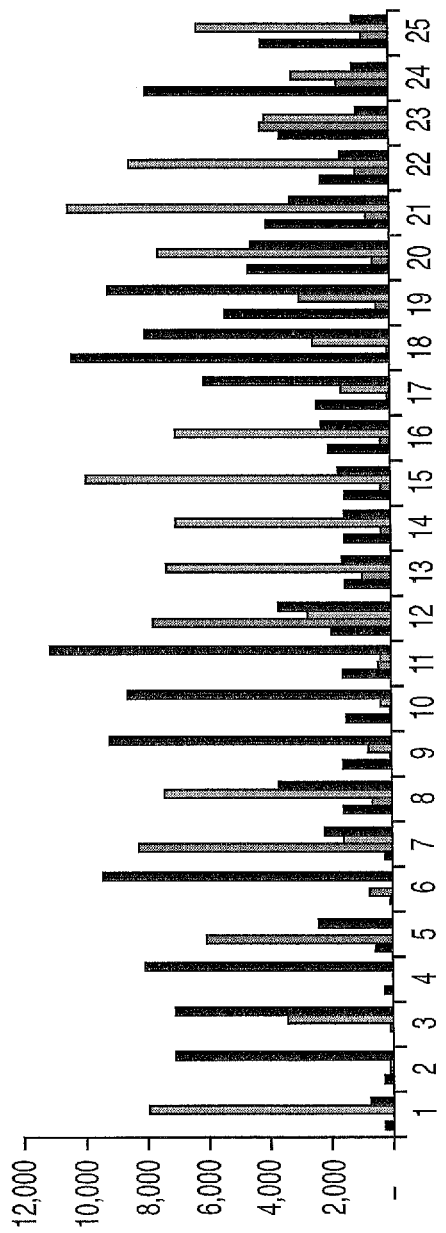
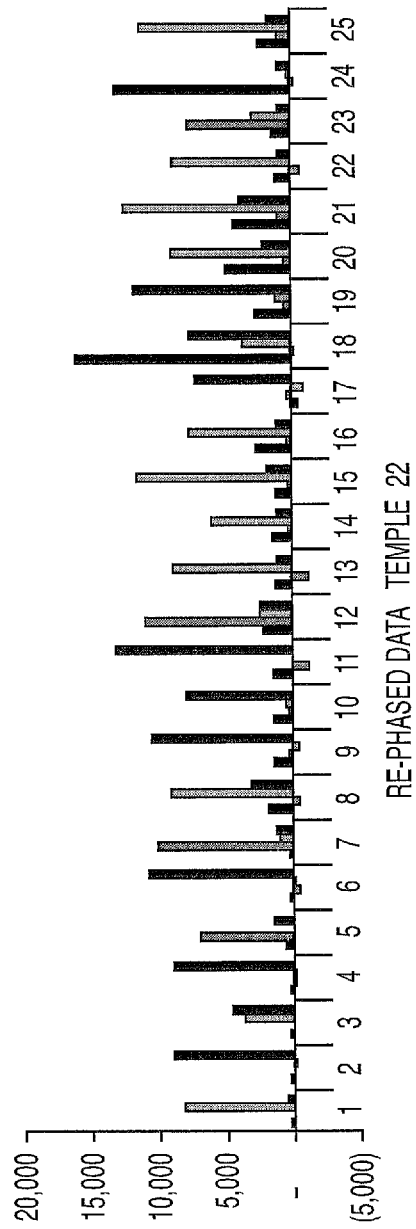
FIG. 34A INSTRUMENT DATA TEMPL 22
FIG. 34B RE-PHASED DATA TEMPLE 22

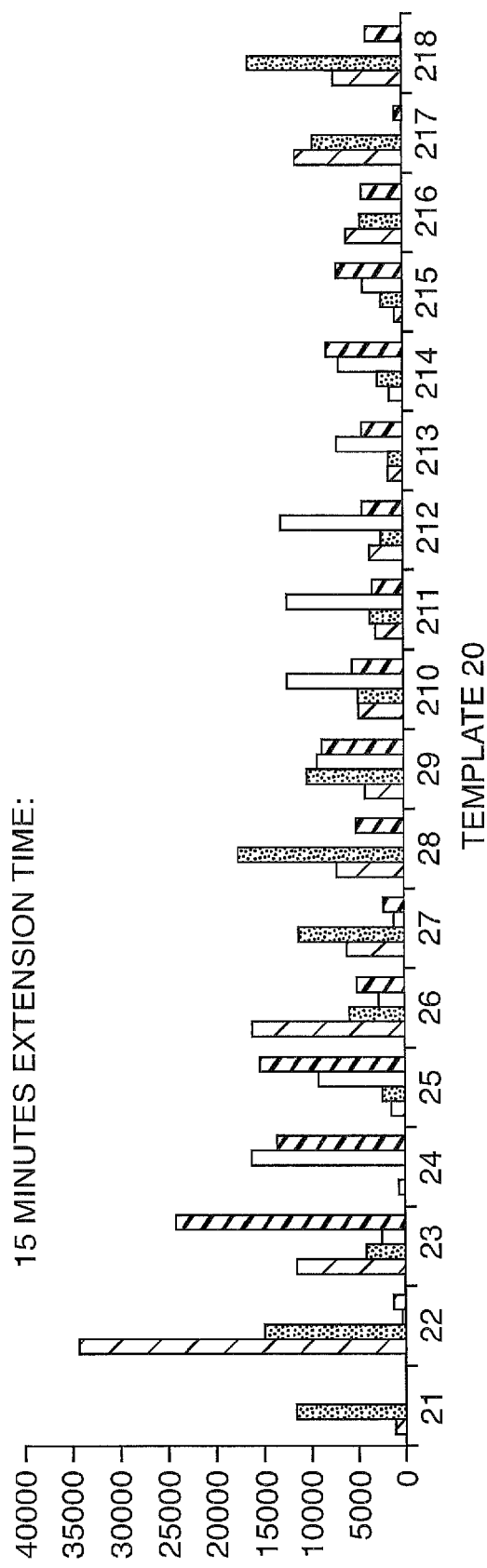
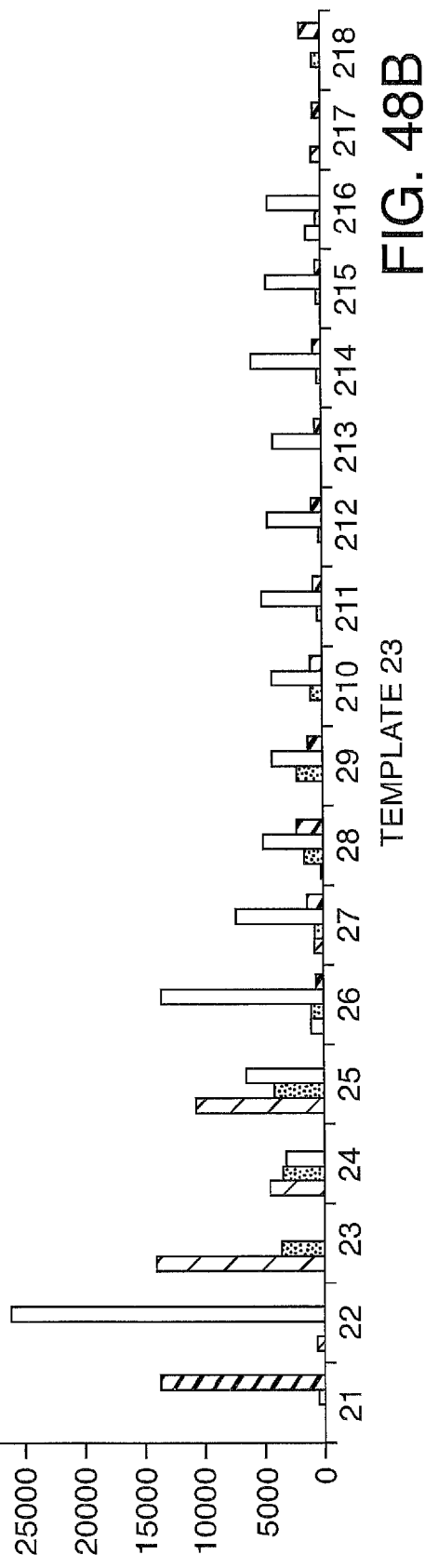

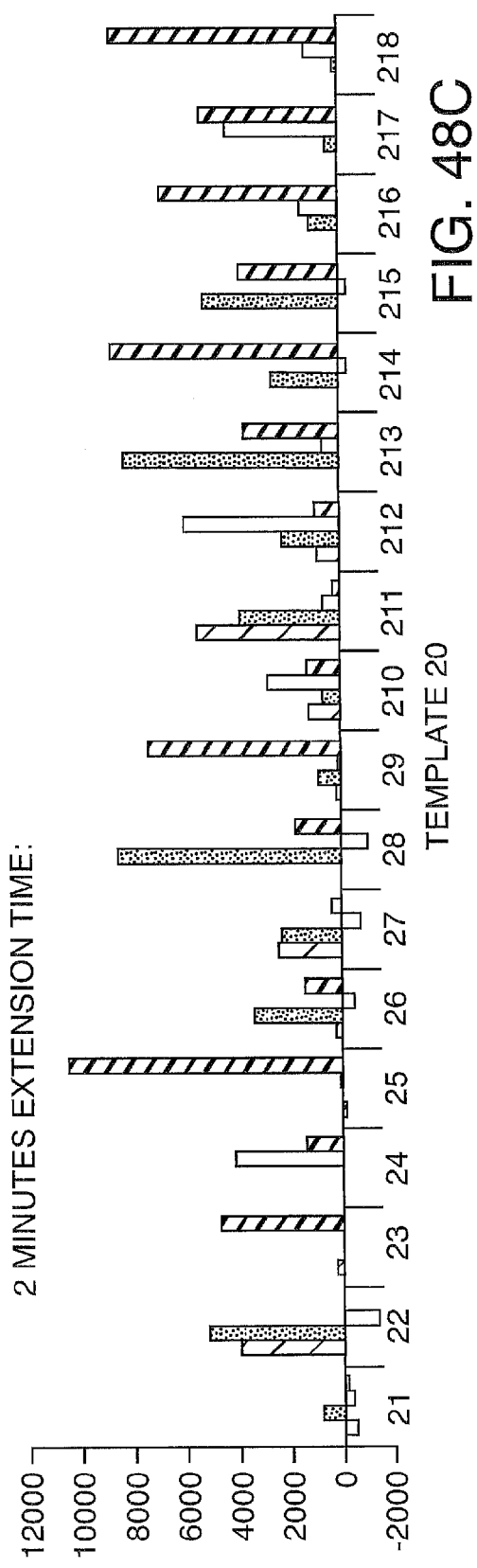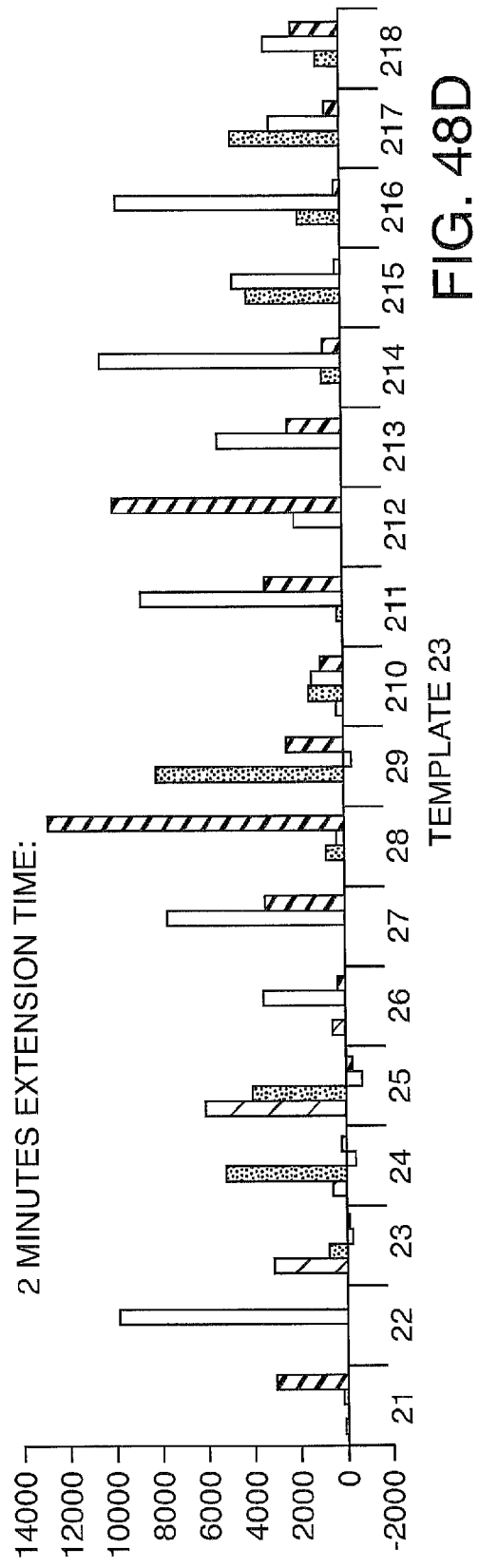

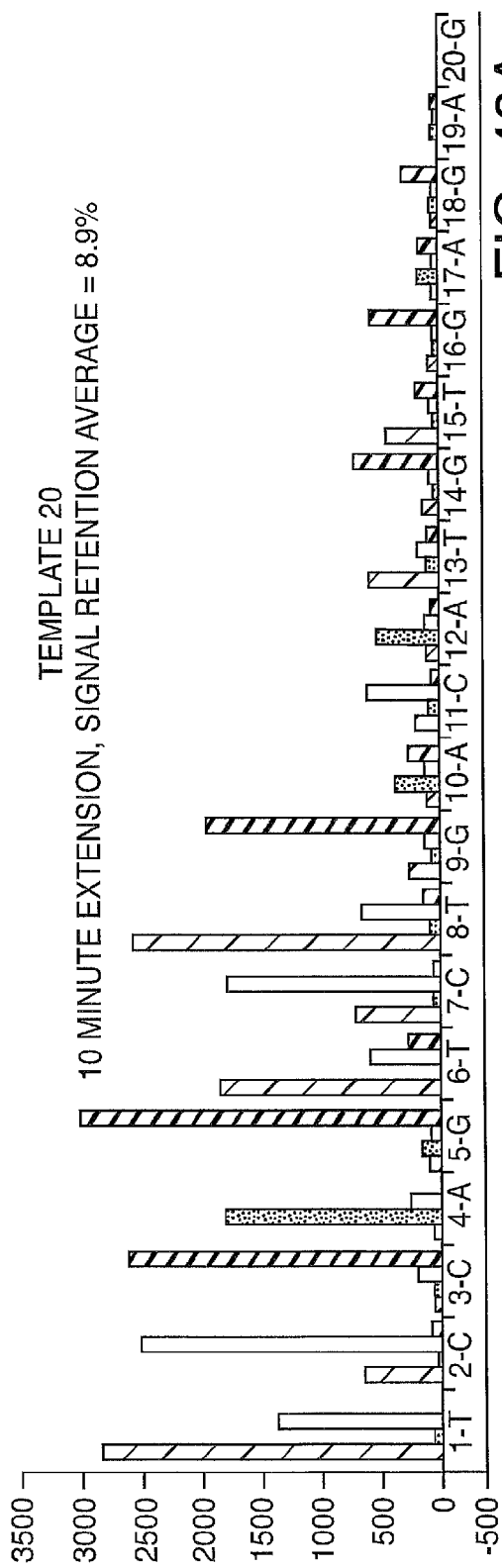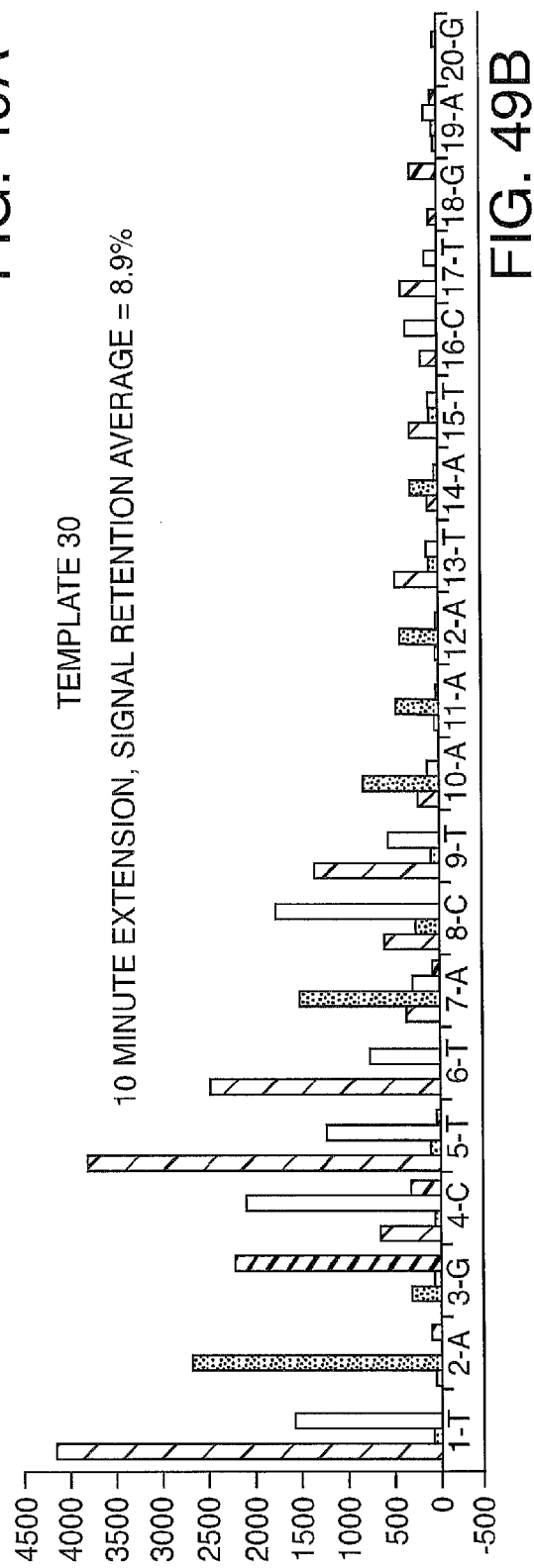

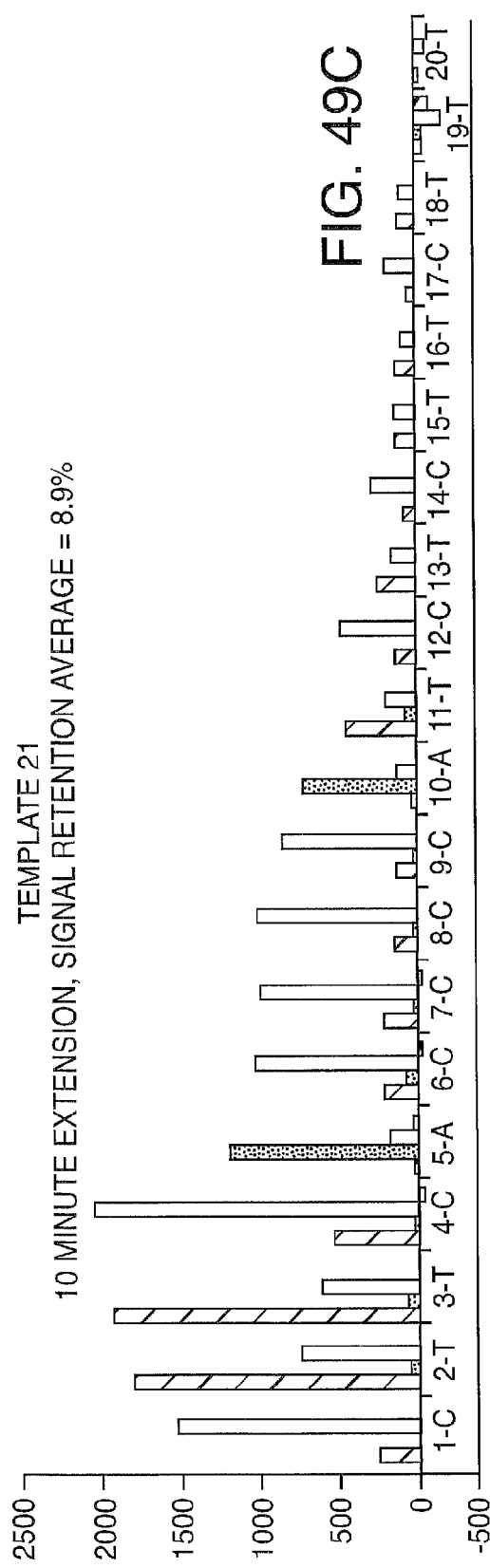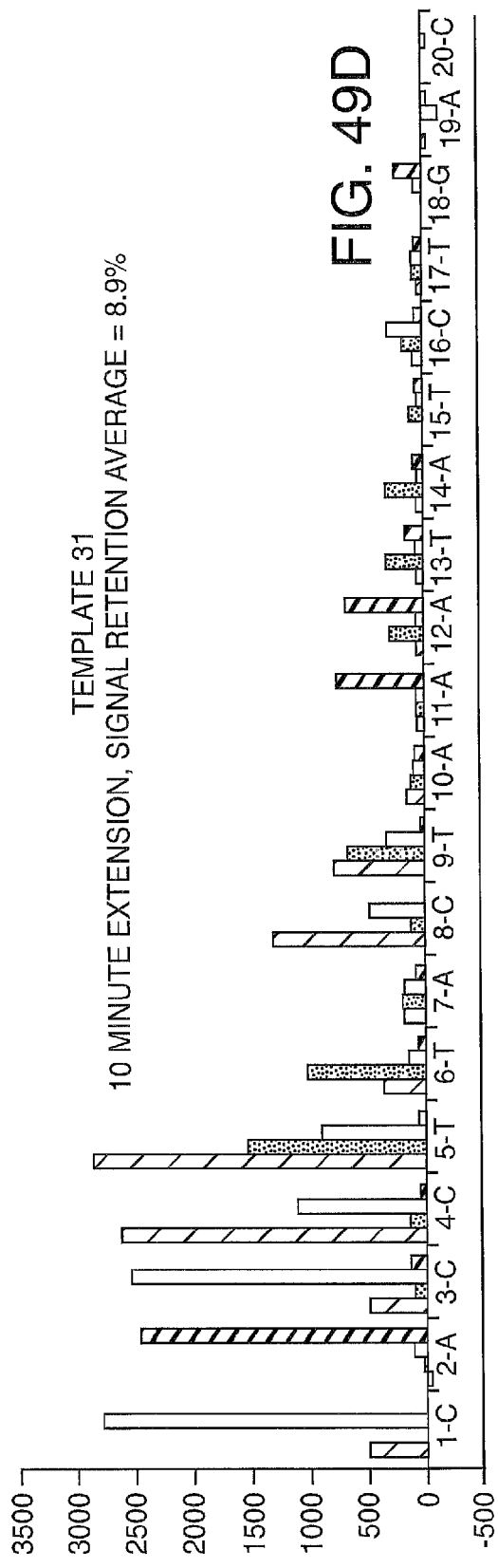

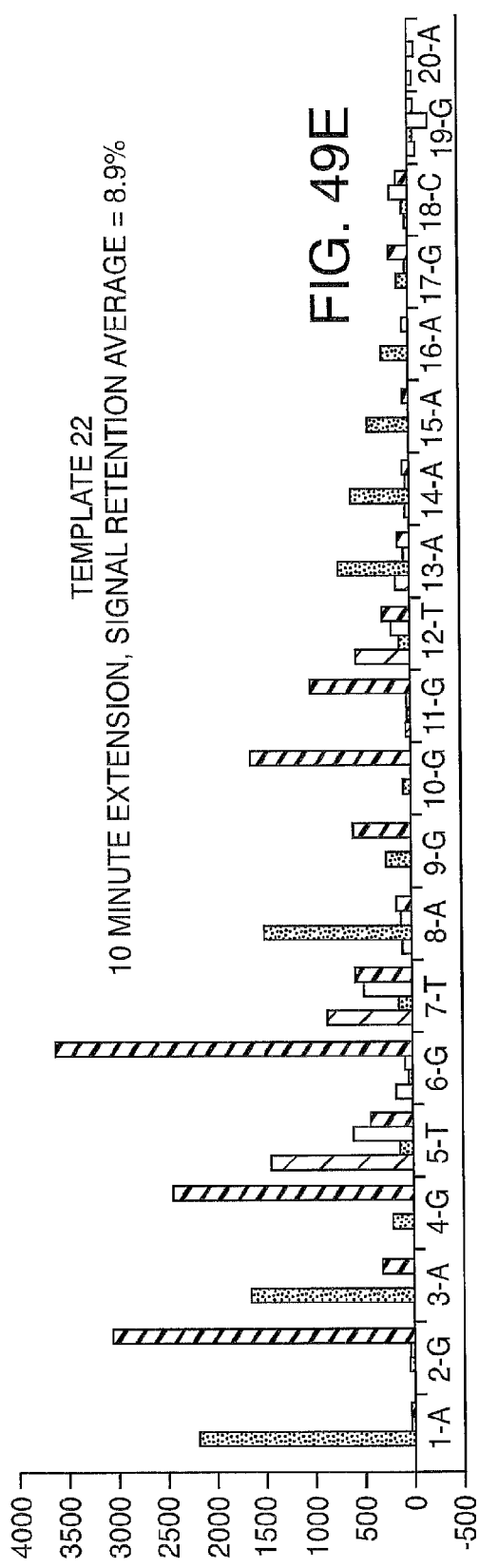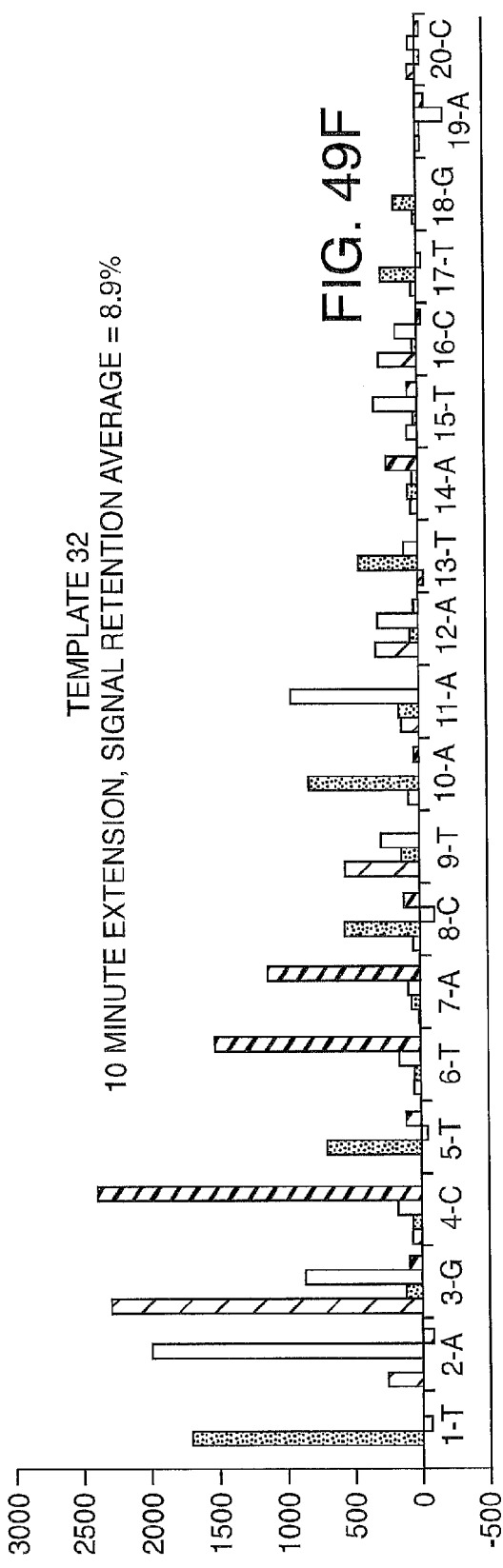

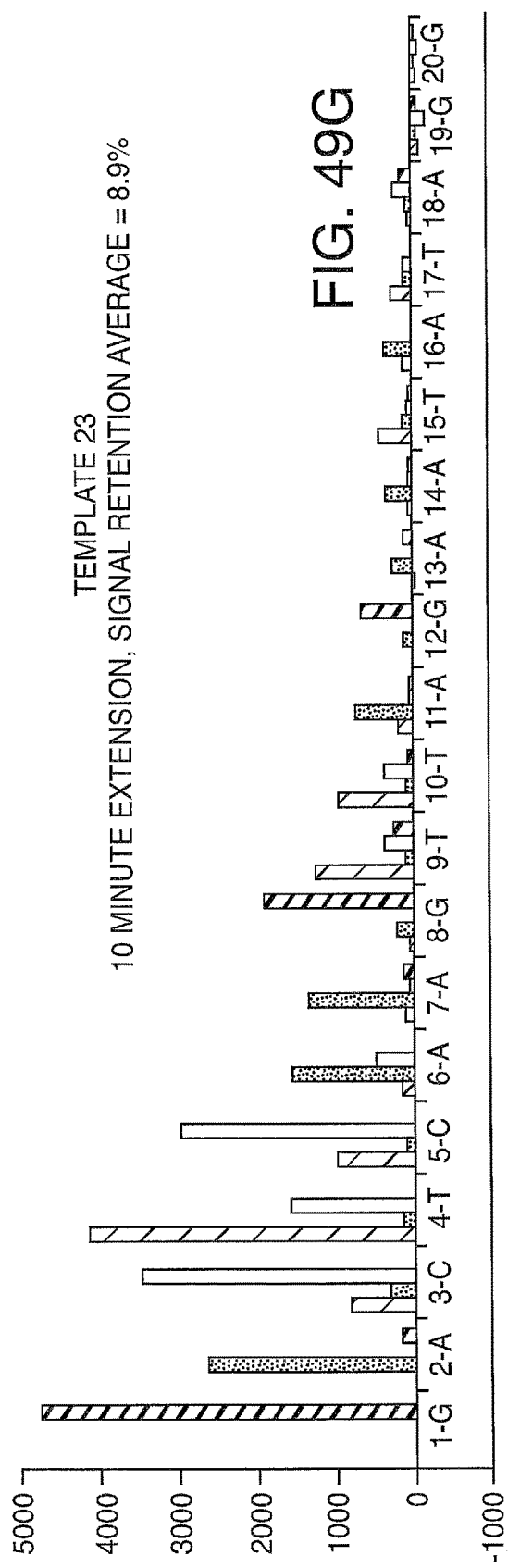
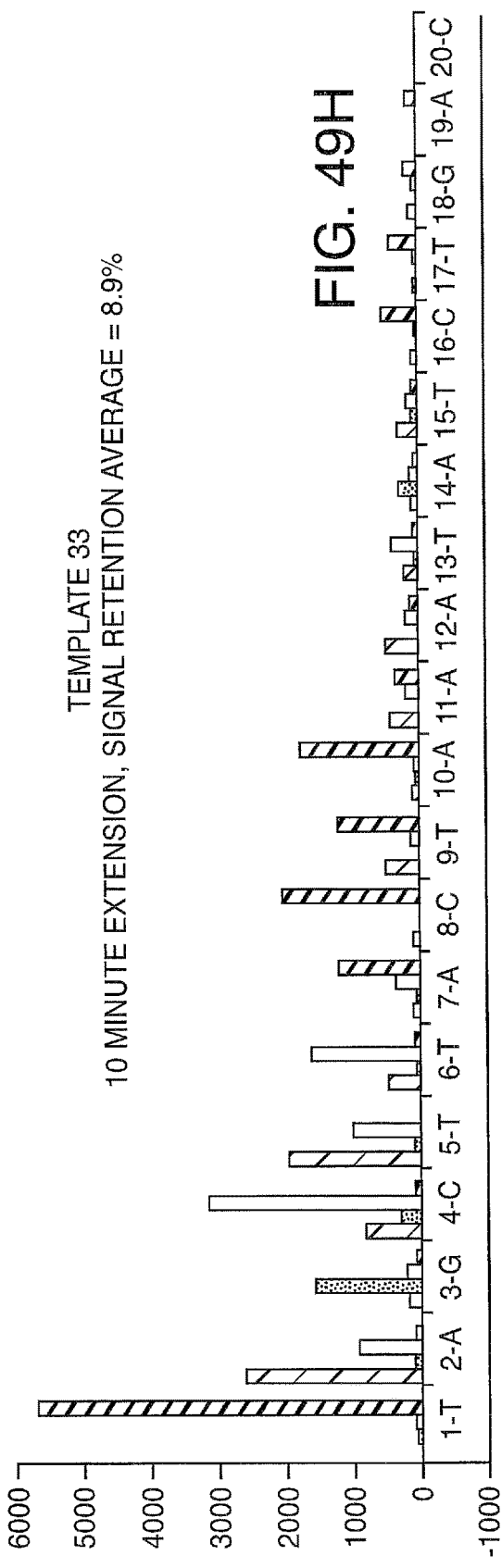

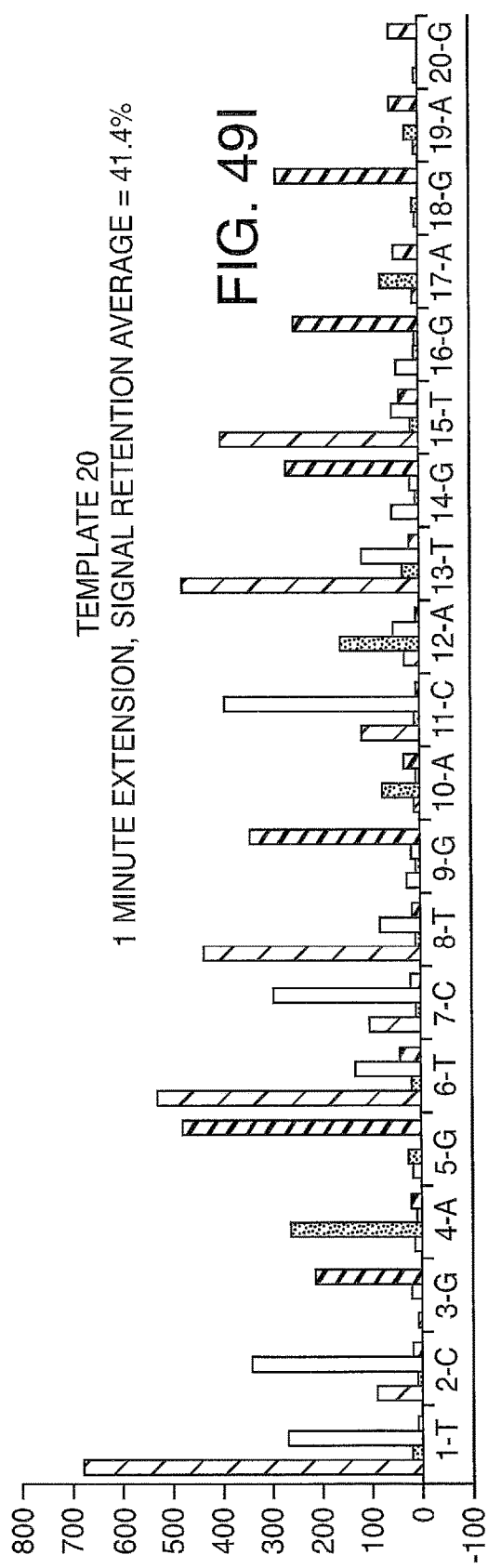
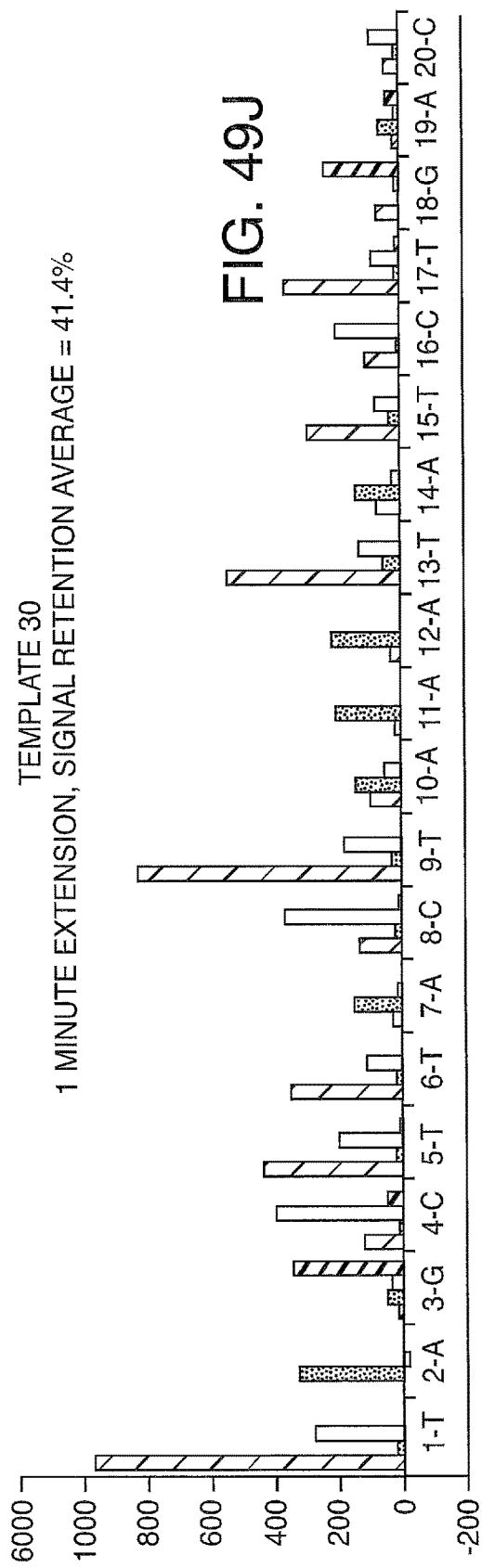

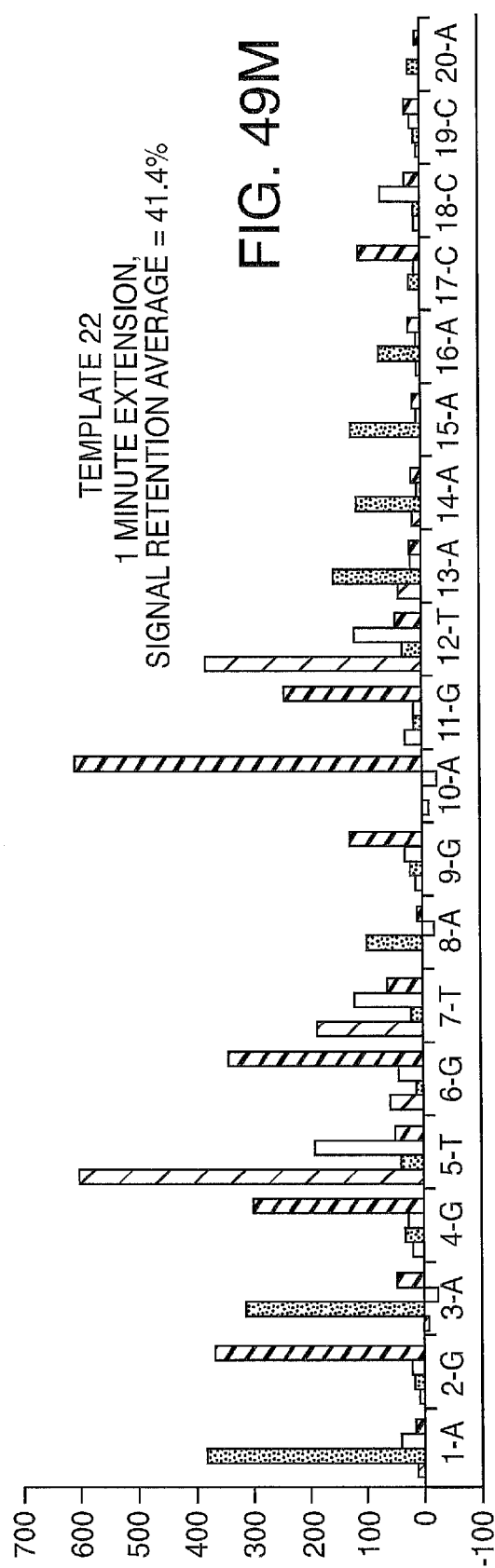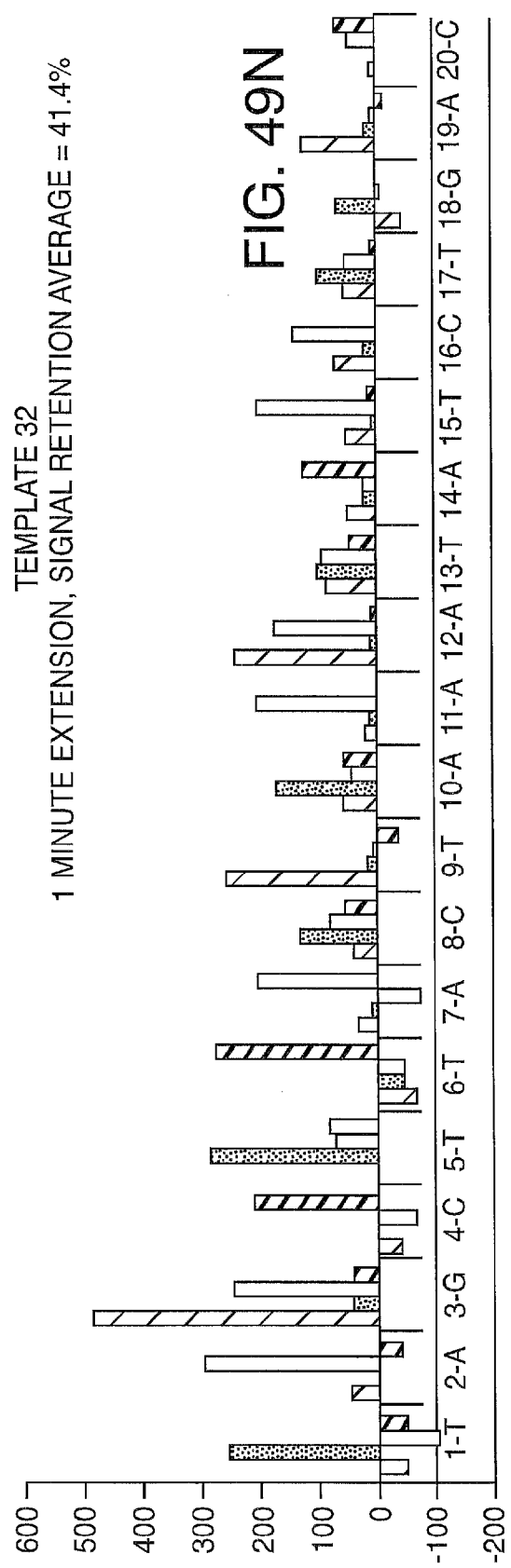

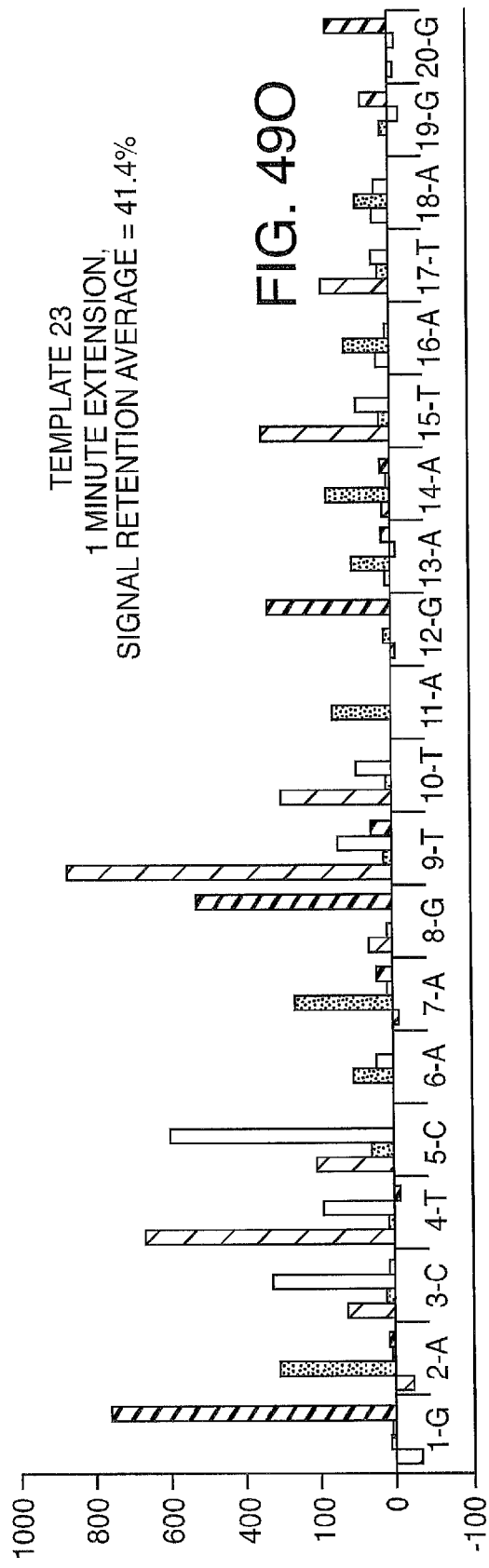
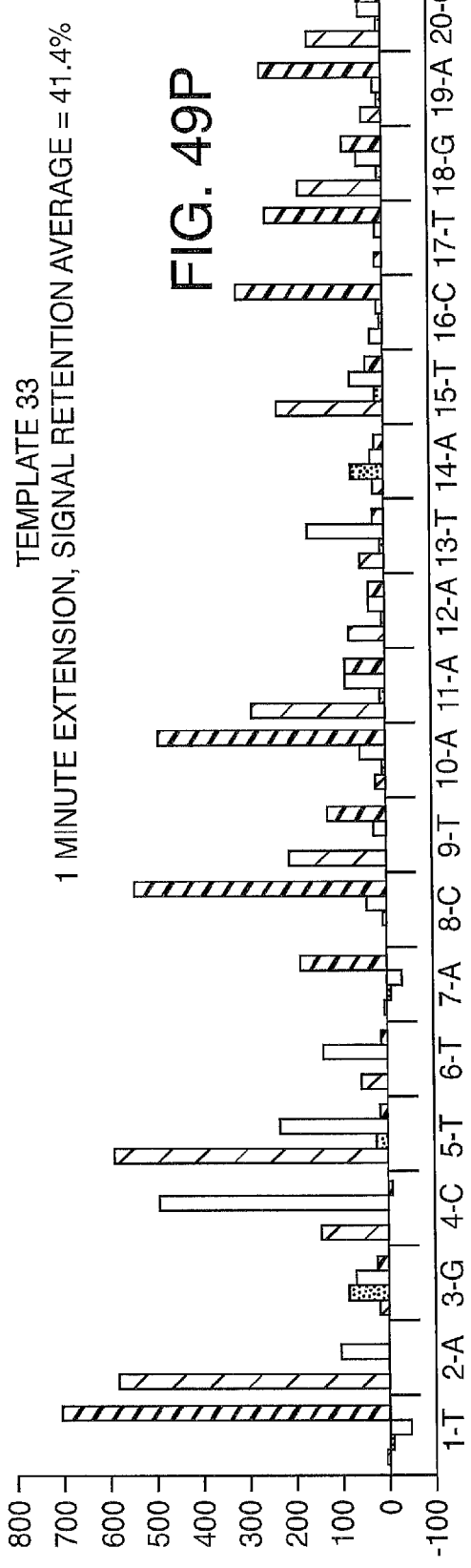
FIG. 49O — TEMPLATE 23, 1 MINUTE EXTENSION, SIGNAL RETENTION AVERAGE = 41.4%
FIG. 49P — TEMPLATE 33, 1 MINUTE EXTENSION, SIGNAL RETENTION AVERAGE = 41.4%

SEQUENCE LISTING

```
<160> NUMBER OF SEQ ID NOS: 12

<210> SEQ ID NO 1
<211> LENGTH: 53
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'NH2
<220> FEATURE:
<221> NAME/KEY: stem_loop
<222> LOCATION: (26)..(53)
```

<400> SEQUENCE: 1
catcactctc acatgtcaga ctcgagctga attccgcgtt cgcggaattc agc        53

<210> SEQ ID NO 2
<211> LENGTH: 53
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'NH2
<220> FEATURE:
<221> NAME/KEY: stem_loop
<222> LOCATION: (26)..(53)

<400> SEQUENCE: 2
gcgaaaaaga agagatgggg tgaaggctga attccgcgtt cgcggaattc agc        53

<210> SEQ ID NO 3
<211> LENGTH: 53
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'NH2
<220> FEATURE:
<221> NAME/KEY: stem_loop
<222> LOCATION: (26)..(53)

<400> SEQUENCE: 3
tgatttcgct tttaccctac actctgctga attccgcgtt cgcggaattc agc        53

<210> SEQ ID NO 4
<211> LENGTH: 53
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'NH2
<220> FEATURE:
<221> NAME/KEY: stem_loop
<222> LOCATION: (26)..(53)

<400> SEQUENCE: 4
atcgccctat attctaactt gactcgctga attccgcgtt cgcggaattc agc        53

<210> SEQ ID NO 5
<211> LENGTH: 12
<212> TYPE: DNA
<213> ORGANISM: Artificial Sequence
<220> FEATURE:
<223> OTHER INFORMATION: Synthetic

<400> SEQUENCE: 5
actgactgac tg        12

<210> SEQ ID NO 6
<211> LENGTH: 25
<212> TYPE: DNA
<213> ORGANISM: Artificial Sequence

```
<220> FEATURE:
<223> OTHER INFORMATION: Synthetic

<400> SEQUENCE: 6
tcgagtctga catgtgagag tgatg                                              25

<210> SEQ ID NO 7
<211> LENGTH: 25
<212> TYPE: DNA
<213> ORGANISM: Artificial Sequence
<220> FEATURE:
<223> OTHER INFORMATION: Synthetic

<400> SEQUENCE: 7
cttcacccca tctcttcttt ttcgc                                              25

<210> SEQ ID NO 8
<211> LENGTH: 25
<212> TYPE: DNA
<213> ORGANISM: Artificial Sequence
<220> FEATURE:
<223> OTHER INFORMATION: Synthetic

<400> SEQUENCE: 8
agagtgtagg gtaaaagcga aatca                                              25

<210> SEQ ID NO 9
<211> LENGTH: 25
<212> TYPE: DNA
<213> ORGANISM: Artificial Sequence
<220> FEATURE:
<223> OTHER INFORMATION: Synthetic

<400> SEQUENCE: 9
gagtcaagtt agaatatagg gcgat                                              25

<210> SEQ ID NO 10
<211> LENGTH: 12
<212> TYPE: DNA
<213> ORGANISM: Artificial Sequence
<220> FEATURE:
<223> OTHER INFORMATION: Synthetic

<400> SEQUENCE: 10
agctagctag ct                                                            12

<210> SEQ ID NO 11
<211> LENGTH: 10
<212> TYPE: DNA
<213> ORGANISM: Artificial Sequence
<220> FEATURE:
<223> OTHER INFORMATION: Synthetic

<400> SEQUENCE: 11
tcgtcgtcga                                                               10

<210> SEQ ID NO 12
<211> LENGTH: 18
<212> TYPE: DNA
<213> ORGANISM: Artificial Sequence
<220> FEATURE:
<223> OTHER INFORMATION: Synthetic

<400> SEQUENCE: 12
tctcgacgtc gacgacga                                                      18
```

METHODS AND SOLUTIONS FOR INHIBITING UNDESIRED CLEAVING OF LABELS

FIELD OF THE INVENTION

The invention relates to methods, compositions, devices, systems and kits are described including, without limitation, reagents, mixtures, data processing steps, algorithms, computer readable media, and computer programs, for determining the identity of nucleic acids in nucleotide sequences using, for example, data obtained from sequencing by synthesis methods.

BACKGROUND OF THE INVENTION

Over the past 25 years, the amount of DNA sequence information that has been generated and deposited into Genbank has grows exponentially. Many of the next-generation sequencing technologies use a form of sequencing by synthesis (SBS), wherein specially designed nucleotides and DNA polymerases are used to read the sequence of chip-bound, single-stranded DNA templates in a controlled manner. To attain high throughput, many millions of such template spots are arrayed across a sequencing chip and their sequence is independently read out and recorded.

Devices, equations, and computer systems for forming and using arrays of material on a substrate for DNA sequencing are known (e.g., Ju et al., U.S. Pat. No. 6,664,079; Pirrung et al., U.S. Pat. No. 5,143,854; Hubbell et al, U.S. Pat. No. 5,71,639; Lipshutz et al., U.S. Pat. Nos. 6,957,149, 5,733,729, 6,066,454, 6,228,593 and 6,546,340; Chee et al., U.S. Pat. No. 5,795,716; Domnisoru et al., U.S. Pat. No. 6,598,013; Schermer et al., U.S. Pat. No. 7,209,836; Gavrilov et al., U.S. Pat. Application No. 2007/0194249; Eltoukhy et al., In: IEEE International Conference on Acoustics, Speech and signal processing, (2006) 2:1032-1035; Margulies et al. (2005) Nature 437:376-380; and Gerardo et al. (2008) Nucleic Acids Res. (2008) 36(4):e25). However, there is a continued need for methods and compositions for increasing the fidelity of sequencing nucleic acid sequences.

SUMMARY OF THE INVENTION

The invention provides methods, compositions, devices, systems and kits are described including, without limitation, reagents, mixtures, data processing steps, algorithms, computer readable media, and computer programs, for determining the identity of nucleic acids in nucleotide sequences using, for example, data obtained from sequencing by synthesis methods. The methods of the invention include reducing and/or correcting one or more phenomena that are encountered during nucleotide sequencing, such as using sequencing by synthesis methods. These phenomena include, without limitation, sequence lead, sequence lag, spectral crosstalk, light from neighboring spots, and noise resulting from variations in illumination and/or filter responses.

In one embodiment, the present invention contemplates a set of data processing steps that may be used to analyze images of a hexagonal array of spots or beads on a surface. In one embodiment, the steps comprise a) field flattening and background subtraction, b) spot location in the array, c) image sharpening, d) spot brightness determination, e) neighbor influence elimination, and f) color crosstalk elimination. Each of these steps is described in more detail below.

Of course, in one embodiment, the present invention contemplates using a subset of these steps (in the same order or in a different order) as well as additional processing steps. The result of the analysis may be used to make measurements of the output of four different fluorescent dyes for each spot in the array. The methods described may also be generalized for a rectangular or other shaped arrays rather than a hexagonal array.

In one embodiment, the invention provides a method for determining an identity of a nucleic acid at an interrogation position in a nucleotide sequence from data acquired from one or more channels, comprising a) obtaining a data set for one or more probe intensities at one or more nucleic acid positions in the sequence, wherein each probe corresponds to a nucleic acid, b) determining the ratio contribution to probe intensity at the interrogation position from probe intensities at the interrogation position and at one or both of i) at least one subsequent nucleic acid positions in the sequence, and ii) at least one preceding nucleic acid positions in the sequence, and c) applying the ratio contribution to probe intensity to the data set to arrive at an identity for a nucleic acid at the interrogation position in the nucleotide sequence. In a particular embodiment, the step of determining the ratio contribution to probe intensity comprises measuring the rate (that is, the fraction of template molecules in an ensemble of identical template molecules) at which a lag, such as Gi, occurs at one or more nucleotide position in the nucleotide sequence, such as at each nucleotide position in the nucleotide sequence. In another embodiment, the step of determining the ratio contribution to probe intensity comprises measuring the rate (fraction) at which a lead, such as Di, occurs at one or more nucleotide positions in the nucleotide sequence. In yet another embodiment, the method further comprises calling a nucleic acid at the interrogation position in the nucleotide sequence. In a further embodiment, the method comprises repeating steps b) and c) to arrive at an identity for a nucleic acid at more than one interrogation position in the nucleotide sequence.

While not intending to limit the invention's method to particular steps, in one embodiment, the method further comprises a) applying a sequence lead-lag compensation equation to determine the ratio contribution to probe intensity from probe at i) the interrogation position, ii) each position preceding the interrogation position, and iii) each position subsequent to the interrogation position, and b) summing up the ratio contribution to probe intensity. In an alternative embodiment, the step of applying of the ratio contribution to probe intensity comprises a) comparing probe intensities from the one or more channels at the interrogation position, b) selecting the highest probe intensity of the compared probe intensities, and c) calling a nucleic acid, which corresponds to the selected probe, at the interrogation position.

It is not intended to limit the invention to a particular mathematical formula. Nonetheless, in one embodiment, the method comprises applying a sequence lead-lag compensation equation to the ratio contribution to probe intensity at a plurality of positions in the sequence. In one particular embodiment, the sequence lead-lag compensation equation is determined by applying equation $$\begin{bmatrix} I_{M1} \\ I_{M2} \\ \vdots \\ I_{MN} \end{bmatrix} = K_{Lead/Lag} \begin{bmatrix} I_{A1} \\ I_{A2} \\ \vdots \\ I_{AN} \end{bmatrix}$$

where $I_{M1}$ is a probe intensity measured at position 1 in the sequence, $I_{M2}$ is a probe intensity measured at position 2 in the sequence, $I_{MN}$ is a probe intensity measured at position N in the sequence, $I_{A1}$ is the actual probe intensity at position 1 in the sequence, $I_{A2}$ is the actual probe intensity at position 2 in the sequence, $I_{AN}$ is the actual probe intensity at position N in the sequence, where $$K_{Lead/Lag} = \begin{bmatrix} R_{Lag/Lead,1} & R_{+1Lead,1} & R_{+2Lead,1} & R_{+3Lead,1} & \cdots & R_{+(N-1)Lead,1} \\ R_{-1Lag,2} & R_{Lag/Lead,2} & R_{+1Lead,2} & R_{+2Lead,2} & \cdots & R_{+(N-2)Lead,2} \\ R_{-2Lag,3} & R_{-1Lag,3} & R_{Lag/Lead,3} & R_{+1Lead,3} & \cdots & R_{+(N-3)Lead,3} \\ R_{-3Lag,4} & R_{-2Lag,4} & R_{-1Lag,4} & R_{Lag/Lead,4} & \cdots & R_{+(N-4)Lead,4} \\ \vdots & \vdots & \vdots & \vdots & \ddots & \vdots \\ R_{-(N-1)Lag,N} & R_{-(N-2)Lag,N} & R_{-(N-3)Lag,N} & R_{-(N-4)Lag,N} & \cdots & R_{Lag/Lead,N} \end{bmatrix}$$

where $R_{Lag/Lead,1}$ is the ratio between reduced probe intensity for nucleic acid at position 1 to actual probe intensity at the nucleic acid at position 1, $R_{+1Lead,1}$ the ratio contribution to probe intensity at nucleic acid position 1 from probe at nucleic acid position 2, $R_{+2Lead,1}$ is the ratio contribution to probe intensity at nucleic acid position 1 from probe at nucleic acid position 3, $R_{+3Lead,1}$ the ratio contribution to probe intensity at nucleic acid position 1 from probe at nucleic acid position 4, $R_{+(N-1)Lead,1}$ is the ratio contribution to probe intensity at nucleic acid position 1 from probe at nucleic acid position 1+(N-1), $R_{-1Lag,2}$ is the ratio contribution to probe intensity at nucleic acid position 2 from probe at nucleic acid position 1, $R_{Lag/Lead,2}$ is the ratio between reduced probe intensity for nucleic acid at position 2 to actual probe intensity at the nucleic acid at position 2, $R_{+1Lead,2}$ the ratio contribution to probe intensity at nucleic acid position 2 from probe at nucleic acid position 3, $R_{+2Lead,2}$ is the ratio contribution to probe intensity at nucleic acid position 2 from probe at nucleic acid position 4, $R_{+(N-2)Lead,2}$ the ratio contribution to probe intensity at nucleic add position 2 from probe at nucleic acid position 2+(N-2), $R_{-2Lag,3}$ is the ratio contribution to probe intensity at nucleic add position 3 from probe at nucleic acid position 1, $R_{-1Lag,3}$ is the ratio contribution to probe intensity at nucleic acid position 3 from probe at nucleic acid position 2, $R_{Lag/Lead,3}$ is the ratio between reduced probe intensity for nucleic add at position 3 to actual probe intensity at the nucleic add at position 3, $R_{+1Lead,3}$ is the ratio contribution to probe intensity at nucleic acid position 3 from probe at nucleic acid position 4, $R_{+(N-3)Lead,3}$ is the ratio contribution to probe intensity at nucleic acid position 3 from probe at nucleic add position 3+(N-3), $R_{-3Lag,4}$ is the ratio contribution to probe intensity at nucleic acid position 4 from probe at nucleic add position 1, $R_{-2Lag,4}$ is the ratio contribution to probe intensity at nucleic acid position 4 from probe at nucleic acid position 2, $R_{-1Lag,4}$ is the ratio contribution to probe intensity at nucleic acid position 4 form probe at nucleic acid position 3, $R_{Lag/Lead,4}$ is the ratio between reduced probe intensity for nucleic acid at position 4 to actual probe intensity at the nucleic acid at position 4, $R_{+(N-4)Lead,4}$ is the ratio contribution to probe intensity at nucleic acid position 4 from probe at nucleic acid position 4+(N-4), $R_{-(N-1)Lag,N}$ the ratio contribution to probe intensity at nucleic acid position N from probe at nucleic acid position N-(N-1), $R_{-(N-2)Lag,N}$ the ratio contribution to probe intensity at nucleic acid position N from probe at nucleic acid position N-(N-2), $R_{-(N-3)Lag,N}$ contribution to probe intensity at nucleic acid position N from probe at nucleic add position N-(N-3), $R_{-(N-4)Lag,N}$ is the ratio contribution to probe intensity at nucleic acid position N from probe at nucleic acid position N-(N-4), and $R_{Lag/Lead,N}$ the ratio between reduced probe intensity for nucleic acid at position N to actual probe intensity at the nucleic acid at position N.

In a further embodiment, the sequence lead-lag compensation equation is determined by applying equation $$\begin{bmatrix} I_{M1} \\ I_{M2} \\ \vdots \\ I_{MN} \end{bmatrix} = K_{Lead/Lag} \begin{bmatrix} I_{A1} \\ I_{A2} \\ \vdots \\ I_{AN} \end{bmatrix}.$$

In a particular embodiment, the nucleic acid comprises a base selected from the group of adenine (A), guanine (G), cytosine (C), thymine (T), and uracil (U), and the probe is detectable using any means such as color in the visible spectrum (e.g., fluorescence), radioactivity, and the like.

While not intending to limit the invention's methods to particular steps, in one embodiment, the methods further comprise field flattening of background data for the data set. This may be accomplished by, for example, a) obtaining a first data set for a plurality of pixel intensities of a first raw image of a probe at a first concentration on a solid support, wherein the first raw image is produced using a first spectral filter for detecting a first probe, b) obtaining a second data set for a plurality of pixel intensities of a second smoothed image of the probe uniformly spread on the solid support or other uniformly radiating substrate, wherein the second smoothed image is produced using a low pass filter, c) determining a field flattening intensity value for a plurality of pixels of the first raw image, and d) generating a third field flattened image of the probe on the solid support using the field flattening intensity of the plurality of pixels, wherein the correlation of intensity of a plurality of pixels to their spatial location on the third field flattened image is reduced compared to the intensity of a plurality of pixels at a corresponding location on the first raw image. In a particular embodiment, the background intensities are removed from both the first and second data sets so that the lowest intensity data point is at 0.

Although the field flattening methods are not intended to be limited to any particular equation, in one embodiment, the field flattening intensity value of a pixel is determined by equation $$F_{x,y} = R_{x,y} M_{x0,y0} / M_{x,y}$$

where
- $F_{x,y}$ is a field flattening intensity value,
- $R_{x,y}$ is the intensity of a pixel of the plurality of pixels on the first raw image,
- $M_{x,y}$ is the intensity of a pixel of the plurality of pixels on the second smoothed image at a corresponding spatial location to the pixel on the first raw image, and
- $M_{x0,y0}$ is the intensity of a reference pixel on the second smoothed image or is an arbitrary scale factor.

In one embodiment the scale factor $M_{x0,y0}$ may also include a factor accounting for different exposure times or lighting intensities. In another embodiment, such as where a camera system has a proportional response to changes in exposure times or lighting conditions, the following equation may be used $$M_{x0,y0} = M_0 E_{(second\ image)} / E_{(first\ image)}$$

where $E_{(first\ image)}$ is the exposure or lighting level used during measurement of the first image, $E_{(second\ image)}$ is the exposure or lighting level used for the second image and $M_0$ is an arbitrary constant. In a further embodiment, the method further comprises repeating steps a) to d), using a second spectral filter for detecting a second probe. In an alternative embodiment, the method further comprises repeating steps a) to d), using the probe at a second concentration on the solid support. The solid support is exemplified, but not limited to, a microscope slide and silicon chip.

Also without limiting the invention's methods to particular steps, in one embodiment, the methods further comprise reducing spectral crosstalk in the one or more channels, by a) determining spectral crosstalk factors for each of the one or more probes in its corresponding channel from one or more adjacent: channels, b) applying the spectral crosstalk factors to determine a spectral crosstalk matrix, and c) applying the spectral crosstalk matrix to the data set for the one or more probe intensities. In a particular embodiment, the step of reducing spectral crosstalk comprises a) determining probe intensity for one or more probes from one or more channels, wherein each channel corresponds to a probe, b) determining the ratios of the probe intensities in the one or more channels to arrive at signature ratios for the probe intensity in the channels, c) applying the signature ratios in a matrix equation, and d) inverting the matrix equation to arrive at an inverted matrix. In one embodiment, the method further comprises e) applying the inverted matrix to data from the one or more channels.

While not intending to limit reducing spectral crosstalk to any particular equation, in one embodiment, the step of determining spectral crosstalk matrix comprises using equation $$\begin{bmatrix} M_A \\ M_B \\ M_C \\ M_D \end{bmatrix} = K \begin{bmatrix} A \\ B \\ C \\ D \end{bmatrix}$$

where $$K = \begin{bmatrix} 1 & R_{AB} & 0 & 0 \\ R_{BA} & 1 & R_{BC} & 0 \\ 0 & R_{CB} & 1 & R_{CD} \\ 0 & 0 & R_{DC} & 1 \end{bmatrix}.$$

and where
- $M_A$ is the observed intensity in the channel for probe A,
- $M_B$ is the observed intensity in the channel for probe B,
- $M_C$ is the observed intensity in the channel for probe C,
- $M_D$ is the observed intensity in the channel for probe D,
- A is the actual probe intensity of probe A,
- B is the actual probe intensity of probe B,
- C is the actual probe intensity of probe C,
- D is the actual probe intensity of probe D,
- $R_{AB}$ is the ratio between (a) the portion of intensity in the channel for probe A that is contributed by probe B, and (b) the actual probe intensity of probe B,
- $R_{BA}$ is the ratio between (a) the portion of intensity in the channel for probe B that is contributed by probe A, and (b) the actual probe intensity of probe A,
- $R_{BC}$ is the ratio between (a) the portion of intensity in the channel for probe B that is contributed by probe C, and (b) the actual probe intensity of probe C,
- $R_{CB}$ is the ratio between (a) the portion of intensity in a channel for probe C that is contributed by probe B, and (b) the actual probe intensity of probe B,
- $R_{CD}$ is the ratio between (a) the portion of intensity in a channel for probe C that is contributed by probe D, and (b) the actual probe intensity of probe D, and
- $R_{DC}$ is the ratio between (a) the portion of intensity in a channel for probe D that is contributed by probe C, and (b) the actual probe intensity of probe C.

The above equation is solved to determine spectral crosstalk matrix $K^{-1}$ and an estimate of the actual intensities of the probes (A, B, C and D) using equation $$\begin{bmatrix} A \\ B \\ C \\ D \end{bmatrix} = K^{-1} \begin{bmatrix} M_A \\ M_B \\ M_C \\ M_D \end{bmatrix}$$

In an alternative embodiment, the equation is solved to determine and/or estimate for actual probe intensities A, B, C and D.

The invention further provides an algorithm for processing data for nucleic acids in a nucleotide sequence, wherein the data is acquired from one or more channels, the algorithm comprising a) determining the ratio contribution to probe intensity in the one or more channels for one or more interrogation positions, from probe intensities at the interrogation position and at one or both of i) at least one subsequent nucleic acid positions in the sequence, and ii) at least one preceding nucleic acid positions in the sequence, b) processing data from the one or more channels to correct for sequence lead and sequence lag, and c) reconstructing the data in the one or more channels. In one embodiment, the step of processing data comprises applying the ratio contribution to probe intensity to determine, for the probe at the one or more interrogation positions, a sequence lead-lag compensation equation. Without limiting the invention to any particular equation, in one embodiment, the sequence lead-lag compensation equation is determined by applying equation $$\begin{bmatrix} I_{M1} \\ I_{M2} \\ \vdots \\ I_{MN} \end{bmatrix} = K_{Lead/Lag} \begin{bmatrix} I_{A1} \\ I_{A2} \\ \vdots \\ I_{AN} \end{bmatrix}$$

where $I_{M1}$ is a probe intensity measured at position 1 in the sequence, $I_{M2}$ is a probe intensity measured at position 2 in the sequence, $I_{MN}$ is a probe intensity measured at position N in the sequence, $I_{A1}$ is the actual probe intensity at position 1 in the sequence, $I_{A2}$ is the actual probe intensity at position 2 in the sequence, $I_{AN}$ is the actual probe intensity at position N in the sequence, In an alternative embodiment, the sequence lead-lag compensation equation is determined by applying equation $$K_{Lead/Lag} = \begin{bmatrix} R_{Lag/Lead,1} & R_{+1Lead,1} & R_{+2Lead,1} & R_{+3Lead,1} & \cdots & R_{+(N-1)Lead,1} \\ R_{-1Lag,2} & R_{Lag/Lead,2} & R_{+1Lead,2} & R_{+2Lead,2} & \cdots & R_{+(N-2)Lead,2} \\ R_{-2Lag,3} & R_{-1Lag,3} & R_{Lag/Lead,3} & R_{+1Lead,3} & \cdots & R_{+(N-3)Lead,3} \\ R_{-3Lag,4} & R_{-2Lag,4} & R_{-1Lag,4} & R_{Lag/Lead,4} & \cdots & R_{+(N-4)Lead,4} \\ \vdots & \vdots & \vdots & \vdots & \ddots & \vdots \\ R_{-(N-1)Lag,N} & R_{-(N-2)Lag,N} & R_{-(N-3)Lag,N} & R_{-(N-4)Lag,N} & \cdots & R_{Lag/Lead,N} \end{bmatrix}$$

where $R_{Lag/Lead,1}$ is the ratio between reduced probe intensity for nucleic acid at position 1 to actual probe intensity at the nucleic acid at position 1, $R_{+1Lead,1}$ is the ratio contribution to probe intensity at nucleic acid position 1 from probe at nucleic acid position 2, $R_{+2Lead,1}$ is the ratio contribution to probe intensity at nucleic acid position 1 from probe at nucleic acid position 3, $R_{+3Lead,1}$ is the ratio contribution to probe intensity at nucleic acid position 1 from probe at nucleic acid position 4, $R_{+(N-1)Lead,1}$ is the ratio contribution to probe intensity at nucleic acid position 1 from probe at nucleic acid position 1+(N−1), $R_{-1Lag,2}$ is the ratio contribution to probe intensity at nucleic acid position 2 from probe at nucleic acid position 1, $R_{Lag/Lead,2}$ is the ratio between reduced probe intensity for nucleic acid at position 2 to actual probe intensity at the nucleic acid at position 2, $R_{+1Lead,2}$ is the ratio contribution to probe intensity at nucleic acid position 2 from probe at nucleic acid position 3, $R_{+2Lead,2}$ is the ratio contribution to probe intensity at nucleic acid position 2 from probe at nucleic acid position 4, $R_{+(N-2)Lead,2}$ is the ratio contribution to probe intensity at nucleic acid position 2 from probe at nucleic add position 2+(N−2), $R_{-2Lag,3}$ is the ratio contribution to probe intensity at nucleic acid position 3 from probe at nucleic acid position 1, $R_{-1Lag,3}$ is the ratio contribution to probe intensity at nucleic acid position 3 from probe at nucleic acid position 2, $R_{Lag/Lead,3}$ is the ratio between reduced probe intensity for nucleic acid at position 3 to actual probe intensity at the nucleic acid at position 3, $R_{+1Lead,3}$ is the ratio contribution to probe intensity at nucleic acid position 3 from probe at nucleic acid position 4, $R_{+(N-3)Lead,3}$ is the ratio contribution to probe intensity at nucleic acid position 3 from probe at nucleic acid position 3+(N−3), $R_{-3Lag,4}$ is the ratio contribution to probe intensity at nucleic acid position 4 from probe at nucleic acid position 1, $R_{-2Lag,4}$ is the ratio contribution to probe intensity at nucleic acid position 4 from probe at nucleic acid position 2, $R_{-1Lag,4}$ is the ratio contribution to probe intensity at nucleic acid position 4 from probe at nucleic acid position 3, $R_{Lag/Lead,4}$ is the ratio between reduced probe intensity for nucleic acid at position 4 to actual probe intensity at the nucleic acid at position 4, $R_{+(N-4)Lead,4}$ is the ratio contribution to probe intensity at nucleic acid position 4 from probe at nucleic acid position 4+(N−4), $R_{-(N-1)Lag,N}$ the ratio contribution to probe intensity at nucleic acid position N from probe at nucleic acid position N−(N−1), $R_{-(N-2)Lag,N}$ is the ratio contribution to probe intensity at nucleic acid position N from probe at nucleic acid position N−(N−2), $R_{-(N-3)Lag,N}$ the ratio contribution to probe intensity at nucleic acid position N from probe at nucleic acid position N−(N−3), $R_{-(N-4)Lag,N}$ ratio contribution to probe intensity at nucleic acid position N from probe at nucleic acid position N−(N−4), and $R_{Lag/Lead,N}$ the ratio between reduced probe intensity for nucleic acid at position N to actual probe intensity at the nucleic acid at position N.

In another alternative embodiment, the sequence lead-lag compensation equation is determined by applying equation $$\begin{bmatrix} I_{M1} \\ I_{M2} \\ \vdots \\ I_{MN} \end{bmatrix} = K_{Lead/Lag} \begin{bmatrix} I_{A1} \\ I_{A2} \\ \vdots \\ I_{AN} \end{bmatrix}.$$

While not necessary, it may be desirable to also include field flattening of background data in the algorithm and/or reducing spectral crosstalk between the data comprised in a plurality of channels. Dephasing correction (i.e., correction for lead-lag effects), field flattening and spectral crosstalk correction may be carried out in any order. Thus, in one embodiment, the field flattening is carried out before spectral crosstalk correction. In an alternative embodiment, spectral crosstalk correction is carried out before dephasing correction.

The invention also provides a computer readable medium containing a computer program for performing one or more of the method steps disclosed herein.

Also provided by the invention is a computer program product for processing data for nucleic acids in a nucleotide sequence to determine an identity of a nucleic acid at an interrogation position in the nucleotide sequence, the computer program product comprising a) computer code that inputs data from one or more channels for one or more probe intensities, wherein each channel corresponds to a probe, and each probe corresponds to a nucleic acid, b) computer code that applies to the input data a sequence lead-lag compensation equation to correct for sequence lead and sequence lag, c) computer code that compares probe intensities in the one or more channels that have been corrected for sequence lead and sequence lag, d) computer code that determines the highest probe intensity of the compared probe intensities, and e) computer code that identifies a nucleic acid at the interrogation position according to the highest probe intensity. Optionally, the computer program product may further comprise computer code that applies field flattening of background data and/or that reduces spectral crosstalk between data comprised in the one or more channels.

The invention also provides an apparatus that processes data for nucleic acids in a nucleotide sequence to determine an identity of a nucleic acid at an interrogation position in the nucleotide sequence, the apparatus comprising a) means for inputting data from one or more channels for one or more probe intensities, wherein each channel corresponds to a probe, and each probe corresponds to a nucleic acid, b) means for applying to the input data a sequence lead-lag compensation equation to correct for sequence lead and sequence lag, c) means for comparing probe intensities in the one or more; channels that have been corrected for sequence lead and sequence lag, d) means for determining the highest probe intensity of the compared probe intensities, and e) means for identifying a nucleic acid at the interrogation position according to the highest probe intensity. Though not necessary, if may be desirable to also include means for applying field flattening of background data and/or for reducing spectral crosstalk between data comprised in the one or more channels.

Additionally provided herein is a system for processing data to determine an identity of a nucleic acid at an interrogation position in the nucleotide sequence, the system comprising a) a processor, and b) a computer readable medium readable by the processor, the computer readable medium storing a computer program that comprises i) code that receives as input a plurality of probe intensities at various positions in a nucleotide sequence, ii) code that applies to the input data a sequence lead-lag compensation equation to correct for sequence lead and sequence lag, and iii) code that identifies a nucleic acid at one or more interrogation position according to the corrected data. While net necessary, it may be desirable to additionally include in the computer readable medium code that applies field Battening of background data and/or that reduces spectral crosstalk between data comprised in the one ore more channels.

The invention also provides a method for field flattening an image of a probe on a solid support, comprising a) obtaining a first data set for a plurality of pixel intensities of a first raw image of a probe at a first concentration on a solid support, wherein die first raw image is produced using a first spectral filter for detecting a first probe, b) obtaining a second data set for a plurality of pixel intensities of a second smoothed image of the probe on the solid support, wherein the second smoothed image is produced using a low-pass filter, c) determining a field flattening intensity value for a plurality of pixels of the first raw image, and d) generating a third field flattened image of the probe on the solid support using the field flattening intensity of the plurality of pixels, wherein the correlation of intensity of a plurality of pixels to their spatial location on the third field flattened image is reduced compared to the intensity of a plurality of pixels at a corresponding location on the first raw image. Without, intending to limit the invention to any particular equation, in one embodiment, the field flattening intensity value of a pixel is determined by equation $$F_{x,y} = R_{x,y} M_{x0,y0} / M_{x,y}$$

where $F_{x,y}$ is a field flattening intensity value, $R_{x,y}$ is the intensity of a pixel of the plurality of pixels on the first raw image, $M_{x,y}$ is the intensity of a pixel of the plurality of pixels on the second smoothed image at a corresponding spatial location to the pixel on the first raw image, and $M_{x0,y0}$ is the intensity of a reference pixel on the second smoothed image, or is any other scale factor of interest.

In one embodiment, it may be desirable to repeat, steps a) to d), using a second spectral filter for detecting a second probe. Alternatively, or in addition, it may be desirable to repeat steps a) to d), using the probe at a second concentration on the solid support. In one embodiment, the probe is fluorescent and corresponds to a nucleic acid that comprises a base selected from the group of adenine (A), guanine (G), cytosine (C), thymine (T), and uracil (U). The solid support may comprise a microscope slide, silicon chip, and the like.

The invention also provides a method for reducing spectral crosstalk in one or more channels that deliver data for determining the identity of a nucleic acid at an interrogation position in a nucleotide sequence, comprising a) obtaining a data set for one or more probe intensities at one or more nucleic acid positions in the sequence, wherein each probe corresponds to a nucleic acid, b) determining spectral crosstalk factors for each of the one or more probes in its corresponding channel from one or more adjacent channels, c) applying the spectral crosstalk factors to determine a spectral crosstalk matrix, and d) applying the spectral crosstalk matrix to the data set to arrive at an identity for a nucleic acid at the interrogation position in the nucleotide sequence. In one embodiment, the step of determining spectral crosstalk factors comprises determining a ratio between (a) the portion of probe intensity in a first channel of a first probe that is contributed by a second probe in a second channel adjacent to the first channel, and (b) the actual probe intensity of the second probe in the second channel in a particular embodiment, the method further comprises determining the ratio between (a) the portion of probe intensity in the first channel of the first probe that is contributed by a third probe in a third channel adjacent to the first channel, and (b) the actual probe intensity of the third probe in the third channel. Without limiting the type of equation used, in one embodiment, the step of determining spectral crosstalk matrix comprises using equation $$\begin{bmatrix} M_A \\ M_B \\ M_C \\ M_D \end{bmatrix} = K \begin{bmatrix} A \\ B \\ C \\ D \end{bmatrix}$$

where $$K = \begin{bmatrix} 1 & R_{AB} & 0 & 0 \\ R_{BA} & 1 & R_{BC} & 0 \\ 0 & R_{CB} & 1 & R_{CD} \\ 0 & 0 & R_{DC} & 1 \end{bmatrix}$$

and where
  $M_A$ is the observed probe intensity of probe A,
  $M_B$ is the observed probe intensity of probe B,
  $M_C$ is the observed probe intensity of probe C,
  $M_D$ is the observed probe intensity of probe D,
  A is the actual probe intensity of probe A,
  B is the actual probe intensity of probe B,
  C is the actual probe intensity of probe C,
  D is the actual probe intensity of probe D,
  $R_{AB}$ is the ratio between (a) the portion of intensity in the channel for probe A that is contributed by probe B, and (b) the actual probe intensity of probe B,
  $R_{BA}$ is the ratio between (a) the portion of intensity in the channel for probe B that is contributed by probe A, and (b) the actual probe intensity of probe A,
  $R_{BC}$ is the ratio between (a) the portion of intensity in the channel for probe B that is contributed by probe C, and (b) the actual probe intensity of probe C,
  $R_{CB}$ is the ratio between (a) the portion of intensity in a channel for probe C that is contributed by probe B, and (b) the actual probe intensity of probe B,
  $R_{CD}$ is the ratio between (a) the portion of intensity in a channel for probe C that is contributed by probe D, and (b) the actual probe intensity of probe D, and
  $R_{DC}$ is the ratio between (a) the portion of intensity in a channel for probe D that is contributed by probe C, and (b) the actual probe intensity of probe C.
In a further embodiment, the equation is solved to determine spectral crosstalk matrix $K^{-1}$ and an estimate of the actual intensity or probes (A, B, C and D) using equation $$\begin{bmatrix} A \\ B \\ C \\ D \end{bmatrix} = K^{-1} \begin{bmatrix} M_A \\ M_B \\ M_C \\ M_D \end{bmatrix}$$

In a particular embodiment, the order of the data correction methods described herein is 1) field flattening, 2) color crosstalk correction and 3) dephasing correction. When field flattening precedes color crosstalk correction, then the same crosstalk parameters may be used for the entire image. When color crosstalk correction precedes dephasing correction, the dephasing correction will be more accurate as the intensity data from the different channels will more precisely represent actual probe intensities.

As noted above, the present invention contemplates reducing some of these phenomenon that make accurate base calling difficult. One problem addressed in one embodiment of the present invention is the problem created by using a cleaving agent. In one embodiment, a cleaving agent scavenger is employed to address leftover cleaving agent which might prematurely cleave in the next cycle. Thus, the present invention contemplates in one embodiment a method of incorporating labeled nucleotides into nucleic acid, comprising: a) providing a plurality of nucleic acid template molecules, a polymerase, a cleaving agent, a cleaving agent scavenger, and a plurality of nucleotide analogues wherein each nucleotide analogue is labeled with a unique label and contains a removable chemical moiety sapping the 3'-OH group; b) incorporating a first nucleotide analogue with said polymerase; c) detecting the label of the incorporated nucleotide analogue; d) removing the chemical moiety of the incorporated nucleotide analogue capping the 3'-OH group with said cleaving agent; and f) incorporating a second nucleotide analogue in the presence of said cleaving agent scavenger. With regard to step f), the scavenger can, by way of example, be put into the solution used to incorporate nucleotides in the next round (indeed, in one embodiment, the present invention contemplates compositions comprising 1) the scavenger(s) and one or more labeled or unlabeled nucleotides, 2) the scavenger(s) and polymerase, 3) the scavenger(s) and one or more nucleotides with or without 3-OH capping groups). Alternatively, the scavenger can be in a separate solution that is used prior to the incorporation solution (with residual scavenger present at the time of incorporation). In one embodiment, the present invention contemplates wash steps after step b) and after step d).

It is not intended that the present invention be limited by the nature of the chemistry of the removable chemical moiety. A variety of chemistries are contemplated (and described below in more detail). In one embodiment, said removable chemical moiety comprises a disulfide bond. In another embodiment, said removable chemical moiety comprises an azido group (e.g. an azidomethyl ether). It is preferred that said moiety capping the 3'-OH is not a fluorescent moiety.

It is also not intended that the present invention be limited by the nature of the cleaving agent. In the case of azido-group-containing nucleotides (e.g. 3'-O-azidomethyl ether nucleotides), several types of cleaving agents can be used. In principle, any reducing agent capable of converting the azido group into an amine is suitable for this purpose. The amine undergoes spontaneous conversion to hydroxyl group to enable next nucleotide incorporation. Examples of cleaving agents include: a) Catalytic hydrogenation over $PtO_2$ or Pd/C; b) Reduction with $LiAlH_4$, $HCO_2NH_4$-10% Pd/C, NaBH$_4$/CoCl$_2$.6H$_2$O, Zn/NH$_4$Cl, Fe/NH$_4$Cl; and c) Reduction with phosphines; e.g., tri-n-butyl-phosphine, triphenyl phosphine and its sulfonated versions (i.e., tris(3-sulfophenyl)-phosphine, TPPTS), and tri(carboxyethyl)phosphine (TCEP) and its salts. Most preferred cleaving reagents are soluble in water and are highly selective reducing agents. Water soluble phosphines are particularly preferred. In one embodiment, said cleaving agent is a phosphine Tris(2-carboxy-ethyl)phosphine.

It is also not intended that the present invention be limited by the nature of the cleaving agent scavenger. A variety of chemistries are contemplated (and are described below and in the figures) and more than one type of chemistry can be used together (e.g. two different scavengers). In a preferred embodiment, said cleaving agent scavenger does not contain a nucleic acid base. In one embodiment, said cleaving agent scavenger comprises a disulfide bond (e.g. cystamine or one of the other disulfide-containing compounds shown in FIG. 37). Cystamine is also known as 2,2'-Dithiobisethanamine, 2-Aminoethyl disulfide, or Decarboxycystine, and is available commercially from Sigma-Aldrich. Alternatively, the present invention contemplates in one embodiment that said cleaving agent scavenger comprises an azido group (e.g. an azidomethyl group, an azidoethyl ether group, etc.). In a preferred embodiment, said scavenger is 11-Azido-3,6,9-trioxaundecane-1-amine (which is also known as: 1-Amino-11-azido-3,6,9-trioxaundecane, 2-{2-[2-(2-Azidoethoxy)ethoxy]ethylamine, or O-(2-Aminoethyl)-O'-(2-azidoethyl-diethylene glycol, and which is available commercially from Sigma-Aldrich).

It is not intended that the present invention be limited by where the first and second nucleotides are incorporated. In one embodiment, they are incorporated into a primer [e.g. prior to step b), the present invention contemplates in one embodiment hybridizing a primer to said plurality of nucleic acid template molecules, such that said first nucleotide analogue is incorporated into said primer at step b)], in another embodiment, they are incorporated into the template molecules [e.g. said nucleic acid template molecules comprise a self-priming hairpin, such that said first nucleotide analogue is incorporated into said template molecules at step b)].

In some embodiments, two cites of cleavage are contemplated, i.e. cleavage occurs at two locations on the nucleotide analogue. Thus, in one embodiment, the present invention contemplates a method of incorporating labeled nucleotides into nucleic acid, comprising: a) providing a plurality of nucleic add template molecules, a polymerase, a cleaving agent, a cleaving agent scavenger, and a plurality of nucleotide analogues selected from the group consisting of cytosine, thymine, deaza-adenine and deaza-guanine, wherein each nucleotide analogue comprises a unique label attached through a cleavable linker to a 5-position of cytosine or thymine or to a 7-position of deaza-adenine or deaza-guanine, and wherein each nucleotide analogue contains a removable chemical moiety capping the 3'-OH group; b) incorporating a first nucleotide analogue with said polymerase; c) detecting the label of the incorporated nucleotide analogue; d) removing the chemical moiety of the incorporated nucleotide analogue capping the 3'-OH group and cleaving the cleavable linker with said cleaving agent; and e) incorporating a second nucleotide analogue in the presence of said cleaving agent scavenger.

Again, it is not intended that the present invention be limited by where the first and second nucleotides are incorporated. In one embodiment, they are incorporated into a primer [e.g. prior to step b), the present invention contemplates in one embodiment hybridizing a primer to said plurality of nucleic acid template molecules, such that said first nucleotide analogue is incorporated into said primer at step b)]. In another embodiment, they are incorporated into the template molecules [e.g. said nucleic acid template molecules comprise a self-priming hairpin, such that said first nucleotide analogue is incorporated into said template molecules at step b)].

Again, it is not intended that the present invention be limited by the nature of the chemistry of the removable chemical moiety. A variety of chemistries are contemplated (and described below in more detail) and the chemistry need not be the same chemistry as used in the cleavable linker attaching the label. In one embodiment, said removable chemical moiety comprises a disulfide bond. In another embodiment, said removable chemical moiety comprises an azido group (e.g. an azidomethyl ether). It is preferred that said moiety capping the 3'-OH is not a fluorescent moiety.

Similarly, a variety of chemistries are contemplated for the cleavable linker attaching the label to the nucleotide analogue (and these are described in more detail below). In one embodiment, said cleavable linker comprises a disulfide bond. As noted above, the present invention contemplates embodiments wherein the chemistries for the cleavage at the two cites is the same, as well as embodiments where it is different. For example, in one embodiment, said removable chemical moiety comprises an azido group (e.g. an azidomethyl ether) and said cleavable linker (which attaches the label) comprises a disulfide bond. In another embodiment, this is reversed (the cleavable linker comprises an azido group and the removable chemical moiety comprises a disulfide bond.

Again, it is also not intended that the present invention be limited by the nature of the cleaving agent. However, in one embodiment, said cleaving agent is a phosphine (e.g. Tris (2-carboxy-ethyl)phosphine). Again, a variety of cleaving agent scavengers are contemplated (discussed above). In a preferred embodiment, said cleaving agent scavenger does not contain a nucleic acid base.

In one embodiment, the present invention contemplates incorporating nucleotides having only one location for cleavage (e.g. the cleavable linker attaching the label). Thus, in one embodiment, the present invention contemplates a method of incorporating labeled nucleotides into nucleic acid, comprising: a) providing a plurality of nucleic acid template molecules, a polymerase, a cleaving agent, a cleaving agent scavenger, and a plurality of nucleotide analogues wherein each nucleotide analogue is labeled with a unique label, said label attached by a cleavable linker; b) incorporating a first nucleotide analogue with said polymerase; c) detecting the label of the incorporated nucleotide analogue; d) removing the label of the incorporated nucleotide analogue by cleaving the cleavable linker with said cleaving agent; and e) incorporating a second nucleotide analogue in the presence of said cleaving agent scavenger.

Again, it is not intended that the present invention be limited by where the first and second nucleotides are incorporated. In one embodiment, they are incorporated into a primer [e.g. prior to step b), the present invention contemplates in one embodiment hybridizing a primer to said plurality of nucleic acid template molecules, such that said first nucleotide analogue is incorporated into said primer at step b)]. In another embodiment, they are incorporated into the template molecules [e.g. said nucleic acid template molecules comprise a self-priming hairpin, such that said first nucleotide analogue is incorporated into said template molecules at step b)].

Again, a variety of chemistries are contemplated for the cleavable linker (e.g. wherein said cleavable linker comprises a disulfide bond, azido group, or some other chemical group). However, in a preferred embodiment, the chemistry of the cleavable linker dictates the chemistry of the scavenger (e.g. wherein said cleaving agent scavenger comprises a disulfide bond, it is preferred that the scavenger also comprise a disulfide bond, such as where said scavenger is cystamine or other similar compound).

In one embodiment, the present invention contemplates carrying out nucleotide incorporation in a device, including automated devices. Solutions comprising various combinations of biomolecules are contemplated; such solutions can be, in one embodiment, conveniently be stored in reservoirs which are in fluid communication with a reaction chamber (e.g. flow cells, microchannels, etc.). A series of steps can be carried out to introduce these solutions (and the reagents they contain) into the reaction chamber (e.g. by valving) to carry out the reaction(s). Thus, in one embodiment, the present invention contemplates a method of incorporating labeled nucleotides into nucleic acid, comprising: a) providing i) a reaction chamber (e.g. a flow cell) comprising plurality of nucleic acid template molecules bound to a solid support, ii) a first solution comprising polymerase and a plurality of nucleotide analogues wherein each nucleotide analogue is labeled with a unique label and contains a removable chemical moiety capping the 3'-OH group, iii) a second solution comprising a cleaving agent, and iv) a cleaving agent scavenger, b) introducing said first solution into said reaction chamber under conditions wherein a first nucleotide analogue is incorporated by said polymerase; c) detecting the label of the incorporated nucleotide analogue; d) introducing said second solution into said reaction change under conditions such that the chemical moiety of the incorporated nucleotide analogue capping the 3'-OH group is removed by said cleaving agent; and e) introducing said cleaving agent scavenger into said reaction chamber.

It is not intended that the present invention be limited by the way in which the cleaving agent scavenger is stored or introduced into the reaction chamber. In one embodiment, said cleaving agent scavenger is in a third solution and said scavenger is introduced into said reaction chamber in step e) by introducing said third solution. In another embodiment, the above-indicated method further comprises the step f) re-introducing said first solution into said reaction chamber under conditions such that a second nucleotide analogue is incorporated by said polymerase (and this first solution may contain the scavenger if desired). In another embodiment, separate steps [i.e. step e) and step f)] are not required; rather, a single step is contemplated wherein said cleaving agent scavenger is in said first solution and said introducing of step e) comprises introducing said first solution comprising said scavenger (in this embodiment, a second nucleotide analogue is incorporated in the presence of said cleaving agent scavenger). In some embodiments, additional wash steps are employed to remove reagents between steps [e.g. wash steps after step b), and step d)], although the usefulness of the scavenger has been discovered empirically, since residual cleaving agent is difficult to remove with a practical number of washes (discussed more below).

Again, it is not intended that the present invention be limited by where the first and second nucleotides are incorporated. In one embodiment, they are incorporated into a primer [e.g. prior to step b), the present invention contemplates in one embodiment hybridizing a primer to said plurality of nucleic acid template molecules, such that said first nucleotide analogue is incorporated into said primer at step b)]. In another embodiment, they are incorporated into the template molecules [e.g. said nucleic acid template molecules comprise a self-priming hairpin, such that said first nucleotide analogue is incorporated into said template molecules at step b)].

Again, it is not intended that the present invention be limited by the nature of the chemical moiety capping the 3'-OH on the nucleotide analogue. In one embodiment, said removable chemical moiety comprises a disulfide bond. In one embodiment, said removable chemical moiety comprises an azido group (e.g., an azidomethyl ether). It is preferred that said moiety capping the 3'-OH is not a fluorescent moiety.

Again, if is also not intended that the present invention be limited by the nature of the cleaving agent. However, in one embodiment, said cleaving agent is a phosphine (e.g. Tris (2-carboxy-ethyl)phosphine). Again, a variety of cleaving agent scavengers are contemplated (discussed above). In a preferred, embodiment, said cleaving agent scavenger does not contain a nucleic acid base.

In some embodiments, the reaction in the device is directed at cleavage at two locations on the nucleotide analogue(s). Thus, in one embodiment, the present invention contemplates a method of incorporating labeled nucleotides into nucleic acid, comprising: a) providing i) a reaction chamber comprising plurality of nucleic acid template molecules bound to a solid support, ii) a first solution comprising polymerase and a plurality of nucleotide analogues selected from the group consisting of cytosine, thymine, deaza-adenine and deaza-guanine, wherein each nucleotide analogue comprises a unique label attached through a cleavable linker to a 5-position of cytosine or thymine or to a 7-position of deaza-adenine or deaza-guanine, and wherein each nucleotide analogue is labeled with a unique label and contains a removable chemical moiety capping the 3'-OH group, iii) a second solution comprising a cleaving agent, and iv) a cleaving agent scavenger; b) introducing said first solution into said reaction chamber under conditions wherein a first nucleotide analogue is incorporated by said polymerase; c) detecting the label of the incorporated nucleotide analogue; d) introducing said second solution into said reaction change under conditions such that the chemical moiety of the incorporated nucleotide analogue capping the 3'-OH group is removed and said cleavable linker is cleaved by said cleaving agent; and e) introducing said cleaving agent scavenger into said reaction chamber (e.g. flow cell or the like).

Again, it is not intended that the present invention be limited by the way in which the cleaving agent scavenger is stored or introduced into the reaction chamber. In one embodiment, said cleaving agent scavenger is in a third solution and said scavenger is introduced into said reaction chamber in step e) by introducing said third solution. In another embodiment, the above-indicated method further comprises the step f) re-introducing said first solution into said reaction chamber under conditions such that a second nucleotide analogue is incorporated by said polymerase (and this first solution may contain the scavenger if desired). In another embodiment, separate steps [i.e. step e) and step 0] are not required; rather, a single step is contemplated wherein said cleaving agent scavenger is in said first solution and said introducing of step e) comprises introducing said first solution comprising said scavenger (in this embodiment, a second nucleotide analogue is incorporated in the presence of said cleaving agent scavenger). In some embodiments, additional wash steps are employed to remove reagents between steps [e.g. wash steps after step b).

Again, it is not intended that the present invention be limited by where the first and second nucleotides are incorporated. In one embodiment, they are incorporated into a primer [e.g. prior to step b), the present invention contemplates in one embodiment hybridizing a primer to said plurality of nucleic acid template molecules, such that said first nucleotide analogue is incorporated into said primer at step b)]. In another embodiment, they are incorporated into the template molecules [e.g. said nucleic acid template molecules comprise a self-priming hairpin, such that said first nucleotide analogue is incorporated into said template molecules at step b)].

Again, it is not intended that the present invention be limited by the native of the chemical moiety capping the 3'-OH on the nucleotide analogue. In one embodiment, said removable chemical moiety comprises a disulfide bond. In one embodiment, said removable chemical moiety comprises an azido group (e.g., an azidomethyl ether). It is preferred that said moiety capping the 3'-OH is not a fluorescent moiety.

Again, the chemistry of the cleavable linker (which attaches the label) may be the same or different vis-à-vis the removable chemical capping moiety. Thus, in one embodiment, the linker and the capping group comprise a disulfide bond. Yet, in another embodiment, said removable chemical moiety comprises an azido group and said cleavable linker comprises a disulfide bond (or the reverse, i.e. the capping group comprises a disulfide bond and the cleavable linker comprises an azido group).

Again, it is also not intended that the present invention be limited by the nature of the cleaving agent. However, in one embodiment, said cleaving agent is a phosphine (e.g. Tris (2-carboxy-ethyl)phosphine). Again, a variety of cleaving agent scavengers are contemplated (discussed above). In a preferred embodiment, said cleaving agent scavenger does not contain a nucleic acid base.

In some embodiments, the present invention contemplates a reaction in the device wherein only a single cite of cleavage on the nucleotide analogue is targeted (e.g. a cleavable linker attaching the label). Thus, in one embodiment, the present invention contemplates a method of incorporating labeled nucleotides into nucleic acid, comprising: a) providing i) a reaction chamber comprising plurality of nucleic acid template molecules bound to a solid support, ii) a first solution comprising polymerase and a plurality of nucleotide analogues wherein each nucleotide analogue is labeled with a unique label, said label attached via a cleavable linker, iii) a second solution comprising a cleaving agent, and iv) a cleaving agent scavenger; b) introducing said first solution into said reaction chamber under conditions wherein a first nucleotide analogue is incorporated by said polymerase; c) detecting the label of the incorporated nucleotide analogue; d) introducing said second solution into said reaction change under conditions such that the label of the incorporated nucleotide analogue is removed by cleaving said cleavable linker with said cleaving agent; and e) introducing said cleaving agent scavenger into said reaction chamber.

Again, it is not intended that the present invention be limited by where the first and second nucleotides are incorporated. In one embodiment, they are incorporated into a primer [e.g. prior to step b), the present invention contemplates in one embodiment hybridizing a primer to said plurality of nucleic acid template molecules, such that said first nucleotide analogue is incorporated into said primer at step b)]. In another embodiment, they are incorporated into the template molecules [e.g. said nucleic acid template molecules comprise a self-priming hairpin, such that said first nucleotide analogue is incorporated into said template molecules at step b)].

A variety of chemistries for the cleavable linker are contemplated. In one embodiment, said cleavable linker comprises a disulfide bond.

In one embodiment, the chemistry used in the cleavable linker controls the chemistry of the scavenger. For example, in one embodiments where the linker comprises a disulfide bond, said cleaving agent scavenger comprises a disulfide bond. In one embodiment, where the linker comprises an azido group, said cleaving agent scavenger comprises an azido group. In a preferred embodiment, said cleaving agent scavenger does not contain a nucleic acid base.

The present invention contemplates methods, kits, devices, systems and compositions. In one embodiment, the present invention contemplates a composition comprising cleaving agent scavenger and one or more nucleotide analogues (unlabeled or labeled as herein described). In one embodiment, said composition further comprises polymerase. In one embodiment, the present invention contemplates a composition comprising cleaving agent scavenger and polymerase, and (optionally) one or more nucleotide analogues (unlabeled or labeled as herein described).

In one embodiment, the present invention contemplates a reaction chamber (e.g. a flow cell, flow channels, etc.) comprising a solution, said solution comprising cleaving agent scavenger and one or more nucleotide analogues (labeled or unlabeled as herein described). In one embodiment, said solution further comprises polymerase. In one embodiment, said solution comprises cleaving agent scavenger and polymerase, and (optionally) one or more nucleotide analogues (unlabeled or labeled as herein described).

In one embodiment, the present invention contemplates kits, said kits comprising a solution comprising cleaving agent scavenger and one or more nucleotide analogues (labeled or unlabeled as herein described) and (optionally) polymerase. Alternatively, said kits comprise a solution comprising cleaving agent scavenger and polymerase, and (optionally) one or more nucleotide analogues (unlabeled or labeled as herein described). Preferably, such kits also provide instructions for carrying out incorporation reactions, as well as wash buffers and the like.

In one embodiment, the present invention contemplates a system comprising reservoirs in fluid communication with a reaction chamber, at least one of said reservoirs comprising a solution comprising cleaving agent scavenger and one or more nucleotide analogues (labeled or unlabeled as herein described) and (optionally) polymerase. Alternatively, at least one of said reservoirs comprises a solution comprising cleaving agent scavenger and polymerase, and (optionally) one or more nucleotide analogues (unlabeled or labeled as herein described). Preferably, such solutions can be introduced by automated means (e.g. valving).

As described herein, the present invention contemplates embodiments wherein nucleotides used in extension reactions contain linkers, spacers and chemical groups. The presence of these spacers and groups may affect the ability of the sequencing polymerases to incorporate the subsequent nucleotide. The present invention contemplates a number of ways to minimize or eliminate this undesirable effect, including but not limited to: a) reducing the amount of labeled nucleotides incorporated in the template; b) reducing the size of the spacer arm or eliminate it completely by carefully designing nucleotide analogs; and c) change the reactivity of the spacer arm groups or their charge by performing a chemical "capping" step, where specific reagent is added to react only with groups on the spacer arm.

Reducing the amount of labeled nucleotides that are incorporated can be accomplished by reducing the concentration of labeled nucleotides in the extension solution, and/or by mixing labeled nucleotides (reversible terminators) with non-labeled reversibly terminating nucleotides (e.g. where the non-labeled nucleotides are employed in ratios between 1:1 and 1000:1 relative to the labeled nucleotides, but more preferably in ratios between 10:1 and 100:1). In contrast to labeled nucleotides, non-labeled reversible terminator nucleotides after cleavage convert to native nucleotide (and therefore do not present problems for polymerases). Thus, in one embodiment, the present invention contemplates a composition comprising i) a first plurality of nucleotide analogues wherein each nucleotide analogue is labeled with a unique label and contains a removable chemical moiety capping the 3'-OH group; and ii) a second plurality of nucleotide analogues wherein each nucleotide analogue is unlabeled and contains a removable chemical moiety capping the 3'-OH group. In one embodiment, the composition further comprises polymerase. In a preferred embodiment, said nucleotide analogues are in solution. In one embodiment, the second plurality of nucleotide analogues is present in said solution at a high concentration than said first plurality of nucleotide analogues. In one embodiment, said second plurality of nucleotide analogues is present at a concentration between 1 uM and 100 uM. In one embodiment, said first plurality of nucleotide analogues is present at a concentration between 1 nM and 1 uM.

It is not intended that the composition be limited by the number or nature of nucleotide analogues in said composition. However, in a preferred embodiment, said first plurality of nucleotide analogues comprises four different nucleotide analogues (for example, in one embodiment, the four nucleotodes are either (i) aA, aC, aG, and aT, or (ii) aA, aC, aG, and aU). In a preferred embodiment, said second plurality of (unlabeled) nucleotide analogues comprises four different nucleotide analogues (for example, either (i) aA, aC, aG, and aT, or (ii) aA, aC, aG, and aU).

It is also not intended that the composition be limited by the nature of the label. However, in one embodiment, each of said four different nucleotide analogues comprises a unique (preferably cleavable) label, said label selected from the group consisting of BODIPY, Rhodamine, Carboxyrhodamine, and Cyanine (see FIG. 36, which shows these labels in the context of a cleavable disulfide bond).

It is also not intended that the composition be limited by the chemistry of the removable chemical moiety, which may, by way of example, comprise a disulfide bond or an azido group (e.g. an azidomethyl ether). The chemistry may be the same or different vis-à-vis the cleavable linker. For example, said removable chemical moiety comprises an aside group and said cleavable linker comprises a disulfide bond.

In one embodiment, the present invention contemplates a composition comprising i) a first plurality of nucleotide analogues comprising four different (for example, in one embodiment, the four nucleotides are either (i) aA, aC, aG, and aT, or (ii) aA, aC, aG, and aU) nucleotide analogues, wherein each different nucleotide analogue is labeled with a unique (preferably cleavable) label and contains a removable chemical moiety capping the 3'-OH group; and ii) a second plurality of nucleotide analogues comprising four different (for example, in one embodiment, the four nucleotides are either (i) aA, aC, aG, and aT, or (ii) aA, aC, aG, and aU) nucleotide analogues, wherein each nucleotide analogue is unlabeled and contains a removable chemical moiety capping the 3'-OH group. Again, this composition may further comprise a polymerase and it is preferred that the reagents (e.g. said nucleotide analogues and optionally said polymerase) are in solution.

It is not intended that the composition be limited by the particular linkages. However, in a preferred embodiment, the nucleotide analogues selected from the group consisting of cytosine, thymine, deaza-adenine and deaza-quanine and each comprising a unique (preferably) label attached through a cleavable linker to a 5-position of cytosine or thymine or to a 7-position of deaza-adenine or deaza-guanine.

In one embodiment, the second plurality of nucleotide analogues is present in said solution at a high concentration than said first plurality of nucleotide analogues. In one embodiment, said second plurality of nucleotide analogues is present at a concentration between 1 uM and 100 uM. In one embodiment, said first plurality of nucleotide analogues is present at a concentration between 1 nM and 1 uM.

In one embodiment, the present invention contemplates kits, said kits comprising a mixture of labeled and unlabeled nucleotide analogues (preferably both containing groups capping the 3'-OH—such as an azido group) and (optionally) polymerase. In one embodiment, the present invention contemplates a mixture of 4 labeled and 4 unlabeled nucleotide analogues as herein described) and (optionally) polymerase. The mixture can be provided dry or in solution in the kit (along with appropriate instructions for extension reactions). Preferably, the unlabeled nucleotide analogues are present in the mixture in a greater amount than the labeled nucleotide analogues.

The above-indicated solutions provide advantages in incorporation reactions. Thus, in one embodiment, the present invention contemplates a method of incorporating labeled nucleotides into nucleic acid, comprising: a) providing i) a reaction chamber comprising plurality of nucleic acid template molecules bound to a solid support, ii) a solution comprising a first plurality of nucleotide analogues wherein each nucleotide analogue is labeled with a unique (preferably cleavable) label and contains a removable chemical moiety capping the 3'-OH group, and a second plurality of nucleotide analogues wherein each nucleotide analogue is unlabeled and contains a removable chemical moiety capping the 3'-OH group; and iii) polymerase; b) introducing said solution into said reaction chamber under conditions wherein a nucleotide analogue of said first plurality of nucleotide analogues is incorporated by said polymerase (e.g. the polymerase can be added separately or together with other reagents; regardless, it is preferred that said polymerase is in said solution prior to step b); and c) detecting the label of the incorporated nucleotide analogue. The method may comprise additional steps (cleavage of the capping group, washing, etc.) and may repeat steps (e.g. in order to incorporate subsequent, e.g. a second, third, fourth, etc., nucleotide analogues).

It is not intended that the present invention be limited by where the first (or subsequent) nucleotides are incorporated. In one embodiment, they are incorporated into a primer [e.g. prior to step b), the present invention contemplates in one embodiment hybridizing a primer to said plurality of nucleic acid template molecules, such that said first nucleotide analogue is incorporated into said primer at step b)]. In another embodiment, they are incorporated into the template molecules [e.g. said nucleic acid template molecules comprise a self-priming hairpin, such that said first nucleotide analogue is incorporated into said template molecules at step b)].

In one embodiment, the second plurality of nucleotide analogues is present in said solution at a high concentration than said first plurality of nucleotide analogues. In one embodiment, said second plurality of nucleotide analogues is present at a concentration between 1 uM and 100 uM. In one embodiment, said first plurality of nucleotide analogues is present at a concentration between 1 nM and 1 uM.

In a preferred embodiment, said first plurality of nucleotide analogues comprises four different nucleotide analogues and said second plurality of nucleotide analogues comprises four different nucleotide analogues. In one embodiment, each of said four different nucleotide analogues of said first plurality of labeled analogues comprises a unique label, said label selected from the group consisting of BODIPY, Rhodamine, Carboxyrhodamine, and Cyanine.

Again, it is not intended that the present invention be limited by the nature of the chemical moiety capping the 3'-OH on the nucleotide analogue or the (preferably cleavable) linker attaching the label. In one embodiment, said removable chemical moiety comprises a disulfide bond. In one embodiment, said removable chemical moiety comprises an azido group (e.g., an azidomethyl ether). In one embodiment, said removable chemical moiety comprises an azido group and said cleavable linker comprises a disulfide bond. In another embodiment, these chemistries are reversed. Again, it is preferred that said moiety capping the 3'-OH is not a fluorescent moiety.

Increasing the number of bases that can be sequenced, i.e. increasing read lengths is desirable. However, as one proceeds to larger and larger read lengths, one often encounters a reduction in signal. In one embodiment, the present invention contemplates reducing extension fetes (e.g. extension times of 5-15 minutes are reduced to 1-2 minutes) in order to maintain signal strength at longer read lengths (greater than 20 bases, more preferably greater than 30 bases, etc.). This reduction in extension times can be combined with other methods herein described (e.g. the use of mixtures of labeled and unlabeled nucleotides) to improve performance and increase the retention in signal. Signal retention is defined as the ratio of signals at the end of the run to the signals at the beginning of the run.

BRIEF DESCRIPTION OF THE DRAWINGS

FIG. 2A shows a three dimensional translucent view of a flow cell, comprising fluid tubing connections, cartridge heaters, and O-ring seal. FIG. 2B is a two dimensional drawing of a side view of a flow cell (200), showing an array or slide (201) with spaced spots on the surface (representing positions for biomolecules and/or anchoring molecules), said array positioned (e.g. inverted) in a fluid channel (202) such that solutions of buffers and/or reagents can be introduced over the surface under conditions whereby reactions and/or washing can be achieved. The arrows show one particular direction of fluid flow, with entrance (204) and exit ports (205), as well as one particular method of sealing (O-ring seal 203). FIG. 2C is a drawing depicting beads (206) in the wells (207) of the slide (or chip 208), which preferably comprises nucleic acid to be sequenced (not shown), said slide positioned in a flow cell for contact with reagents in the solution traveling through the flow cell. The single dark arrow shows reagent flow in the flow cell. The many light arrow heads represent detection (e.g. light imaging) from the back of the slide (or chip).

FIGS. 4A-8 show a schematic for steps involved in sample preparation FIG. 4A and highly parallel sequencing steps FIG. 4B for embodiments of the invention.

FIG. 5 shows a general structure of embodiments of cleavable fluorophore nucleotide conjugates with reversible terminator functionality. The 3'-OH group is reversibly blocked by an allyl ether function and the fluorophore is attached via a cleavable allyl carbamate linker (both shown in frames). After incorporation and signal readout, the fluorophore and the 3-O-allyl protective groups are cleaved by aqueous solution of Pd (0).

FIG. 6 shows a cleavage mechanism for trimethyl lock based compounds.

FIG. 7 shows a cleavage mechanism for 1,6-rearrangement based compounds.

FIG. 8 is a schematic flow chart for re-phasing.

FIG. 9A shows actual fluorescent levels, FIG. 9B shows measured fluorescent levels.

FIG. 27 shows exemplary nucleotide structures with 3'-OH group protection that can be cleaved by mild oxidation reactions.

FIG. 32A is raw data and FIG. 32B is data with the color crosstalk removed.

FIG. 33A shows 16-base-long sequence data, and FIG. 33B shows the same data after applying the lead/lag compensation algorithm.

FIG. 34A shows 25-base-long sequence data and FIG. 34B shows the same data after applying the lead/lag compensation algorithm.

FIG. 41A shows an embossing surface 80 with extensions 81 and a slide (or chip) 82. FIG. 41B shows the application of the embossing surface into the slide (or chip) showing a compressed structure 83. FIG. 41C shows the separated embossing surface and the newly embossed slide (or chip) with indentations. FIG. 41D shows the acceptance of microbeads 84 comprising nucleic acid 85 into the embossed indentations 86 of the slide (or chip).

FIGS. 48A-D show that using a mixture of labeled and unlabeled nucleotides (e.g. a mixture of labeled and non-labeled reversible terminators) and controlling extension time can improve performance (e.g. increase retention of signal) on an automated sequencing device. With additional control provided (e.g. by reducing extension time from 15 minutes to 2 minutes), the incorporation rate of labeled nucleotides can be controlled and results in improved fidelity and performance. FIGS. 48A and 48B show the results for 15 minutes. FIGS. 48C and 48D show the results for 2 minutes.

FIGS. 49A-P show that using a mixture of labeled and unlabeled nucleotides (e.g. a mixture of labeled and non-labeled reversible terminators) and controlling extension time can improve performance (e.g. increase retention of signal) on an automated sequencing device. FIGS. 49A, 49B, 49C, 49D, 49E, 49F, 49G and 49H show the results with 10 minute extension (for templates 20, 30, 21, 31,22, 32, 23 and 33, respectively). FIGS. 49I, 49J, 49K, 49L, 49M, 49N, 49O and 49P show the results with 1 minute extension (for templates 20, 30, 21,31, 23 and 33, respectively). With additional control provided (e.g. by reducing extension time from 10 minutes to 1 minute), the incorporation rate of labeled nucleotides can be controlled and results in improved fidelity and performance. Signal retention is defined as the ratio of signals at the end of the run to the signals at the beginning of the run.

DEFINITIONS

Figure 1:
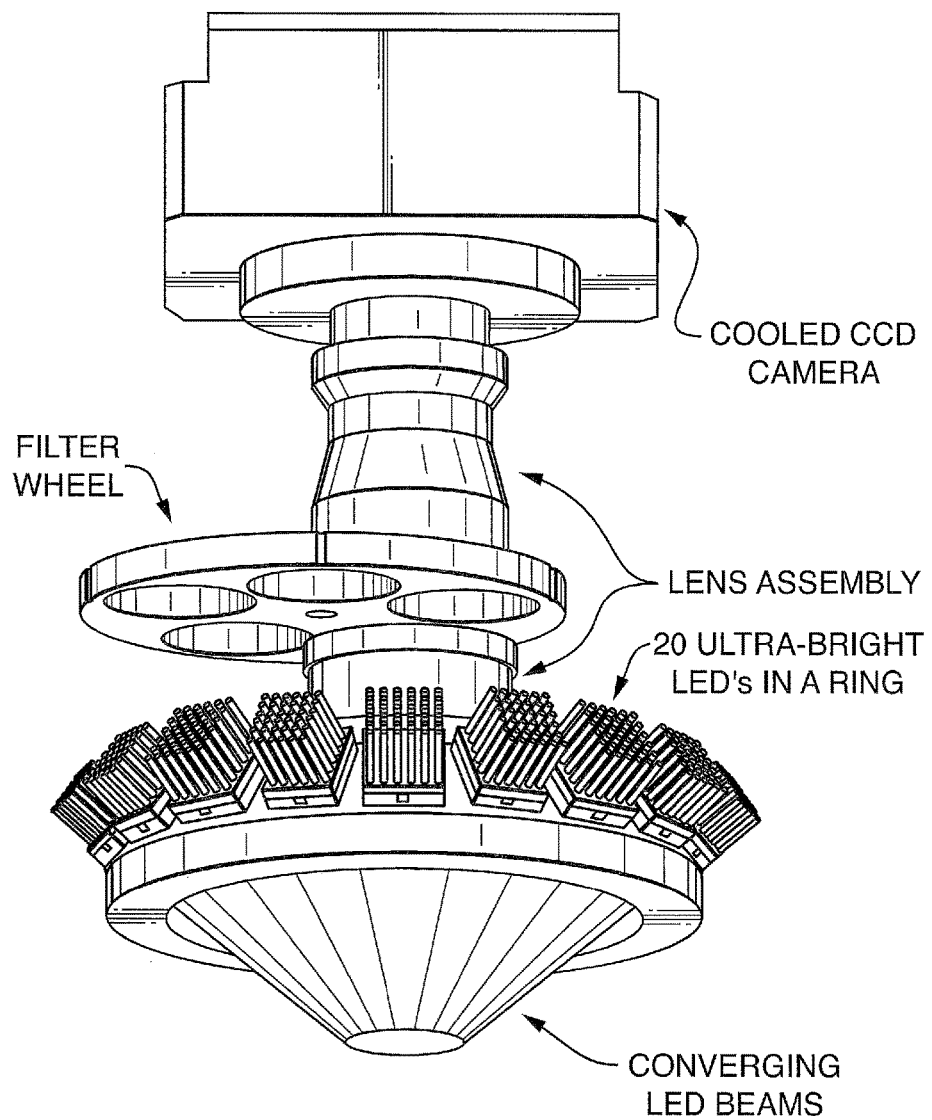
FIG. 1 schematically shows one embodiment of the imaging system of the present invention, said embodiment comprising a) a circular array of LEDs configured such that the emitted light converges on a region or platform (e.g. a position for a sample, flow cell, etc.) so as to excite fluorescence of fluorescent material, b) a lens assembly positioned above the region so as to capture at least a portion of said fluorescence, c) a filter wheel comprising bandpass filters, and d) light collection means (in this case a cooled CCD camera), wherein said filter wheel is positioned between the region where the light converges and the light collection means.

To facilitate understanding of the invention, a number of terms are defined below, and others are found elsewhere in the specification.

The term "plurality" means two or more.

The term "nucleotide sequence" refers to a polymer comprising deoxyribonucleotides (in DNA) or ribonucleotides (in RNA).

The term "interrogation position" when made in reference to a nucleotide sequence refers to a location of interest in the sequence, such as the location at which the identity of a nucleic acid is sought to be determined.

The term "preceding nucleic acid" when made in reference to a first nucleic acid in relation to a second nucleic acid that is located at an interrogation position in a nucleotide sequence refers to a nucleic acid that is inserted during synthesis into the nucleotide sequence before the insertion of the second nucleic acid at the interrogation position. The term "subsequent nucleic acid" when made in reference to a third nucleic acid in relation to the second nucleic acid at the interrogation position refers to a nucleic acid that is inserted during synthesis into the nucleotide sequence after the insertion of the second nucleic acid at the interrogation position.

The terms "probe" and "label" are interchangeably used to describe a chemical moiety that, when attached to a composition of interest, acts as a marker for the presence of the composition of interest. Probes are exemplified by fluorescent moieties such as 5-carboxyfluorescein, 6-carboxyrhodamine-6G, N,N,N',N'-tetramethyl-6-carboxyrhodamine, and 6-carboxy-X-rhodamine. Probes also include a fluorescence energy transfer tag that comprises an energy transfer donor and an energy transfer acceptor. The energy transfer donor is exemplified by 5-carboxyfluorescein and cyanine, and the energy transfer acceptor is exemplified by dichlorocarboxyfluorescein, dichloro-6-carboxyrhodamine-6G, dichloro-N,N,N',N'-tetramethyl-6-carboxyrhodamine, and dichloro-6-carboxy-X-rhodamine. The mass tag is exemplified by a 2-nitro-a-methyl-benzyl group, 2-nitro-a-methyl-3-fluorobenzyl group, 2-nitro-a-methyl-3,4-difluorobenzyl group, and 2-nitro-a-methyl-3,4-dimethoxybenzyl group.

The term "probe corresponds to a nucleotide" means that the probe serves as a marker for the presence of the nucleotide. Thus, detecting the presence of the probe also detects the presence of the nucleotide.

The term "field flattening" when in reference to pixel intensity of an image refers to reducing differences in pixel intensity between two or more pixels at different spatial locations on the image of a uniformly radiating surface.

The terms "reducing," "decreasing" and grammatical equivalents when in reference to the level of a molecule and/or phenomenon (e.g., light intensity, chemical concentration, correlation between two event, etc.) in a first sample relative to a second sample, mean that the quantity of molecule and/or phenomenon in the first sample is lower than in the second sample by any amount that is statistically significant using any art-accepted statistical method of analysis. In some embodiments, the quantity of molecule and/or phenomenon in the first sample is at least 10% lower than, at least 25% lower than, at least 50% lower than, at least 75% lower than, and/or at least 90% lower than the quantity of the same molecule and/or phenomenon in a second sample. The term "reducing" includes, but does not require, a 100% lowering in the quantity of the molecule and/or phenomenon in the first sample compared to the second sample.

The terms "increasing," "elevating" and grammatical equivalents when in reference to the level of a molecule and/or phenomenon (e.g., light intensity, chemical concentration, correlation between two event, etc.) in a first sample relative to a second sample, mean that the quantity of molecule and/or phenomenon in the first sample is higher than in the second sample by any amount that is statistically significant using any art-accepted statistical method of analysis. In some embodiments, the quantity of the molecule and/or phenomenon in the first sample is at least 10% greater than, at least 25% greater than, at least 50% greater than, at least 75% greater than, and/or at least 90% greater than the quantity of the same molecule and/or phenomenon in a second sample.

"Spectral" is a term that refers to electromagnetic radiation. In one embodiment, the electromagnetic radiation is in the visible light region (wavelength of approximately 400-700 nanometers), such as that emitted by fluorescent moieties.

The terms "spectral filter" and "color filter" are interchangeably used to refer to a filter for detection of a particular range of electromagnetic wavelengths, such as in the visible region. The terms "spectral crosstalk" and "color crosstalk" refer to any phenomenon by which a spectral signal, or a digital signal that corresponds to a spectral signal, that is transmitted and measured in one channel of transmission creates an undesired effect in another channel. For example, spectral crosstalk may occur when exciting only a green dye, resulting in a signal that is visible in the yellow channel as well as in the green channel. Using methods disclosed herein, if this spectral crosstalk is calibrated, it may be removed from subsequent measurements even if the dyes are mixed in unknown quantities.

The term "low pass filter" refers to a filter that passes slowly spatially varying intensity signals but reduces signals with higher spatial variation than a desired cutoff value. Exemplary software for carrying out these steps is shown Appendix C, which is a source code for creating a flat map calibration image.

The term "computer readable medium" refers to a medium, such as a compact optical disc, that is used to store and retrieve digital data.

One element is in "fluid communication" or "fluidic communication" with another element when it is attached through a channel, tube or other conduit that permits the passage of liquid, gas, vapor and the like. "Tubing" can be made of a variety of materials, including put not limited to various plastics, metals and composites. Tubing can be rigid or flexible. Tubing can be "attached" in a detachable mode or a fixed mode. Tubing is typically attached by sliding into or over (both of which are examples of "slidably engaging") other tubing or connectors.

DESCRIPTION OF THE INVENTION

For further clarity, the invention is described below under the following headings
A. Sequencing By Synthesis; B. Device Embodiments and Elements; C. Nucleotides; D. Reducing Lead And Lag; E. Dephasing; F. Field Flattening; G. Spot Location in the Array; H. Image Sharpening; I. Spot Brightness Determination; J. Neighbor Influence Elimination; K. Spectral Crosstalk Calibration; L. Base Calls; and M. Software Appendices A-C A. Sequencing by Synthesis The invention relates to methods and compositions for determining the identity of nucleic acids in nucleotide sequences using, for example, data obtained from sequencing by synthesis methods. Methods of DNA sequencing are generally described in Metzker, Genome Res. (2005) 15(12): 1767-1776 and Shendure et al. (2004) Nature Reviews Genetics 5: 335-344. The Sanger sequencing method or chain termination or dideoxy method is a technique that uses an enzymatic procedure to synthesize DNA chains of varying length in different reactions that contain diluted concentrations of individual dideoxy nucleotides mixed in with normal nucleotides. DNA replication is stopped at positions that axe occupied by one of the dideoxy nucleotide bases resulting in a distribution of nucleotide fragments since the normal nucleotides will properly incorporate. Unnatural ddNTP terminators replace the OH with an H at the 3'-position of the deoxyribose molecule and irreversibly terminate DNA polymerase activity. The resulting fragment lengths are determined to decipher the ultimate sequence. Electrophoretic separation of the deoxyribonucleotide triphosphate (dNTP) fragments may be accomplished with single-base resolution.

In sequencing by synthesis, nucleotides conjugated with fluorescent markers that incorporate into a growing double-stranded nucleic acid from the single strand are detected. For example, one may immobilize template DNA on a solid surface by its 5'end. One may accomplish this by annealing a sequencing primer to a consensus sequence and introducing DNA polymerase and fluorescent nucleotide conjugates (alternatively, a self-priming hairpin can be introduced by PCR or ligation to the template). One detects nucleotide incorporation using a laser microarray scanner or fluorescent microscope by correlating a particular fluorescent marker to a specific nucleotide. After each nucleotide is incorporated and the fluorescent signal is detected, one bleaches or removes the fluorescent moiety from the nucleotide conjugate so as to prevent the accumulation of a background signal.

In one embodiment, the present invention contemplates DNA sequencing by synthesis using an automated instrument, as well as methods and compositions useful for sequencing using such an instrument. In one embodiment, the instrument comprises a flow cell (FIGS. 2A and 2B) with at least two fluidics ports, a substrate with sequenceable nucleic acid molecules attached to the substrate, reagent and waste reservoirs and fluidic system connecting the reservoirs to the flowcell (FIG. 3A-B). The flowcell is interfaced with a detection system to monitor the incorporation of the nucleotides.

In one embodiment, the sequencing by synthesis is carried out using reversibly terminating nucleotides and polymerase. The nucleotides comprise a protective group at their 3'-OH which prevents multiple incorporations and allows for accurate decoding of the sequence. Once incorporated the protective groups can be cleaved with high efficiency and specificity to allow subsequent nucleotide incorporations. The nucleotides may also comprise a detectable label which can be cleaved after the detection.

In one embodiment, the present invention contemplates a series of method steps, which an instrument for automated sequencing by synthesis may carry out. In one embodiment, the process is comprised of the following reagent reservoirs: 1) Extend A (reversibly terminated labeled nucleotides and polymerase); 2) Extend B (reversibly terminated unlabeled nucleotides and polymerase, but lacking labeled nucleotide analogues); 3) Wash solution 1 (e.g. in one embodiment comprising a detergent, such as polysorbate 20, in a citrate solution, such as saline sodium citrate); 4) Cleave solution; 5) Wash solution 2 (e.g. in one embodiment, comprising a detergent, such as polysorbate 20 in a buffer comprising tris(hydroxymethyl)aminomethane or "Tris"). Of course, the present invention is not limited to particular concentrations of reagents in these solutions (and other buffers and detergents can be employed). Nonetheless, in order to achieve high throughput rates, the incorporation reactions and the cleavage reactions are desired to be fast. In one embodiment, high reaction rates are achieved by increasing the concentration of reagents, agitation, pH or temperature (or the combination of all these factors). The incorporation rate in addition is dependent on the specific activity and processivity of the polymerase used. In one particular embodiment (which is provided by way of a non-limiting example), the reagents solutions have the following compositions and concentration ranges:
1) Extend A—reversibly terminated (3'-O-Azidomethyl) labeled (1 nM to 1 uM) and non-labeled nucleotides (1 uM to 100 uM) and a first polymerase (1-500 ug/ml)); 2) Extend B—reversibly terminated non-labeled nucleotides (1 uM to 100 uM) and a second polymerase (1-500 ug/ml)); 3) Wash solution 1 (3×SSC, 0.02% Tween 20); 4) Cleave solution (50-100 mM TCEP); 5) Wash solution 2 (100 mM Tris-HCl, 0.02% Tween 20, 10 mM KCl 20 mM (NH2)2SO$_4$. In one embodiment, the first polymerase incorporates labeled nucleotides better than the second polymerase, which incorporates unlabeled nucleotides more efficiently. Examples of commercially available polymerases that can be used include Therminator I-III. These polymerases are derived from *Thermococcus* sp. and carry mutations allowing for incorporation of modified nucleotides. Examples of these polymerases are listed in Table below:

| Terminator I | NEB cat. # M0261L | 9° N A485L (exo-) DNA Polymerase |
|---|---|---|
| Terminator II | NEB cat. # M0266L | 9° N A485L/Y409V (exo-) DNA Polymerase |
| Terminator III | NEB cat. # M0333L | 9° N L408S/Y409A/P410V (exo-) DNA Polymerase |

Other polymerases derived from 9 deg N parent polymerase or *Thermococcus* sp. could also be used. Other suitable polymerase families could conceivably be used after introducing mutation controlling the steric gate and enabling reversible terminators incorporation.

In one embodiment, the sequenceable DNA (preferably loaded on the chip or slide) is subjected to these solutions and compositions in the instrument, and the sequencing is performed using automated protocol. Again, it is not intended that the present invention be limited to a precise protocol or series of method steps. The order and number of steps can vary, as well as the time taken for each step. By way of a non-limiting example, in one embodiment, the instrument protocol comprises (and is configured) as follows:

1. Extend A—0.5-5 minutes (delivery+agitation)
2. ExtendB—1-20 minutes (delivery+agitation)
3. Wash 2—5-10 minutes (10-20× delivery and agitation followed by flow cell evacuation)
4. Image
5. Cleave—1-5 minutes (delivery+agitation)
6. Wash 1—5-10 minutes (10-20× delivery and agitation followed by flow cell evacuation)
7. Wash 2—5-10 minutes (10-20× delivery and agitation followed by flow cell evacuation)
8. Go to step 1

The cycle may be repeated as desired and images may be taken and subsequently analyzed to decode the DNA sequence present at each location.

In one embodiment of the above indicated cycle, eight nucleotide analogues are employed; four (A, T, C, G) cleavably labeled and reversibly terminated; four (A, T, G, C) unlabeled but reversibly terminated. In one embodiment the concentration of the labeled analogues is at a relatively low concentration [e.g. just enough to be incorporated into a substantial portion (e.g. so the label is visible and detected) of the plurality of primers, whether they be detached primers or self-priming hairpins on the template]. By contrast, the unlabeled analogues, in one embodiment, are employed in a relatively high concentration (e.g. in order to drive the extensions to completion, and avoid primers, whether they be detached primers or self-priming hairpins, that lack incorporation of a first nucleotide analogue). It has been found empirically that the use of unlabeled nucleotides improves read lengths, and reduces lead and lag (discussed below).

One example of a currently optimized protocol running on Beta instrument using 3'-O-azidomethyl/disulfide labeled nucleotides and non-labeled 3'-O-azidomethyl nucleotides is shown

| Nucleotide | Labeled nucleotides [nM] | Un-labeled nucleotides [nM] |
|---|---|---|
| dCTP | 30 | 250 |
| dATP | 20 | 250 |
| dGTP | 30 | 250 |
| TTP | 30 | 250 | in the Table (above), wherein un-labeled nucleotides are employed in ratios between 8.33 to 1 and 12.5 to 1 (relative to labeled nucleotides). In one embodiment, the labeling (i.e. incorporation) step uses Kapa RevTerm polymerase (from Kapa Biosystems, Woburn, Mass.) at 2 µg/ml and is performed at 55 deg C. for 1-2 minutes. This is followed by synchronization step where only non-labeled nucleotides are used at 25 µM concentration and a polymerase derived from 9 deg N (*Thermococcus* sp). at 25 µg/ml is used. This step is also carried out at 55 deg C. Thus, unlabeled nucleotide analogues can be employed together with labeled nucleotides, as well as in steps where no labeled nucleotides are employed.

B. Device

In one embodiment, the present invention contemplates using an optical system, for exciting and measuring fluorescence on or in samples comprising fluorescent materials (e.g., fluorescent labels, dyes or pigments). In a further embodiment, a device is used to detect fluorescent labels on nucleic acid. In another embodiment, the device comprises a fluorescent detection system and a flow cell for processing biomolecules (e.g., nucleic acid samples) arrayed on a "chip" or other surface (e.g., microscope slide, etc.). The flow cell permits the user to perform biological reactions, including but not limited to, hybridization and sequencing of nucleic acids.

It is not intended that the present invention be limited to particular light sources. By way of example only, the system can employ ultra-bright LEDs (such as those available from Philips Lumileds Lighting Co., San Jose, Calif.) of different colors to excite dyes attached to the arrayed nucleic acids. These LEDs are more cost effective and have a longer life than conventionally used gas or solid state lasers. Other non-lasing sources of lights such as incandescent or fluorescent lamps may also be used.

FIG. 1 shows a useful configuration of the LEDs, whereby the emitted light converges on a region or platform (e.g., suitable for positioning the flow cell or sample). However, linear arrays of LEDs can also be used.

It is not intended that the present invention be limited to particular light collection devices. By way of example only, the system may employ a high sensitivity CCD camera (such as those available from Roper Scientific, Inc., Photometric division, Tucson Ariz. or those available from Apogee Instruments, Roseville, Calif.) to image the fluorescent dyes and make measurements of their intensity. The CCD cameras may also be cooled to increase their sensitivity to low noise level signals. These may also be CMOS, vidicon or other types of electronic camera systems.

Since LED illumination light is not a collimated beam as from lasers, it is therefore an appropriate choice for imaging a larger area of many nucleic acid spots. To get sufficient light and therefore fluorescent signals over the larger area, the area seen by each pixel of the camera must be of sufficient size to allow enough fluorescent dye molecules to create a sufficient signal (for example, an Apogee U13 CCD available has 1.3 megapixels of 16 microns in size, while the Apogee U32 has 3.2 megapixels of 6.8 microns in size).

To increase capacity and efficiency, the present invention contemplates in one embodiment, a two flow cell system (e.g. while one chip in a first flow cell is undergoing one or more reaction steps, a second chip in a second flow cell is being scanned and imaged) with a single camera. In yet another embodiment of an imaging system, two flow cells and two cameras are employed.

Figure 2A:
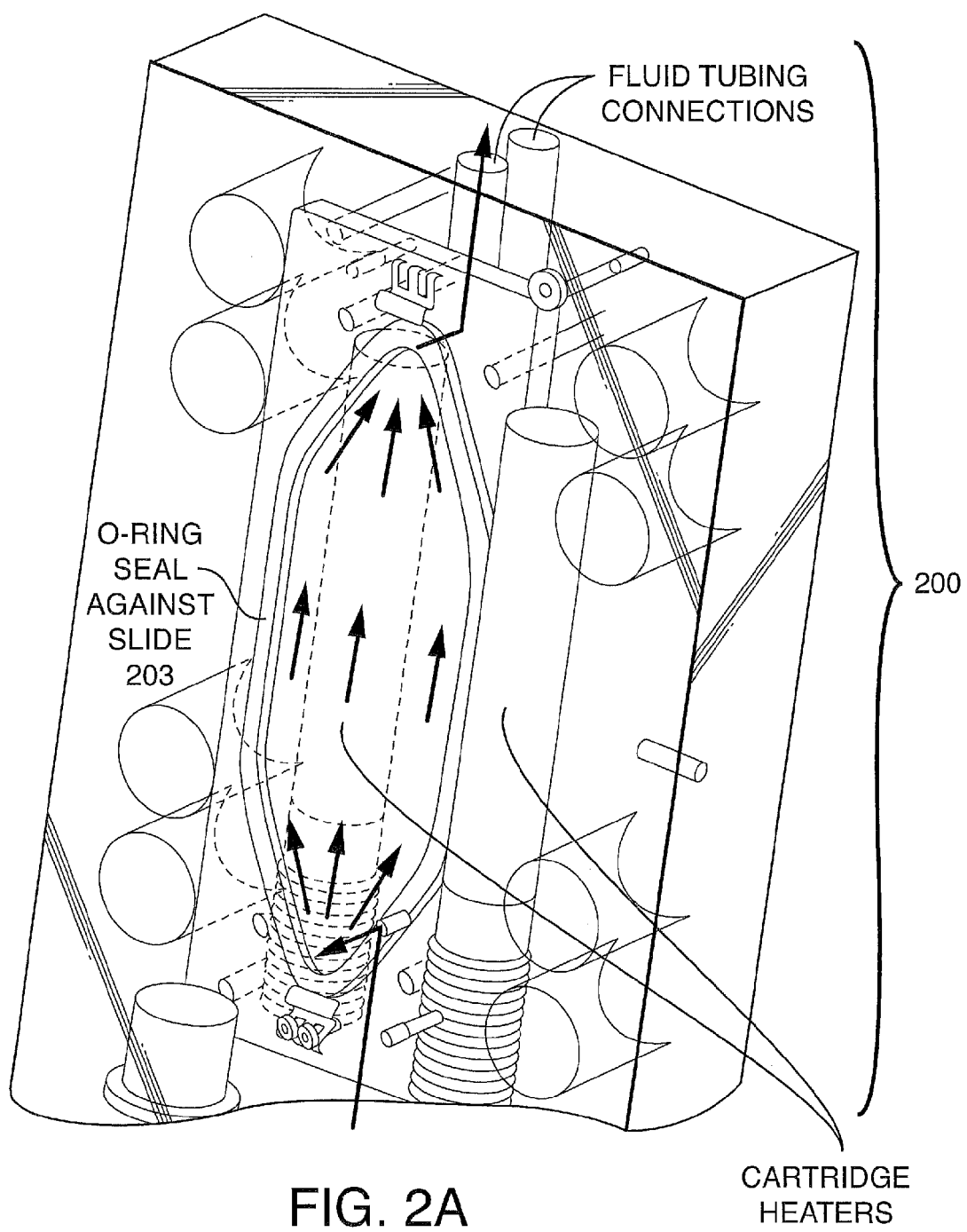
FIGS. 2A-C schematically show one embodiment of a flow cell (200).
Figure 2B:
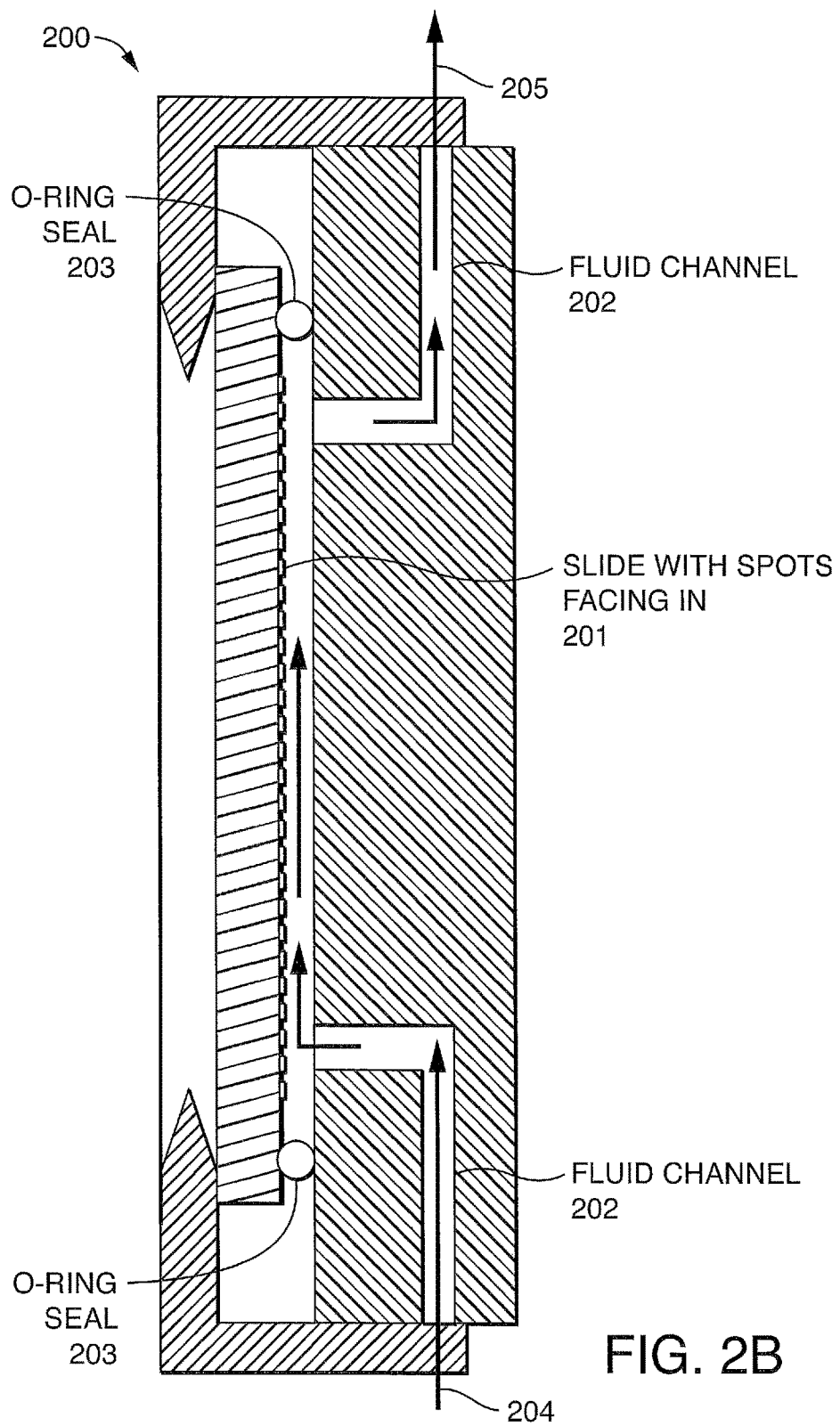
Figure 2C:
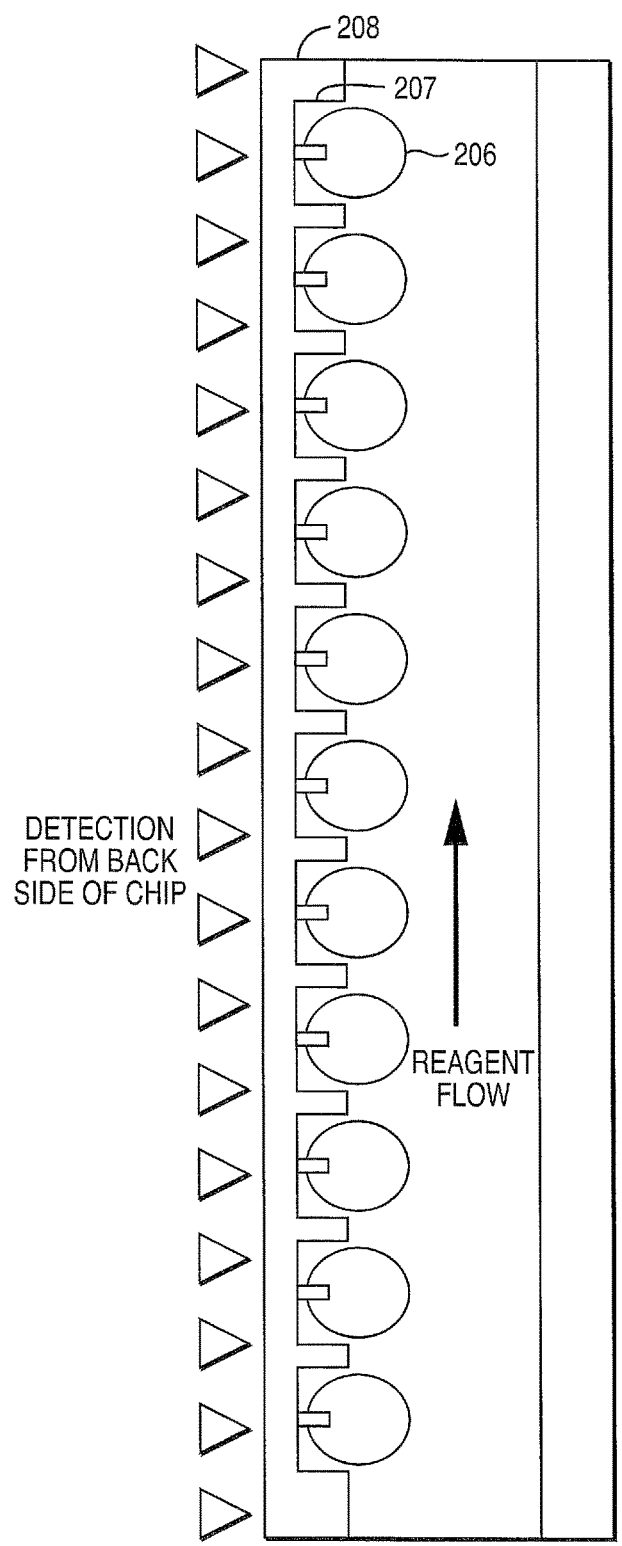
Figure 3A:
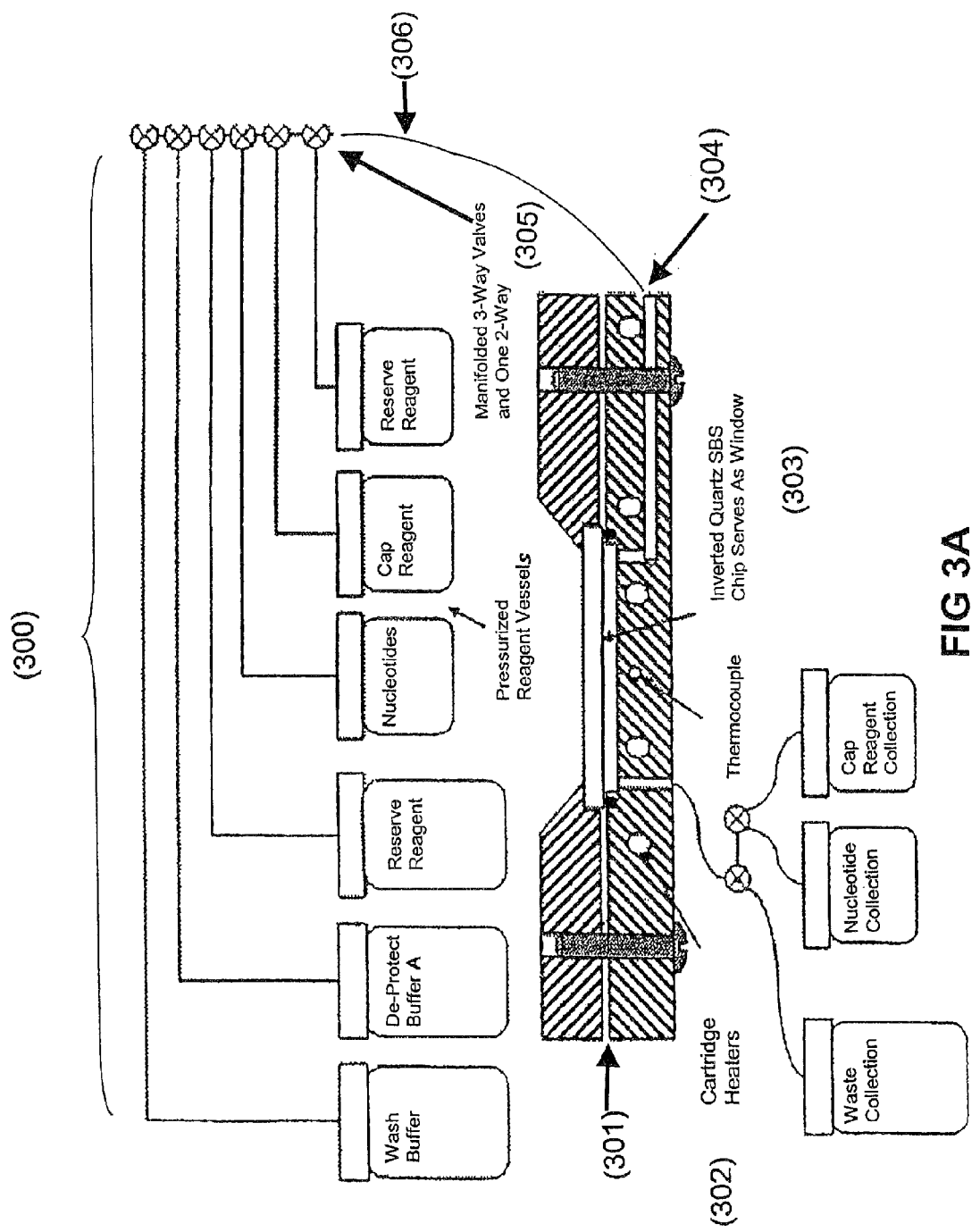
FIG. 3A schematically shows one embodiment of a fluidics system (300), comprising a variety of illustrative reagent and buffer reservoirs in communication (via tubing (306) or other channeling into a manifold comprising valves (305)) with one embodiment of a flow cell (comprising a side entrance port (301) and one or more heaters 302), wherein the array or chip (303) is inverted and the exit port (304) is on the bottom, thereby permitting the fluid channel to be drained at least in part by gravity so that waste can be readily collected into a reservoir. 3B shows another embodiment of the system (310), showing the flow cell (311) in relationship to the illumination and optics (312).
Figure 3B:
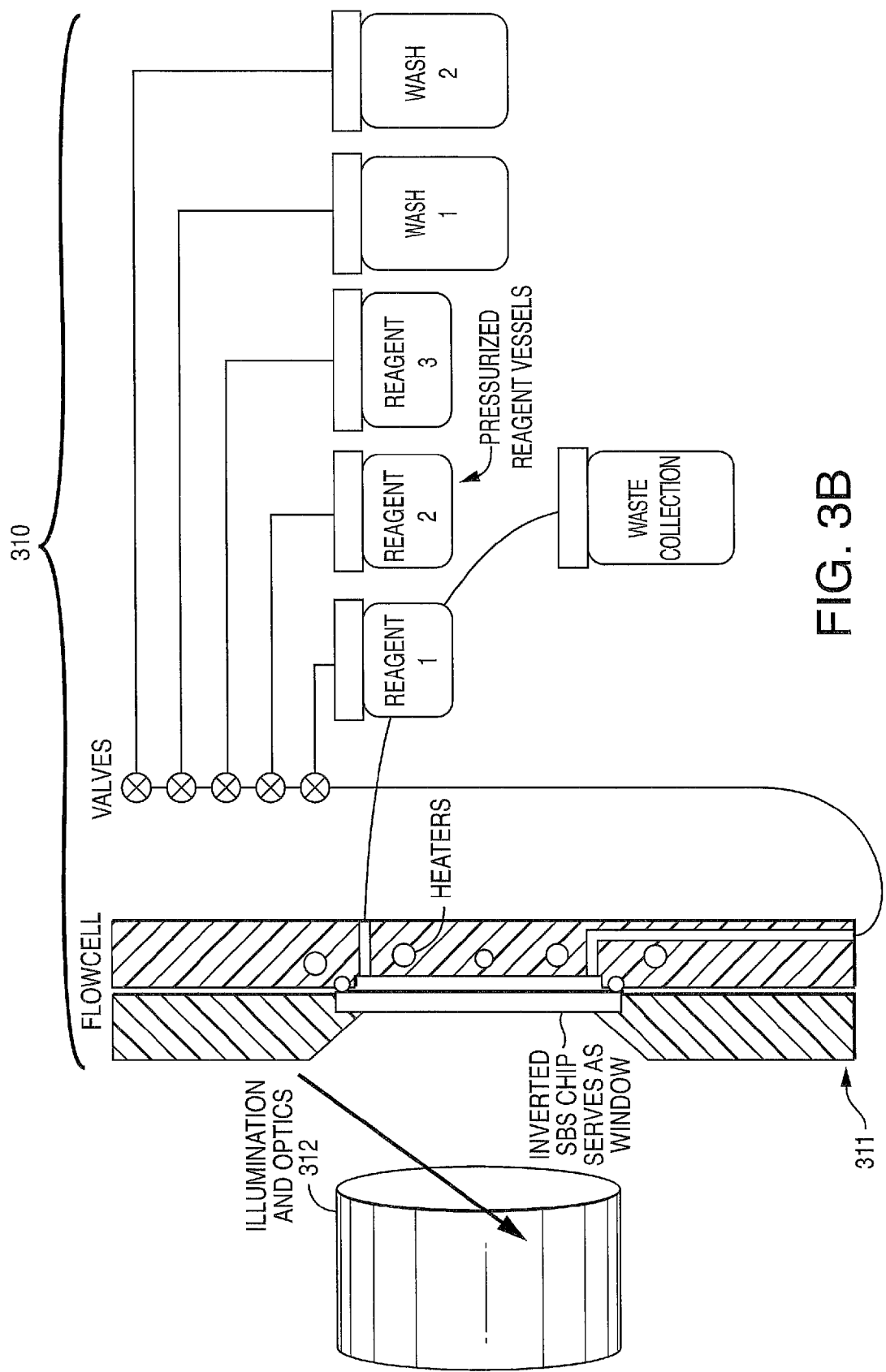

In one embodiment, the chip containing the array of nucleic acid spots is processed in a transparent flow cell incorporated within the instrument, which flows reagent past the spots and produces the signals required for sequencing (see FIGS. 2A and 2B). In a particular embodiment, the chip remains in the flow cell while it is imaged by the LED detector. The flow cell and associated reagents adds the nucleic acids, enzymes, buffers, etc. that are required to produce the fluorescent signals for each sequencing step, then the flow cell delivers the required reagents to remove the fluorescent signals in preparation for the next cycle. Measurement by the detector occurs between these two steps. In order for reactions to take place, the flow channels are configured to be of sufficient dimensions. For example, the flow-cell fluid channel formed by the array and the flat surface of the flow cell are at least 0.1 mm in depth (more particularly 0.5 mm in depth) and the volume formed by the chip, the block and the seal is at least 100 microliters in volume (more particularly, between 100 and 700 microliters, and still more particularly, between 150 and 300 microliters, e.g. 200 microliters, in volume).

In one embodiment, the flow cell is motionless (i.e., not moved during reactions or imaging). On the other hand, the flow cell can readily be mounted on a rotary or one or more linear stages, permitting movement. For example, in a two flow cell embodiment, the two flow cells may move up and down (or side to side) across the imaging system. Movement may be desired where additional processes are desired (e.g., where exposure to UV light is desired for photochemical reactions within the flow cell, such as removal of photo-cleavable fluorescent labels), when multiple flow cells share a single camera, or when the field of view of the detection system is smaller than the desired area to be measured on the flow cell. The detector system may also be moved instead of or in addition to the flow cell.

In a further embodiment, the flow cell is in fluid communication with a fluidics system (see illustrative system shown in FIG. 3A-B. In one embodiment, each bottle is pressurized with a small positive gas pressure. Opening the appropriate valve allows reagent to flow from the source bottle through the flow cell to the appropriate collection vessel(s). In one embodiment, the nucleotides and polymerase solutions are recovered in a separate collection bottle for re-use in a subsequent cycle. In one embodiment, hazardous waste is recovered in a separate collection bottle. The bottle and valve configuration allow the wash fluid to flush the entire valve train for the system as well as the flow cell. In one embodiment, the process steps comprise: 1) flushing the system with wash reagent, 2) introducing nucleotides (e.g. flowing a nucleotide cocktail) and polymerase, 3) flushing the system with wash reagent, 4) introducing de-blocking reagent (enzyme or compounds capable of removing protective groups in order to permit nucleic acid extension by a polymerase), 5) imaging, 6) introducing label removing reagent (enzyme or compounds capable of removing fluorescent labels), and 7) flushing the system with wash reagent.

The system can be made to include a user interface system. The Labview (National Instruments, Austin, Tex.) system is available and provides software for computer controlled systems. Galil Motion Control (Rocklin, Calif.) provides motion control systems that can be interfaced to control the instrument.

C. Nucleotides

The invention's compositions and methods contemplate using nucleotide sequences that contain nucleotides. The terms "nucleotide" and "nucleic acid" refer to constituents of nucleic acids (DNA and RNA) that contain a purine or pyrimide base, such as adenine (A), guanine (G), cytosine (C), uracil (U), or thymine (T)), covalently linked to a sugar, such as D-ribose (in RNA) or D-2-deoxyribose (in DNA), with the addition of from one to three phosphate groups that are linked in series to each other and linked to the sugar. The term "nucleotide" includes native nucleotides and modified nucleotides.

"Native nucleotide" refers to a nucleotide occurring in nature, such as in the DNA and RNA of cells. In contrast, "modified nucleotide" refers to a nucleotide that has been modified by man, such as using chemical and/or molecular biological techniques compared to the native nucleotide. The terms also include nucleotide analogs attached to one or more probes to facilitate the determination of the incorporation of the corresponding nucleotide into the nucleotide sequence. In one embodiment, nucleotide analogues are synthesized by linking a unique label through a cleavable linker to the nucleotide base or an analogue of the nucleotide base, such as to the 5-position of the pyrimidines (T, C and U) and to the 7-position of the purines (G and A), to use a small cleavable chemical moiety to cap the 3'-OH group of the deoxyribose or ribose to make it nonreactive, and to incorporate the nucleotide analogues into the growing nucleotide sequence strand as terminators, such as reversible terminators and irreversible terminators. Detection of the unique label will yield the sequence identity of the nucleotide. Upon removing the label and the 3'-OH capping group, the polymerase reaction will proceed to incorporate the next nucleotide analogue and detect the next base. Exemplary fluorescent moieties and fluorescent semiconductor crystals are described in Ju et al., U.S. Pat. No. 6,664,079, hereby incorporated by reference.

Other nucleotide analogs that contain markers, particularly cleavable markers, are also contemplated, such as those configured using allyl groups, azido groups, and the like, and which are further described below. The nucleotide compositions of the invention are particularly useful in massively parallel DNA Sequencing By Synthesis (SBS) approaches utilizing fluorophores as markers.

a. Allyl Analogs

Cleavable fluorescent nucleotides with photo-cleavable linkers having reversible terminator allyl groups have been described in Ruparel et al. (2005) Proc. Natl. Acad. Sci. 102(17) 5932-7. Similar, fluorescent nucleotide conjugates have been described in Bi et al. (2006) J. Am. Chem. Soc. 128(8) 2542-3. In one embodiment, the invention contemplates using nucleotide analogs with cleavable markers conveniently configured with allyl groups. In a particular embodiment, the exposed amine groups of incorporated nucleotides are capped during sequencing. In other embodiments, the nucleotide derivatives comprise two or more allyl ethers and synthetic intermediates thereto.

Figure 5:
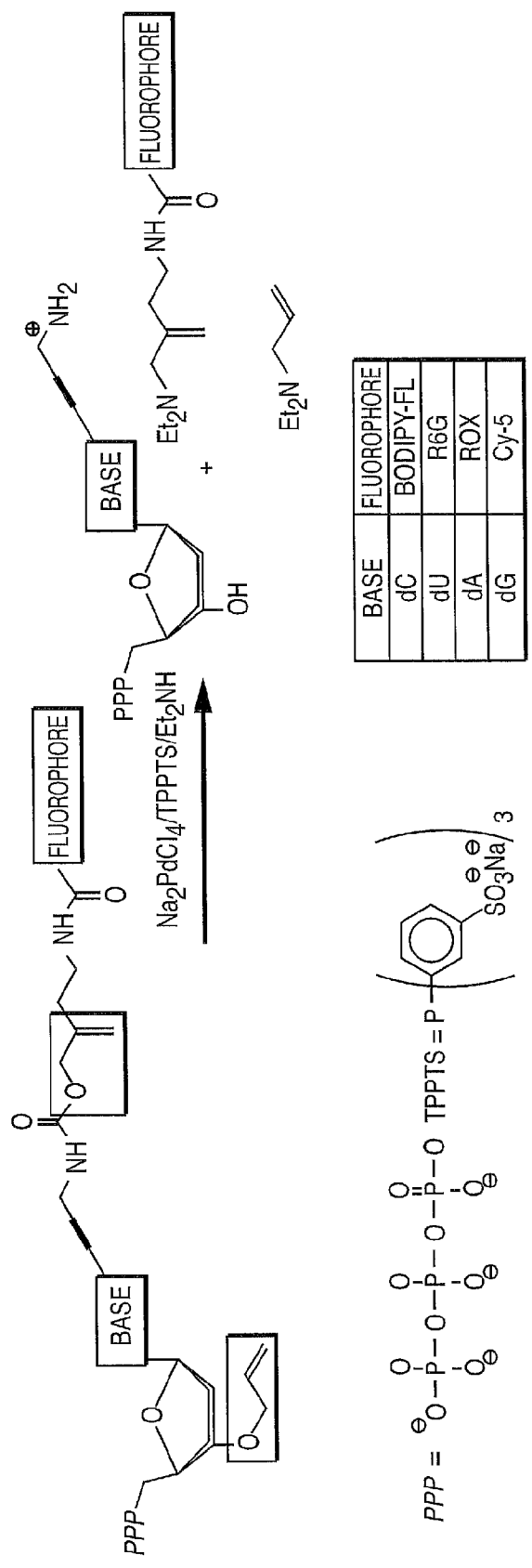

Sample preparation and parallel sequencing steps are exemplified, but not limited, to those illustrated in FIGS. 4A-B and 5. FIG. 4A shows how one isolates and prepares the DNA prior to sequencing and FIG. 4B shows the sequencing cycle. One isolates DNA from a biological source and shears it by a mechanical device to the desired average size. One end-repairs, A-tails, and circularizes the fragments using a dT-tailed linker about 100 nucleotides in length. The linker consists of two outward directed primer recognition sequences and an arbitrary sequence of about 100 bases between the priming sites. After ligation, one decomposes noncircular sequences by treatment with an endonuclease. One dilutes the circular DNA fragments to prepare them for head-based emulsion PCR using a biotinylated forward primer and a bead-attached reverse primer carrying an azido group on its 5'-end. One performs emulsion PCR. An aqueous mix containing all the necessary components for PCR plus primer-bound beads and template DNA are stirred together with an oil/detergent mix to create microemulsions. The aqueous compartments contain an average of less than one template molecule and less than one bead. The microemulsions are temperature-cycled as in a conventional PCR. If a DNA template and bead are present together in a single aqueous compartment, the bead-bound oligonucleotides act as primers for amplification. One breaks the emulsion and subjects the mixture to an enrichment step by using streptavidin coated magnetic beads. One denatures the nucleic acid immobilized on the beads generating single stranded amplicons to which a self-priming hairpin moiety is then ligated.

The beads are then arrayed on a chip surface and the sequencing by synthesis reactions are performed. Each cycle comprises steps that are used to read out the DNA sequence (See FIG. 4, B). One subjects the array segment to the fluorescent nucleotide conjugate with a hydroxyl-protecting group on the 3' end. One scans the array and the fluorescent output of each of the fluorescent markers and measures the output for each position. One exposes the array to conditions for cleavage of the fluorescent marker and the hydroxyl-protecting group. The entire process is repeated with another set of nucleotide bases unit the sequence of each position is determined. As the sequence data is generated, one collects the sequence information and aligns the reference sequences for diagnosis. One may use computer software and a database of previously known mutations and corresponding sequences to correlate them to the sequence with known mutations.

The PCR approach described above ensures that instead of sequencing of the entire pool of templates, one performs clonal or digital sequencing, resulting in much higher sensitivity for detection of mutations. For example, if a spontaneous mutation is present at only 5% of the population and the remaining 95% of the gene copies are wild types it is difficult to detect the mutated DNA using a conventional pool sequencing approach because of insufficient sensitivity. In the applicants' approach, one dilutes the input sample so that each PCR emulsion bubble contains at most a single template, which is then subjected to sequencing. If one performs this process on 1,000 unique clones, then one on average detects mutant sequences (present in 5% of amplicons) in 50 reactions and wild type sequence in 95% of the reactions.

b. Azido Analogs

Nucleotide analogs that contain cleavable markers configured using azido groups are also useful in the invention's methods and compositions. The nucleotide analogs are exemplified by nucleotide compositions comprising compounds of the following general structure:

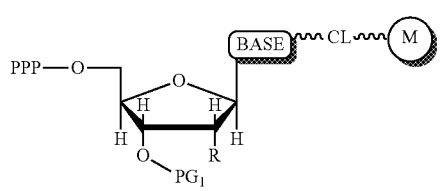

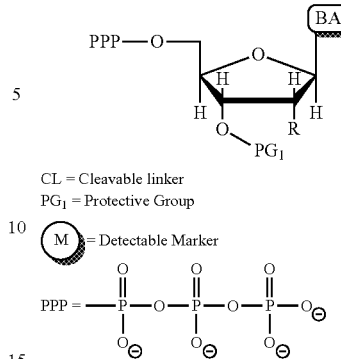

CL = Cleavable linker
PG$_1$ = Protective Group
(M) = Detectable Marker $$PPP = -\overset{O}{\underset{O_\ominus}{\overset{\|}{P}}}-O-\overset{O}{\underset{O_\ominus}{\overset{\|}{P}}}-O-\overset{O}{\underset{O_\ominus}{\overset{\|}{P}}}-O_\ominus$$

Where PG1 stands for protective group that is selectively removable and, and CL stands for cleavable linker, which is also selectively cleavable, and R is selected from the group of H, OH, F, NH$_2$. Several particular embodiments of this invention are contemplated. In one embodiment these nucleotide compositions can be incorporated into the nucleic acid by nucleic acids modifying enzymes in a controlled fashion to decode the identity of the bases encoded by the marker moiety M. Once the identity of the base has been decoded, then the marker moiety can be cleaved off and removed. This invention contemplates the use of the cleavable linkers based on the "trimethyl lock" mechanism or the "1,6-rearrangement" mechanism. The 3'-O-protective groups which act as reversible terminators can also be cleaved off to enable addition of the next nucleotide. This invention contemplates the use of azidomethyl, methylaminoxy, disulfide and allyl groups as reversible 3'-OH terminators.

Methods for synthesizing exemplary nucleotide analogs that contain cleavable markers configured using azido groups are described in Examples 2-11 and shown in FIGS. 20-26.

The invention contemplates the use of the cleavable linkers based on the "trimethyl lock" mechanism or the "1,6-rearrangement" mechanism. The 3'-O-protective groups which act as reversible terminators can also be cleaved off to enable addition of the next nucleotide. The invention contemplates the use of azidomethyl, aminooxy, methylaminoxy and allyl groups as reversible 3'-OH terminators.

i. Cleavable Linkers (Cl)

Cleavable linkers are exemplified by trimethyl lock based linkers and 1,6-rearrengement linkers as further described below.

1. Trimethyl Lock Based Linkers

Cleavable linkers are the linkers linking the marker molecule M to the base and these can be selectively cleaved using specific cleaving agents. Specifically, this invention contemplates the use of a "trimethyl lock" structure as the cleavage mechanism. These structures are well known in the chemical arts and have been used before in controlled drug release applications. The general structures of cleavable trimethyl lock based linker utilized in particular embodiments of the present invention are shown below:

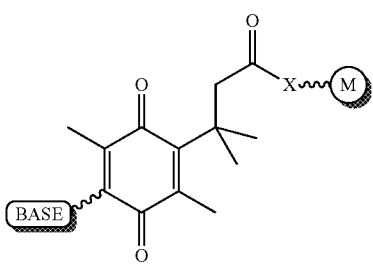

The above shows exemplary embodiment A where BASE is selected from any ribo- or deoxyribo-nucleobases: adenosine, cytidine, guanosine, thymidine and analogs, M is a detectable marker, and X is a divalent group selected from NH, O, S.

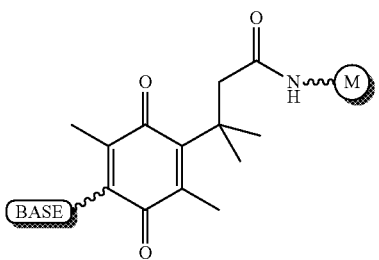

The above shows exemplary embodiment B where BASE is selected torn any ribo- or deoxyribo-nucleobases: adenosine, cytidine, guanosine, thymidine and analogs, M is a detectable marker, and X is NH.

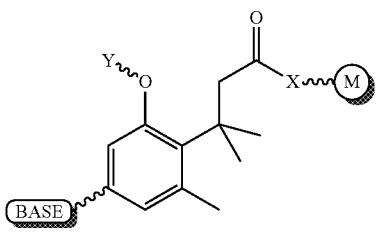

The above shows exemplary embodiment C where BASE is selected from any ribo- or deoxyribo-nucleobases: adenosine, cytidine, guanosine, thymidine and analogs, M is a detectable marker, and X is a divalent group selected from NH, O, S, and Y is a selectively removable protective group.

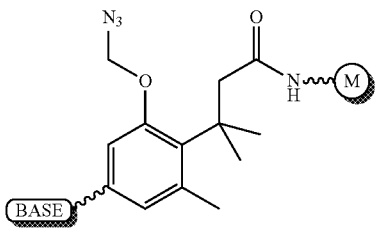

The shove shows exemplary embodiment D where BASE is selected from any ribo- or deoxyribo-nucleobases: adenosine, cytidine, guanosine, thymidine and analogs, M is a detectable marker, X is NH, and Y is an azidomethyl group.

Figure 6:
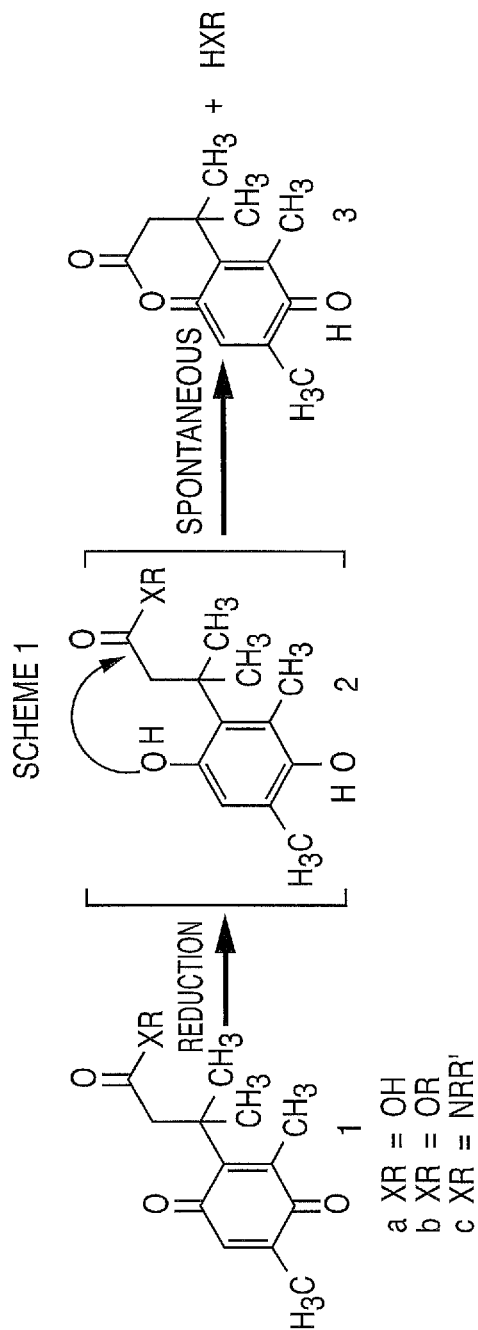

The cleavage mechanism for the trimethyl lock based compounds is shown schematically in FIG. 6. This phenomenon has been previously described in the chemical literature and used as for basic research studies (Borchardt and Cohen (1972). J. Am. Chem. Soc. 94(26): 9166-9174, Wang et al. (1996) Bioorg. Chem. 24: 39-49), as caging agents for controlled drug delivery (Wang et al. (1997). J. Org. Chem. 62(5): 1363-1367) and as protective groups in organic synthesis (Wang et al. (1995). J. Org. Chem. 60(3): 539-543).

The linkers in the present invention leverage the ability of the trimethyl lock system to create cleavably linked nucleotides.

2. 1,6-Rearrengement Linkers

The invention contemplates another category of cleavable linkers linking the detectable marker moiety to the nucleotide that are based on 1,6 quinone methide rearrangement mechanism (Carl et al. (1981), J. Med. Chem. 24(5):479-480; Duimstra et al. (2005). J. Am. Chem. Soc. 127(37): 12847-12855). These structures are well known in the chemical arts and they have been used before for the controlled drug release applications and for chemical synthesis (Azoulay et al. (2006) Bioorganic & Medicinal Chemistry Letters 16(12): 3147-3149; Murata et al. (2006) Tetrahedron Letters 47(13): 2147-2150). The general structures of cleavable 1,6 rearrangement mechanism based linker utilized in some embodiments of the present invention are shown below:

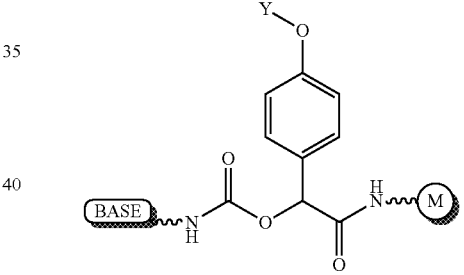

The above shows exemplary embodiment E, where BASE is selected from any ribo- or deoxyribo-nucleobases: adenosine, cytidine, guanosine, thymidine and analogs, M is a detectable marker and Y is a selectively removable protective group.

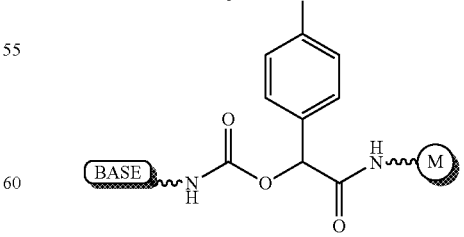

The above shows exemplary embodiment F, where BASE is selected from any ribo- or deoxyribo-nucleobases: adenosine, cytidine, guanosine, thymidine and analogs, M is a detectable marker.

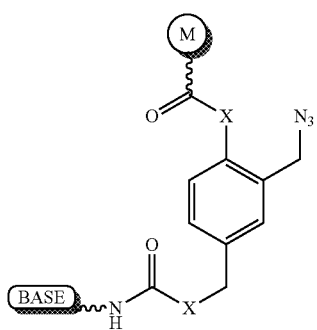

The above shows exemplary embodiment G where BASE is selected from any ribo- or deoxyribo-nucleobases; adenosine, cytidine, guanosine, thymidine and analogs, M is a detectable marker, and X is a divalent group selected from the following: NH, O, S.

Figure 7:
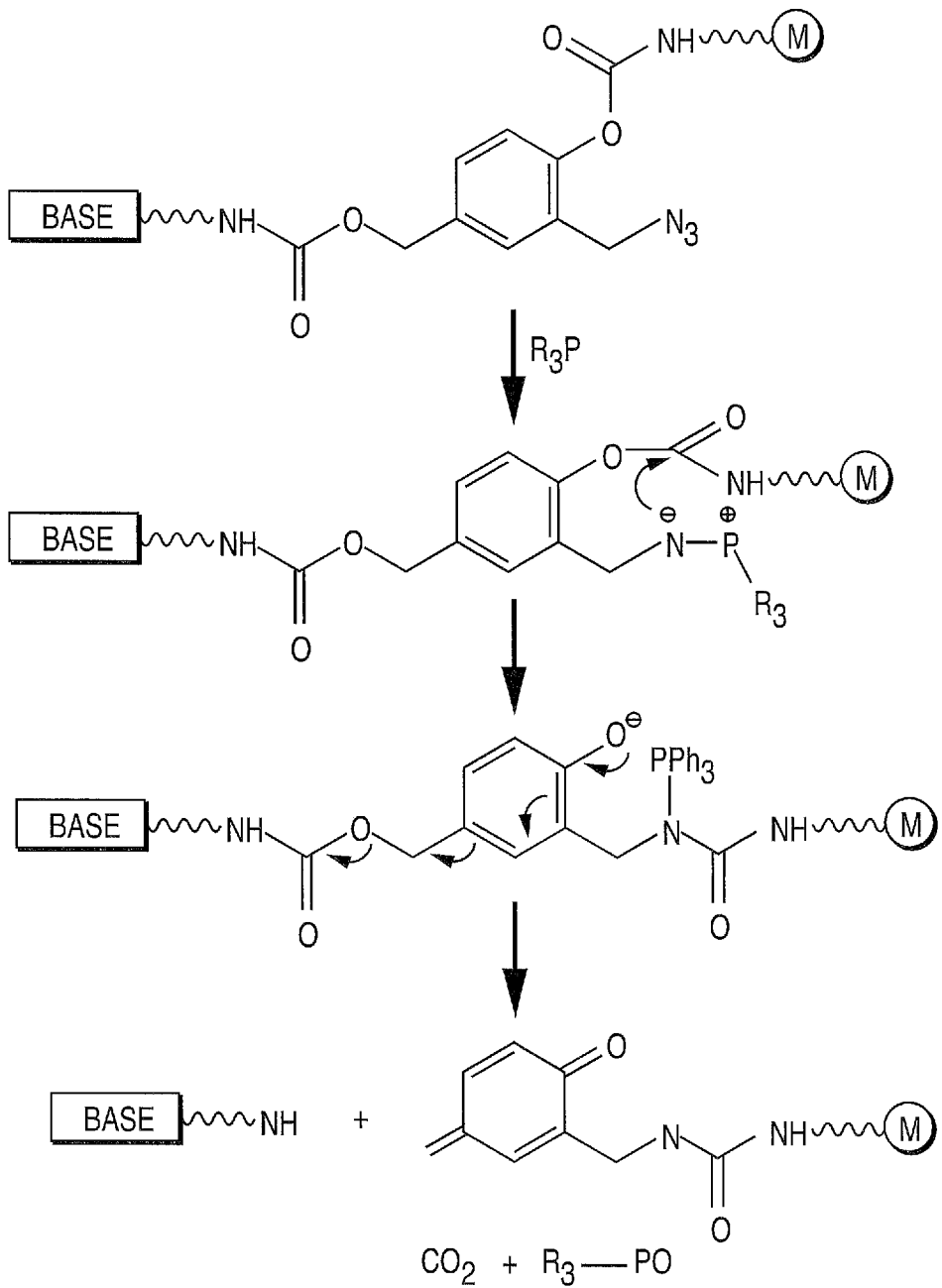

FIG. 7 shows an exemplary cleavage mechanism for the cleavable linker described in the following exemplary embodiment G.

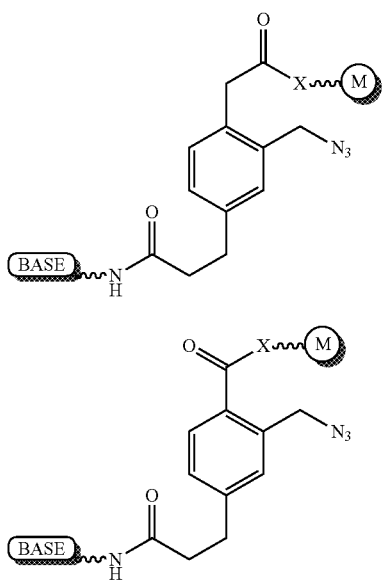

The above shows exemplary embodiment H where BASE is selected from any ribo- or deoxyribo-nucleobases: adenosine, cytidine, guanosine, thymidine and analogs, M is a detectable marker, and X is a divalent group selected from the following: NH, O, S. The cleavage is driven here by the reducing agent and nucleophilic attack of the resulting amino group on the carbonyl followed by cyclization. This mechanism has been used before for the development of protective groups for applications in the carbohydrate and nucleoside chemistry (Wada et al. (2001). Tetrahedron Letters 42(6): 1069-1072; Xu et al. (2002) Carbohydrate Research 337(2): 87-91).

The cleavable linker attachment to the base moiety can be achieved in variety of ways that are well known in the art. Among these is the use of linkers based on 1) propargylamino nucleosides, 2) aminoallyl nucleosides, and 3) propargylhydroxy nucleosides.

ii. Protective Groups (PG1)

The invention contemplates nucleotide compositions comprising the following protective groups (PG1) that reside on the 3'-OH groups of the nucleotides; 1) 3'-O-Azidomethyl ethers, 2) 3'-O-disulfide, 3) 3'-O-methylaminoxy, and 4) 3'-O-allyl.

With respect to the 3'-O-Azidomethyl ethers, exemplary protective groups that reside on the 3'-OH groups of the nucleotides that are within the scope of this invention are 3'-O-azidomethyl groups. These groups can be removed using mild reducing agents, such as Tris(2-carboxyethyl) phosphine (TCEP).

With respect to the 3'-O-disulfide group, the 3'-O-disulfide group can be removed under mild oxidative conditions, for example using in using mild reducing agents, such as Tris(2-carboxy-ethyl)phosphine (TCEP).

With respect to the 3'-O-methylaminoxy group, the 3'-O-methylaminoxy (3'-O—CH2-NH2) group can be removed under mild oxidative conditions, for example using in situ generated nitrous acid (such as from sodium nitrite).

As to the 3'-O-allyl group, this protective group can be removed using a variety of reducing agents, including transition metal complexes (Pd, Rh).

c. 3'-O-Protected Nucleosides and Nucleotides

The invention contemplates compositions comprising compounds of the following general structure:

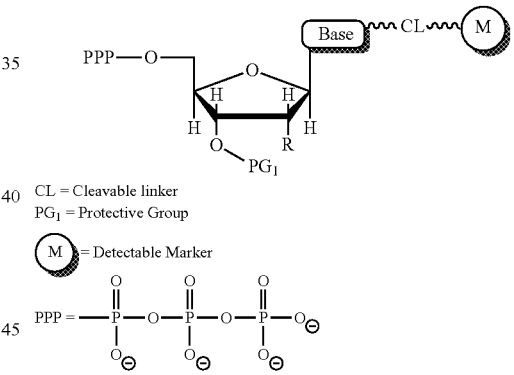

CL = Cleavable linker
PG₁ = Protective Group
Ⓜ = Detectable Marker $$PPP = \begin{array}{c} O \\ \parallel \\ -P-O- \\ | \\ O_\ominus \end{array} \begin{array}{c} O \\ \parallel \\ -P-O- \\ | \\ O_\ominus \end{array} \begin{array}{c} O \\ \parallel \\ -P-O_\ominus \\ | \\ O_\ominus \end{array}$$

PG1 stands for protective group that is selectively removable and, and CL stands for cleavable linker, which is also selectively cleavable. In one embodiment these nucleotide compositions can be incorporated into the nucleic acid by nucleic acids modifying enzymes in a controlled fashion for example to decode the identity of the bases encoded by the marker moiety M. Once the identity of the base has been decoded, then the marker moiety can be cleaved off and removed. In one embodiment, the invention contemplates the use of cleavable protection for 3'-OH in nucleotides for reversible terminators for SBS.

Figure 28:
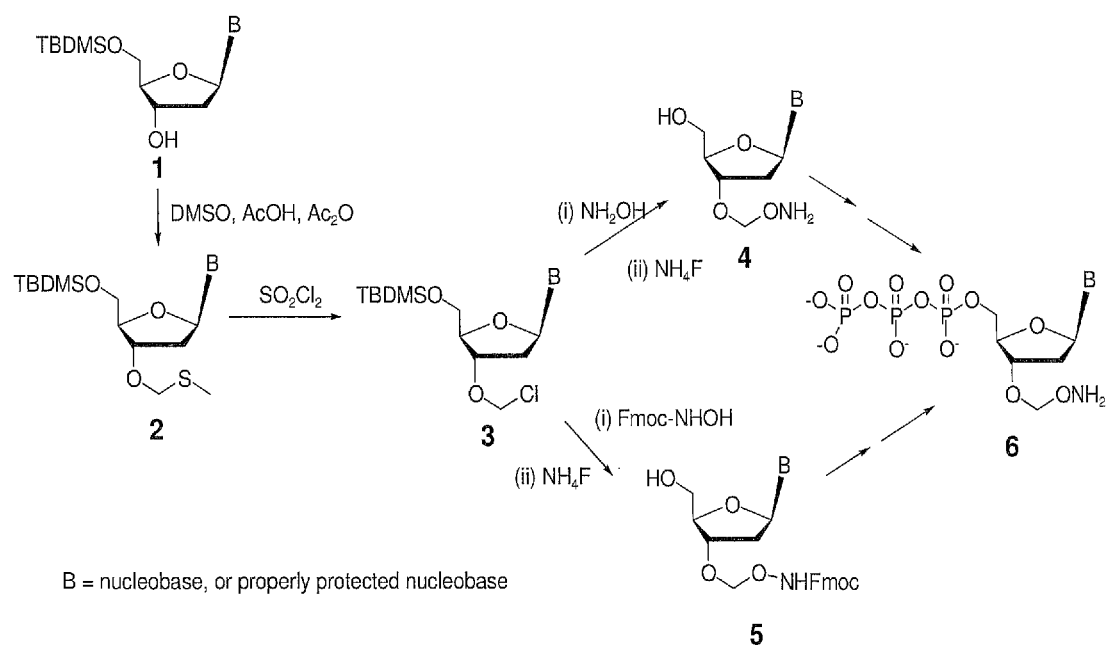
FIG. 28 shows an exemplary general synthetic pathway to install 3'-O amino hemiacetal group ($—CH_2ONH_2$) and conversion to nucleotides.
Figure 29:
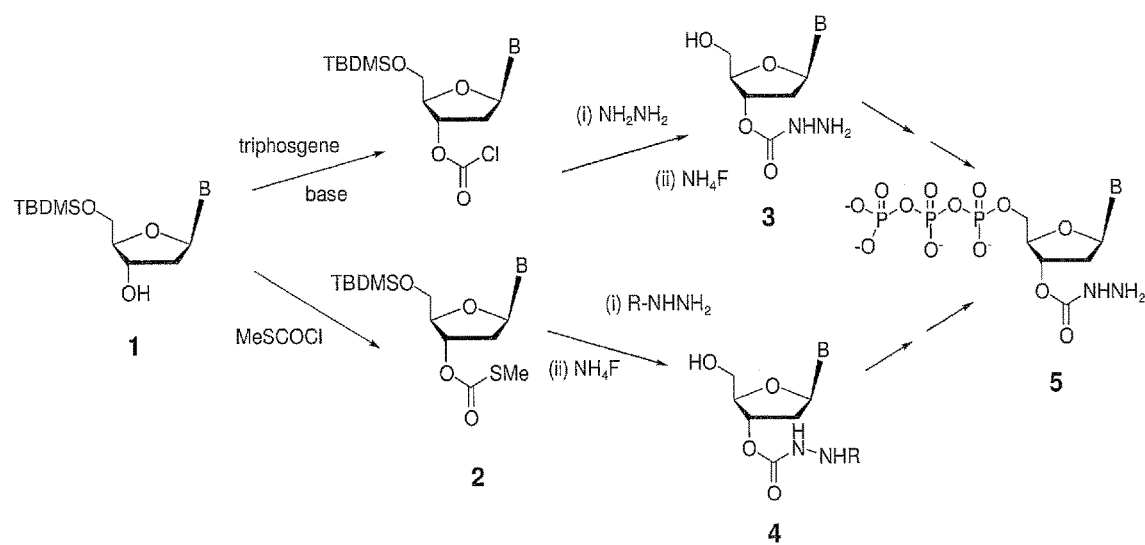
FIG. 29 shows an exemplary synthetic pathway to prepare 3'-O carbazate ($—CH_2ONH_2$) nucleotide analogues
Figure 30:
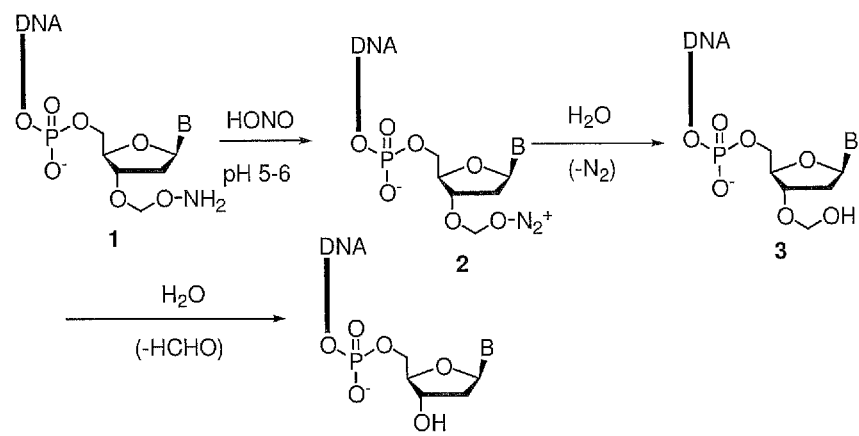
FIG. 30 shows an exemplary mechanism of 3'-O amino hemiacetal ($—CH_2ONH_2$) nucleotides deprotection reaction to generate free 3'-OH group.
Figure 31:
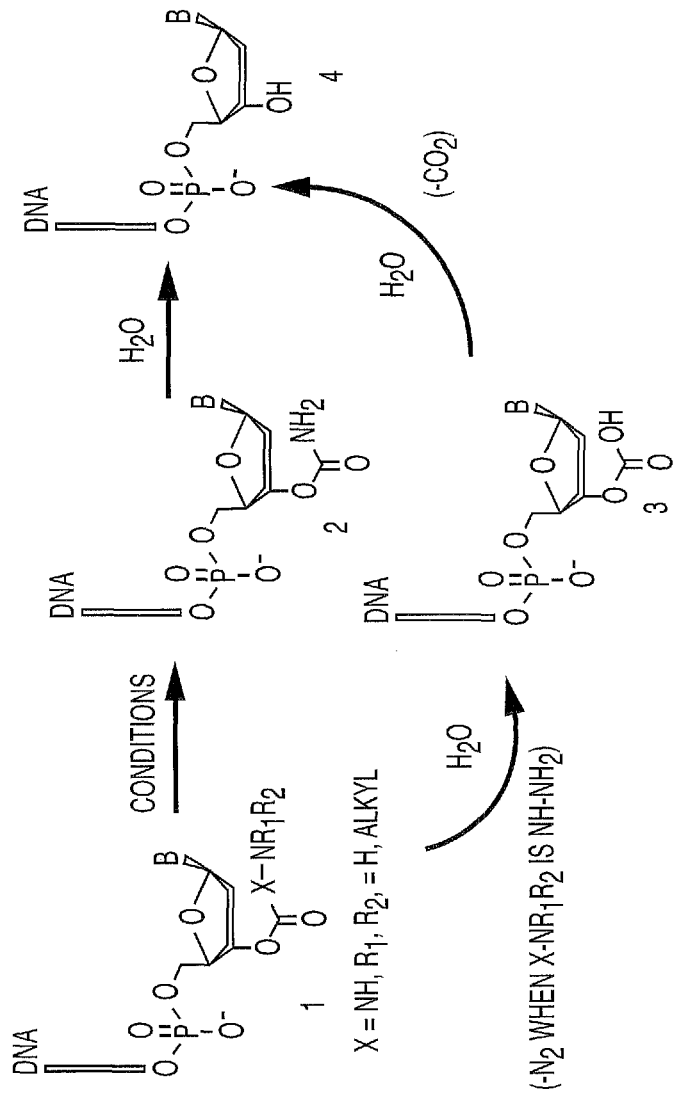
FIG. 31 shows an exemplary mechanism of 3'-O-carbazate ($—C(O)NHNH_2$) nucleotides deprotection. The reaction may be fast due to higher entropy contribution of the leaving molecular nitrogen and carbon dioxide gas.

Examples of PG1 protective groups are shown in FIG. 27. As an illustration, the synthesis of one of the embodiments in such classes of nucleotide-3'-O—(CH₂ONH₂)-dNTPs is presented in FIG. 28. Briefly, the protected 3'-methylthiomethyl nucleoside (1) upon treatment with SO₂Cl₂ produce activated product (2) which after reaction with hydroxylamine or its N-Fmoc protected compound install aminoxy group. The later compounds can be triphosphorylated to result in nucleotides. Other compounds and exemplary synthesis pathways within the scope of the invention are shown in FIGS. 29-31.

D. Reducing Lead and Lag

Figure 35:
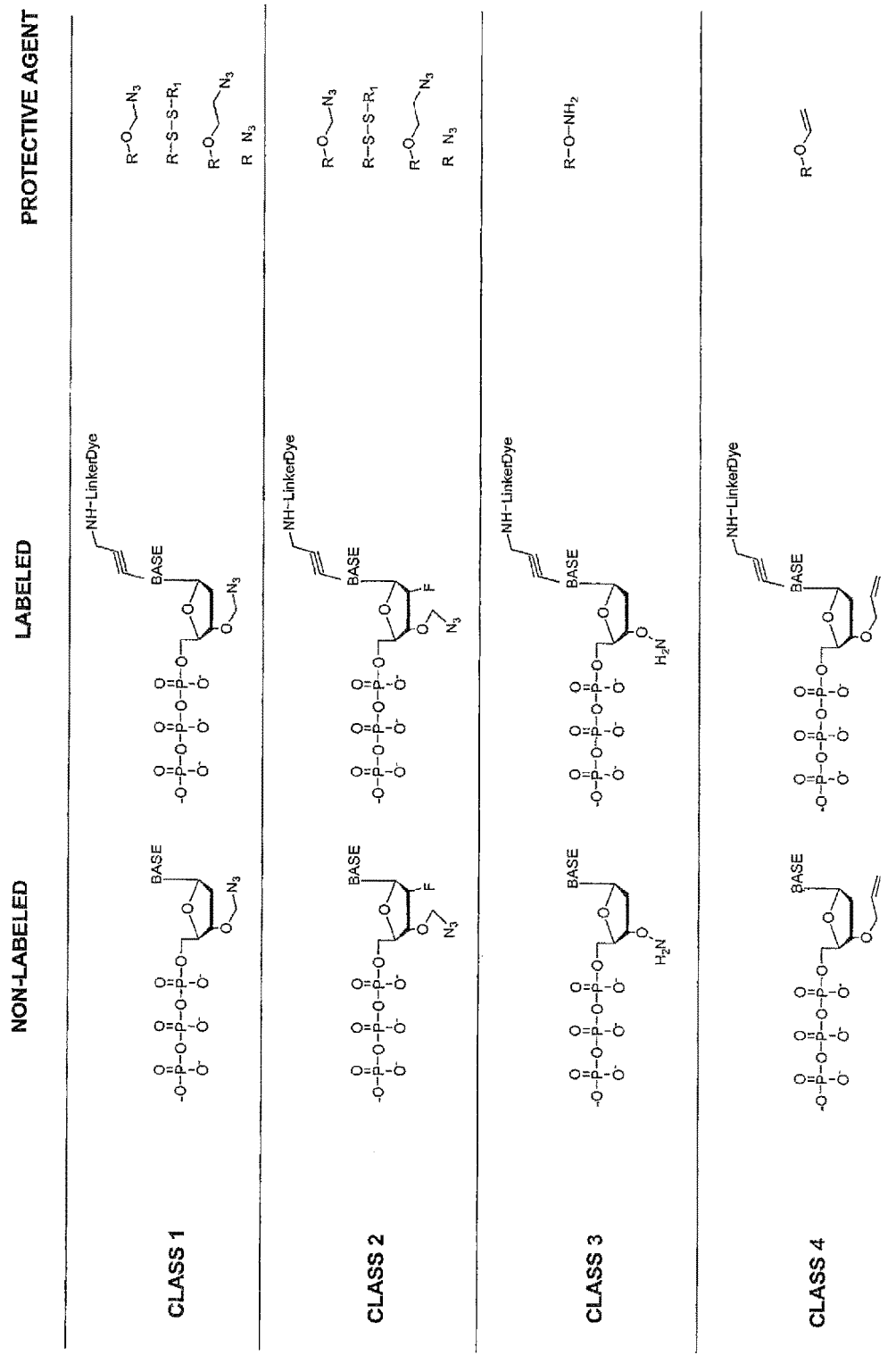
FIG. 35 provides examples of chemical structures of the reversibly terminating nucleotides used in sequencing. These examples include: 3'-O-azidomethyl nucleotides, 3'-O-aminoxy nucleotides, 3'-O-allyl nucleotides; and disulfide nucleotides.
Figure 36:
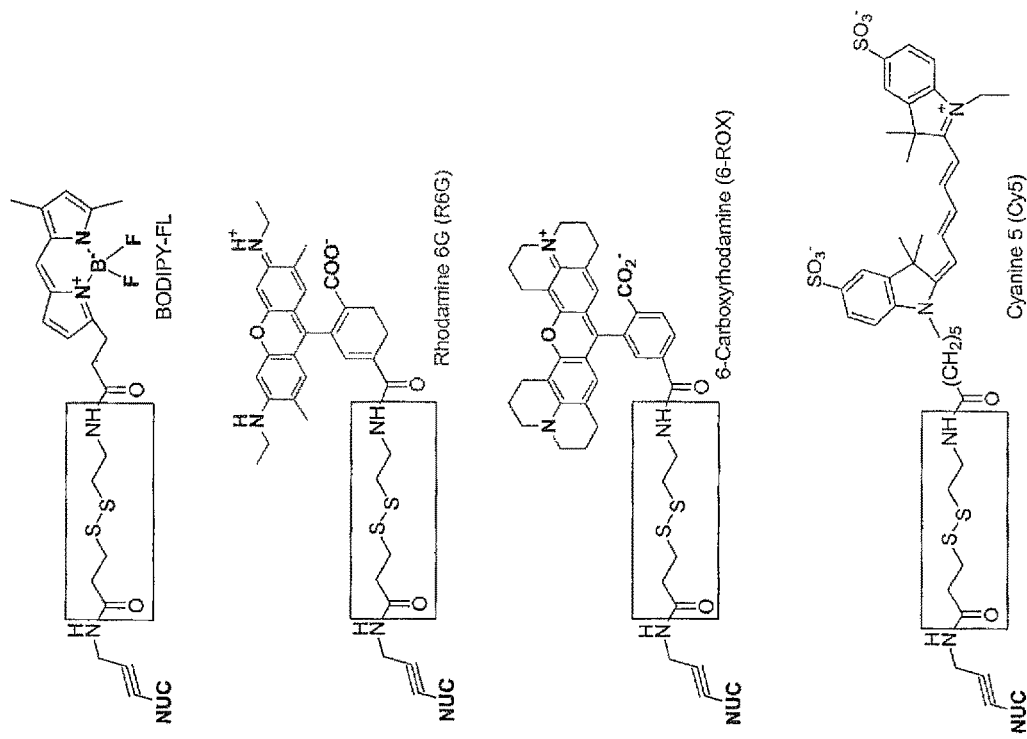
FIG. 36 provides examples of dyes conjugated to reversibly terminating nucleotides via a cleavable linker.

The cleaving agent is designed to cleave the 3'-OH or the dye attached to the nucleotide or both the 3'-OH and the dye. A variety of chemistries may be used for these attachments. FIG. 35 shows various possible chemistries for the 3"-OH group. FIG. 36 shows disulfide linkers for attaching the dye. Importantly, for any particular nucleotide, the chemistries may be same or may be different. For example, in one embodiment, the 3'-OH group can carry an azidomethyl ether and yet the dye can be attached via an azido linker. In another embodiment, however, the 3'-OH group can carry an azidomethyl ether and yet the dye can be attached via a disulfide linker. Both the azidomethyl ether and the disulfide linker are cleavable by TCEP (Tris-carboxyethyl)phosphine, although the disulfide linker cleaves much faster than the 3'-O-azidomethyl ether.

The cleaving agent is used at relatively high concentration (50-100 mM) to achieve fast cleavage. It is important for the sequencing process to remove any traces of cleaving agent in the wash steps, as these traces could interact with the Extend A and B solution (see the discussion of these solutions above) in the next cycle and create native nucleotides. This is highly undesirable as this leads to sequence dephasing (lead and lag) and limits useful read lengths.

One approach might be to increase the number of washes. However, it has been found empirically that increased washing cycles after cleavage step have only minimal effect on the sequencing performance unless very high numbers of washes are used (see Example 14). Such an approach would slow down the process considerably.

The present invention, in one embodiment, contemplates a different approach to solving the problem. In one embodiment, the present invention contemplates novel compositions to be used in one or more of the solutions employed in the sequencing by synthesis method (or in a new, additional separate solution) that reduce, minimize and/or inhibit the cleaving agent and the "pre-cleaving" effect. In one embodiment, a cleavage agent "scavenger" is contemplated. The cleavage agent scavenger is designed to react with any leftover cleaving reagent remaining in the flow cell or the fluidics (e.g. tubing) by inefficient or incomplete washing. In one preferred embodiment, the scavenger agent is added to the wash solution directly after the cleave step. In another embodiment the scavenger is added to the Extend A solution. In yet another embodiment the scavenger agent is added to Extend B solution. The scavenger requirements are as follows; 1) solubility; 2) fast and specific reaction with the cleaving agent. In the embodiments where the scavenger is added to Extend A or B solution, there is the additional requirement of lack of inhibition of polymerase reaction and lack of reactivity with functional groups on the nucleotides, dyes or polymerase.

Figure 37:
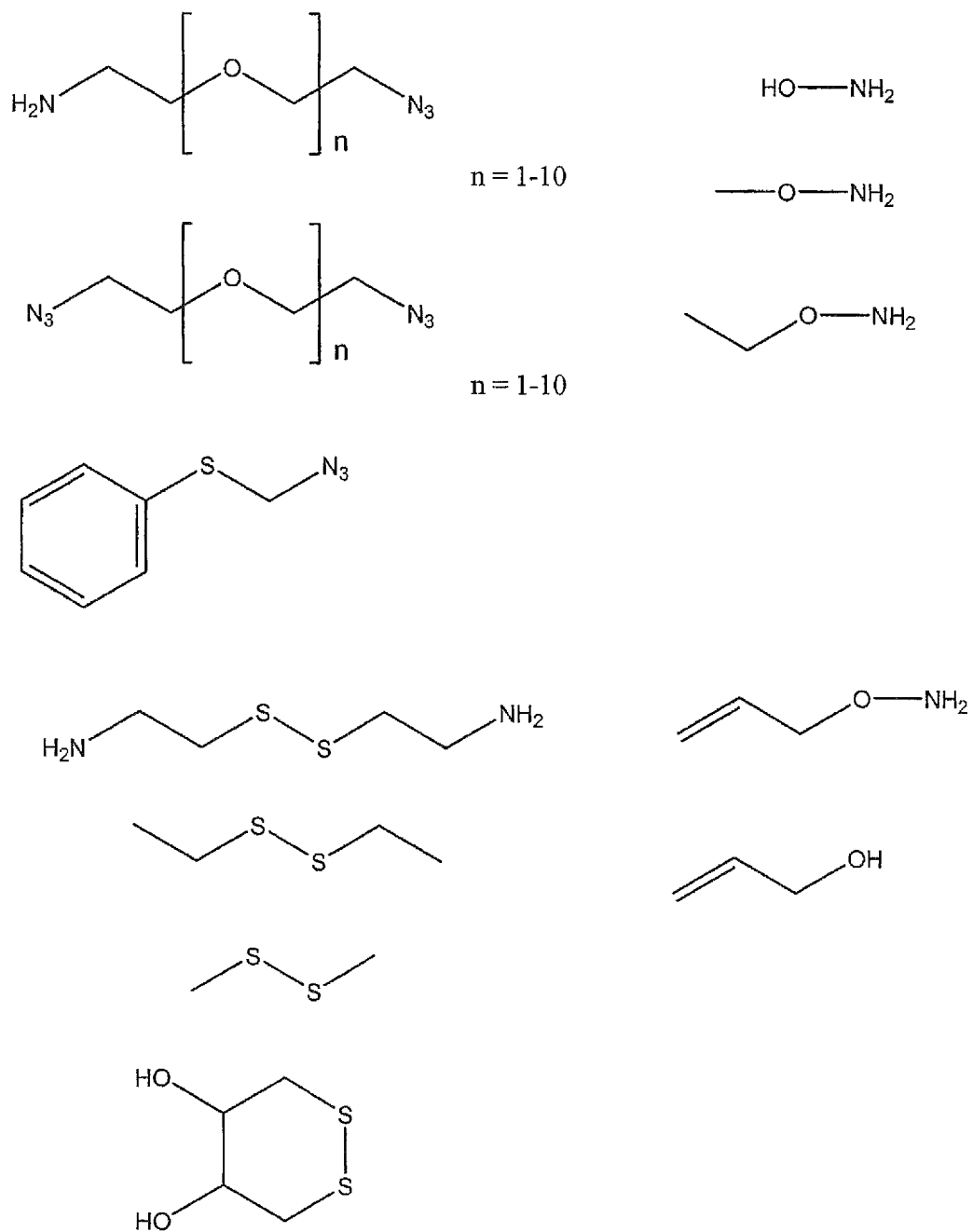
FIG. 37 provides examples of compounds useful as cleaving agent "scavengers."

In one particular embodiment, the scavenger agent mimicks the structure of the protective group present on the 3'-OH location of the nucleotide. In another embodiment, the scavenger mimicks only the reactivity of the protective group. For example, in case of 3'-O-azidomethyl nucleotides scavenger compounds could comprise azidomethyl, azidoethyl ethers or disulfide compounds. In case of 3'-O—NH2 nucleotides the scavengers could be any aminoxy compounds, such, as hydroxylamine. In case of 3'-O-allyl nucleotides the scavengers could be any allyl ether or disulfide compounds. FIG. 37 provides examples of cleaving agent "scavengers." It has been found empirically (see Example 15), that the use of such compounds improves base calling accuracy, without the need for additional wash steps (and in particular, without the need for high numbers of wash cycles).

E. Dephasing

Many next-generation DNA sequencing systems read the sequence of millions of different single-stranded DNA fragments in parallel by using a polymerase enzyme to incorporate fluorescently labeled DNA nucleotides into the complementary strand one cycle at a time. However, incorporation errors can shift the phase of some of the templates, so base read outs may lead ahead or lag behind the cycle number. The invention provides a model and methods to account for incorporation errors and show how the model may be inverted to correct this dephasing and extend read lengths.

Although fluorescence-based, single-molecule sequencing on a chip has been demonstrated, it is very sensitive to polymerase incorporation errors. This may be reduced and therefore reliability of sequence read out may be increased if each spot on a chip is an ensemble of identical template molecules. Polymerase errors (such as the incorporation of the wrong complementary nucleotide or no incorporation at all) are inevitable, but infrequent. Therefore, the superposition of all of the fluorescent signals from template molecules within an ensemble will primarily be from the correct nucleotide. As the number of cycles gets large, however, certain errors can accumulate within an ensemble and contribute to possible miscalling of the correct nucleotide.

For our analysis, we assume that a set of reversibly terminated and cleavably labeled nucleotides with four different dye colors (one for each nucleotide type: A, C, G and T) are used for sequence read out. The methods described herein may also be applied to other types of SBS processes such as pyrosequencing. If the SBS process works without mis-incorporations, then for each cycle only a single nucleotide type is incorporated into every strand in an ensemble. During a read out phase, the color of each ensemble is measured, then during a cleavage phase, the terminator and dyes are cleaved off and the chip is ready for the next, cycle. Thus, the position of the base being read out on every template on the chip is synchronized with the cycle number.

Because of impurities, limited polymerase efficiencies and other errors, some of the templates within an ensemble may get out of phase with the cycle number. For example, the base that is incorporated in the $i^{th}$ cycle may be complementary to the $i-1^{st}$ position or the $i+1^{st}$ position in the template rather than the expected $i^{th}$ position. The invention's methods provide computational re-phasing of the dephased data. FIG. 8 is a schematic flow chart for re-phasing. Additional data demonstrating the efficacy of the invention's methods is discussed below, including FIGS. 9A-B-19 and Example 11 (FIGS. 33A-B-34A-B).

d. Sequence Lead

Polymerases that have an increased capacity for incorporating 3' reversibly terminated nucleotide analogs continue to have a preference for incorporating native nucleotides. This means that even though nucleotide analogs may be extremely pure, any residual nucleotides with 3'-OH (non-terminated) will be incorporated at a much higher rate and therefore appear to be more prevalent. The incorporation of non-terminated nucleotides has the effect of skipping a base, as a second incorporation (the next base) will occur in the same cycle. Thus, the fluorescent measurement for that template will exhibit the dye from the following base rather than the expected base at that cycle number. Since that template now exhibits a "lead," it will continue to do so, even if all future nucleotides are reversibly terminated.

Figure 9A:
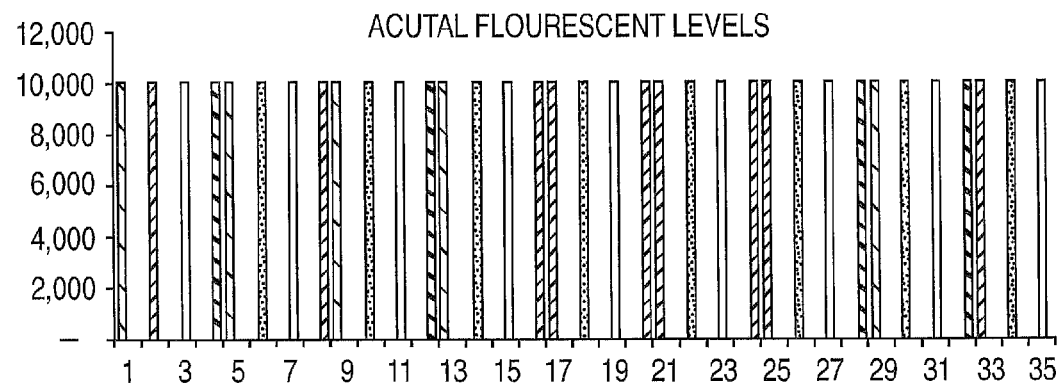
FIG. 9A-B shows simulated data showing sequence lead due to incorporation of small amounts of non-terminated nucleotides mixed with the reversibly terminated nucleotides.
Figure 9B:
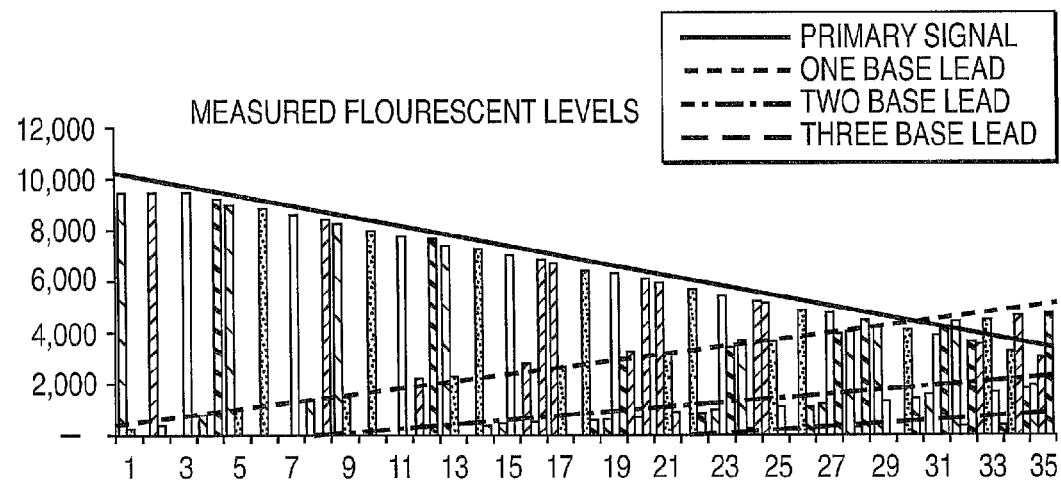

This effect is cumulative and shown in simulated 3O data in FIG. 9 for a non-terminated nucleotide incorporation rate of 2% as compared to the terminated nucleotide analog rate and a repeated 35 base sequence of the sequence ACT-GACTGACTG [SEQ ID NO: 5] . . . . Here we make the assumption that each of the nucleotides has the same nonterminated incorporation rate thereby allowing us to use a linear model. Again, the actual nucleotide purity may well be better than say 99.5%, but the apparent non-terminated incorporation rate may be 2% depending on the polymerase. In the example in FIG. 9A-B, the model tells us the amount of signal due to the sequence lead effect. In cycle 20, the model calculates that we have 60% of the signal from the primary base at the 20th position (red), 32.4% of the signal from the base at the 21st position (blue), 6.7% of the signal from the base at the 22nd position (green), 0.8% of the signal from the base at the 23rd position (yellow), and 0.07% of the signal from the base at the 24th position (red). An interesting observation is that with the lead effect, the primary base signal (actual base at that cycle) does not have a 100% signal as some templates are already "reading out" subsequent bases on that strand. Thus at the end of a run, we can "look forward" and shift back the lead signals and correct the primary signals. We denote the contributions at the $i^{th}$ cycle as $R_{0Lead,i}$, $R_{+1Lead,i}$, $R_{+2Lead,i}$, $R_{+3Lead,i}$, etc, for the ratio between the reduced signal for the $i^{th}$ base to the actual $i^{th}$ base population, the ratio contribution to the $i^{th}$ base signal from the $i+1^{st}$ a base, the ratio contribution to the $i^{th}$ base signal from the $i+2^{nd}$ base, etc. Because the amount of lead changes with each cycle, there will be a different set of ratios for each cycle.

e. Sequence Lag

Figure 10:
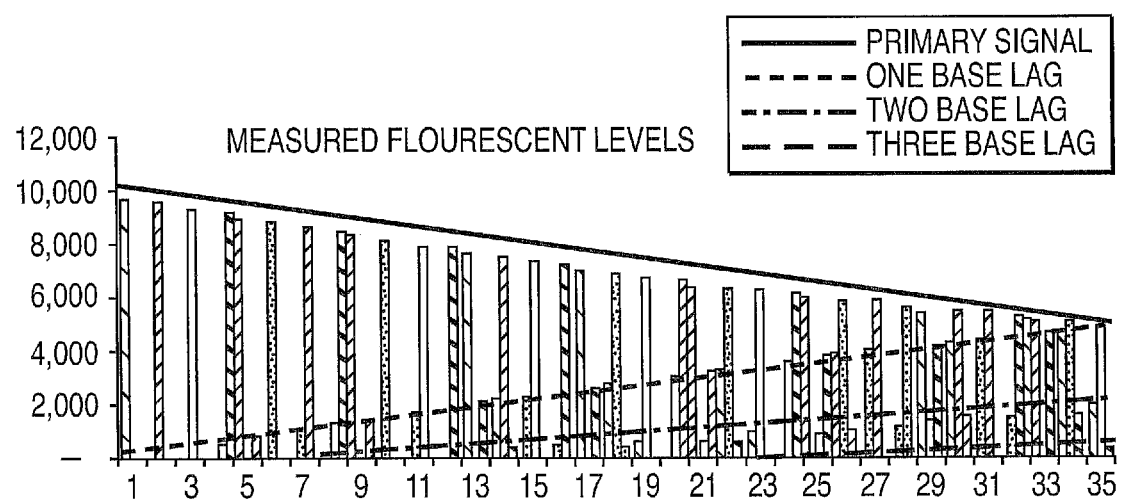
FIG. 10 shows simulated data showing sequence lag due to finite incorporation efficiency.

We developed a model for de-phasing due to sequence lag. This is caused by limited incorporation efficiency where some small percentage of the templates do not get a base incorporated in the cycle. FIG. 10 shows simulated data for a 98% incorporation efficiency for the same template sequence as in FIG. 9A-B. We denote the contributions at the $i^{th}$ cycle as $R_{0Lag,i}$, $R_{1Lag,i}$, $R_{-2Lag,i}$, $R_{-3Lag,i}$, etc., for the ratio between the reduced signal for the $i^{th}$ base to the actual $i^{th}$ base population, the ratio contribution to the $i^{th}$ base signal from the $i-1^{st}$ base, the ratio contribution to the $i^{th}$ base signal from the $i-2^{nd}$ base, etc.

f. Nucleotide Incorporation Events

As discussed above, every time there is an available site for the polymerase to incorporate a nucleotide on a template, there are three possible outcomes: First, no nucleotide is incorporated—Event No-I. If no nucleotide is incorporated due for example to polymerase inefficiency, then the site remains available for the next cycle. We term this a "lag" event as it has the effect of causing a readout in the next cycle that will from the position behind or lagging the cycle number. Second, a reversibly terminated nucleotide is incorporated—Event T-I. If as expected, a reversibly terminated nucleotide is incorporated, then the nucleotide readout is in sync with the cycle number. In the next cycle, the next, consecutive template nucleotide position will be available for incorporation. Third, a non-terminated (native) nucleotide is incorporated—Event N-I. If a non-terminated nucleotide is incorporated, then during that same cycle, there is a second opportunity for another nucleotide to be incorporated at the subsequent position in the template strand. We term this a "lead" event as it has the effect of causing a readout of a nucleotide that is at a position that is ahead of or leading the cycle number. This second incorporation event is subject to the same three possible outcomes (No-I, T-I or N-I); thus, N-I events are recursive.

We will use the variable $G_i$ to represent the rate at which a lag occurs at template position i and similarly $D_i$ for the lead rate at position i. The analysis assumes that these rates may vary from position to position depending on the identity of the nucleotide that is to be incorporated, but we have assumed that all incorporation events for a particular nucleotide have the same lag and lead rates, even if the incorporation is not the first one in a cycle (it follows an N-I event). The fluorescent signal that will be generated from an incorporation event at a template location i is proportional to $(1-G_i-D_i)$, so at every $i_{th}$ incorporation event, the three types of events (No-I, T-I and N-I) will occur at the following rates: Event No-I at rate $G_i$, Event T-I at rate $(1-G_i-D_i)$, and Event N-I at rate $D_i$.

g. Signals Produced in Each Cycle

Figure 11:
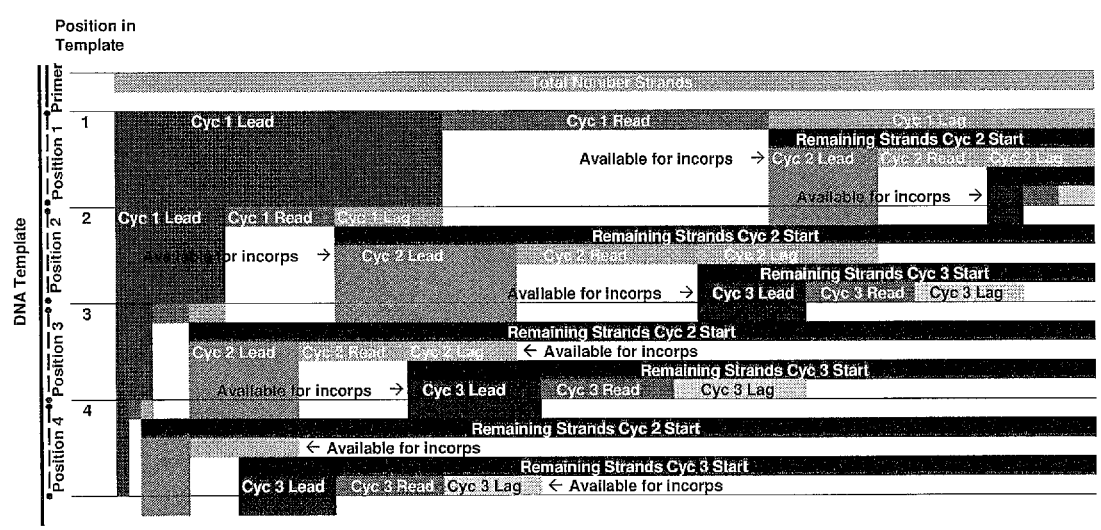
FIG. 11 is a chart of an exemplary sequence of extension events using an exemplary 4 templates positions and 3 cycles.

Although there are only three potential outcomes from an incorporation event, all of the combined events from multiple cycles in a template can be fairly complex. FIG. 11 may be used to better visualize the sequence of extension events. For simplicity, only 4 templates positions and only 3 cycles are illustrated in FIG. 11. The numbered regions in the vertical direction along the left edge indicate the nucleotide position along the strand. The horizontal direction symbolizes the relative number of strands in an ensemble that undergo events No-I, T-I or N-I (lag, readout or lead). The various events for cycle 1 in the sequence process are shown in shades of blue, events for cycle 2 are shown in red and events in cycle 3 are shown in green.

For clarity in FIG. 11, we have designated each of the three possible events (No-I, T-I and N-I) to occur at the same rate for every cycle. In an actual system, the lead and lag rate are both likely to be much smaller values. The chart is easier to understand if it is viewed one color at a time. The blue regions represent events that occur during the first cycle. At position 1 of the template, the entire ensemble of templates are available for extensions, thus (light blue) undergo a lag (no incorporation), (medium blue) are read out and (dark blue) undergo a lead. The portion of templates that experienced a lag (light blue) during the first cycle, remain available during the second cycle for incorporations. The portion of the templates that experienced a readout (medium blue) comprises the signal that is read during cycle 1 at position 1. This portion will progress in synchrony and allow incorporations to occur at position 2 during the second cycle. The portion of fee templates that experienced a lead at position 1 will have a second incorporation event during cycle 1 at the second position of the template. This incorporation again will be split equally into the three possible events. A portion of the templates will remain unextended (lag), a portion will generate a signal (readout) and a portion will undergo a lead and produce a third set of incorporation events at position 3. This process will continue during cycle 1. Although lead events may continue down the entire length of the template during cycle 1, in practical terms, the effects after about 4 lead events are negligible.

Figure 12:
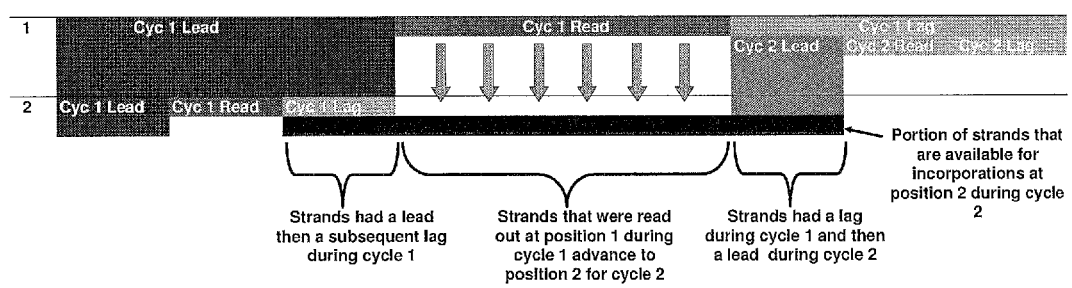
FIG. 12 is a chart of an exemplary sequence of extension events.

In cycle 2 (red colors), the only strands that are available to be extended at position 2 are those for which one of three events occurred (see FIG. 12): (1) strands that were read out at position 1 during cycle 1, (2) strands that experienced both a lead at position 1 and a lag at position 2 during cycle 1, and (3) stands that experienced a lag at position 1 during cycle 1 along with a subsequent lead at position 1 during cycle 2. A portion of these strands will also experience a cycle 2 lead to the third position, however, since they have "caught up" to the other strands with available sites at the second position, they are lumped together with them and further leads are considered as portions of the combined population.

Similar events occur at each template position during cycle 2. The events of cycle 3 (green shades) follow very similar patterns to those described for cycle 2.

h. Mathematical Models of Dephasing and Rephasing

We may derive general equations that describe all the incorporation events at each position and for each cycle. If we denote the relative magnitude (out of 1) of the number of strands that remain unincorporated for position i at the end of a cycle j as $R_{i,j}$, and the number of strands that are available for incorporation in the next cycle as $A_{i,j}$ then $$R_{i,j} = R_{i,j-1} - A_{i,j-1}(1 - G_i) \quad (1)$$

and $$A_{i,j} = R_{i,j} - R_{i,j-1} + A_{i-1,j} D_{i-1} \quad (2)$$

Figure 13:
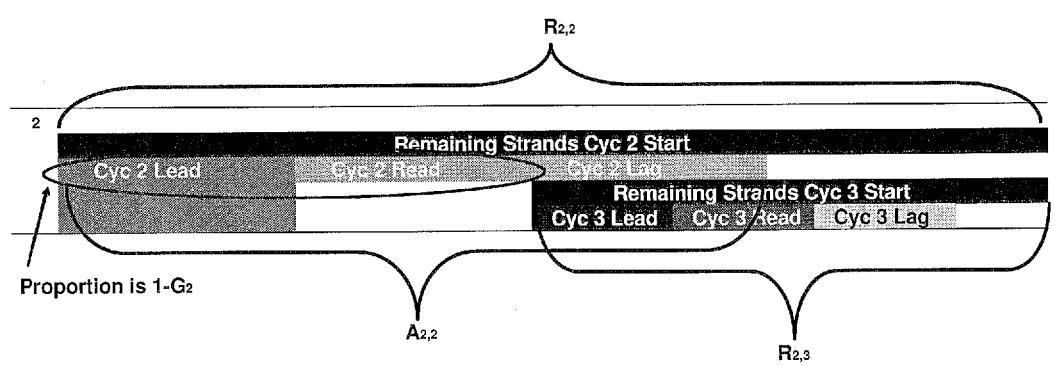
FIG. 13 shows a first portion of the chart of FIG. 11.

To explain the derivation of Equation 1, we use the example in FIG. 13, which shows a portion of the chart from FIG. 11. Only cycles 2 and 3 are shown for position 2. $R_{2,3}$ is comprised of $R_{2,2}$ minus a portion $(1-G_2)$ of $A_{2,2}$.

Figure 14:
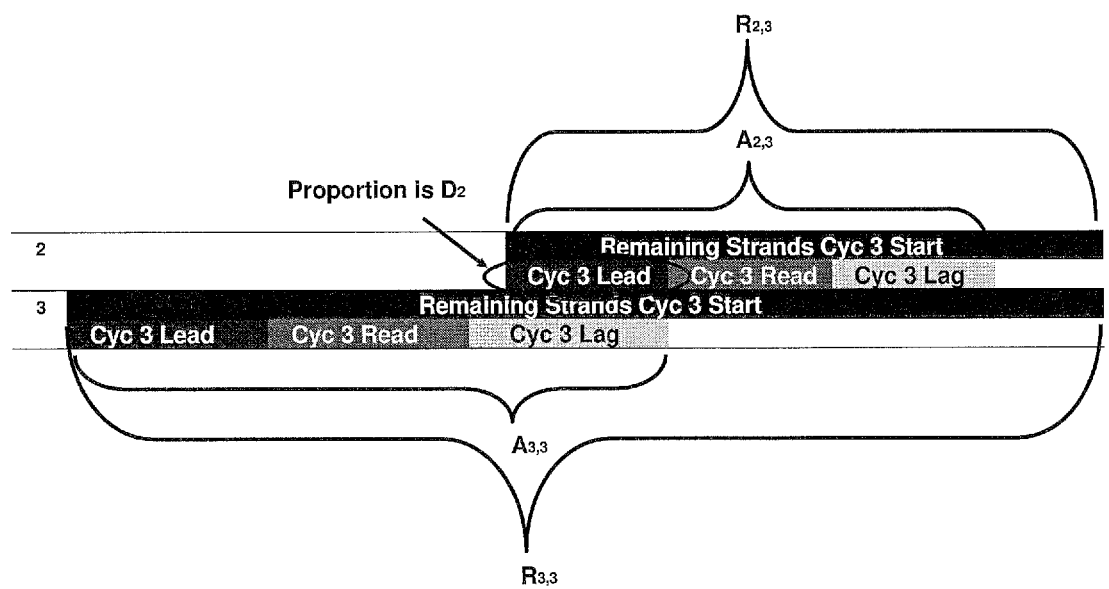
FIG. 14 shows a second portion of the chart of FIG. 11.

To explain the derivation of Equation 2, we use the example in FIG. 14, which shows a portion of the chart from FIG. 11. Only cycle 3 is shown for positions 2 and 3. $A_{3,3}$ is comprised of $R_{3,3}$ minus $R_{2,3}$ plus the lead portion $(D_2)$ of $A_{2,3}$.

It should be noted that for any particular cycle and position, the number of available stands, $A_{i,j}$, is generally fewer than the number of remaining strands, $R_{i,j}$, since some templates at the particular position are still lagging and unavailable, but may "catch up" in future cycles.

The signal that is produced, $S_{i,j}$, at the $i^{th}$ position at the end of the $j^{th}$ cycle comes from the proportion of the stands that are available, $A_{i,j}$, that, undergo event T-I $$S_{i,j} = A_{i,j}(1 - D_i - G_i) \quad (3)$$

In one embodiment, the model is used to apply the lead-lag compensation based on calibration of parameters, before or during the test, and to provide an initial estimate of the base identity at each location as determined during the sequencing run. In a particular embodiment, $G_i$ and $D_i$ for each nucleotide may be pre-calibrated or measured during the sequencing procedure. In general, the model is constructed with lag parameters that are applied to each cycle and lead parameters that are recursively applied to each cycle.

In a particular embodiment, the lead-lag matrix is formulated after an initial draft sequence is measured. This allows application of the proper set of $G_i$ and $D_i$ parameters to each cycle based on the nucleotides identified at each position in the draft sequence. In a further embodiment, the re-phasing of data is iterated using the result of one re-phasing calculation to select an updated set of $G_i$ and $D_i$ parameters for the next iteration.

i. Simulated Dephased Sequencing Data

We may use the relationships derived in the previous section to generate sequence data that simulate the signals that might occur when portions of every incorporation undergo a lead and a lag.

Figure 15:
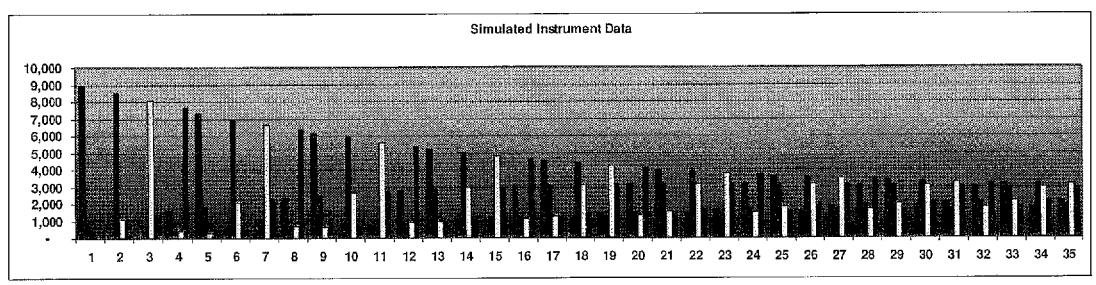
FIG. 15 shows data generated from the iterative application of equations 1-3 using parameters in Table 1.

As an example, we use the lead and lag factors below and generate simulated sequence data assuming the maximum signal from the template is 10,000 counts and the template has a 35 base repeating sequence of the sequence AGCTAGCTAGCT [SEQ ID NO: 10]. FIG. 15 shows data generated from the iterative application of equations 1-3 using the parameters in Table 1.

TABLE 1

| Lead Factors and Lag Factors for Nucleotides | | | | |
|---|---|---|---|---|
| | A | G | C | T |
| Lead Factors | 4.10% | 4.20% | 4.30% | 4.40% |
| Lag Factors | 1.10% | 1.20% | 1.30% | 1.40% |

FIG. 15 shows that with the presence of a lead and lag component, there is a cumulative effect that reduces the signal from the expected nucleotide at a particular cycle and "spreads" some of the signal forwards and backwards. As the number of cycles increases, it becomes more and more difficult to directly read the correct base from the graph, thereby limiting the effective read length of the template.

ii. Re-Phasing Sequencing Data

Data herein (Example 11, FIGS. 33A-B-34A-B) demonstrate that applying the methods and the below described equations of the invention, exemplary 16-base and 25-base nucleotide sequences were sequenced with high fidelity. The high quality of the data, particularly in the last several bases in FIG. 34A-B, demonstrates that the read length will not be limited by signal decline. Thus, it is contemplated that the invention's methods are applicable to sequences containing at least 16 nucleotides, at least 25 nucleotides, at least 35 nucleotides, at least 50 nucleotides, at least 100 nucleotides, at least 1,000 nucleotides, and at least 10,000 nucleotides. Further description of the equations used to re-phase sequencing data is described as follows.

We constructed a matrix equation that describes a model for the reduced measured signal, $I_{Mi}$, from the lead and lag effect in the $i^{th}$ cycle from the original template populations, $I_{Ai}$, for all cycles, i=1 to N. Here each of the intensity matrices ($[I_{Ai}]$ and $[I_{Mi}]$) have N rows (one for each cycle) and four columns (one for each color).

$$\begin{bmatrix} I_{M1} \\ I_{M2} \\ \vdots \\ I_{MN} \end{bmatrix} = K_{Lead/Lag} \begin{bmatrix} I_{A1} \\ I_{A2} \\ \vdots \\ I_{AN} \end{bmatrix}, \quad (4)$$

where the lead/lag matrix, $K_{Lead/Lag}$, is a square N×N matrix of the following form:

$$K_{Lead/Lag} = \begin{bmatrix} R_{Lag/Lead,1} & R_{+1Lead,1} & R_{+2Lead,1} & R_{+3Lead,1} & \cdots & R_{+(N-1)Lead,1} \\ R_{-1Lag,2} & R_{Lag/Lead,2} & R_{+1Lead,2} & R_{+2Lead,2} & \cdots & R_{+(N-2)Lead,2} \\ R_{-2Lag,3} & R_{-1Lag,3} & R_{Lag/Lead,3} & R_{+1Lead,3} & \cdots & R_{+(N-3)Lead,3} \\ R_{-3Lag,4} & R_{-2Lag,4} & R_{-1Lag,4} & R_{Lag/Lead,4} & \cdots & R_{+(N-4)Lead,4} \\ \vdots & \vdots & \vdots & \vdots & \ddots & \vdots \\ R_{-(N-1)Lag,N} & R_{-(N-2)Lag,N} & R_{-(N-3)Lag,N} & R_{-(N-4)Lag,N} & \cdots & R_{Lag/Lead,N} \end{bmatrix} \quad (5)$$

The diagonal terms, $R_{Lag/Lead,i}$, in the $K_{Lead/Lag}$ matrix above is the fractional remaining signal in the $i^{th}$ cycle from the $i^{th}$ position of the templates after all of the leads and lags to that point. Each of the terms in the upper triangular portion of the matrix, $R_{+kLead,i}$, is the fractional contribution to the signal in the $i^{th}$ cycle from k positions forward of the $i^{th}$ position. Each of the terms in the lower triangular portion of the matrix, $R_{-kLag,i}$ is the fractional contribution to the signal in the $i^{th}$ cycle from k positions before the $i^{th}$ position. In most systems, the terms with k greater than about 4 (5 positions or more away from the position corresponding to the cycle number) are negligible. The diagonal terms are close to 1 for the earlier cycles and do not drop below about 0.25 for the later cycles. Thus, this matrix is invertable.

In order to compensate for both sequence leads and lags, we solved for $[I_{Ai}]$ in Equation 4 by taking the inverse, $K_{Lead/Lag}^{-1}$, of $K_{Lead/Lag}$ (Equation 5) to get an estimate of the actual template population $[I_{Ai}]$:

$$\begin{bmatrix} I_{A1} \\ I_{A2} \\ \vdots \\ I_{AN} \end{bmatrix} = K_{Lead/Lag}^{-1} \begin{bmatrix} I_{M1} \\ I_{M2} \\ \vdots \\ I_{MN} \end{bmatrix}. \quad (6)$$

When the lead rates for all the nucleotides are identical and the lag rates for all of the nucleotides are identical, then the lead/lag matrix, $K_{Lead/Lag}$, does not depend on the sequence. This makes Equation 6 linear and the inverse of the matrix is deterministic. In this case the inverse of the lead/lag model gives the correction matrix, $K_{Lead/Lag}^{-1}$, which is applied just once at the end of a run and takes into account all of the signals from the first to the last base.

If on the other hand the lead and lag factors vary from one nucleotide to the next, then the lead/lag matrix, $K_{Lead/Lag}$, depends on the actual sequence (solution of $[I_{Ai}]$ in Equation 6) and the problem is non linear. In other words, we need to determine an estimate for the true value of the intensities of each base in the sequence when the governing equations depend on this solution.

To solve the non-linear problem, one can estimate a solution and iterate until the solutions converge. We may use the raw out-of-phase sequence data to make an initial estimate of the sequence by taking the maximum value at each cycle, using this information to determine the lead and lag rates for each position, construct a lead/lag matrix ($K_{Lead/Lag}$), take the inverse of that matrix and solve for the corrected, re-phased sequence. We can then use the new sequence to make a new estimate of the lead/lag matrix, etc. As long as the various lead and lag factors are fairly close to one another, this method should converge in about two or three iterations.

iii. Additional Factors

The above method is a very powerful way of "cleaning up" sequence data that has been dephased due to the lead and lag phenomena. The matrix condition number determines when matrix manipulations will be sensitive to small numerical variations. A matrix condition near 1 means the matrix is well behaved, while a large condition number means the matrix is ill-conditioned or sensitive to small numerical inaccuracies.

Figures 16A, 16B:
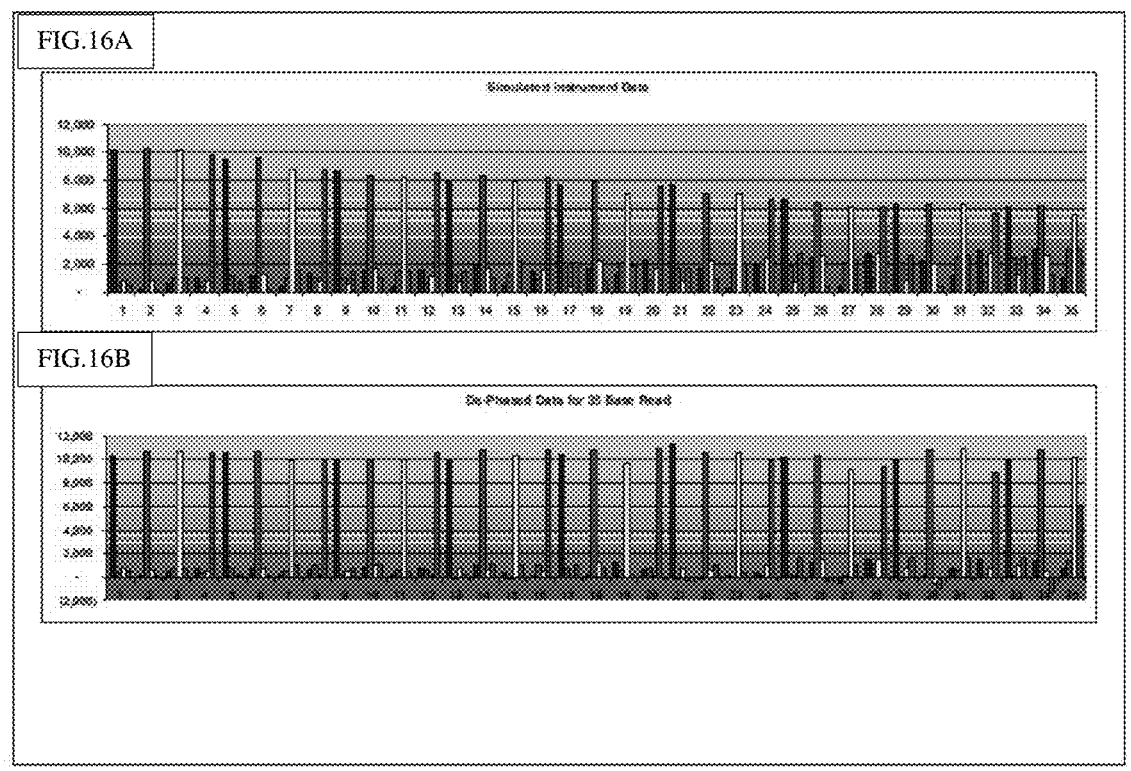
FIG. 16A shows simulated base read data with 10% noise added and lead and lag factors of 1% each.
FIG. 16B shows reconstructed data with the lead and the lag removed.
Figures 17A, 17B, 17C:
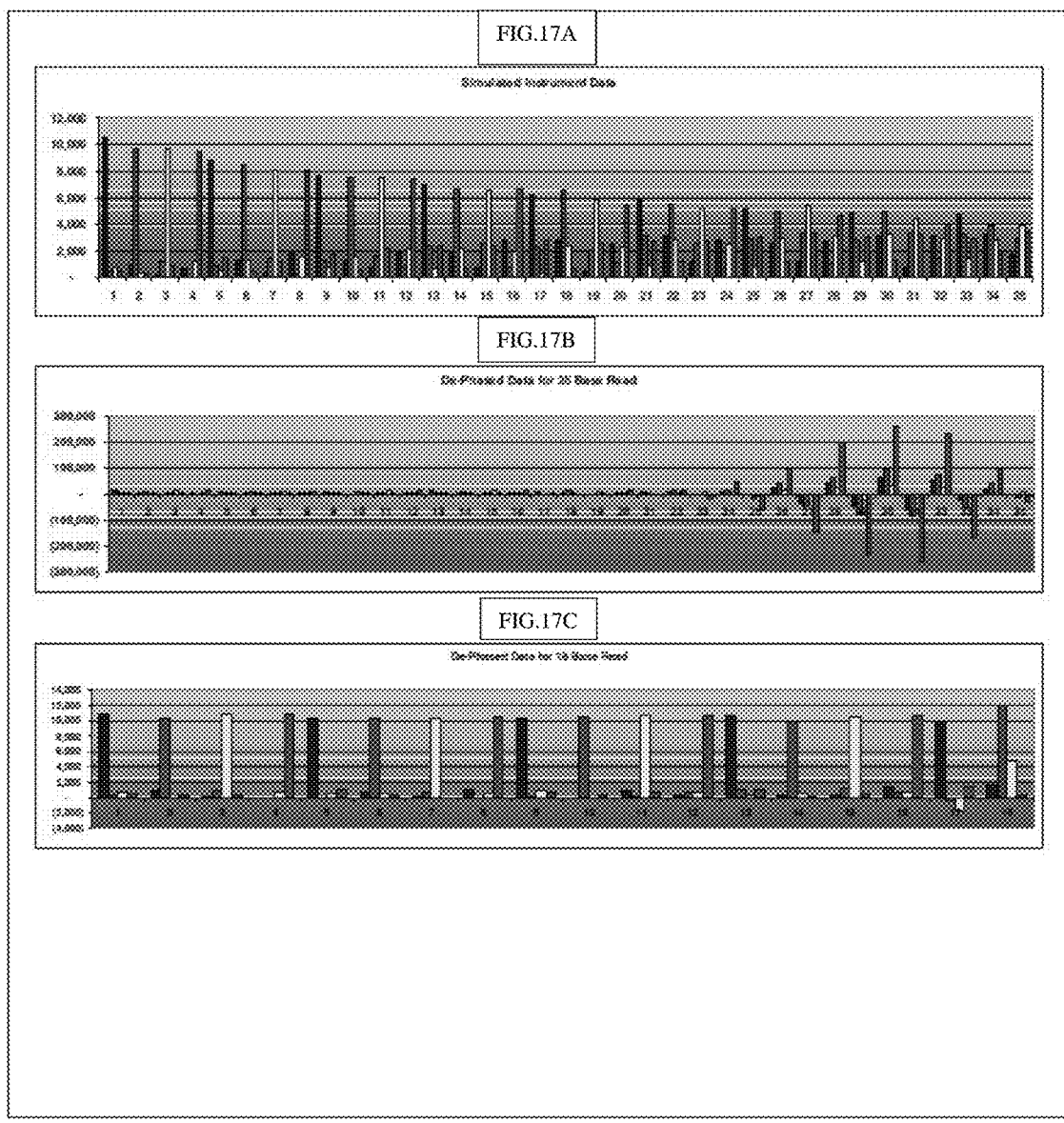
FIG. 17A shows simulated base read data with 10% noise added and lead and lag factors of 1.75% each.
FIG. 17B shows that attempted reconstruction is poor as the lead/lag matrix is ill-conditioned.
FIG. 17C shows reconstructed data with the lead and lag removed for only the first 18 bases. The 18-base lead/lag matrix is relatively well behaved and a more precise reconstruction may be performed.
Figure 18:
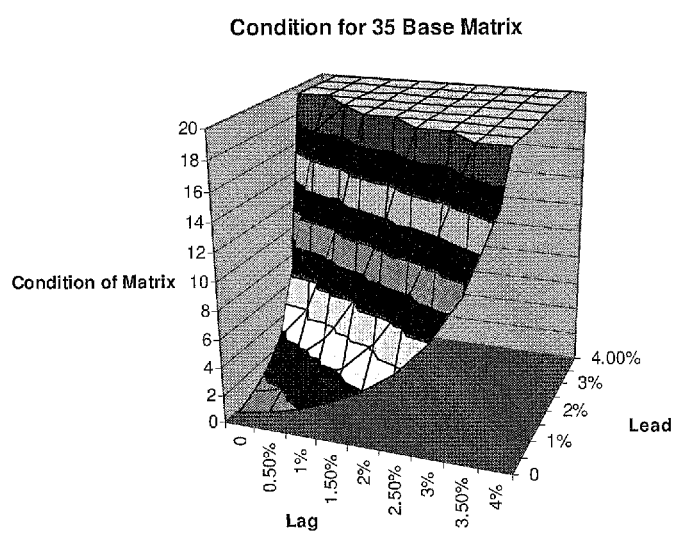
FIG. 18 shows lead/lag matrix conditions for various lead and lag parameters for a 35 base read. In one embodiment, a condition number below 20 produces accurate reconstruction.

FIG. 16A shows a simulated 35 base read data with 10% noise added and lead and lag factors of 1% each. FIG. 16B shows an accurate lead/lag compensation reconstruction using the inverse lead/lag matrix, $K^{-1}_{Lead/Lag}$. The condition number for this lead/lag matrix is 5. FIG. 17A shows the same exemplary 35 base sequence with 10% noise and a lead and lag factor of 1.75% each and FIG. 17B shows the reconstruction. Here, the condition number is 550 and reconstruction is poor. In order to have a fairly precise reconstruction of the data, lead/lag matrices desirably have a condition below about 20. FIG. 18 plots the matrix condition numbers below 20 for 35 base lead/lag matrices with various values of lead and lag. Because the lead/lag matrix is calculated independent of the DNA sequence in a template for the case where nucleotides all have equal lead ratios and equal lag ratios, we are able to determine our ability to accurately call bases without consideration of the A, C, T, and G content of the templates.

Even if a 35 base lead/lag matrix is ill-conditioned and produces poor reconstruction, smaller matrices from a portion of the same data may still be well behaved. For example, FIG. 17C shows the reconstruction of the first 18 bases for a lead and lag of 1.75% each (same conditions that produced the poor reconstruction for the 35 base read). Here the 18×18 lead/lag matrix has a condition number of 3.7. The matrix becomes ill-conditioning when cumulative contributions from the lead or lag or both generate signals that are on the order of the signal from the true base (where the position equals the cycle number).

Figure 19:
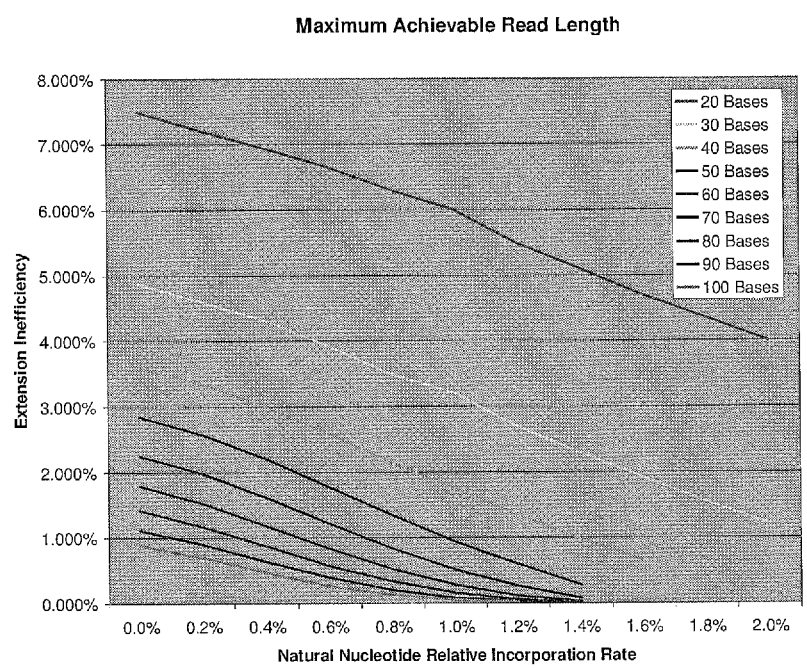
FIG. 19 shows exemplary read length for various values of lead and lag.

The above shows that changing the read length can provide an accurate reconstruction of earlier portions of the data. Thus, we can plot the lead and lag factors that will cause matrices of different sizes (read lengths) to have a condition number of 20 (the point where matrices become too ill-conditioned for precise reconstruction). For example, if a 23×23 matrix produces a condition number of 20, then we would restrict, the read length to a maximum of 23 as reconstruction using the 24th base (as well as any additional bases) would likely create a matrix that is too ill-conditioned to accurately reconstruct the data. FIG. 19 shows the read lengths for various lead and lag factors. This plot provides a method for predicting the read length obtainable from a sequencing system based on two factors: the purity of the nucleotides (major contributor to the lead) and the polymerase incorporation efficiency (major contributor to the lag). This result also shows that if both the lead and lag factors are below about 0.5%, this results in reconstruction of a 100-base read.

F. Field Fattening

In one embodiment, when a chip of uniform dye concentration is imaged, it may be desirable that all of the pixels in the resultant image have nearly the same intensity, with variations reflecting only the relatively small distribution inherent in the camera's optical system. In practice, however, the inventors have found that variations in illumination and filter response produce a significant spatially correlated pattern in an image. The inventors have also found that the pattern is highly reproducible and has a linear response to changes in dye concentration and camera exposure. These conditions lead to the following algorithm for removing this spatial correlation between pixel intensity and location of the pixel on the solid substrate.

First, for each machine and each filter, we image the pattern of a spatially uniform fluorescence on a dyed microscope slide. Second, the image is smoothed using a low-pass filter. In the resultant smoothed image, M, we choose an origin point, $M_{x0,y0}$. The choice of the point is fairly arbitrary but it is selected from a region in which the smoothed images of all of the filters have low intensity gradients to minimize the impact of changes in the system. Third, the intensity of each pixel at a point in a raw image ($R_{x,y}$) is replaced by its field-flattening value, $F_{x,y}$, where $F_{x,y} = R_{x,y} M_{x0,y0}/M_{x,y}$, and $M_{x,y}$ is the value of the model image at the same spatial location as the raw image pixel. The resultant "Field Flattened" image, F, has intensities that are now solely dependent on the camera exposure and dye concentration, and do not have any correlation with the spatial location of the pixel in the image.

The invention's algorithms and equations for field flattening are distinguished from those described by, for example Eltoukhy et al. (2006), since the algorithms of Eltoukhy et al. relate to signal noise that is uncollrelated to system parameters (e.g., uneven light source). In contrast, the signal noise that is corrected by the invention's methods is correlated to the signal's position across the solid substrate. In one embodiment, each pixel is corrected (i.e., field flattened) based on a previously calibrated baseline intensity at that pixel position and a scaling factor based on for example a longer exposure time.

G. Spot Location in the Array

In one embodiment, the present invention contemplates a processing step (preferably in a series of processing steps as discussed above) for locating the spots in the array. In one embodiment, the spot locating image processing algorithm uses the fact that the spots on the chip are in a regular hexagonal pattern along vertical columns and diagonal rows. To find the columns of spots, image pixel values are summed along the vertical direction. This results in a one-dimensional set of data that resembles a sinusoidal pattern. The peaks of the pattern are measured and used to determine the period and phase of the pattern. There are then used to guide a search to determine a set of equations for vertical lines that approximately bisect each of the spots in a column. The result is a set of equations for parallel lines (slope, intercept, and spacing) at regular spacing. A number of these lines are then probed to establish a second sinusoidal-like pattern of intensities along the lines. These are then used to determine the period, angle and phase of the diagonal lines that bisect each of the spots. These second set of lines are at a 60 degree angle from the vertical lines. The intersection of the diagonal set of lines and the vertical set of lines give an estimate for the subpixel locations of each of the spot centers.

H. Image Sharpening

In one embodiment, the present invention contemplates a processing step (preferably in a series of processing steps as discussed above) to sharpen the image of the spots on the array. This is particularly useful if chips are constructed with tightly packed spots. In such a case, it might be beneficial to run the images through a sharpening filter in order to reduce the amount of blur or spread for each of the spots. This will reduce the amount of light energy blooming into adjacent spots. Similarly, if the optics for the system cannot sufficiently resolve spots on the chip, then the application of a sharpening filter may also help to precisely analyze the images. A number of sharpening algorithms may be used to narrow the spread of the spots. One embodiment uses a Wiener filter (as described, for example, in The Image Processing Handbook, by John C. Russ, Published by CRC Press, 2006, ISBN 0849372542, 9780849372544, 817 pages) to make the diameter of the spots smaller and remove light energy from adjacent spots.

I. Spot Brightness Determination

In one embodiment, the present invention contemplates a processing step (preferably in a series of processing steps as discussed above) to determine spot brightness. In one embodiment, the pixels that surround each of the subpixel locations of the spots are summed to determine an estimate for the spot brightness. The local set of pixels that is selected depends on both the diameter of the spots and the location within the pixel of the subpixel center location. For example, if the subpixel location is close to the top of the pixel that contains the center, then more pixels above the pixel that contains the center are counted than pixels below the pixel containing the center.

In one embodiment, the above method for making spot brightness measurements is repeated independently for each of the four different color channels (four separate images) and the sharpening and neighbor influence (see below) correction calculations are applied, then the color crosstalk correction is applied (see below). In one embodiment, the result of the color crosstalk calculation produces a list of four values (one for each dye color) for each spot in the images that may be used to call the base for that sequencing cycle.

J. Neighbor Influence Elimination

In addition to each of the spots expanding beyond its physical bounds, the light from one spot (bead) may illuminate an adjacent spot and make it appear to have more of the color of its neighbors. This might happen because light being emitted from one bead make impinge on an adjacent bead, be reflected within the bead and then reemitted from that bead. This neighbor influence may be eliminated by, in one embodiment, constructing an influence or "spreading" matrix, then applying the inverse of this matrix to the data. To formulate the solution to the neighbor influence problem from spot data that is in hexagonal form, it is convenient to first put the data into a rectilinear array. This is done by shifting the even vertical columns up by ½ of a pixel as shown below. Thus, a two-dimensional rectilinear matrix, whose elements represent the magnitude of each spot in the original image of the hexagonal array of spots, may be used. To further facilitate matrix manipulations, the rectilinear spot matrix may be made into a spot vector by stacking the columns from the two-dimensional matrix under one another to form a one dimensional array or vector. In other words, the second column is appended to the bottom of the first, the third to the bottom of the second, etc., thereby generating $1 \times N^2$ vector formed from an N×N spot matrix.

In one embodiment a "spreading matrix" is next formed that represents the magnitude of the influence from a spot to neighboring spots. In a general formulation, a central spot may be thought of as influencing the nearest six neighbors surrounding the central spot by a fraction, A, of the central spot brightness, the next nearest neighbors by a smaller fraction, B, etc. If the central spot is very bright, then its neighbors may appear to be emitting their own light of the same color as the central spot, even if they actually generate none of their own light in that color. The spreading matrix is formulated such that if it is applied to an ideal image of single element spots (each spot is an idealized point and does not extend beyond one element of the matrix), then the resultant matrix will have spots that have been spread across several elements due to the neighbor influence phenomenon. Thus, the spreading matrix is a model for the influence of any spot in the image to any other spot in the image.

For hexagonal arrayed spots that have been make into a one-dimensional vector with dimensions $N^2 \times 1$ (in other words, a concatenation of all the columns of the matrix), the spreading matrix, S, may be formulated as a $N^2 \times N^2$ matrix. An example 25×25 spreading matrix corresponding to a 5×5 spot image that has the three levels of neighbor influence (A for the closest 6 neighbors, B for the next closest 6 and C for the third closest 6) is shown below.

The method described above for removing the neighbor influence can generate sizable spreading matrices on the order of $N^4$ and therefore may be computationally intensive for typical images. Since the influence of spots that are relatively far from the spot of interest have relatively negligible influence, it is possible to reduce the size of the spreading matrices used for the calculation and perform the calculation on smaller subsections of the image at a time. This ears significantly reduce the computational complexity and computer memory requirements for the calculation. It should be understood that the methods set forth above may be generalized in algorithms that are more efficient or operate on smaller portions of the image.

K. Spectral Crosstalk Calibration

In one embodiment, it may be desirable to correct the data to account for color crosstalk. This may be done using methods known in the art (e.g., U.S. Pat. No. 7,209,836 incorporated by reference) as well as methods disclosed herein (See Example 10, FIG. 32A-B). For example, a four-color fluorescent detection system (for detection of the exemplary colors blue, green, yellow and red) has one detector channel for each of the four different color dyes. However, because the dyes have fairly broad spectra, there is some detection of dyes in adjacent color channels. For example, when exciting only a green dye, a signal is visible in the yellow channel as well as the green channel. If this spectral crosstalk is calibrated, it may be removed from subsequent measurements even if the dyes are mixed in unknown quantities. To determine actual fluorescent intensities for the four colors, A, B, C and D from measured detector outputs, $M_A$, $M_B$, $M_C$, $M_D$ in corresponding chan-

| 1 | A | C | 0 | 0 | A | A | B | 0 | 0 | B | C | 0 | 0 | 0 | 0 | 0 | 0 | 0 | 0 | 0 | 0 | 0 | 0 | 0 |
| A | 1 | A | C | 0 | B | A | A | B | 0 | C | B | C | 0 | 0 | 0 | 0 | 0 | 0 | 0 | 0 | 0 | 0 | 0 | 0 |
| C | A | 1 | A | C | 0 | B | A | A | B | 0 | B | C | B | C | 0 | 0 | 0 | 0 | 0 | 0 | 0 | 0 | 0 | 0 |
| 0 | C | A | 1 | A | 0 | 0 | B | A | A | 0 | 0 | C | B | C | 0 | 0 | 0 | 0 | 0 | 0 | 0 | 0 | 0 | 0 |
| 0 | 0 | C | A | 1 | 0 | 0 | 0 | B | A | 0 | 0 | 0 | C | B | 0 | 0 | 0 | 0 | 0 | 0 | 0 | 0 | 0 | 0 |
| A | B | 0 | 0 | 0 | 1 | A | C | 0 | 0 | A | B | 0 | 0 | 0 | B | C | 0 | 0 | 0 | 0 | 0 | 0 | 0 | 0 |
| A | A | B | 0 | 0 | A | 1 | A | C | 0 | A | A | B | 0 | 0 | C | B | C | 0 | 0 | 0 | 0 | 0 | 0 | 0 |
| B | A | A | B | 0 | C | A | 1 | A | C | B | A | A | B | 0 | 0 | C | B | C | 0 | 0 | 0 | 0 | 0 | 0 |
| 0 | B | A | A | B | 0 | C | A | 1 | A | 0 | B | A | A | B | 0 | 0 | C | B | C | 0 | 0 | 0 | 0 | 0 |
| 0 | 0 | B | A | A | 0 | 0 | C | A | 1 | 0 | 0 | B | A | A | 0 | 0 | 0 | C | B | 0 | 0 | 0 | 0 | 0 |
| B | C | 0 | 0 | 0 | A | A | B | 0 | 0 | 1 | A | C | 0 | 0 | A | A | B | 0 | 0 | B | C | 0 | 0 | 0 |
| C | B | C | 0 | 0 | B | A | A | B | 0 | A | 1 | A | C | 0 | B | A | A | B | 0 | C | B | C | 0 | 0 |
| 0 | C | B | C | 0 | 0 | B | A | A | B | C | A | 1 | A | C | 0 | B | A | A | B | 0 | C | B | C | 0 |
| 0 | 0 | C | B | C | 0 | 0 | B | A | A | 0 | C | A | 1 | A | 0 | 0 | B | A | A | 0 | 0 | C | B | C |
| 0 | 0 | 0 | C | B | 0 | 0 | 0 | B | A | 0 | 0 | C | A | 1 | 0 | 0 | 0 | B | A | 0 | 0 | 0 | C | B |
| 0 | 0 | 0 | 0 | 0 | B | C | 0 | 0 | 0 | A | B | 0 | 0 | 0 | 1 | A | C | 0 | 0 | A | B | 0 | 0 | 0 |
| 0 | 0 | 0 | 0 | 0 | C | B | C | 0 | 0 | A | A | B | 0 | 0 | A | 1 | A | C | 0 | A | A | B | 0 | 0 |
| 0 | 0 | 0 | 0 | 0 | 0 | C | B | C | 0 | B | A | A | B | 0 | C | A | 1 | A | C | B | A | A | B | 0 |
| 0 | 0 | 0 | 0 | 0 | 0 | 0 | C | B | C | 0 | B | A | A | B | 0 | C | A | 1 | A | 0 | B | A | A | B |
| 0 | 0 | 0 | 0 | 0 | 0 | 0 | 0 | C | B | 0 | 0 | B | A | A | 0 | 0 | C | A | 1 | 0 | 0 | B | A | A |
| 0 | 0 | 0 | 0 | 0 | 0 | 0 | 0 | 0 | 0 | B | C | 0 | 0 | 0 | A | A | B | 0 | 0 | 1 | A | C | 0 | 0 |
| 0 | 0 | 0 | 0 | 0 | 0 | 0 | 0 | 0 | 0 | C | B | C | 0 | 0 | B | A | A | B | 0 | A | 1 | A | C | 0 |
| 0 | 0 | 0 | 0 | 0 | 0 | 0 | 0 | 0 | 0 | 0 | C | B | C | 0 | 0 | B | A | A | B | C | A | 1 | A | C |
| 0 | 0 | 0 | 0 | 0 | 0 | 0 | 0 | 0 | 0 | 0 | 0 | C | B | C | 0 | 0 | B | A | A | 0 | C | A | 1 | A |
| 0 | 0 | 0 | 0 | 0 | 0 | 0 | 0 | 0 | 0 | 0 | 0 | 0 | C | B | 0 | 0 | 0 | B | A | 0 | 0 | C | A | 1 |

If the spreading matrix, S, is inverted, $S^{-1}$, it may be used to eliminate the neighbor influence modeled by the spreading matrix. If we multiply the measured spot matrix (in the form of a vector), $v_{spot}$, by the in verse of the spreading matrix, $S^{-1}$, we can generate an estimate for the spot matrix with the neighbor influence removed, $v_{uninfluenced}$ $$v_{uninfluenced} = S^{-1} v_{spot}$$

nels, one needs to know all of the spectral crosstalk factors: $R_{AB}$, $R_{BA}$, $R_{BC}$, $R_{CB}$, $R_{CD}$, and $R_{DC}$. For example, $R_{AB}$ is the ratio between the portion of the signal in the A channel coming from the B dye and the actual intensity of the B dye. If for instance $R_{AB}$ is 20%, then the A channel will have an additional signal equal to 0.2 times the actual B dye intensity in the B channel. Thus for channel B, the observed measurement, $M_B$, is the direct measurement of B and the two contributions from The adjacent channels (if any): $M_B = B + R_{BA}A + R_{BC}C$ (6). For the four channels, this may be written in matrix form:

$$\begin{bmatrix} M_A \\ M_B \\ M_C \\ M_D \end{bmatrix} = K \begin{bmatrix} A \\ B \\ C \\ D \end{bmatrix} \quad (7)$$

where $$K = \begin{bmatrix} 1 & R_{AB} & 0 & 0 \\ R_{BA} & 1 & R_{BC} & 0 \\ 0 & R_{CB} & 1 & R_{CD} \\ 0 & 0 & R_{DC} & 1 \end{bmatrix}.$$

Each of the six spectral crosstalk factors may be determined through an experiment with pure dyes. We want to solve for the actual fluorescent signals, A, B, C and D given the detector measurements, $M_A$, $M_B$, $M_C$, $M_D$. Thus, we want to solve the above matrix Equation (7). This is equation (8):

$$\begin{bmatrix} A \\ B \\ C \\ D \end{bmatrix} = K^{-1} \begin{bmatrix} M_A \\ M_B \\ M_C \\ M_D \end{bmatrix}$$

where $K^{-1}$ is the inverse of matrix K. Although the inverse of matrix K may be written out in terms of the six spectral crosstalk factors, it is somewhat complex and is best performed by plugging in the numbers and letting the computer take the inverse. The results are discussed in Example 10 which demonstrate that a base in the sequence would have been miscalled were the spectral crosstalk calibration not performed.

Any multicolor sequencing by synthesis device may be calibrated using the above equations and the resultant spectral crosstalk matrix may be used in all four color measurements from the device. In one embodiment, if we also include information on the relative magnitude of each of the four colors, then we can also correct for differences in perceived dye brightness from one channel to the next. Multiplying the matrix K by a diagonal matrix, whose diagonal terms are the relative brightness for each dye, produces a new matrix K whose inverse will automatically scale the dyes to be consistent with one another.

K. Base Calls

As discussed above, at each sequencing by synthesis cycle, the signals that are observed in the four color channels are used to both determine the most likely base at that cycle (base call) and to determine a quality score for the base call. Because of a number of factors, it may not always be the case that the brightest color in the raw data indicates the most likely base. Thus, it may be desirable to correct for at least one, and more particularly all, of the following phenomena that were discussed supra: field flattening, spectral crosstalk, sequence lead and sequence lag. After the correction factors (field flattening, spectral crosstalk and/or lead-lag compensation) have been applied, a base is called based on the maximum signal between the four channels. The output of the base calls may be a file similar to a FASTA format. In one embodiment, this file is also accompanied by a quality score file.

To optimize the alignment and assembly of the data into contigs, it is desirable to have a precise quality score associated with each base call. A quality file may be generated that encodes quality scores for each cycle. Preserving the information for all four bases is also desirable to allow the sequence alignment software to examine several likely calls instead of only the one with the highest signal.

M. Software Appendices A-C

The below software Appendices A, B and C (copyright Intelligent Bio-Systems, Inc., 34 Bear Hill Road, Waltham, Mass. 02451) provide source code for implementing the present invention. Appendix A is a source code for collecting a raw image using a flat map calibration image, as exemplified by the code under FlattenImageInArray and AdjustRawValue. Appendix B is a source code for applying the inverse cross-talk array to four filter images. In particular, the FindBeadIntensities method calls ProcessOneBead to apply the spectral crosstalk correction matrix. Appendix C is a source code for creating a flat map calibration image. In one embodiment, this is a process that uses a combination of automated and manual steps. The automated steps are exemplified by the emoveSpikesWithSlope and LocalSmoothing methods. The manual steps are exemplified by ImageJ to replace spikes in the calibration image with smoothed data. The manual and automated steps may be carried out in any order. In a particular embodiment, the manual steps are carried out before the automated steps.

a.     Appendix A

```csharp
using System;
using System.Collections.Generic;
using System.ComponentModel;
using System.Data;
using System.Drawing;
using System.Text;
using System.Windows.Forms;
using System.IO;

namespace IBS
{
    /// <summary>
    /// Remove spatially correlated intensity variations in an image that occur due to
    /// differences in how the imaging light hits a slide and how the fluorescing light
    /// is passed through the filters to the camera (and any other related issues like
    /// lens issues).
    /// </summary>
    public class FlattenImage
    {
```

```
// constructor for static members of class
public FlattenImage()
{
    if (!m_isInitialized)
    {
        m_isInitialized = LoadParameters(); // get parameters from .ini file
    }

}

/// <summary>
/// Load image flattening parameters for all filters
/// </summary>
/// <returns>true on success</returns>
static bool LoadParameters()
{
    // initialize all static arrays
    if (m_calibrationImage == null)
    {
        m_calibrationImage = new ImageData[Camera.FilterCnt];
        m_backgroundConstant = new ushort[Camera.FilterCnt];
        m_primaryRow = new int[Camera.FilterCnt];
        m_primaryCol = new int[Camera.FilterCnt];
        m_topDeadZone = new int[Camera.FilterCnt];

for (int filter = 0; filter < Camera.FilterCnt; ++filter)
        {
            m_calibrationImage[filter] = null;
        }
    } for (int filter = 0; filter < Camera.FilterCnt; ++filter)
    {
        if (LoadSingleFilterParameters(filter) == false)
            return false;

if (filter > 0 &&
            (m_calibrationImage[filter].RowCount !=
    m_calibrationImage[filter - 1].RowCount ||
                m_calibrationImage[filter].ColCount !=
    m_calibrationImage[filter - 1].ColCount))
            Log.IBSEvent("Warning: Image Flattening calibration image for " +
                ((Til.Data.FilterIndex)filter).ToString() + " filter has different size than another filter");
    } return true;

}
/// <summary>
/// Get parameters for flatenning an image from .ini file.
/// </summary>
/// <param name="filter"></param>
/// <returns>true if parameters all loaded, else false</returns>
```

```
static bool LoadSingleFilterParameters(int filter)
{
    // get calibrationParameterFilePath from .ini file
    string calibrationParameterFilePath;
    calibrationParameterFilePath =
Program.resourceIni.ReadStringValue("IMAGE_PROCESSING",
"Flatten_Image_Parameter_File_" + TileData.FilterName[filter]);
    if (calibrationParameterFilePath.Length < 1)
    {
        Log.IBSEvent("Resource.ini file is missing
Flatten_Image_Parameter_File entry in the IMAGE_PROCESSING section for the " +
TileData.FilterName[filter] + " filter");
        return false;
    }

// get cal parameters in file
    try
    {
        // Create an instance of StreamReader to read from a file.
        // The using statement also closes the StreamReader.
        using (StreamReader sr = new
StreamReader(calibrationParameterFilePath))
        {
            String calibrationImageFilepath;
            int rowCount, colCount;
            string line;

// parameters are in the form valueName=value so find '='
            // and grab value that follows
            line = sr.ReadLine();
            rowCount = int.Parse(line.Substring(line.IndexOf("=") +
1));
            line = sr.ReadLine();
            colCount = int.Parse(line.Substring(line.IndexOf("=") +
1));
            line = sr.ReadLine();
            m_backgroundConstant[filter] =
ushort.Parse(line.Substring(line.IndexOf("=") + 1));
            line = sr.ReadLine();
            m_primaryRow[filter] =
int.Parse(line.Substring(line.IndexOf("=") + 1));
            line = sr.ReadLine();
            m_primaryCol[filter] =
int.Parse(line.Substring(line.IndexOf("=") + 1));
            line = sr.ReadLine();
            m_topDeadZone[filter] =
int.Parse(line.Substring(line.IndexOf("=") + 1));

calibrationImageFilepath = sr.ReadLine();

// create calibration image array of sufficient size
            if (m_calibrationImage[filter] == null ||
                m_calibrationImage[filter].RowCount < rowCount ||
                m_calibrationImage[filter].ColCount < colCount
                )
                m_calibrationImage[filter] = new ImageData(rowCount,
colCount);
```

```csharp
            // load calibration array from file
            if
(m_calibrationImage[filter].LoadFromFile(calibrationImageFilepath) == false)
                return false;

} // end using (StreamReader)

}
    catch (Exception e)
    {
        // Let the user know what went wrong.
        Log.IBSEvent("Could not load flatten image parameter file (or
its embedded calibration image). Error=" + e.Message);
        return false;
    } return true;

}

/// <summary>
/// Read raw image from file, remove spatially-correlated intensities,
/// save flattened image in a file and an array
/// </summary>
/// <param name="filter">image was snapped using this filter</param>
/// <param name="imageFilepath">full path to raw image file</param>
/// <param name="adjustedFilenamePrefix">prefix to put onto flattened
image file</param>
/// <param name="flatImage">array in which to store flattened
image</param>
/// <returns>full path of flattened image file</returns>
public string FlattenImageInFile(int filter, string imageFilepath,
string adjustedFilenamePrefix, ImageData flatImage)
{
    ushort rawValue, flatValue;

// If necessary, load flattening parameters-this should have
happened in static constructor but
    // this way the user can catch errors in .ini file and fix them
without exiting rapid.exe
    if (!m_isInitialized)
    {
        if (!LoadParameters())
            return ""; // parameter load failed
    }

// make sure that receiving array can hold all of the image data
from the raw file
    flatImage.Resize(m_calibrationImage[filter].RowCount,
m_calibrationImage[filter].ColCount);

// create filename for adjusted image
    String adjustedImageFilepath;
    adjustedImageFilepath = imageFilepath.Substring(0,
imageFilepath.LastIndexOf("\\") + 1) +
        adjustedFilenamePrefix + "_" +
        imageFilepath.Substring(imageFilepath.LastIndexOf("\\") + 1);
```

```csharp
            // open raw image for reading from, and adjusted image for writing to
            FileStream rawImageFileStream = null, adjustedImageFileStream = null;
            BinaryReader rawImageReader;
            BinaryWriter adjustedImageWriter;

try
            {
                rawImageFileStream = File.OpenRead(imageFilepath);
                rawImageReader = new BinaryReader(rawImageFileStream);

adjustedImageFileStream = File.OpenWrite(adjustedImageFilepath);
                adjustedImageWriter = new BinaryWriter(adjustedImageFileStream);

// get each raw pixel and write out its adjusted value
                m_curFilter = filter;
                for (int row = 0; row < m_calibrationImage[filter].RowCount; ++row)
                {
                    for (int col = 0; col < m_calibrationImage[filter].ColCount; ++col)
                    {
                        rawValue = rawImageReader.ReadUInt16();
                        flatValue = AdjustRawValue(row, col, rawValue);
                        adjustedImageWriter.Write(flatValue);
                        flatImage.Pixel[row, col] = flatValue;
                    }
                }

}
            catch (Exception e)
            {
                Log.IBSEvent("Could not flatten image in file=" + imageFilepath + " error=" + e.Message);
            }
            finally
            {
                if (rawImageFileStream != null)
                    rawImageFileStream.Close();

if (adjustedImageFileStream != null)
                    adjustedImageFileStream.Close();
            } return adjustedImageFilepath;
        }

/// <summary>
        /// remove spatially-correlated intensities in 'image'
        /// </summary>
        /// <param name="filter">camera used this filer to capture the raw image</param>
        /// <param name="image">2-D array that is to be flattened in-place</param>
        /// <returns>true on sucess, otherwise false</returns>
```

```
public bool FlattenImageInArray(int filter, ImageData image)
{
    if (image == null)
        return true; // there is nothing to flatten // If necessary, load flattening parameters
    if (!m_isInitialized)
    {
        if (!LoadParameters())
            return false; // parameter load failed
    } if (m_calibrationImage[filter].ColCount != image.ColCount ||
        m_calibrationImage[filter].RowCount != image.RowCount)
    {
        Log.IBSEvent("Cannot flatten image because raw image size does not match flattening calibration image");
        return false;
    }

// replace each raw pixel with its adjusted value
    m_curFilter = filter;
    m_peakValue =
m_calibrationImage[m_curFilter].Pixel[m_primaryRow[m_curFilter],
m_primaryCol[m_curFilter]];
    for (int row = 0; row < image.RowCount; ++row)
    {
        for (int col = 0; col < image.ColCount; ++col)
        {
            image.Pixel[row, col] = AdjustRawValue(row, col,
image.Pixel[row, col]);
        }
    } return true;

}

/// <summary>
/// Final value = (raw pixel - background) * FlatMapPeakValue /
FlatMapValueAtRawPixel'sLocation.
/// We include checks to make sure we never go below 0 or exceed
maximum value for pixel's
/// type.
/// </summary>
/// <param name="row"></param>
/// <param name="col"></param>
/// <param name="rawValueUShort"></param>
/// <returns></returns>
private ushort AdjustRawValue(int row, int col, ushort rawValueUShort)
{
    double adjustedVal;
    double calRatio;

if (rawValueUShort < m_backgroundConstant[m_curFilter])
        rawValueUShort = 0;
    else
```

```
                rawValueUShort -= m_backgroundConstant[m_curFilter];

calRatio = (double)rawValueUShort /
(double)m_calibrationImage[m_curFilter].Pixel[row, col];

adjustedVal = calRatio * m_peakValue;

if (adjustedVal > ushort.MaxValue)
                return ushort.MaxValue;
            else
                return (ushort)adjustedVal;
        }

// member variables are all static because they are loaded only once.  However, the class
        // is not static because we don't want the .Net framework to load this class if the user
        // does not require it.  All arrays are indexed by a camera filter index (blue, green, yellow, red)

static ImageData[] m_calibrationImage; // smooth calibration images for spatial equalization
        static ushort[] m_backgroundConstant; // camera's pixel value when shutter is closed
        static int[] m_primaryRow, m_primaryCol; // pixel in calibration image that we will use for mapping raw images to (for flattening intensity across the image)
        static int[] m_topDeadZone; // this many rows at the top of the image cannot be calibrated
        static bool m_isInitialized = false; // set to true after first call of constructor initializes all of the static parameters int m_curFilter; // minor hack to avoid passing this parameter around so much
        double m_peakValue; // value in the calibration image that we have chosen to scale all other values by (= m_calibrationImage[m_primaryRow, m_primaryCol])

}
} b.      Appendix B
using System;
using System.Collections;
using System.Text;
using System.IO;
using System.Collections.Generic;
using System.Diagnostics; // just for Stopwatch namespace IBS
{
    /// <summary>
    /// Used to find all of the spots in an image
    /// </summary>
    public class SpotFinder
    {
```

```
            }
        {
            // print average of either side of spike
            uint avg;
            avg  = (uint)m_grid[gridRow, gridCol - 1];
            avg += (uint)m_grid[gridRow, gridCol + 1];
            avg /= 2;
            //m_paramStream.Write("*" + avg.ToString() + " ");
            m_paramStream.Write(avg.ToString() + " ");
        }
        else
            m_paramStream.Write(m_grid[gridRow, gridCol].ToString() + " ");
    }
    m_paramStream.Write(m_grid[gridRow, m_gridColMax - 1].ToString() + " ");
    m_paramStream.WriteLine();
    } m_paramStream.WriteLine();
}

**** end of old code ************************/
```

```
        const string m_macroDataFilePath = "c:\\LineDisplayData.txt"; // pv todo - just use if some debug flag is set in .ini file
        const int m_defaultLineRoiSize = 60; // if no regions are defined, use this as roiLineWidth and height of line search roi ////////////////////////////////////////////////////////////////////////////////////////////////////////
        // Internal Classes  (basically just useful data structures and sorting interface classes) //////////////////////////////////////////////////
        ////////////////////////////////////////////////////////////// public class LineData
        {
            public double m_slope;
            public double m_intercept;
        //  public double m_sigma; // measurement of noise in slope & intercept
        //  public bool m_bVerticalFit;  // If true, we fit a vertical line (X = mY + b). If false, we fit usual y = mx + b

};

public class BeadCenterData: IComparer<BeadCenterData>
        {
            public double m_y;
            public double m_xc;
            public double m_interceptEstimate; // axis intercept assuming a known slope thru (m_y,m_xc)
            public int m_lineNumber; // for grouping points into a line
        //  public double m_intensity; // estimated intensity at bead center at (m_xc, m_y)

// default sorting method is by row (y)
            public int Compare (BeadCenterData x, BeadCenterData y)
            {
                // To be really safe we should first check for x or y == null but that
                // should never happen so to save time, I'm skipping that check.
                if (x.m_y < y.m_y)
                    return -1;
                else if (x.m_y > y.m_y)
                    return 1;
                else
                    return 0;
            }

};

/// <summary>
        /// useful for sorting intercept while still keeping track of which line the intercept is associated with
        /// </summary>
        public class LineDataExt
        {
```

```
        public LineDataExt(int lineNumber, double lineIntercept, int
lineSize, int lineFirstPoint)
        {
            this.lineNum = lineNumber;
            this.intercept = lineIntercept;
            this.size = lineSize;
            this.firstPoint = lineFirstPoint;
            this.mergedLineNum = null;
        } public int lineNum; // line number
        public double intercept; // line intercept
        public int size; // # of data points in the line (note that the
points are usually, but not always, on contiguous rows)
        public int firstPoint; // index into m_vertPoint of first point of
the line. WARNING: This is only valid if m_vertPoints hasn't been sorted since
this assignment.
        public List<int> mergedLineNum; // list of line numbers that have
been merged with this line due to common intercept

}

/////////////////////////////////////////////////////////////////////////////////
///////////////////////////
        // member variables
/////////////////////////////////////////////////////////////////////////////////
////
        ///////////////////////////////////////////////

// Every intersection of a vertical line and a diagonal line defines
the center of a bead in the image
        public double m_vertLinePeriod; // all beads are on a nearly vertical
line characterized by these three parameters
        public double m_vertLineSlope;
        public double m_vertLineIntercept;

//public double m_vertBeadPeriod; // Avg # of pixels between bead
centers on a vertical line = sqrt(dx*dx + dy*dy).
        // Note: due to image rotation, this may be slightly different than the
of rows between bead centers public double m_diagLinePeriod; // all beads are also on a diagonal
line characterized by these three parameters
        public double m_diagLineSlope;
        public double m_diagLineIntercept;

// Private members
        int m_iSmoothWindow; // average this # of pixels before looking for a
bead peak (actually +/-m_iSmoothWindow/2 so total # of pixels =
m_iSmoothWindow+1)
        int m_iSpotWidth; // a priori estimate of roiLineWidth (in pixels) of a
bead in the image
        int m_iSpotHeight; // a priori estimate of height (in pixels) of a bead
in the image
        double m_dPredictedPeriod; // expected # of pixels between each bead
center
```

```
        List<BeadCenterData> m_vertPoints;   // points that go through
approximately vertical lines(depending on image rotation)
        List<BeadCenterData> m_diagPoints;   // points that go through diagonal
lines(due to the honeycomb structure of the plate that the beads are sitting
on)

List<LineData> m_vertLines;   // best fit vertical lines through bead
centers
        List<LineData> m_diagLines;   // best fit diagonal lines through bead
centers double[,] m_crosstalk;
        RegionData[] m_regionData;
        RegionData m_region; // current entry in m_regionData
        int m_definedRegionCount; // # of regions defined in .ini file (if zero
then automatically define single region for the entire image)

bool m_IsFirstRegion; // true if this is first region of the first tile
of the snap image command (i.e. if true, we do not have any estimate of the
slope or period in the images. if false, we can use previous tile's data to
guide us)

//////////////////////////////////////////////////////////////////////////////
///////////////////////////
        // Public  Constructor & Methods
//////////////////////////////////////////////////////////////////////////////
//////
        ////////////////////////////////////////////////////// public SpotFinder()
        {
            // load cross talk parameters from .ini file. pv todo - make this
static and reload once at start of a protocol
            m_crosstalk = new double[Camera.FilterCnt, Camera.FilterCnt];

m_crosstalk[(int)TileData.FilterIndex.red,
(int)TileData.FilterIndex.red] =
Program.resourceIni.ReadDoubleValue("IMAGE_PROCESSING", "Crosstalk_Red_to_Red",
1.0);
            m_crosstalk[(int)TileData.FilterIndex.red,
(int)TileData.FilterIndex.yellow] =
Program.resourceIni.ReadDoubleValue("IMAGE_PROCESSING",
"Crosstalk_Red_to_Yellow", 0.0);
            m_crosstalk[(int)TileData.FilterIndex.red,
(int)TileData.FilterIndex.green] =
Program.resourceIni.ReadDoubleValue("IMAGE_PROCESSING",
"Crosstalk_Red_to_Green", 0.0);
            m_crosstalk[(int)TileData.FilterIndex.red,
(int)TileData.FilterIndex.blue] =
Program.resourceIni.ReadDoubleValue("IMAGE_PROCESSING",
"Crosstalk_Red_to_Blue", 0.0);

m_crosstalk[(int)TileData.FilterIndex.yellow,
(int)TileData.FilterIndex.red] =
Program.resourceIni.ReadDoubleValue("IMAGE_PROCESSING",
"Crosstalk_Yellow_to_Red", 0.0);
```

```
        m_crosstalk[(int)TileData.FilterIndex.yellow,
(int)TileData.FilterIndex.yellow] =
Program.resourceIni.ReadDoubleValue("IMAGE_PROCESSING",
"Crosstalk_Yellow_to_Yellow", 1.0);
        m_crosstalk[(int)TileData.FilterIndex.yellow,
(int)TileData.FilterIndex.green] =
Program.resourceIni.ReadDoubleValue("IMAGE_PROCESSING",
"Crosstalk_Yellow_to_Green", 0.0);
        m_crosstalk[(int)TileData.FilterIndex.yellow,
(int)TileData.FilterIndex.blue] =
Program.resourceIni.ReadDoubleValue("IMAGE_PROCESSING",
"Crosstalk_Yellow_to_Blue", 0.0);

m_crosstalk[(int)TileData.FilterIndex.green,
(int)TileData.FilterIndex.red] =
Program.resourceIni.ReadDoubleValue("IMAGE_PROCESSING",
"Crosstalk_Green_to_Red", 0.0);
        m_crosstalk[(int)TileData.FilterIndex.green,
(int)TileData.FilterIndex.yellow] =
Program.resourceIni.ReadDoubleValue("IMAGE_PROCESSING",
"Crosstalk_Green_to_Yellow", 0.0);
        m_crosstalk[(int)TileData.FilterIndex.green,
(int)TileData.FilterIndex.green] =
Program.resourceIni.ReadDoubleValue("IMAGE_PROCESSING",
"Crosstalk_Green_to_Green", 1.0);
        m_crosstalk[(int)TileData.FilterIndex.green,
(int)TileData.FilterIndex.blue] =
Program.resourceIni.ReadDoubleValue("IMAGE_PROCESSING",
"Crosstalk_Green_to_Blue", 0.0);

m_crosstalk[(int)TileData.FilterIndex.blue,
(int)TileData.FilterIndex.red] =
Program.resourceIni.ReadDoubleValue("IMAGE_PROCESSING",
"Crosstalk_Blue_to_Red", 0.0);
        m_crosstalk[(int)TileData.FilterIndex.blue,
(int)TileData.FilterIndex.yellow] =
Program.resourceIni.ReadDoubleValue("IMAGE_PROCESSING",
"Crosstalk_Blue_to_Yellow", 0.0);
        m_crosstalk[(int)TileData.FilterIndex.blue,
(int)TileData.FilterIndex.green] =
Program.resourceIni.ReadDoubleValue("IMAGE_PROCESSING",
"Crosstalk_Blue_to_Green", 0.0);
        m_crosstalk[(int)TileData.FilterIndex.blue,
(int)TileData.FilterIndex.blue] =
Program.resourceIni.ReadDoubleValue("IMAGE_PROCESSING",
"Crosstalk_Blue_to_Blue", 1.0);

// load geometric mask parameters from .ini file that are
independent of region
        m_iSpotWidth = Program.resourceIni.ReadIntValue("GEOMETRIC_MASK",
"spot_width", 3);
        m_iSpotHeight = Program.resourceIni.ReadIntValue("GEOMETRIC_MASK",
"spot_height", 3);
        m_iSmoothWindow =
Program.resourceIni.ReadIntValue("GEOMETRIC_MASK", "smooth_window", 12);
        m_dPredictedPeriod =
Program.resourceIni.ReadDoubleValue("GEOMETRIC_MASK", "expected_period",
3.62785);
```

```
            // load parameters that divide an image up into separate regions
            m_definedRegionCount =
Program.resourceIni.ReadIntValue("GEOMETRIC_MASK", "Region_Count", 0);
            m_regionData = new RegionData[Math.Max(1, m_definedRegionCount)];

// determine biggest line search roi in the regions
            int maxLineRoiWidth = -1; // # of pixels in area in which we will
be searching for horizontal and vertical lines
            int maxLineRoiHeight = -1;
            if (m_definedRegionCount < 1)
            {
                // If m_definedRegionCount == 0 then we will define region in
ImageProcessor::FindBeadLocationsAndIntensities()
                // but we can allocate line finding members here because we
know the default line finding size.
                maxLineRoiWidth = maxLineRoiHeight = m_defaultLineRoiSize;
            }
            else
            {
                for (int i = 1; i <= m_definedRegionCount; ++i)
                {
                    m_regionData[i - 1] = new RegionData();
                    m_regionData[i - 1].LoadParameters(i);
                    int width, height;
                    width = m_regionData[i - 1].m_xLineRoiStop - m_regionData[i
- 1].m_xLineRoiStart;
                    if (width > maxLineRoiWidth)
                        maxLineRoiWidth = width;

height = m_regionData[i - 1].m_yLineRoiStop -
m_regionData[i - 1].m_yLineRoiStart;
                    if (height > maxLineRoiHeight)
                        maxLineRoiHeight = height;

}
            }

// allocate space for line finding parameters
            // 3/2 is a fudge factor. roiWidth/spotWidth = points per row,
roiHeight = # of rows.
            int maxBeadCountEstimate = (3 * maxLineRoiWidth * maxLineRoiHeight)
/ (2 * m_iSpotWidth);
            m_vertPoints = new List<BeadCenterData>(maxBeadCountEstimate);
            m_diagPoints = new List<BeadCenterData>(maxBeadCountEstimate);
            m_vertLines = new List<LineData>(maxLineRoiWidth); // there can't
be more than 1 line per column ( roiWidth / spotWidth would be a more realistic
estimate)
            m_diagLines = new List<LineData>((int)(1.415 * maxLineRoiWidth));
// there will be about sqrt(2) more diagonal lines than there are vertical
lines m_IsFirstRegion = true;

}

/// <summary>
        /// Find basic parameters that define the location of all of the beads
in an image
```

```
        /// (or in a region of the image). Assumes that beads are in a repeating
        /// honeycomb pattern in which each bead has a neighbor directly above and below itself plus
        /// four neighbors at 60 degree angles off to the left and right side. The honeycomb pattern may be
        /// rotated slightly (typically not more than 3 degrees) in the image. It is also
        /// assumed that each bead has at least one pixel spacing between each neighbors.
        /// See 3/7/07 notes for more details about bead model.
        /// </summary>
        /// <param name="tile">Contains all the filter images of the tile we are finding beads in</param>
        /// <returns>true on success, otherwise false</returns>
        public bool FindBeadLocationsWithGeometricMask(TileData tile)
        {
            long[] timingMs = new long[20]; // just for debug timing
            string[] timingName = new string[20];
            int timingCnt = 0;

Stopwatch st = new Stopwatch();

st.Start();

// We use to add images together but now we just set ImageSum equal
            // to the brightest image (because each filter shifts the pixels
            // so we cannot add them)
            if (tile.SumImages(m_region.m_xLineRoiStart, m_region.m_xLineRoiStop,
                    m_region.m_yLineRoiStart, m_region.m_yLineRoiStop) == false)
                return false;

// Within the line-finding ROI, set very bright spots to 0.
            RemoveDustSpots(tile);

st.Stop();
            timingMs[timingCnt] = st.ElapsedMilliseconds;
            timingName[timingCnt++] = "Sum Images and remove dust spots ";
            st.Reset();
            st.Start();

// find center of beads along vertical lines and assign a line number to each bead
            if (FindVerticalLinePoints(tile.ImageSum, m_region.m_xLineRoiStart, m_region.m_xLineRoiStop,
                    m_region.m_yLineRoiStart, m_region.m_yLineRoiStop) == false)
                return false;

st.Stop();
            timingMs[timingCnt] = st.ElapsedMilliseconds;
            timingName[timingCnt++] = "FindVerticalLinePoints ";
            st.Reset();
            st.Start();

// find a common slope, period, and base x-intercept for vertical points
            if (GlobalFitLine(m_vertPoints, true) == false)
                return false;
```

```
            st.Stop();
            timingMs[timingCnt] = st.ElapsedMilliseconds;
            timingName[timingCnt++] = "GlobalFitLine ";
            st.Reset();
            st.Start();

//// average # of pixels between bead centers on a vertical line =
m_vertBeadPeriod
            //if (CalculateLinePeriod() == false)
            //    return false;

//st.Stop();
            //timingMs[timingCnt] = st.ElapsedMilliseconds;
            //timingName[timingCnt++] = "CalculateLinePeriod ";
            //st.Reset();
            //st.Start();

bool diagonalSwitch = false;
            if (diagonalSwitch) // old method that rotates image to find
diagonal lines
            {
                // fit diagonal lines to all beads - this will populate
m_diagonalPoints
                if (FindDiagonalLinePoints(tile.ImageSum,
m_region.m_xLineRoiStart, m_region.m_xLineRoiStop,
                    m_region.m_yLineRoiStart, m_region.m_yLineRoiStop) == false)
                    return false;

st.Stop();
                timingMs[timingCnt] = st.ElapsedMilliseconds;
                timingName[timingCnt++] = "FindDiagonalLinePoints ";
                st.Reset();
                st.Start();
            }
            else // new way
            {
                if (FindDiagonalPointsAlongVerticalLines(tile) == false)
                    return false;

st.Stop();
                timingMs[timingCnt] = st.ElapsedMilliseconds;
                timingName[timingCnt++] = "FindDiagonalPointsAlongVerticalLines
";
                st.Reset();
                st.Start();
            }

// find common parameters that define all diagonal lines
            //if (GlobalFitLineIntercept(m_diagPoints) == false)
            //    return false;
            if (GlobalFitLine(m_diagPoints, false) == false)
                return false;

st.Stop();
            timingMs[timingCnt] = st.ElapsedMilliseconds;
            timingName[timingCnt++] = "GlobalFitLineIntercept ";
            //st.Reset();
            //st.Start();
```

```csharp
            // just for debug, print sample line data (for ImageJ display) and timing data
            StreamWriter macroStream = null;
            StreamWriter timingFile = null;
            try
            {
                // save timings to a file
                timingFile = File.AppendText("C:\\pvTiming.txt");
                timingFile.WriteLine("");
                timingFile.WriteLine("");
                timingFile.WriteLine("New Run:  ");
                for (int i = 0; i < timingCnt; ++i)
                    timingFile.WriteLine("{0,5} ms   {1}", timingMs[i].ToString(), timingName[i]);

// save sample line data so we can display them in ImageJ using DrawLines plugin
                macroStream = File.CreateText(m_macroDataFilePath);

if (Program.resourceIni.ReadBoolValue("DEBUG_FLAGS", "show_vertical_lines", false))
                    foreach (LineData line in m_vertLines)
                        macroStream.WriteLine("{0} 0 {1} {2}",
                            line.m_intercept,
                            (line.m_slope * (tile.RowCount - 1)) + line.m_intercept,
                            tile.RowCount - 1);

if (Program.resourceIni.ReadBoolValue("DEBUG_FLAGS", "show_vertical_points", false))
                    foreach (BeadCenterData bead in m_vertPoints)
                    {
                        if (bead.m_lineNumber == int.MaxValue)
                        {
                            //  draw square to show this point was on a bad line
                            // macroStream.WriteLine(bead.m_xc + " " +
                            //   bead.m_y + " " + bead.m_lineNumber); // line number tells ImageJ macro to draw a square (see DrawLine.java plugin)
                        }
                        else
                        {   // draw circle at center of the bead
                            macroStream.WriteLine(bead.m_xc + " " + bead.m_y);
                        }
                    } if (Program.resourceIni.ReadBoolValue("DEBUG_FLAGS", "show_diagonal_lines", false))
                    foreach (LineData line in m_diagLines)
                        macroStream.WriteLine("0 {0} {1} {2}",
                            line.m_intercept,
                            tile.ColCount - 1,
                            (line.m_slope * (tile.ColCount - 1)) + line.m_intercept
```

```
                            };
            if (Program.resourceIni.ReadBoolValue("DEBUG_FLAGS",
"show_diagonal_points", false))
                foreach (BeadCenterData bead in m_diagPoints)
                {
                    if (bead.m_lineNumber == int.MaxValue)
                    {
                        // draw circle to show this was a rejected diagonal
point
                        // macroStream.WriteLine(bead.m_xc + " " +
                        //   bead.m_y); // + " " + bead.m_lineNumber); //
line number tells imageJ macro to draw a square (see DrawLine.java plugin)

}
                    else
                    {
                        // draw square to distinguish these diagonal points
from vertical points
                        macroStream.WriteLine(bead.m_xc + " " +
                            bead.m_y + " " + bead.m_lineNumber); // line
number tells imageJ macro to draw a square (see DrawLine.java plugin)
                    }
                }

}
        catch (Exception e)
        {
            Log.IBSEvent("could not write out timings or test lines for
ImageJ. error = " + e.Message);
        }
        finally
        {
            if (macroStream != null)
                macroStream.Close();
            if (timingFile != null)
                timingFile.Close();
        } return true;

} // end FindBeadLocationsWithGeometricMask()

//////////////////////////////////////////////////////////////////////////
///////////////////////////
        // Private Methods
//////////////////////////////////////////////////////////////////////////
///////////////////////////

/// <summary>
        /// Find peaks along each vertical line. Each peak represents the
location where
        /// a diagonal line crosses the vertical line. Save these locations as
bead centers
        /// in m_diagPoints. Also assigns a line number to each m_diagPoint
bead center.
```

```
            /// </summary>
            /// <returns></returns>
            bool FindDiagonalPointsAlongVerticalLines(TileData tile)
            {
                int roiRowCount = m_region.m_yLineRoiStop -
m_region.m_yLineRoiStart + 1;
                int[] sum = new int[roiRowCount]; // intensity at each point along
the vertical line (we will search this array to find peaks = bead centers)
                int lastLineInRoi; // max vertical line number that is inside of
bead finding roi
                int zy; // zero-based index into sum[]; zy = current row -
m_region.m_yLineRoiStart
                double xExact; // x value where a vertical line intersects a row
(without any rounding to closest column)
                int x; // column in image that is closest to current xExact
                int localSum; // temporary value that we error check before adding
to sum[]
                int smoothingBeadCount = 5; // at each row, we sum pixels from 5
beads (i.e. 5 vertical lines)
                // to get a smoothed value for the central vertical line.
                double twoLinePeriod = 2 * m_region.m_verticalPeriod;

// Basic algorithm: Go down each vertical line in the roi. Where
the line intersects a row,
                // sum the horizontal pixels closest to the line. Also sum the
horizontal pixels on the +/-2
                // vertical lines closest to the current vertical line. Note that
the honeycomb pattern of the
                // beads means that for line number = v, the next comparable line
is v + 2 (or v - 2).
                // This sum is used as the horizontal intensity on the vertical
line at that row. Once all of
                // the rows in the roi have been processed for a single line, then
we go back and find subpixel peak
                // intensities (just like we searched columns for peak intensities
to find vertical peaks).
                // The peaks are stored as bead centers in m_diagPoints.

m_diagPoints.Clear();

// Recall that for vertical lines: x = Slope*y + Intercept +
lineNumber*Period so we can
                // solve for last vertical line number in the roi by rearranging
this equation and plugging
                // in the first row (y) and last column (x) of the roi.
                lastLineInRoi = (int)((m_region.m_xLineRoiStop -
(m_region.m_verticalSlope * m_region.m_yLineRoiStart) -
                    m_region.m_verticalIntercept) / m_region.m_verticalPeriod);

// go down each line, getting horizontal sum at each row
                for (int lineNum = 0; lineNum <= lastLineInRoi; ++lineNum)
                {
                    zy = 0;
                    // sum horizontally at each row
                    for (int y = m_region.m_yLineRoiStart; y <=
m_region.m_yLineRoiStop; ++y, ++zy)
                    {
                        // Ignore following comment, missing beads should just
lower amplitude of peak without changing signal-to-noise ratio.
```

```
                // We are about to sum pixels that are near 5 lines. But if a line has a missing bead
                // then the pixels are just background noise and can hide a peak. To compensate for this,
                // we try to count missing beads and adjust the total to make is comparable to rows that
                // have no missing beads.
                // int goodBeadCount = 0;

sum[zy] = 0;
                // (lineNum - 4) represents the line that is two to the left of the current line in the image
                xExact = (int)((m_region.m_verticalSlope * m_region.m_yLineRoiStart) + m_region.m_verticalIntercept +
                    ((lineNum - 4) * m_region.m_verticalPeriod));
                // sum 3 pixels closest to 5 vertical lines
                for (int i = 0; i < smoothingBeadCount; ++i)
                {
                    x = (int)Math.Round(xExact);
                    if ((x - 1 > 0) && (x + 1 < tile.m_imageSum.ColCount))
                    {
                        // summing region is within the image size
                        localSum = tile.m_imageSum.Pixel[y, x] + tile.m_imageSum.Pixel[y, x - 1] +
                            tile.m_imageSum.Pixel[y, x + 1]; // sum for 3 columns about the vertical line sum[zy] += localSum;
                        //if (localSum > 3300) // = average background * 3. pv todo - how should we set the background value??
                        //{
                        //    sum[zy] += localSum;
                        //    ++goodBeadCount;
                        //}
                    } xExact += twoLinePeriod; // skip every other line to match honeycomb pattern of beads
                }

// compensate for missing beads
                //if (goodBeadCount > 0)
                //    sum[zy] *= (smoothingBeadCount / goodBeadCount); // the ratio of smoothing/good will be 1, unless there are some missing beads.
                // pv todo - and an else for dealing with goodBeadCount == 0
            }

// Find all peaks along the current vertical line
            for (int d = 0; d < sum.Length; ) // note that d is incremented inside the loop
            {
                // add next peak to m_diagPoints
                d = FindNextDiagonalPeak(d, sum, lineNum); // returns line index just after the peak
            }

} // end for (each vertical line in roi)
```

```
        AssignDiagonalLineNumbers();

// just for debug, save diagonal point data to a file
        //StreamWriter macroStream = null;
        //try
        //{
        //    macroStream = File.AppendText(m_macroDataFilePath);
        //    if (macroStream != null)
        //    {
        //        for (int i = 0; i < m_diagPoints.Count; ++i)
        //        {
        //            // writing just the x and y tells imageJ plugin DrawLine to draw a circle centered on the point
        //            if (m_diagPoints[i].m_lineNumber == int.MaxValue)
        //            {
        //                // the -1 will draw square to show this point was on a bad line
        //                //macroStream.WriteLine(m_diagPoints[i].m_xc.ToString() + " " +
        //                //    m_diagPoints[i].m_y + " -1");
        //            }
        //            else
        //            {
        //                macroStream.WriteLine(m_diagPoints[i].m_xc.ToString() + " " +
        //                    m_diagPoints[i].m_y); // + " " + m_diagPoints[i].m_lineNumber);
        //            }
        //        }
        //    }
        //}
        //catch (Exception e)
        //{
        //    Log.IBSEvent("FindDiagonalPointsAlongVerticalLines could not write diagonal points to macro file <" +
        //        m_macroDataFilePath + "> error = " + e.Message);
        //}
        //finally
        //{
        //    if (macroStream != null)
        //        macroStream.Close();
        //} return true;
    }

/// <summary>
    /// Starting at location d in line, find the next peak value that is within
    /// a search length equal to slightly more that a bead's width.
    /// Create a bead Center for the peak and add it to m_diagLinePoints.
    /// Uses the same core algorithm as FindBestXFromRunningAverage.
    /// </summary>
    /// <param name="dBegin">staring index in 'line'</param>
    /// <param name="line">intensities along a line in which we are looking for the next intensity peak</param>
```

```
        /// <param name="lineNumber">vertical line number that we are searching
along</param>
        /// <returns>index of first entry in line after the peak (if no peak
found, return dBegin+1)</returns>
        private int FindNextDiagonalPeak(int dBegin, int[] line, int
lineNumber)
        {
            int d; // index into line[] of a diagonal point if (line.Length < 3)
                return line.Length; // no 3-point parabolic peak can be found
in this line so skip to end of the line int peakD; // d of brightest value of sum that has lower values on
either side
            // (i.e. line[peak2x-1] and line[peak2x+1] are both less than
line[peak2x])
            double peakValue;  // brightest intensity seen so far
            bool bSinglePeak;  // if true, we found a normal 1 pixel peak. If
false, we found a peak that is 2 (or more) pixels wide
            int searchLength; // # of pixels in a row to search when looking
for the peak value of a bead searchLength = (int)((1.33 * m_iSpotWidth) + 1.5); // make sure we
get a full peak, but not two peaks in
            int lastD = dBegin + searchLength - 1; // stopping entry in line so
we don't override one peak with the next peak
            if (lastD >= line.Length - 1) // make sure that search length
doesn't overrun the # of points in the line
                lastD = line.Length - 2;  // Note that line.Count is always >=
3 peakD = -1; // no peak is yet found
            peakValue = 0;
            bSinglePeak = false;
            for (d = dBegin + 1; d <= lastD; ++d)
            {
                if (peakValue < line[d] &&
                    line[d - 1] < line[d] &&
                    line[d + 1] < line[d])
                {
                    // single pixel peak found
                    bSinglePeak = true;
                    peakValue = line[d];
                    peakD = d;
                    // we know that line[d+1] is not a peak so we don't have to
check it
                    ++d;
                }
                else if (peakValue < line[d] && line[d] == line[d + 1])
                {
                    // double pixel peak found
                    bSinglePeak = false;
                    peakValue = line[d];
                    peakD = d;
                    // we know that line[d+1] is not a peak so we don't have to
check it
                    ++d;
                }
```

```
            }

// peakD is now the index of the best peak in the searchLength (or
-1 if no peak found)

if (peakD > 0)
            {
                if (bSinglePeak)
                {
                    BeadCenterData beadCenter = new BeadCenterData();
                    // Assume bead center curve is a parabola (near its peak)
and
                    // from that assumption, calculate peak location's y
coordinate
                    double shift; // subpixel peak estimate (the value of
'shift' begins at the start of the roi)
                    shift = EstimateSubPixelPeakWithUnitaryXDiff(peakD,
line[peakD - 1],
                                                                              line[peakD],
line[peakD + 1]);
                    beadCenter.m_y = m_region.m_yLineRoiStart + shift;
                    // assume x & y are on line that has been fit to the line's
vertical points
                    beadCenter.m_xc = (m_region.m_verticalSlope *
beadCenter.m_y) + m_region.m_verticalIntercept
                                            + (m_region.m_verticalPeriod *
lineNumber);
                    beadCenter.m_interceptEstimate = beadCenter.m_y -
m_region.m_diagonalSlope * beadCenter.m_xc; // recall that diagonal slope was
set back when we found vertical line slopes
                    m_diagPoints.Add(beadCenter); // we will define diagonal
line numbers later
                    return peakD + 1;
                }
                else // peak is 2 or more rows long (peak is at peakD + 1 or
more rows)
                {
                    // check if we have a simple double pixel peak
                    if (line[peakD - 1] < line[peakD] &&
                        (peakD + 2) < searchLength &&
                        line[peakD + 2] < line[peakD])
                    {
                        // Peak is in exact middle of two pixels (peakD and
peakD+1).
                        // Note that this assumes that line[peak2x-
1]==line[peak2x+2], which is not usually
                        // exactly true but close enough for our purposes.
                        BeadCenterData beadCenter = new BeadCenterData();
                        beadCenter.m_y = m_region.m_yLineRoiStart + peakD +
0.5;
                        // assume x & y are on line that has been fit to the
line's vertical points
                        beadCenter.m_xc = (m_region.m_verticalSlope *
beadCenter.m_y) + m_region.m_verticalIntercept
                                            + (m_region.m_verticalPeriod *
lineNumber);
```

```
                        beadCenter.m_interceptEstimate = beadCenter.m_y -
m_region.m_diagonalSlope * beadCenter.m_xc; // recall that diagonal slope was
set back when we found vertical line slopes
                        m_diagPoints.Add(beadCenter); // we will define
diagonal line numbers later return peakD + 2; // peakD + 1 is end of this 2 pixel
wide peak }
                    else
                        return peakD + 3; // peak is 3 pixels wide (or wider),
just reject this unexpected result

}

}
            else
                return dBegin + 1; // no peak found

}

/// <summary>
        /// Assign a diagonal line number to each diagonal point in
m_diagPoints.
        /// Mark bads points (i.e. any point that does not fall on a line that
is an integral period
        /// away from the longest line) by setting their line number to
int.MaxValue. This will be used by
        /// GlobalFitLineIntercept to screen out bad points. (I'm assuming that
screening out bad
        /// points is faster than deleting them from the collection).
        /// </summary>
        void AssignDiagonalLineNumbers()
        {
            int i;
            int lineNumber; // 0-based index of current line
            int pointCount; // # of points in current line
            double interceptSum; // sum of all intercepts of points on current
diagonal line
            int maxLineNumber = 2 * (m_region.m_yLineRoiStop -
m_region.m_yLineRoiStart + 1); // max # of lines in ROI (factor of 2 to account
for badly placed beads)
            double[] interceptAvg = new double[maxLineNumber]; // average y
intercept of each diagonal line
            int[] linePointCount = new int[maxLineNumber]; // # of points in
each diagonal line // sort points by their estimated y intercepts
            //Comparison<BeadCenterData> compareByInterceptEstimate;
            //compareByInterceptEstimate = new
Comparison<BeadCenterData>(CompareByInterceptEstimate);
            m_diagPoints.Sort(new
Comparison<BeadCenterData>(CompareByInterceptEstimate));

// Label every point with its line number.
```

```
            // A jump in the estimated y intercept indicates that we have
jumped to a new line.
            // If the previous line has too few points, eliminate all points
from the short line.
            lineNumber = 0;
            pointCount = 0;
            interceptSum = 0;
            //minPointsPerLine = 2; // use inter-line period check rather than
line length to screen diagonal lines
            //int iLineBegin = 0;
            for (i = 0; i < m_diagPoints.Count - 1; ++i)
            {
                // current point is part of current line
                m_diagPoints[i].m_lineNumber = lineNumber;
                interceptSum += m_diagPoints[i].m_interceptEstimate;
                ++pointCount;

if (((m_diagPoints[i + 1].m_interceptEstimate -
m_diagPoints[i].m_interceptEstimate) > 0.7) ||
                    ((m_diagPoints[i + 1].m_interceptEstimate - (interceptSum
/ pointCount)) > 0.5))
                {
                //// we are at the end of a line, mark short lines by
forcing their line number to -1
                //// but don't delete them (yet)

//// we are at the end of a line's data so check if current
line
                //// is big enough to keep
                //if (pointCount >= 10)
                //{
                //    // good line, go on to the next one
                //    ++lineNumber;
                //    iLineBegin = i + 1;
                //}
                //else
                //{
                //    // bad line, delete all points in this short line
                //    m_diagPoints.RemoveRange(iLineBegin, (i - iLineBegin)
+ 1);
                //    i = iLineBegin - 1; // back up to end of the previous
line so for-loop increment makes next i == iLineBegin
                //    // note that we do not increment lineNumber because
we are going
                //    // to re-use on the next line (that is not too short)
                //}
                linePointCount[lineNumber] = pointCount;
                interceptAvg[lineNumber++] = interceptSum / pointCount;
                pointCount = 0;
                interceptSum = 0;
                if (lineNumber >= maxLineNumber)
                {
                    Log.IBSEvent("Found more diagonal lines than expected.
Check that beads are properly placed in chip");
                    break;
                }
            }
```

```
            }

// assign line to last point
            if (i < m_diagPoints.Count)
            {
                m_diagPoints[i].m_lineNumber = lineNumber;
                interceptSum += m_diagPoints[i].m_interceptEstimate;
                ++pointCount;
                linePointCount[lineNumber] = pointCount;
                interceptAvg[lineNumber++] = interceptSum / pointCount;
            }

// determine line with the most points and assume that it's intercept is good
            int bigLine = 0;
            for (i = 1; i < lineNumber; ++i)
            {
                if (linePointCount[bigLine] < linePointCount[i])
                    bigLine = i;
            }

// Calculate line number based on how many integer periods a line is from the
            // biggest line. If a line is not close to an integer period, then mark it as
            // a bad line by setting its line number to int.MaxValue.
            int[] trueLineNumber = new int[maxLineNumber];
            double goodIntercept = interceptAvg[bigLine];  // just used to save accessing array
            double distance; // distance from biggest line's y intercept to current line's y intercept
            double error;    // how far is line from being an integer period away from biggest line
            int multiple;    // closest number of integer periods between the intercepts
            for (i = 0; i < lineNumber; ++i)
            {
                distance = interceptAvg[i] - goodIntercept;
                // We cannot calculate the period error with a simple % operation because we
                // need the Round operation.
                multiple = (int)Math.Round(distance / m_region.m_diagonalPeriod); // Note that multiple can be positive or negative
                error = distance - (multiple * m_region.m_diagonalPeriod);

if (Math.Abs(error) < 0.7)
                    trueLineNumber[i] = bigLine + multiple; // good line
                else
                    trueLineNumber[i] = int.MaxValue; // bad line
            }

// The problem with the above method is that if m_region.m_diagonalPeriod is off by a small
            // amount, then this error gets multiplied for lines that are a long way from the bigLine.
            // This problem shows up more if we are using big ROI's. To avoid this issue, we will check
```

```
                // the periodicity of each bad line against the closest good line. If we do this starting at
                // the central bigLine and work our way out, then we will propagate goodLine across the entire
                // array of lines.

// Check for lines that are bad in comparision to bigLine, but are good in comparision to closer,
                // local lines.
                int lastGood = bigLine; // most local good line
                for (i = bigLine + 1; i < lineNumber; ++i)
                {
                    if (trueLineNumber[i] != int.MaxValue)
                        lastGood = i;
                    else
                    {
                        // i is a bad line with respect to bigLine. Check if it is good with respect
                        // to the lastGood line.
                        distance = interceptAvg[i] - interceptAvg[lastGood];   // interceptAvg is sorted from smallest to largest so distance is always positive // We cannot calculate the period error with a simple % operation because we
                        // need the Round operation.
                        multiple = (int)Math.Round(distance / m_region.m_diagonalPeriod); // this multiple is always positive
                        error = distance - (multiple * m_region.m_diagonalPeriod);

if (Math.Abs(error) < 0.4) // since this is a local line, we only allow a relatively small error window
                            trueLineNumber[i] = trueLineNumber[lastGood] + multiple; // good line
                        // else i is really a bad line

}
                }

// repeat procedure but this time to the opposite direction from the bigLine
                lastGood = bigLine; // most local good line
                for (i = bigLine - 1; i >= 0; --i)
                {
                    if (trueLineNumber[i] != int.MaxValue)
                        lastGood = i;
                    else
                    {
                        // i is a bad line with respect to bigLine. Check if it is good with respect
                        // to the lastGood line.
                        distance = interceptAvg[lastGood] - interceptAvg[i];   // interceptAvg is sorted from smallest to largest so distance is always positive // We cannot calculate the period error with a simple % operation because we
                        // need the Round operation.
                        multiple = (int)Math.Round(distance / m_region.m_diagonalPeriod); // this multiple is always positive
                        error = distance - (multiple * m_region.m_diagonalPeriod);
```

```
                if (Math.Abs(error) < 0.4) // since this is a local line,
we only allow a relatively small error window
                    trueLineNumber[i] = trueLineNumber[lastGood] -
multiple; // good line
                // else i is really a bad line

}
        }

// pv todo - just for debug, we renumber the lines so we always
start at 0
        int firstGoodLine = 0;
        while (trueLineNumber[firstGoodLine] == int.MaxValue)
            ++firstGoodLine;

for (i = firstGoodLine; i < lineNumber; ++i)
        {
            if (trueLineNumber[i] != int.MaxValue)
                trueLineNumber[i] -= firstGoodLine;
        }

// assign true line numbers to all points
        for (i = 0; i < m_diagPoints.Count; ++i)
        {
            m_diagPoints[i].m_lineNumber =
trueLineNumber[m_diagPoints[i].m_lineNumber];
        }

}

/// <summary>
    /// Comparison delegate function for comparing beads by their line
number
    /// </summary>
    /// <param name="x"></param>
    /// <param name="y"></param>
    /// <returns></returns>
    private int CompareByLineNumber(BeadCenterData x, BeadCenterData y)
    {
        // To be really safe we should first check for x or y == null but
that
        // should never happen so to save time, I'm skipping that check.
        if (x.m_lineNumber < y.m_lineNumber)
            return -1;
        else if (x.m_lineNumber > y.m_lineNumber)
            return 1;
        else
            return 0;
    }

/// <summary>
    /// Comparison delegate function for comparing beads by their intercept
    /// </summary>
    /// <param name="x"></param>
    /// <param name="y"></param>
    /// <returns></returns>
```

```csharp
        private int CompareByInterceptEstimate(BeadCenterData x, BeadCenterData y)
        {
            // To be really safe we should first check for x or y == null but that
            // should never happen so to save time, I'm skipping that check.
            if (x.m_interceptEstimate < y.m_interceptEstimate)
                return -1;
            else if (x.m_interceptEstimate > y.m_interceptEstimate)
                return 1;
            else
                return 0;
        }

/*      We redefined this from a Comparison delegate to the default IComparer interface for
 *      BeadCenterData so that we could sort sub-sets of lists of beads.
 *      Why Microsoft doesn't allow Comparision delegates for sub-set sorting is beyond me.
 *
        /// <summary>
        /// Comparison delegate function for comparing beads by their row #
        /// </summary>
        /// <param name="x"></param>
        /// <param name="y"></param>
        /// <returns></returns>
        private int CompareByY(BeadCenterData x, BeadCenterData y)
        {
            // To be really safe we should first check for x or y == null but that
            // should never happen so to save time, I'm skipping that check.
            if (x.m_y < y.m_y)
                return -1;
            else if (x.m_y > y.m_y)
                return 1;
            else
                return 0;
        }
*/

/// <summary>
        /// Comparison delegate function for comparing lines by their intercept
        /// </summary>
        /// <param name="x"></param>
        /// <param name="y"></param>
        /// <returns></returns>
        private int CompareByIntercept(LineDataExt x, LineDataExt y)
        {
            // To be really safe we should first check for x or y == null but that
            // should never happen so to save time, I'm skipping that check.
            if (x.intercept < y.intercept)
                return -1;
            else if (x.intercept > y.intercept)
                return 1;
            else
                return 0;
```

```
        }

/// <summary>
        /// The vertical fit is better than diagonal fit so use vertical slope and period to
        /// calculate diagonal slope and period. Then use those two parameters to find best
        /// fit of diagonal intercept parameter.
        /// See 05-22-07 notes for detailed drawings and derivations.
        /// </summary>
        /// <param name="diagPoints"></param>
        /// <returns></returns>
        private bool GlobalFitLineIntercept(List<BeadCenterData> diagPoints)
        {
            // We are fitting all diagonal lines to the equation: Y = (slope * X) + intercept + (lineNumber * period)
            // where lineNumber goes in order of increasing y_intercept and
            // y_intercept = intercept + (lineNumber * period).
            // In other words, the period is the distance between adjacent diagonal lines along the Y axis.
            double intercept, slope, period; // basic linear parameters of diagonal lines
            double sumIntercept; // sum of intercept's calculated for each diagonal point
            int beadCount; // # of beads summed in sumIntercept
            double theta; // angle that vertical line makes with Y axis (positive in direction of X axis) == vertical atan(dx/dy)
            double verticalLinePeriod; // distance between adjacent vertical lines along the X axis.

// The current region's diagonal slope and period are now set as soon as we calculate vertical line parameters in GlobalFitLine()
            //// Convert vertical line parameters to diagonal line parameters assuming
            //// that even if the images are rotated, there is still a 60 degree angle
            //// between bead centers due to the honeycomb packing of the beads.
            //// See 05-22-07 notes for detailed drawings and derivation.
            //theta = Math.Atan(m_vertLines[0].m_slope);
            //slope = Math.Tan((Math.PI / 6.0) - theta); // diagonal line angle = 30 degrees - vertical line angle
            //verticalLinePeriod = (m_vertLines[1].m_intercept - m_vertLines[0].m_intercept);
            //period = verticalLinePeriod * Math.Cos(theta) / Math.Sin((2 * Math.PI / 3) - theta);

// Since Y = (slope * X) + intercept + (lineNumber * period), we can now calculate
            // and sum all intercepts. Note that all lines (and therefor all points) have a
            // common intercept parameter because each line's Y_intercept is calculated by
            // adding the lineNumber*period to the common intercept parameter to get the
            // unique Y_intercept for each line.
            sumIntercept = 0.0;
```

```
            beadCount = 0;
            for (int i = 0; i < diagPoints.Count; ++i)
            {
                // screen out bad points
                if (diagPoints[i].m_lineNumber == int.MaxValue)
                {
                    //Log.IBSEvent("In GlobalFitLineIntercept, diagonal point "
+ i.ToString() + " has unassigned line number", true);
                    //diagPoints.RemoveAt(i);
                    //--i;
                    continue; // point was marked previously as bad point
                } sumIntercept += diagPoints[i].m_y - (m_region.m_diagonalSlope *
diagPoints[i].m_xc) - (diagPoints[i].m_lineNumber * m_region.m_diagonalPeriod);
                ++beadCount;

}

// pv todo - I think I will have to fit diagPeriod too. (see hack
in GlobalFitLine assignment of diag period)

// calc best fit of intercept parameter
            if (beadCount > 0)
                m_region.m_diagonalIntercept = (sumIntercept / beadCount);
            else
            {
                Log.IBSEvent("In GlobalFitLineIntercept, no good diagonal
points found");
                return false; // This should never happen
            } m_diagLinePeriod = m_region.m_diagonalPeriod; // pv todo - replace
obsolete m_diagLinePeriod with m_region values
            m_diagLineSlope = m_region.m_diagonalSlope;
            m_diagLineIntercept = m_region.m_diagonalIntercept;

// generate some lines so we can see how things look - pv todo -
only do this if some debug flag is on in .ini file
            m_diagLines.Clear();
            LineData currentLine;
            int firstLine = (int)((m_region.m_yLineRoiStart -
(m_region.m_diagonalSlope * m_region.m_xLineRoiStop) -
m_region.m_diagonalIntercept) / m_region.m_diagonalPeriod);
            int lastLine = (int)((m_region.m_yLineRoiStop -
(m_region.m_diagonalSlope * m_region.m_xLineRoiStart) -
m_region.m_diagonalIntercept) / m_region.m_diagonalPeriod);
            for (int i = firstLine; i <= lastLine; ++i)
            {
                currentLine = new LineData();
                currentLine.m_slope = m_region.m_diagonalSlope;
                currentLine.m_intercept = m_region.m_diagonalIntercept + (i *
m_region.m_diagonalPeriod);

m_diagLines.Add(currentLine);
            }
```

```
        return true;

} // end GlobalFitLineIntercept()

/// <summary>
    /// Find bead centers of points that lie on diagonal lines in the
image.
    /// Uses the same basic algorithm as FindVerticalLinePoints but we have
to go to a lot of work to
    /// get effective subpixel sampling to get accurate smoothing along a
diagonal.
    ///
    /// See 5-18-07 notes for drawing and discussion of our rotated ROI in
which we will be searching
    /// for points on diagonal lines. Basic idea: the hexagonal bead nest
pattern means that there is
    /// is a line of beads at an angle about 30 degrees from the horizontal
(just like the vertical beads
    /// were about 90 degrees from the horizontal). If we sum a bunch of
points along 30 degree lines, we will
    /// get good smoothing just like summing along columns gave good
vertical line smoothing.
    /// </summary>
    /// <param name="image"></param>
    /// <param name="startX"></param>
    /// <param name="stopX"></param>
    /// <param name="startY"></param>
    /// <param name="stopY"></param>
    /// <returns></returns>
    private bool FindDiagonalLinePoints(ImageData image, int startX, int
stopX, int startY, int stopY)
    {
        int widthROI, heightROI; // roiLineWidth and height, in pixels, of
rotated ROI (for vertical points this would be the columns and rows)
        double rotatedStartX, rotatedStartY; // location in image of start
of rotated ROI (its upper, left corner).
        BeadCenterData point = new BeadCenterData(); // location of current
point on a diagonal line
        double centerX, centerY; // center of usual (non-rotated) ROI
        double vectorX, vectorY; // vector from Center of non-rotated ROI
to starting point of non-rotated ROI
        double angleROI; // angle that diagonal ROI is rotated (about -60
degrees)
        double angleDiag;   // angle of our smoothing lines (about 30
degrees). (also the expected angle of all diagonal lines).
        // By definition, angleDiag - angleROI = 90 degrees
        double cosROI, sinROI; // sin and cosine of angleROI
        double cosDiag, sinDiag; // sin and cosine of angle Diag
        double slopeDiag; // nominal slope of diagonal lines, i.e.
tan(angleDiag)
        int row, col;  // row and column of rotated ROI
        double length; // distance, in pixels, from starting corner of
rotated ROI - i.e., from (rotatedStartX, rotatedStartY)
        double angle; // angle within ROI from start of ROI to current
row,col
        double x0, y0; // point in image where current search region of
rotated ROI begins (where we begin to look for the next diagonal point)
```

```
            double peakColumnOffset = 0; // distance, in columns, from start of
current search region to where peak was found.
            // note that these are columns aligned with rotated ROI
            //std::vector<CBeadCenterData>::iterator itPoint;
            int i;

int lineNumber; // 0-based index of current line
            int pointCount; // # of points in current line
            //std::vector<CBeadCenterData>::iterator it, itNext, itLineBegin;
// pointers to points that make up a line
            int minPointsPerLine; // minimum # of points per line // open file that holds data that ImageJ macro will use
            //StreamWriter macroStream = null; // pv todo -just for debug to
show bead locations in imageJ, perhaps use based on .ini flag?
            //try
            //{
            //    macroStream = File.AppendText(m_macroDataFilePath);
            //}
            //catch (Exception e)
            //{
            //    Log.IBSEvent("Could not open ImageJ Macro Data File <" +
m_macroDataFilePath +
            //        "> for writing horizontal points. Error = " + e.Message);
            //    macroStream = null;
            //}
            m_diagPoints.Clear();

// Rotate starting point of normal ROI by about -60 degrees to
align it with diagonal lines in the image
            // Rotate about center of normal ROI so our diagonal ROI overlaps
as much as possible
            // with normal ROI
            centerX = (double)(startX + stopX) / 2.0; // center of normal ROI =
pivot point of rotation
            centerY = (double)(startY + stopY) / 2.0;
            // now find vector from Center point to normal starting point
            vectorX = startX - centerX;
            vectorY = startY - centerY;
            // determine angle that we need to rotate rotate to align it with
diagonal lines in the image.
            // Due to hexagonal pattern of bead nests, we know that diagonal
lines are -60 from vertical lines.
            angleROI = Math.Atan(-m_vertLines[0].m_slope) - (Math.PI / 3.0);
            cosROI = Math.Cos(angleROI); // save frequently used sine and
cosine values
            sinROI = Math.Sin(angleROI);

rotatedStartX = centerX + vectorX * cosROI - vectorY * sinROI;
            rotatedStartY = centerY + vectorX * sinROI + vectorY * cosROI;

// diagonal lines are 90 degrees ahead of the ROI rotation
            angleDiag = angleROI + (Math.PI / 2.0);
            cosDiag = Math.Cos(angleDiag);
            sinDiag = Math.Sin(angleDiag);
            slopeDiag = sinDiag / cosDiag; // slope of a line = tangent of
line's angle
```

```
            // Note that we will be doing an independent fit of the slopes of
the diagonal lines later on.
            // slopeDiag is just our current best estimate based on the
vertical lines.

// search the entire rotated ROI for diagonal line points (just
like we did for vertical points)
            heightROI = stopY - startY + 1;
            widthROI = stopX - startX + 1;
            for (row = 0; row < heightROI; ++row)
            {
                for (col = 0; col < widthROI; ) // note that col increment is
handled in the loop,
                {                                              // depending on
where we find a point // calc point in image where current search region begins
by finding the
                    // vector from the start of the ROI to the current
(row,col)
                    length = Math.Sqrt((double)row * row + col * col);
                    angle = angleROI + Math.Atan2((double)row, (double)col);
                    x0 = rotatedStartX + length * Math.Cos(angle);
                    y0 = rotatedStartY + length * Math.Sin(angle);

// search local region for a diagonal point
                    if (FindRotatedPeak(image, x0, y0, cosROI, sinROI, cosDiag,
sinDiag, ref point, ref peakColumnOffset))
                    {
                        // project point to its y-intercept. We will use this
later to group points into common lines
                        point.m_interceptEstimate = point.m_y - slopeDiag *
point.m_xc;

m_diagPoints.Add(point);
                        //if (macroStream != null)
                        //    macroStream.WriteLine(point.m_xc.ToString() + " "
+ point.m_y.ToString() + " 0"); // trailing 0 makes ImageJ macro draw a square
(instead of a circle for vertical pts)

col += (int)(peakColumnOffset + 0.5); // move to a
column just beyond current peak. This saves us from finding the same peak
multiple times.
                        point = new BeadCenterData(); // get ready for adding
next point
                    }
                    else
                        col++; // no point found in this search region } // end for (each col)

} // end for (each row)

// sort points by their estimated y intercepts
            m_diagPoints.Sort(new
Comparison<BeadCenterData>(CompareByInterceptEstimate));

// Label every point with its line number.
```

```
            // A jump in the estimated y intercept indicates that we have
jumped to a new line.
            // If the previous line has too few points, eliminate all points
from the short line.
            lineNumber = 0;
            pointCount = 1;
            minPointsPerLine = 2 * heightROI / 3; // there should be about 1
point for every row so use 67% of rows as a minimum criterion
            int iLineBegin = 0;
            for (i = 0; i < m_diagPoints.Count - 1; ++i)
            {
                // current point is part of current line
                m_diagPoints[i].m_lineNumber = lineNumber;
                ++pointCount;
                //
                //      lineEndFlag = fabs(itNext->m_xc - it->m_xc);
                //      if (lineEndFlag > 2)

if (Math.Abs(m_diagPoints[i + 1].m_interceptEstimate -
m_diagPoints[i].m_interceptEstimate) > 0.5)
                {
                    // we are at the end of a line's data so check if current
line
                    // is big enough to keep
                    if (pointCount >= minPointsPerLine)
                    {
                        // good line, go on to the next one
                        ++lineNumber;
                        iLineBegin = i + 1;
                    }
                    else
                    {
                        // bad line, delete all points in this short line
                        m_diagPoints.RemoveRange(iLineBegin, (i - iLineBegin) +
1);
                        i = iLineBegin - 1; // back up to end of the previous
line so for-loop increment makes next i == iLineBegin
                        // note that we do not increment lineNumber because we
are going
                        // to re-use on the next line (that is not too short)

}
                    pointCount = 0;

}

}

// assign line to last point
            if (i < m_diagPoints.Count)
            {
                m_diagPoints[i].m_lineNumber = lineNumber;
                ++pointCount;
            }

// check if last line is too short
            if (pointCount < minPointsPerLine)
            {
```

```
                    m_diagPoints.RemoveRange(iLineBegin, m_diagPoints.Count - iLineBegin); // erase last short line
            }

//// just for debug, save diagonal point data to a file
            //try
            //{
            //    if (macroStream != null)
            //    {
            //        for (i = 0; i < m_diagPoints.Count; ++i)
            //        {
            //            // writing just the x and y tells imageJ plugin DrawLine to draw a circle centered on the point
            //            macroStream.WriteLine(m_diagPoints[i].m_xc.ToString() + " " +
            //                m_diagPoints[i].m_y); // + " " + m_diagPoints[i].m_lineNumber);
            //        }
            //    }
            //}
            //catch (Exception e)
            //{
            //    Log.IBSEvent("FindDiagonalLinePoints could not write diagonal points to macro file <" +
            //        m_macroDataFilePath + "> error = " + e.Message);
            //}
            //finally
            //{
            //    if (macroStream != null)
            //        macroStream.Close();
            //} return true;

} // end FindDiagonalLinePoints()

//
        /// <summary>
        /// Finds a diagonal point within a local search region using the same basic algorithm as FindBestXFromRunningAverage().
        /// There is a search region that is slightly bigger than a bead.
        /// The search region is aligned with the rotated ROI. At each point in the search region, we smooth
        /// many pixels along a line that is perpendicular to the
        /// search region. In FindBestXFromRunningAverage, the perpendicular line was oriented along a single column in the
        /// image but in this procedure, due to the rotated ROI, the smoothing line is oriented with the diagonal lines.
        ///
        /// Another complication is that, because we are not sampling along a simple column, we need to use sub-pixel sampling
        /// (about 10 times per pixel)
        /// to get an accurate estimate of the average intensity along the diagonal line. This is, in effect, a Monte Carlo
        /// method, e.g. we generate many hits along a line to get a good sampling without ever exactly measuring a full pixel.
        /// </summary>
        /// <param name="Image"></param>
```

```
/// <param name="xStart"></param>
/// <param name="yStart"></param>
/// <param name="cosROI"></param>
/// <param name="sinROI"></param>
/// <param name="cosDiag"></param>
/// <param name="sinDiag"></param>
/// <param name="point"></param>
/// <param name="?"></param>
/// <returns></returns>
bool FindRotatedPeak(ImageData image,     // pointer to image
                     double xStart, double yStart,   // start of local search region
                     double cosROI, double sinROI,   // angle of ROI
                     double cosDiag, double sinDiag, // expected angle of all diagonal lines = smoothing angle
                     ref BeadCenterData point,       // location of bead center along a diagonal line
                     ref double peakColumnOffset)    // distance to peak with search region (in units of columns)
{
    double x, y; // subpixel point in image that we are currently sampling
    int ix, iy; // integer version of x,y int[] sum = new int[30]; // sum of intensities along local search region
    int col; // index into sum array. The columns in sum[] are aligned with the columns
             // in the rotated ROI (hence its name).
    int searchLength; // how many columns in sum[] we will be using. This is the length of the search region.
    int peakValue; // largest value in sum[] that is not at the very beginning or ending of the search region
    int peakCol; // index of peakValue in sum[]
    bool bSinglePeak; // if true, we found a normal 1 pixel peak. If false, we found a peak that is 2 (or more) pixels wide double sampleRate = 0.1; // distance along smoothing line that we will sample pixels
    double xStep, yStep; // conversion of sampleRate into actual distance (in pixels) that we are moving between samples
    xStep = sampleRate * cosDiag;
    yStep = sampleRate * sinDiag;
    int i; // counts how many steps along the smoothing line we have taken
    int maxSmoothCount; // total number of steps we will take on smoothing line double x0, y0; // location in image of start of sum[]

// Make sure we get a full peak, but not two peaks. Distance between vertical intercepts is shorter
    // than the distance between diagonal lines (by a factor of cosDiag) because we are searching across
    // the columns of the
    // rotated ROI which is perpendicular to the diagonal lines whereas the non-rotated ROI searched for
```

```
            // vertical lines across the natural columns of the image which are
not perpendicular to the vertical
            // lines (unless the camera happens to be really well aligned with
the slide).

searchLength = (int)((1.33 * m_vertLinePeriod / Math.Abs(cosDiag))
+ 0.5); // the 1.33 factor tries to insure that we get at least one peak but
not two peaks within each sum[]
            maxSmoothCount = (int)(((double)(m_iSmoothWindow + m_iSmoothWindow
+ 1)) / sampleRate);

// pv todo - parameterize 29, 30 and 1.33
            if (29 < searchLength) // just defensive programming
            {
                // this should never happen.
                // LogIAEventEx(EVT_COMMAND_IMAGE_PROCESSING, "Bead size is too
large for FindRotatedPeak");
                searchLength = 29;
            }

// smooth image along lines perpendicular to sum[]
            x0 = xStart;
            y0 = yStart;
            for (col = 0; col < searchLength; ++col)
            {
                // x,y = start of smoothing line
                x = x0 - ((double)m_iSmoothWindow) * cosDiag;
                y = y0 - ((double)m_iSmoothWindow) * sinDiag;
                sum[col] = 0;

// sum along smoothing line
                for (i = 0; i < maxSmoothCount; ++i)
                {
                    ix = (int)Math.Floor(x);
                    iy = (int)Math.Floor(y);
                    sum[col] += image.Pixel(iy, ix);
                    x += xStep;
                    y += yStep;
                }

// calc image location of the next column in the search region
                x0 += cosROI;
                y0 += sinROI;

} // end for (each column in sum[])

// sum[] now has smoothed image. Find maximum peak.
            peakCol = -1; // no peak is yet found
            peakValue = 0;
            bSinglePeak = false;
            for (col = 1; col < (searchLength - 1); ++col)
            {
                if (peakValue < sum[col] && sum[col - 1] < sum[col] && sum[col
+ 1] < sum[col])
                {
                    // single pixel peak found
                    bSinglePeak = true;
                    peakValue = sum[col];
```

```
                peakCol = col;
                // we know that sum[col+1] is not a peak so we don't have to check it
                ++col;
            }
            else if (peakValue < sum[col] && sum[col] == sum[col + 1])
            {
                // double pixel peak found
                bSinglePeak = false;
                peakValue = sum[col];
                peakCol = col;
                // we know that sum[col+1] is not a peak so we don't have to check it
                ++col;
            }
        }

// peakCol is now the index of the best peak in sum
        if (peakCol > 0)
        {
            if (bSinglePeak)
            {
                // assume bead center curve is a parabola (near its peak) and
                // from that assumption, calculate peak X location
                peakColumnOffset = EstimateSubPixelPeakWithUnitaryXDiff(peakCol, sum[peakCol - 1], sum[peakCol], sum[peakCol + 1]);
                point.m_xc = xStart + (peakColumnOffset * cosROI);
                point.m_y = yStart + (peakColumnOffset * sinROI);
                return true;
            }
            else // xSearchLength
            {
                // check that we have a simple double pixel peak
                if (sum[peakCol - 1] < sum[peakCol] &&
                    (peakCol + 2) < searchLength &&
                    sum[peakCol + 2] < sum[peakCol])
                {
                    // peak is in exact middle of two pixels
                    peakColumnOffset = peakCol + 0.5;
                    // Note that this assumes that sum[peakCol-1]==sum[peakCol+2], which is not usually
                    // exactly true but close enough for our purposes. We really want this data point
                    // to avoid gaps in our data so that when we assign line numbers to points we can
                    // trace a line down from one row to the next without missing any rows.
                    point.m_xc = xStart + (peakColumnOffset * cosROI);
                    point.m_y = yStart + (peakColumnOffset * sinROI);
                    return true;
                }
                else
                    return false; // peak is 3 pixels wide (or wider).
                // just reject this unexpected result
            }
```

```csharp
        }
        else
            return false; // no peak found

} // end FindRotatedPeak()

/// <summary>
    /// Fit a parabola through three points (x1,f1), (x2,f2), and (x3,f3)
    /// in which x1-x2 = x2-x3 = 1 so they can be eliminated from the equation.
    /// Modified from "Numerical Recipes in Fortran", p.395, 2nd Edition.
    /// </summary>
    /// <param name="x2"></param>
    /// <param name="f1"></param>
    /// <param name="f2"></param>
    /// <param name="f3"></param>
    /// <returns>peak (or trough) x position</returns>
    public static double EstimateSubPixelPeakWithUnitaryXDiff(double x2,
double f1, double f2, double f3)
    {
        double f23, f21; // fi - fj
        double xPeak, shift;

f23 = f2 - f3;
        f21 = f2 - f1;
        shift = (0.5 * (f23 - f21)) / (f23 + f21);
        xPeak = x2 - shift;
        return xPeak;
    }

/*
    /// <summary>
    /// Fit a parabola through three consecutive points in a
    /// list (p1, p2, p3) in which p2 has the largest intensity.
    /// Assume the three points are essentially on a straight vertical
    /// line (i.e. their m_xc values differ mainly due to noise rather
    /// than actual slope of the best-fit line that passes through them).
    ///
    /// We actually it a parabola through three points (a,fa), (b,fb), and
(c,fc)
    /// in which a is set to 0, b = |(p2-p1)|, c = |(p3-p2)|.
    /// fa, fb, and fc are the intensities of each point.
    /// Find peak location and then (using the vertical line that passes
through p1,p2,p3)
    /// translate that back into image (x,y) coordinate to get xPeak, yPeak
    ///
    /// Modified from "Numerical Recipes in Fortran", p.395, 2nd Edition.
    /// </summary>
    /// <param name="p1_i">index into list of point p1</param>
    /// <param name="point">list of points</param>
    /// <returns>subpixel estimate of y location (in the image) of the
peak</returns>
    public double EstimateSubPixelPeakAlongVerticalLine(int p1_i,
List<BeadCenterData> point)
    {
```

```
                double b, c;    // location along line of last two points of the parabola
                double shift;   // distance along line (from p2) to the peak b = point[pl_i + 1].m_y - point[pl_i].m_y;
                c = point[pl_i + 2].m_y - point[pl_i].m_y;
                if ((Math.Abs(b - 1.0) < 0.001) && (Math.Abs(c - 2.0) < 0.001))
                {
                    // most common case in which p1,p2,and p3 are from consecutive rows
                    shift = EstimateSubPixelPeakWithUnitaryXDiff(b, point[pl_i].m_intensity,
                        point[pl_i + 1].m_intensity, point[pl_i + 2].m_intensity);
                }
                else
                {
                    // non-uniform spacing between the points so we have to use the full parabolic interpolation formula
                    double fbc, fba; // intensity difference between 2 points
                    double ba, bc;   // distance along the line between two points ba = b; // recall that 'a' was normalized to 0
                    bc = b - c;
                    fbc = point[pl_i + 1].m_intensity - point[pl_i + 2].m_intensity;
                    fba = point[pl_i + 1].m_intensity - point[pl_i].m_intensity;

shift = b - (((ba * ba * fbc) - (bc * bc * fba)) / (2 * ((ba * fbc) - (bc * fba))));
                } return point[pl_i + 1].m_y + shift; // interpolate between rows;
        }

/// <summary>
        /// Calculate the distance (in pixels) between adjacent bead centers on the same line.
        /// See notes on "Period Algorithm" for drawings that explain shortPeriod and theta
        /// </summary>
        /// <returns></returns>
        private bool CalculateLinePeriod()
        {
            double shortPeriod; // distance along a row between two adjacent vertical lines
            double theta; // angle between bead centers. Would be 30 degrees for a perfect hexagon with no rotation if (m_vertLines.Count < 2)
            {
                Log.IBSEvent("CalculateLinePeriod failed because vertical line count was < 2");
                return false; // this should never happen
            }

// FindVerticalLines forces all of the lines to be parallel so their x intercepts measure the
```

```
        // distance along the x-axis between each line
        shortPeriod = (m_vertLines[m_vertLines.Count - 1].m_intercept -
m_vertLines[0].m_intercept) / (m_vertLines.Count - 1);

// the slope of each vertical line is dx/dy so angle of the slope
says how much the image is rotated
        theta = (30.0 * Math.PI / 180.0) -
Math.Atan(m_vertLines[0].m_slope);

m_vertBeadPeriod = shortPeriod / Math.Cos(theta);
        return true;
    }
*/

/// <summary>
    /// Use all points in linePoints to make a best fit line
    /// If the lines are nearly vertical, we will be fitting:
    /// X = mY + b; rather than the more usual y = mx + b formulation.
    ///
    /// We require that all lines have the same slope and that their
intercepts be a constant
    /// distance apart (i.e. bi+1 - bi = period): Y = mx + b +
line_number*period.
    /// See 4/3/07 Notes for derivation of
    /// the new linear regression equations based on these two
requirements. Basically, we
    /// 1) Set error = Sum {(Y - mx - b - l*p)**2}
    /// 2) Take three partial derivatives of error (with respect to m, b,
and l)
    /// 3) Set each derivative equal to zero.
    /// 4) Solve for 3 equations with 3 unknowns.
    /// </summary>
    /// <param name="linePoints"></param>
    /// <param name="bFitVerticalLine">true if we are fitting vertical line
points (false if we are fitting diagonal line points)</param>
    /// <returns>true on success otherwise false</returns>
    private bool GlobalFitLine(List<BeadCenterData> linePoints, bool
bFitVerticalLine)
    {
        double x, y; // current point
        double xSum, ySum, lSum; // sum all x's, etc.
        double xSquareSum, ySquareSum, lSquareSum; // sum all x*x, y*y, l*l
for each point
        double lxSum, lySum, xySum; // sum of all l*x for each point
        int cnt; // Total number of points
        double a, c, d, e, f, g, h, k, q, r, s, t, u, v; // algebraic
variables in solution equations
        double intercept, slope, period; // basic linear parameters of the
family of lines we are globally fitting
        double m1, m2, m3; // 3 different ways of solving for slope. Used
for a consistency check
        int i;
        int firstLine, lastLine; // first and last line that fit into ROI
(just for display in ImageJ)

// calculate basic summations
        xSum = ySum = lSum = 0;
        xSquareSum = ySquareSum = lSquareSum = 0;
```

```
            lxSum = lySum = xySum = 0;
            cnt = 0;
            for (i = 0; i < linePoints.Count; ++i)
            {
                // defensive programming - this should never happen
                if (linePoints[i].m_lineNumber == int.MaxValue)
                {
                    continue; // rejected point
                }

// adjust for fitting vertical or diagonal line
                if (bFitVerticalLine)
                {
                    x = linePoints[i].m_xc;
                    y = linePoints[i].m_y;
                }
                else
                {
                    x = linePoints[i].m_y;
                    y = linePoints[i].m_xc;
                } xSum += x;
                ySum += y;
                lSum += linePoints[i].m_lineNumber;
                xSquareSum += x * x;
                ySquareSum += y * y;
                lSquareSum += linePoints[i].m_lineNumber *
linePoints[i].m_lineNumber;
                lxSum += linePoints[i].m_lineNumber * x;
                lySum += linePoints[i].m_lineNumber * y;
                xySum += x * y;

++cnt;

} // end for (each point in line)

if (cnt < 2)
            {
                Log.IBSEvent("In GlobalLineFit, cannot fit a line because there
are less than 2 valid points to fit");
                return false;
            }

// put calculations in try/catch to catch unexpected math errors
            try
            {
                // calculate basic variables of the partial derivatives
                a = -(xySum + xySum);
                c = ySquareSum + ySquareSum;
                e = ySum + ySum;
                d = lySum + lySum;
                f = lSum + lSum;
                g = lSquareSum + lSquareSum;
                h = -(lxSum + lxSum);
                k = -(xSum + xSum);

// Calculate variables used to solve 3 simultaneous linear
equations using
```

```
            // Gauss-Jordan elimination
            v = a - (c * h / d);
            q = e - (c * f / d);
            r = d - (c * g / d);

s = a - (c * k / e);
            t = e - (c * 2 * cnt / e);
            u = d - (c * f / e);

// Solve for period (distance between line intercepts)
            period = (v * t - q * s) / (q * u - r * t);

// Solve for intercept of the first line in family of lines
            intercept = -(r * period + v) / q;

// Solve for slope using 3 different equations (just to check for consistency)
            m1 = -(a + e * intercept + d * period) / c;
            m2 = -(k + 2 * cnt * intercept + f * period) / e;
            m3 = -(h + f * intercept + g * period) / d;
            slope = (m1 + m2 + m3) / 3;

if ((Math.Abs(1 - m1 / m2) > 0.0001) || (Math.Abs(1 - m2 / m3) > 0.0001))
            {
                // If a line is nearly vertical this would cause very small m values and hence
                // a false warning. Rule this out and then, if necessary, issue warning
                if (Math.Abs(m1) > 0.01 || Math.Abs(m2) > 0.01 || Math.Abs(m3) > 0.01)
                    Log.IBSEvent("Possible miscalculation in GlobalFitLine");
            }

}
        catch (Exception errorMsg)
        {
            Log.IBSEvent("Illegal math operation in GlobalFitLine. Terminating Spot Finder. Error = " + errorMsg.Message);
            return false;
        }

// add a few sanity checks
        if (period < 2.0)
        {
            Log.IBSEvent("Vertical line period (" + period + ")is too small to process. Spot finding aborted.");
            return false;
        } if (bFitVerticalLine)
        {
            if (Math.Abs(slope) > 0.07)
            {
                Log.IBSEvent("WARNING: Vertical line slope (" + slope + ") exceeds +/- 3 degrees.");
            }
            else if (intercept < -220 || intercept > 4318)
```

```
            {
                    Log.IBSEvent("WARNING; Vertical line intercept (" +
intercept + ") exceeds expected range.");
            }
        }
        else
        {
            // pv todo - add sanity checks for diagonal slope and intercept //if (Math.Abs(slope) > 0.07)
            //{
            //    Log.IBSEvent("WARNING; diagonal line slope (" + slope +
") exceeds +/- 3 degrees.");
            //}
            //else if (intercept < -220 || intercept > 4318)
            //{
            //    Log.IBSEvent("WARNING; Diagonal line intercept (" +
intercept + ") exceeds expected range.");
            //}
        }

// pv todo - use debug flag to determine if we are going to
calculate lines for display in ImageJ HOWEVER, WE MUST KEEP AT LEAST
m_vertLines[0].m_slope for use in PlaceVerticalPointsIntoDiagonalLinePoints
        if (bFitVerticalLine)
        {
            m_vertLinePeriod = period; // pv todo - replace global line
parameters with m_region line parameters
            m_vertLineSlope = slope;
            m_vertLineIntercept = intercept;

// save line data for region
            m_region.m_verticalPeriod = period;
            m_region.m_verticalSlope = slope;
            m_region.m_verticalIntercept = intercept;

// We believe the vertical points are more accurate than the
diagonal points
            // so we will convert vertical line parameters to diagonal line
parameters assuming
            // that even if the images are rotated, there is still a 60
degree angle
            // between bead centers due to the honeycomb packing of the
beads.
            // See 05-22-07 notes for detailed drawings and derivation.
            double theta = Math.Atan(m_region.m_verticalSlope);
            m_region.m_diagonalSlope = Math.Tan((Math.PI / 6.0) - theta);
// diagonal line angle = 30 degrees - vertical line angle
            m_region.m_diagonalPeriod = m_region.m_verticalPeriod *
Math.Cos(theta) / Math.Sin((2 * Math.PI / 3) - theta);
            m_region.m_diagonalPeriod -= 0.07; // pv todo - how do we
predict this offset?

m_vertLines.Clear();
            firstLine = (int)((m_region.m_xLineRoiStart - (slope *
m_region.m_yLineRoiStart) - intercept) / period);
            lastLine = (int)((m_region.m_xLineRoiStop - (slope *
m_region.m_yLineRoiStart) - intercept) / period);
        }
```

```
        else
        {
            m_diagLinePeriod = period;
            m_diagLineSlope = slope;
            m_diagLineIntercept = intercept;

m_region.m_diagonalPeriod = period;
            m_region.m_diagonalSlope = slope;
            m_region.m_diagonalIntercept = intercept;

//m_horizLines.clear();
            m_diagLines.Clear();
            firstLine = (int)((m_region.m_yLineRoiStart -
(m_region.m_diagonalSlope * m_region.m_xLineRoiStop) -
m_region.m_diagonalIntercept) / m_region.m_diagonalPeriod);
            lastLine = (int)((m_region.m_yLineRoiStop -
(m_region.m_diagonalSlope * m_region.m_xLineRoiStart) -
m_region.m_diagonalIntercept) / m_region.m_diagonalPeriod);

}

// generate some lines so we can see how things look
        LineData currentLine;

for (i = firstLine; i <= lastLine; ++i)
        {
            currentLine = new LineData();
            currentLine.m_slope = slope;
            currentLine.m_intercept = intercept + (i * period);

if (bFitVerticalLine)
                m_vertLines.Add(currentLine);
            else
                m_diagLines.Add(currentLine);
            //m_horizLines.push_back(currentLine);

} return true;

} // end GlobalFitLine()

/// <summary>
    /// Find where vertical lines of beads cross each row inside of a
search roi.
    /// </summary>
    /// <param name="image"></param>
    /// <param name="startX">beginning of line search roi</param>
    /// <param name="stopX">end of line search roi</param>
    /// <param name="startY">beginning of line search roi</param>
    /// <param name="stopY">end of line search roi</param>
    /// <returns>true on success</returns>
    private bool FindVerticalLinePoints(ImageData image, int startX, int
stopX, int startY, int stopY)
    {
        int lineNumber; // 0-based index of line passing through current
bead center
```

```
            int x, y; // define outside of for-loops so we can see their values
when an error forces a catch
            double peakIntensity; // estimate of image intensity at peak x
location (summed over the smoothing window)

int[] lastRow;  // last row that a line was found at this column
            // (array index = column in roi where a vertical point has been
found) note that
            // the roi column = full image column - firstX of roi.
            int[] lastRowLineNumber; // line number last found at this roi
column
            double[] lastRowPeak; // sub-pixel peak location of last peak found
at this roi column (set to -1 if no peak exists at this column)
            int roiWidth; // max # of columns in roi
            int i;

BeadCenterData beadCenter = new BeadCenterData();
            StreamWriter macroStream = null; // pv todo -just for debug to show
bead locations in imageJ, perhaps use based on .ini flag?

// basic algorithm:
            // For each row, do a large vertical smoothing then look for peaks
across the row.
            // From one row to the next, try to chain peaks that are within +/-
0.5 pixels of peaks found in  previous row.
            // Track where peaks are found using lastRowPeak[].
            // Every time a peak is found that does not chain with a previous
peak, give it a new lineNumber.
            // When a peak is chained to a previous row, it is assigned the
same lineNumber as the previous row's peak (using lastRowLineNumber[]).
            // Since lines can have up to 3 degrees of slope, if we have not
seen a peak at a column for a long time, do not
            // chain it to a peak that shows up many rows away (track this with
lastRow[]) because two sloped lines
            // can cross the same column.
            //
            // It is very important that we do not give a common line number to
peaks that belong to different lines. On the
            // other hand, it is ok if two chains have different line numbers
but actually belong to the same line in the
            // image - we will sort that out in AssignVerticalLineNumbers().

try
            {
                //macroStream = File.CreateText(m_macroDataFilePath);

m_vertPoints.Clear();

// initialize line tracking arrays
                roiWidth = stopX - startX + 10; // 10 is fudge factor for beads
that start in roi but finish just outside of its boundary-necessary so we don't
have to restrict search width in every call of FindBestXFromRunningAverage
                lastRow = new int[roiWidth];
                lastRowLineNumber = new int[roiWidth];
                lastRowPeak = new double[roiWidth];
                lineNumber = 0;
                for (i = 0; i < roiWidth; ++i)
                {
```

```
            lastRowPeak[i] = -100.0; // fake data to force any
comparison to conclude that there is not a matching peak at this column
            lastRow[i] = startY;
        } for (y = startY; y <= stopY; ++y)
        {
            // find all bead centers that cross the current row (y)
            for (x = startX; x <= stopX; ) // Note: no ++x
            {
                // Find x (assuming no rotation)
                beadCenter.m_xc = FindBestXFromRunningAverage(x, y,
image, out peakIntensity);

//fprintf(fpResults, "%3d %3d  %5.1lf\n", x, y,
beadCenter.m_xc);
                if (beadCenter.m_xc > 0)
                {
                    // bead center found
                    beadCenter.m_y = y;
                    if (y == startY) // first row of search ROI
                    {
                        beadCenter.m_lineNumber = lineNumber; // every
peak on the first row is a new line
                        m_vertPoints.Add(beadCenter);

int col = ((int)beadCenter.m_xc) - startX; //
column within roi that peak was found
                        lastRowLineNumber[col] = lineNumber++;
                        lastRowPeak[col] = beadCenter.m_xc;

}
                    else
                    {
                        // Determine line number of this peak.
Increment lineNumber if
                        // this bead is the start of a new line. Update
lastRow arrays.
                        FindMatchingLine(beadCenter, startX, lastRow,
lastRowLineNumber, lastRowPeak, ref lineNumber);
                        m_vertPoints.Add(beadCenter);
                    } x = (int)(beadCenter.m_xc + 1.0); // go to x just
beyond the bead center we just found
                    beadCenter = new BeadCenterData(); // get ready for
next bead
                }
                else
                    ++x; // bead center not found yet } // end for (each x)

} // end for (each y)
```

```
                // macroStream.WriteLine(beadCenter.m_xc.ToString() + " " +
y.ToString() + " " + beadCenter.m_lineNumber.ToString()); // line number tells
imageJ macro to draw a square (see DrawLine.java plugin)

// Make sure all points are on good lines (mark points on bad
lines
                // by setting their m_lineNumber to -1). Line 'goodness'
defined by
                // matching inter-line spacing to expected vertical line
period.
                if (AssignVerticalLineNumbers(lineNumber) == false)
                    return false;

}
            catch (Exception e)
            {
                Log.IBSEvent("FindVerticalLinePoints error = " + e.Message);
                //if (macroStream != null)
                //    macroStream.Close();
                return false;
            }

//macroStream.Close();
            return true;

} // end FindVerticalLinePoints()

/// <summary>
        /// Find existing line that can chain to beadCenter. If no such line
        /// found then start a new line with this bead. Track what we just did
        /// in the lastRow arrays (see FindVerticalLinePoints for descriptions
        /// of these parameters)
        /// </summary>
        /// <param name="beadCenter"></param>
        /// <param name="roiStartX"></param>
        /// <param name="lastRow">see FindVerticalLinePoints for
descriptions</param>
        /// <param name="lastRowLineNumber"></param>
        /// <param name="lastRowPeak"></param>
        /// <param name="nextLineNumber">If bead does not belong to a pre-
existing line, assign this line number to the bead (and increment it)</param>
        private void FindMatchingLine(BeadCenterData beadCenter, int roiStartX,
int[] lastRow, int[] lastRowLineNumber,
            double[] lastRowPeak, ref int nextLineNumber)
        {
            int col = ((int)beadCenter.m_xc) - roiStartX; // column within roi
that peak was found
            int row = (int)beadCenter.m_y;

// check if current peak (located at beadCenter.m_xc) is close to a
            // peak in the previous row. The row - lastRow check stops us from
            // attaching a peak to a line after too large a gap in the image
            // however, experience has shown that, given the large vertical
smoothing
            // we already do at each point, any gap at all is a sign of poor
quality
            // data so we don't allow any gap.
            // (at 3 degrees, a row gap of 20 = a 1 pixel shift)
```

```
            if ((row - lastRow[col] < 2) && (Math.Abs(lastRowPeak[col] -
beadCenter.m_xc) < 0.5))
            {
                // match found
                beadCenter.m_lineNumber = lastRowLineNumber[col];
                lastRow[col] = row;
                lastRowPeak[col] = beadCenter.m_xc;
            }
            else if ((col > 0) && (row - lastRow[col-1] < 2) &&
(Math.Abs(lastRowPeak[col-1] - beadCenter.m_xc) < 0.5))
            {
                // match found
                beadCenter.m_lineNumber = lastRowLineNumber[col-1];
                lastRow[col - 1] = row;
                lastRowPeak[col-1] = beadCenter.m_xc;
            }
            else if ((row - lastRow[col + 1] < 2) && (Math.Abs(lastRowPeak[col
+ 1] - beadCenter.m_xc) < 0.5))
            {
                // match found
                beadCenter.m_lineNumber = lastRowLineNumber[col + 1];
                lastRow[col + 1] = row;
                lastRowPeak[col + 1] = beadCenter.m_xc;
            }
            else
            {
                // no match found, this is the start of a new line
                beadCenter.m_lineNumber = nextLineNumber;
                lastRowLineNumber[col] = nextLineNumber;
                lastRow[col] = row;
                lastRowPeak[col] = beadCenter.m_xc;
                ++nextLineNumber;
            }

}

/// <summary>
    /// Map raw line numbers for every point into true line numbers.
    /// A true line number is either a flag that the point is NOT part of a
good line
    /// (and so should be used in our global fit) or it is a number that
tells us how many
    /// integer vertical periods this line is from any other line.
    ///
    /// Algorithm Outline:
    ///     Sort m_vertPoints by line number.
    ///     Delete short lines, combine lines that share a common x-
intercept.
    ///     Delete lines that don't fit the expected inter-line period.
    ///     Renumber lines so that line numbers reflect accurate period
separation.
    /// </summary>
    /// <param name="lineCount"># of lines in m_vertPoints[]</param>
    private bool AssignVerticalLineNumbers(int lineCount)
    {
        int i;
        int curLineNum;
```

```
            int lineBegin; // index into m_vertPoints at which the current line begins
            List<LineDataExt> lines; // data about each line in roi that we use to merge good lines and delete bad lines
            int lineSize; // # of points in a line
            List<LineDataExt> mLines; // unique set of lines that remain after merging lines with common intercepts and removing bad lines
            List<LineDataExt> badLines; // lines with bad periods
            int minLineSize; // we will only use process lines that are at least this big (this value changes through out the procedure
            int firstI, lastI; // index into m_vertPoints of first and last point on the current line
            double avgX, avgY; // average x and y position of a line (i.e. its midpoint)
            int[] trueLineNum = new int[lineCount]; // maps line number of each point to its true line number (bad points have lineNumber = int.MaxValue)

if (lineCount < 2)
            {
                Log.IBSEvent("Not enough vertical lines found (line count = " + lineCount +
                    ", vertical point count = " + m_vertPoints.Count + ") to determine bead locations.");
                return false;
            } lines = new List<LineDataExt>(lineCount);
            mLines = new List<LineDataExt>(lineCount);

// sort vertical points by line number. Note that at this point in the program,
            // these line numbers just reflect
            // the order that the beads were found in the roi and are not yet associated with
            // the line's true global line number (in which the line number reflects the # of periods a line
            // is from the global x-intercept position).
            m_vertPoints.Sort(new Comparison<BeadCenterData>(CompareByLineNumber));

// We want to group lines by their x-intercept, but to do that we need
            // a fairly accurate estimate of their slopes.
            if (m_IsFirstRegion)
            {
                // No slope estimate exists so generate one from roi data. This code is only called once for the
                // first roi of the first tile.
                int smallLineCount = 0;
                double[] slope; // slope of each line = dx / dy
                slope = new double[lineCount];

minLineSize = Math.Min(20, (m_region.m_yLineRoiStop - m_region.m_yLineRoiStart) / 2); // at least half the length of the roi
                curLineNum = m_vertPoints[0].m_lineNumber;
                lineBegin = 0;

// calculate slope from every line in point data that is long enough
```

```
                for (i = 1; i < m_vertPoints.Count; ++i)
                {
                    if (m_vertPoints[i].m_lineNumber == curLineNum)
                        continue; // keep moving down the point list until we reach the end of current line // point i is now the start of the next line. So we are ready to
                    // estimate slope of the current line.
                    lineSize = i - lineBegin;
                    if (lineSize < minLineSize)
                    {
                        slope[curLineNum] = double.MaxValue; // after sorting by slope, these short lines will all be at the end of list which makes them easy to exclude from the median calculation
                        ++smallLineCount;
                    }
                    else
                    {
                        // weak lines tend to curl off at start and finish, so estimate slope at
                        // 20% and 80% of full length but to do this we have to sort the points
                        // within a line by row
                        m_vertPoints.Sort(lineBegin, lineSize, new BeadCenterData()); // m_vertPoints was sorted by line number but not sub-ordered by row so we have to do that now
                        firstI = lineBegin + (int)(0.2 * lineSize);
                        lastI = lineBegin + (int)(0.8 * lineSize);
                        slope[curLineNum] = (m_vertPoints[lastI].m_xc - m_vertPoints[firstI].m_xc) / (m_vertPoints[lastI].m_y - m_vertPoints[firstI].m_y);
                    }

// get ready to start moving through points of the next line
                    lineBegin = i;
                    curLineNum = m_vertPoints[i].m_lineNumber;
                }

// add last line
                lineSize = i - lineBegin;
                if (lineSize < minLineSize)
                {
                    slope[curLineNum] = double.MaxValue; // after sorting by slope, these short lines will all be at the end of list which makes them easy to exclude from the median calculation
                    ++smallLineCount;
                }
                else
                {
                    // weak lines tend to curl off at start and finish, so estimate slope at
                    // 20% and 80% of full length
                    m_vertPoints.Sort(lineBegin, lineSize, new BeadCenterData());
                    firstI = lineBegin + (int)(0.2 * lineSize);
                    lastI = lineBegin + (int)(0.8 * lineSize);
```

```
                    slope[curLineNum] = (m_vertPoints[lastI].m_xc -
m_vertPoints[firstI].m_xc) / (m_vertPoints[lastI].m_y -
m_vertPoints[firstI].m_y);
                }
                if (lineCount - smallLineCount < 1)
                {
                    Log.IBSEvent("Not enough long vertical lines found (line count = " + lineCount +
                        ", vertical point count = " + m_vertPoints.Count + ") to determine bead locations.");
                    return false;
                }
                else if (lineCount - smallLineCount < 10)
                {
                    Log.IBSEvent("'Warning: Number of long vertical lines found (long line count = " + (lineCount - smallLineCount) +
                        ", vertical point count = " + m_vertPoints.Count + ") is fewer than optimal.");
                    return false;
                }

// use median slope value as best estimate (excluding short lines)
                Array.Sort(slope);
                m_vertLineSlope = slope[(lineCount - smallLineCount) / 2];

}

// go through point array and find intercept for each line minLineSize = Math.Min(20, (m_region.m_yLineRoiStop - m_region.m_yLineRoiStart) / 2); // relatively small minimum because we will be connecting lines using common intercepts
            curLineNum = m_vertPoints[0].m_lineNumber;
            lineBegin = 0;
            // calculate intercept for every line in point data that is long enough
            for (i = 1; i < m_vertPoints.Count; ++i)
            {
                if (m_vertPoints[i].m_lineNumber == curLineNum)
                    continue; // keep moving down the point list until we reach the end of current line // point i is now the start of the next line. So we are ready to
                // estimate intercept of the current line.
                lineSize = i - lineBegin;
                if (lineSize < minLineSize)
                {
                    // we won't use points with this line number to do global fit
                    trueLineNum[curLineNum] = int.MaxValue;
                }
                else
                {
                    // weak lines tend to curl off at start and finish, so estimate average middle of line at
```

```
                // 20% and 80% of full length
                m_vertPoints.Sort(lineBegin, lineSize, new
BeadCenterData()); // m_vertPoints was sorted by line number but not sub-
ordered by row so we have to do that now
                firstI = lineBegin + (int)(0.2 * lineSize);
                lastI = lineBegin + (int)(0.8 * lineSize);
                avgX = (m_vertPoints[lastI].m_xc +
m_vertPoints[firstI].m_xc) / 2;
                avgY = (m_vertPoints[lastI].m_y + m_vertPoints[firstI].m_y)
/ 2;
                lines.Add(new LineDataExt(curLineNum, avgX -
(m_vertLineSlope * avgY), lineSize, lineBegin));
            }

// get ready to start moving through points of the next line
            lineBegin = i;
            curLineNum = m_vertPoints[i].m_lineNumber;
        }

// add last line
        lineSize = i - lineBegin;
        if (lineSize < minLineSize)
        {
            // we won't use points with this line number to do global fit
            trueLineNum[curLineNum] = int.MaxValue;
        }
        else
        {
            m_vertPoints.Sort(lineBegin, lineSize, new BeadCenterData());
// m_vertPoints was sorted by line number but not sub-ordered by row so we have
to do that now
            firstI = lineBegin + (int)(0.2 * lineSize);
            lastI = lineBegin + (int)(0.8 * lineSize);
            avgX = (m_vertPoints[lastI].m_xc + m_vertPoints[firstI].m_xc) /
2;
            avgY = (m_vertPoints[lastI].m_y + m_vertPoints[firstI].m_y) /
2;
            lines.Add(new LineDataExt(i, avgX - (m_vertLineSlope * avgY),
lineSize, lineBegin));
        }

// sort lines by intercept and merge lines with very similar
intercepts
        lines.Sort(new Comparison<LineDataExt>(CompareByIntercept));

int v; // line index (NOT a line number)
        for (v = 0; v < lines.Count - 1; ++v)
        {
            if ((lines[v + 1].intercept - lines[v].intercept) < 1.0) // pv
todo - we may need to adjust this value
            {
                // merge lines by adding v and v's merged list to v+1's
merged list
                lines[v + 1].mergedLineNum = new List<int>(5); // assume
merged list will be no more than 5 other lines
                lines[v + 1].mergedLineNum.Add(lines[v].lineNum);    // Note
that the merged list is a list of raw line numbers. It is NOT an index into any
list or array.
                if (lines[v].mergedLineNum != null)
```

```
            {
                foreach (int k in lines[v].mergedLineNum)
                    lines[v + 1].mergedLineNum.Add(k);
            }

// finish merge by creating a weighted average of the two
lines' intercepts
                int mergedSize = lines[v].size + lines[v + 1].size;
                lines[v + 1].intercept = ((lines[v + 1].intercept * lines[v
+ 1].size) + (lines[v].intercept * lines[v].size)) / mergedSize;
                lines[v + 1].size = mergedSize;

// note that line[v+1] is not yet added to mLine because it
might wind up being
            // merged itself into line[v+2]
            }
            else
            {
                // line[v] is ready to add to our list of lines that are
fully merged
                mLines.Add(lines[v]);
            }
        }

// add last line because it is either unique or it is all done
being merged with previous lines
        mLines.Add(lines[v]);

if (mLines.Count < 2)
        {
            Log.IBSEvent("Not enough merged vertical lines found (line
count = " + mLines.Count +
                ", vertical point count = " + m_vertPoints.Count + ") to
determine bead locations.");
            return false;
        }

// pull lines with unexpected periods out of mLines and put them
into badLines
        FilterVerticalLinesByPeriod(mLines, out badLines);

if (mLines.Count < 1)
        {
            Log.IBSEvent("Not enough filtered vertical lines found (line
count = " + mLines.Count +
                ", vertical point count = " + m_vertPoints.Count + ") to
determine bead locations.");
            return false;
        }

// mLines now has only lines that are integer periods apart so we
can assign true line numbers.
        // Also sets trueLineNum values for the badLines
        CreateTrueLineNumberMap(mLines, badLines, trueLineNum);

// map raw line numbers into true line numbers for every point
        for (i = 0; i < m_vertPoints.Count; ++i)
            m_vertPoints[i].m_lineNumber =
trueLineNum[m_vertPoints[i].m_lineNumber];
```

```
            return true;
    }

/// <summary>
        /// For every line in goodLines, map its line number to a true line number (i.e. a number that reflects its
        /// periodicity within the ROI - if the true line number of two lines differs by k then the two lines
        /// are exactly k periods apart from each other). Also map the same true line number to its merged lines.
        /// Map all bad lines to int.MaxValue so their points will not be used by GlobalFitLine.
        /// </summary>
        /// <param name="goodLines"></param>
        /// <param name="badLines"></param>
        /// <param name="trueLineNum">mapping from raw line number (i.e. the line number of its
        /// points that was assigned by FindMatchingLine) to a line number that reflects where the line is in the ROI
        /// with respect to the Geometric Mask</param>
        private void CreateTrueLineNumberMap(List<LineDataExt> goodLines, List<LineDataExt> badLines, int[] trueLineNum)
        {
            int i;
            double distance; // # of pixels between the intercepts of two adjacent lines
            int multiple;    // # of integer periods between the intercepts of two adjacent lines // first good line in mLines is the first good line in the ROI so set its true line number to 0
            SetTrueLineNumber(goodLines, 0, trueLineNum, 0); // map mLines[0].lineNum, and all its merged lines, to true line number 0

// bootstrap all other good lines from the previous line
            for (i = 1; i < goodLines.Count; ++i)
            {
                // determine how many periods this line is from the last good line
                distance = goodLines[i].intercept - goodLines[i - 1].intercept;
                multiple = (int)Math.Round(distance / m_dPredictedPeriod); // this is guaranteed to be >= 1
                SetTrueLineNumber(goodLines, i, trueLineNum, trueLineNum[goodLines[i - 1].lineNum] + multiple);
            }

// flag all bad line numbers
            for (i = 0; i < badLines.Count; ++i)
                SetTrueLineNumber(badLines, i, trueLineNum, int.MaxValue);

}

/// <summary>
        /// Map a raw line number (and all lines merged with it) to its final true line number
```

```
    /// </summary>
    /// <param name="mLines"></param>
    /// <param name="rawIndex"></param>
    /// <param name="trueLineNumber">index of this array is a point's raw line number</param>
    /// <param name="trueLine">true line number of a point</param>
    private void SetTrueLineNumber(List<LineDataExt> mLines, int rawIndex, int[] trueLineNumber, int trueLine)
    {
        trueLineNumber[mLines[rawIndex].lineNum] = trueLine;

if (mLines[rawIndex].mergedLineNum != null)
        {
            foreach (int rawLineNumber in mLines[rawIndex].mergedLineNum)
                trueLineNumber[rawLineNumber] = trueLine;
        }
    }

/// <summary>
    /// Delete lines with bad periods from 'goodLines' and add them to badLines.
    /// Note that goodLines have already been merged.
    /// </summary>
    /// <param name="lines">lines to be filtered</param>
    /// <param name="badLines">lines whose periods are not what we expected</param>
    void FilterVerticalLinesByPeriod(List<LineDataExt> goodLines, out List<LineDataExt> badLines)
    {
        double period; // distance between two line intercepts measured in pixels
        int multiple;  // distance between two lines measured in units of periods badLines = new List<LineDataExt>(goodLines.Count);

if (m_vertPoints.Count < 2)
        {
            Log.IBSEvent("# of vertical lines found in region is too few to filter by expected period. Spot finder proceeding anyway.");
            return;
        }

// First Pass:
        // If two consecutive lines are not an integer period apart from each other
        // then add them to badLines
        for (int i = goodLines.Count - 1; i > 0; --i)
        {
            // check if distance between two intercepts is an integer multiple of the expected period
            period = goodLines[i].intercept - goodLines[i-1].intercept;
            multiple = (int)Math.Round(period / m_dPredictedPeriod); // note that multiple will usually be 1 if (Math.Abs(period - (multiple * m_dPredictedPeriod)) >= 1.0)
            {
                badLines.Add(goodLines[i]);
                goodLines.RemoveAt(i);
```

```csharp
                        // If 'i' is 2nd-to-last intercept in line and it has a bad period
                        // then the last intercept in line must also have bad period so add it to the list.
                        if (i == 1)
                        {
                            badLines.Add(goodLines[0]);
                            goodLines.RemoveAt(0);
                        }
                    }
                }

// If we have enough good lines, refine our estimate of the predicted period.
                // This helps when we compare lines in the second pass that are many columns away
                // from each other by minimizing false accumulated error due to small expected period discrepancy.
                if (goodLines.Count > 10)
                {
                    double periodSum = 0;
                    int periodCount = 0;
                    for (int i = goodLines.Count - 1; i > 0; --i)
                    {
                        period = goodLines[i].intercept - goodLines[i - 1].intercept;
                        multiple = (int)Math.Round(period / m_dPredictedPeriod); // note that multiple will usually be 1 periodSum += period;
                        periodCount += multiple;
                    } double newPeriod = periodSum / periodCount;
                    if (Math.Abs(newPeriod - m_dPredictedPeriod) > 0.1)
                        Log.IBSEvent("Changing predicted period from " + m_dPredictedPeriod + " to " + newPeriod);

m_dPredictedPeriod = newPeriod;
                }

// Second Pass:
                // For every 'bad line', determine if the line itself is bad or if
                // its period looked bad because it was next to a truly bad line.
                int minimumGoodCount; // if a 'bad line' actually has a good period with respect to this many other line then we will assume that it is not bad
                minimumGoodCount = Math.Max(10, goodLines.Count / 2);
                double badIntercept;
                int goodCount;

for (int bad = badLines.Count - 1; bad >= 0; --bad)
                {
                    badIntercept = badLines[bad].intercept;
                    // determine period of this line in relation to every other line and count
                    // how many of these periods are good
                    goodCount = 0;
                    for (int i = 0; i < goodLines.Count; ++i)
                    {
```

```
                period = Math.Abs(goodLines[i].intercept - badIntercept);
                multiple = (int)Math.Round(period / m_dPredictedPeriod);
                if (Math.Abs(period - (multiple * m_dPredictedPeriod)) < 0.6)
                {
                    ++goodCount;
                }
            }
            if (goodCount >= minimumGoodCount)
            {
                // Bad line is really good. Redemption lives on!
                goodLines.Add(badLines[bad]);
                badLines.RemoveAt(bad);
            }
        } goodLines.Sort(new Comparison<LineDataExt>(CompareByIntercept));

// Final Pass:
        // We are trying to catch the following scenario. Assume we have a good line (g)
        // and a bad line (b). If b and g are close to each other, either one (or both)
        // might get put into badLines[] in Pass 1 and then get taken out in Pass 2.
        // So now we will look for consecutive lines that are too close to each other and just
        // throw them both out because it is most important that we have only good data for the
        // final global fit.
        double minPeriod = m_dPredictedPeriod - 1;
        for (int i = goodLines.Count - 1; i > 0; --i)
        {
            period = goodLines[i].intercept - goodLines[i - 1].intercept; // this will always be positive because // goodLines are sorted from smallest to largest intercept
            if (period < minPeriod)
            {
                // throw them both out
                badLines.Add(goodLines[i]);
                goodLines.RemoveAt(i);
                badLines.Add(goodLines[i - 1]);
                goodLines.RemoveAt(i - 1);
                --i;
            }
        }
    } private bool FindVerticalLinePoints_old(ImageData image, int startX, int stopX, int startY, int stopY)
    {
        int[] histogramLine = null; // # of bead centers in each line (defined after first row of ROI has been analyzed)
```

```
            double[] previousRowBeadCenter = null; // index = line number,
value = bead center of line on the previous row (defined after first row of ROI
has been analyzed)
            int lineNumber; // 0-based index of line passing through current
bead center
            int x, y; // define outside of for-loops so we can see their values
when an error forces a catch
            double peakIntensity; // estimate of image intensity at peak x
location (summed over the smoothing window)

BeadCenterData beadCenter = new BeadCenterData();
            StreamWriter macroStream = null; // pv todo -just for debug to show
bead locations in imageJ, perhaps use based on .ini flag?

try
            {
                //macroStream = File.CreateText(m_macroDataFilePath);

m_vertPoints.Clear();

for (y = startY; y <= stopY; ++y)
                {
                    lineNumber = 0; // reset line number count at the start of
each row // find all bead centers that cross the current row (y)
                    for (x = startX; x <= stopX; ) // Note: no ++x
                    {
                        // Find x (assuming no rotation)
                        beadCenter.m_xc = FindBestXFromRunningAverage(x, y,
image, out peakIntensity);
                        //      beadCenter.m_intensity = peakIntensity; // pv todo -
delete this if we are  no longer using //fprintf(fpResults, "%3d %3d  %5.1lf\n", x, y,
beadCenter.m_xc);
                        if (beadCenter.m_xc > 0)
                        {
                            // bead center found
                            beadCenter.m_y = y;
                            if (y == startY) // first row of search ROI
                            {
                                m_vertPoints.Add(beadCenter); // we will assign
line numbers and delete bad points after entire first row is done
                            }
                            else
                            {
                                if (FindMatchingLine_old(beadCenter.m_xc,
previousRowBeadCenter, histogramLine, ref lineNumber))
                                {
                                    beadCenter.m_lineNumber = lineNumber;
                                    m_vertPoints.Add(beadCenter);
                                    previousRowBeadCenter[lineNumber] =
beadCenter.m_xc;
                                    ++histogramLine[lineNumber];
                                    ++lineNumber; // next bead has to be on
next line (or greater)
                                }
```

```
                    }
                    x = (int)(beadCenter.m_xc + 1.0); // go to x just
beyond the bead center we just found
                    beadCenter = new BeadCenterData(); // get ready for
next bead
                }
                else
                    ++x; // bead center not found yet } // end for (each x)

if (y == startY)
            {
                // make sure line numbers are consistent with known
period estimation
                if (SetFirstLineNumbers(startX, stopX, out
previousRowBeadCenter, out histogramLine) == false)
                    return false; // did not find enough beads for
analysis (or their frequency did not match m_expectedPeriod)
            }

} // end for (each y)

// macroStream.WriteLine(beadCenter.m_xc.ToString() + " " +
y.ToString() + " " + beadCenter.m_lineNumber.ToString()); // line number tells
imageJ macro to draw a square (see DrawLine.java plugin)

// Delete points that belong to lines that do not have many
data
        // points (we assume these are spurious lines)
        int minLineLength = 2 * (stopY - startY) / 3; // line must
cover 2/3's the height of the search ROI
        for (int shortLine = 0; shortLine < histogramLine.Length;
++shortLine)
        {
            // check if any line is too short
            if (histogramLine[shortLine] < minLineLength &&
histogramLine[shortLine] > 0)
            {
                // delete all points on this short line
                for (int j = m_vertPoints.Count - 1; j >= 0; --j)
                {
                    if (m_vertPoints[j].m_lineNumber == shortLine)
                        m_vertPoints.RemoveAt(j);
                }
            }
        }

//// sort points by their line number (useful for later
processing)
        //Comparison<BeadCenterData> compareByLineNumber;
        //compareByLineNumber = new
Comparison<BeadCenterData>(CompareByLineNumber);
        //m_vertPoints.Sort(compareByLineNumber);
```

```
        }
        catch (Exception e)
        {
            Log.IBSEvent("FindVerticalLinePoints error = " + e.Message);
            //if (macroStream != null)
            //    macroStream.Close();
            return false;
        }

//macroStream.Close();
        return true;

} // end FindVerticalLinePoints_old()

/// <summary>
    /// Find existing line that is within 1 pixel of bead's x position.
    /// This differs from the new findMatchingLine because it cannot generate a
    /// new line if a bead doesn't fit a pre-existing line (so if a line doesn't
    /// begin on the first row, we have lost it forever)
    /// </summary>
    /// <param name="beadCenterX">x of bead we are trying to place on a line</param>
    /// <param name="lineNumber">we know that beadCenterX must be on a line that is equal to, or greater than lineNumber</param>
    /// <returns>true iff matching line found</returns>
    private bool FindMatchingLine_old(double beadCenterX, double[] previousRowBeadCenter, int[] histogramLine, ref int lineNumber)
    {
        double xDiff; // distance between beadCenterX and a line
        int line = lineNumber; // temporary local copy while (true)
        {
            xDiff = previousRowBeadCenter[line] - beadCenterX;
            if (Math.Abs(xDiff) < 0.5)
            {
                lineNumber = line; // bead is very close to line
                return true;
            }
            else if (xDiff > 2 * m_dPredictedPeriod)
            {
                return false; // bead is more than a pixel from any known line
            }
            else
            {
                ++line;
                if (line >= previousRowBeadCenter.Length)
                    return false;
            }
        }
    }

/// <summary>
    /// Analyze beads found in first row of ROI and define line number for each bead.
```

```csharp
/// Also initializes a histogram of # of beads in each line and the
location of the bead center for each line.
/// </summary>
/// <param name="roiStartX">first column in bead searching roi</param>
/// <param name="previousRowBeadCenter">index=line number, value=bead
center of line on previous row</param>
/// <param name="histogramLine">index=line number, value=# of points
with this line number</param>
/// <returns></returns>
private bool SetFirstLineNumbers(int roiStartX, int roiStopX, out
double[] previousRowBeadCenter, out int[] histogramLine)
{
    int i = -1;
    // Note: at this point in the program, every bead in m_vertPoints
    is from the first row of the ROI List<int> badPeriods = null; // list of m_vertPoints indices for
    which the distance from the point to the next point is not an integer multiple
    of the period
    previousRowBeadCenter = null;
    histogramLine = null;
    try
    {

// check for degenerate case
        if (m_vertPoints.Count < 1)
        {
            Log.IBSEvent("ERROR: No beads found in first row of ROI.
            Terminating spot finding for current tile ");
            return false;
        }

// if we have enough data, estimate period
        if (m_vertPoints.Count >= 10)
        {
            EstimateFirstRowPeriod(out badPeriods);  // calculate
            m_dPredictedPeriod from first row of m_VertPoints
        }

// if we have enough data, screen out points that do not match
        predicted period
        if (m_vertPoints.Count > 1)
        {
            FilterFirstRowByPeriod(badPeriods);
        }

// another degenerate case check
        if (m_vertPoints.Count < 1)
        {
            Log.IBSEvent("Not enough good beads found in
            SetFirstLineNumbers, terminating spot finder.");
            previousRowBeadCenter = null;
            histogramLine = null;
            return false;
        }

// At this point, all remaining vertical points are integer
        periods apart from each other
```

```
            // so we can confidently assign line numbers to them. Note that
we purposely try to start numbering
            // at 1 instead of 0. This gives us a little wiggle room latter
on in case a line shows up
            // near the starting edge of the roi that we didn't see in the
first row.

// We have to check in case the first bead is not line #1 due
to missing beads near the start of the roi
            m_vertPoints[0].m_lineNumber =
(int)Math.Round((m_vertPoints[0].m_xc - roiStartX) / m_dPredictedPeriod) + 1;
            int maxLineCount = m_vertPoints[0].m_lineNumber;
            for (i = 1; i < m_vertPoints.Count; ++i)
            {
                // bootstrap line number from one bead to the next. This
avoids possible accumulating error due to actual
                // image's period being slightly different than
m_dPredictedPeriod. The division by m_dPredictedPeriod is
                // necessary because missing beads might cause non-
consecutive numbering.
                m_vertPoints[i].m_lineNumber = m_vertPoints[i -
1].m_lineNumber +
                    (int)Math.Round((m_vertPoints[i].m_xc - m_vertPoints[i
- 1].m_xc) / m_dPredictedPeriod);
                if (maxLineCount < m_vertPoints[i].m_lineNumber)
                    maxLineCount = m_vertPoints[i].m_lineNumber;

}
            ++maxLineCount;
            int theoreticalMaxLineCount = (int)((m_region.m_xLineRoiStop -
m_region.m_xLineRoiStop + 1) / m_dPredictedPeriod);
            maxLineCount = (int)(1.5 * Math.Max(maxLineCount,
theoreticalMaxLineCount));
            // initialize count of beads for each line and estimate of bead
center on the row
            previousRowBeadCenter = new double[maxLineCount];
            histogramLine = new int[maxLineCount];
            for (i = 0; i < maxLineCount; ++i)
            {
                histogramLine[i] = 0;
                previousRowBeadCenter[i] = 0;
            } for (i = 0; i < m_vertPoints.Count; ++i)
            {
                ++histogramLine[m_vertPoints[i].m_lineNumber];
                previousRowBeadCenter[m_vertPoints[i].m_lineNumber] =
m_vertPoints[i].m_xc;
            }

// fill in gaps in previousRowBeadCenter with reasonable values
based on expected period
            for (i = 0; i < maxLineCount; ++i)
            {
                if (histogramLine[i] == 0)
                {
                    // find closest line that has a known bead center
value.
                    bool found = false;
```

```
                                int lineDown = i - 1; // closest line that is less than
i
                                int lineUp = i + 1;   // closest line that is greater
than i
                                while (lineDown >= 0 || lineUp < maxLineCount)
                                {
                                    if ((lineUp < maxLineCount) &&
(histogramLine[lineUp] > 0))
                                    {
                                        previousRowBeadCenter[i] =
previousRowBeadCenter[lineUp] - ((lineUp - i) * m_dPredictedPeriod);
                                        found = true;
                                        break;
                                    }
                                    else if ((lineDown >= 0) &&
(histogramLine[lineDown] > 0))
                                    {
                                        previousRowBeadCenter[i] =
previousRowBeadCenter[lineDown] + ((i - lineDown) * m_dPredictedPeriod);
                                        found = true;
                                        break;
                                    }

--lineDown;
                                    ++lineUp;
                                } if (!found) // this should never happen
                                    Log.IBSEvent("Warning: could not fully initialize
previousRowBeadCenter. Spot finder proceeding anyway.");
                            }
                        }

// pv todo - is it worthwhile to try to estimate period from
first row and use this estimate to
                        //           replace the a priori m_dPredictedPeriod??
                    }
                    catch (Exception e)
                    {
                        Log.IBSEvent("Trouble setting first row line numbers at i = " +
i + " Error = " + e.Message);
                    }
                    return true;
                }

/// <summary>
            /// If we have enough data, calculate m_dPredictedPeriod from first row
of m_VertPoints
            /// </summary>
            /// <param name="badPeriods">list of m_vertPoints indices for which the
point is not an integer multiple of the period</param>
                void EstimateFirstRowPeriod(out List<int> badPeriods)
                {
                    if (m_vertPoints.Count < 10)
                    {
                        Log.IBSEvent("# of beads found in first row (" +
m_vertPoints.Count.ToString() +
```

```
                    ") is too few to estimate the period. Spot finder
proceeding anyway.");
                    badPeriods = null;
                    return;
                }
                else
                    badPeriods = new List<int>(m_vertPoints.Count);

// first, get robust estimate by using median period
                double[] periodList = new double[m_vertPoints.Count - 1]; // index
of periodList matches index of point in m_vertPoints
                double[] sortedPeriodList = new double[m_vertPoints.Count - 1];
                for (int i = 0; i < m_vertPoints.Count - 1; ++i)
                {
                    periodList[i] = m_vertPoints[i + 1].m_xc -
m_vertPoints[i].m_xc;
                    sortedPeriodList[i] = periodList[i];
                }
                Array.Sort(sortedPeriodList);

double medianPeriod = sortedPeriodList[sortedPeriodList.Length /
2];

// sum all periods that are reasonably close to the median period
                // (or close to an integer count of the median period)
                double periodSum = 0;
                double periodCount = 0; // # of periods in the sum
                for (int i = 0; i < periodList.Length; ++i)
                {
                    // check if distance between two bead centers is an integer
multiple of the median period
                    int multiple = (int)Math.Round(periodList[i] / medianPeriod);
// note that multiple will usually be 1
                    double thisPeriod;
                    if (multiple > 1)
                        thisPeriod = periodList[i] / multiple;
                    else
                        thisPeriod = periodList[i];

if (Math.Abs(thisPeriod - medianPeriod) < 0.7)
                    {
                        periodSum += thisPeriod;
                        ++periodCount;
                    }
                    else
                    {
                        badPeriods.Add(i);
                        // If 'i' is 2nd-to-last bead in m_vertPoints and it has a
bad period
                        // (which was measured by the distance from it to the last
bead in m_vertPoints)
                        // then the last bead in m_vertPoints
                        // must also have bad period so add it to the list.
                        if (i == periodList.Length - 1)
                            badPeriods.Add(i + 1);
                    }
                }
```

```
            // if we have enough data, recalculate period estimate
            if (periodCount >= 8)
            {
                double newPeriod = periodSum / periodCount;
                // log big changes
                if (Math.Abs(newPeriod - m_dPredictedPeriod) > 0.02)
                    Log.IBSEvent("Old predicted period = " +
m_dPredictedPeriod.ToString() +
                        " new = " + newPeriod.ToString());
                m_dPredictedPeriod = newPeriod;
            }

}

/// <summary>
        /// if we have enough data, screen out points that do not match
predicted period
        /// </summary>
        void FilterFirstRowByPeriod(List<int> badPeriods)
        {
            double period; // distance between two bead centers if (m_vertPoints.Count < 2)
            {
                Log.IBSEvent("# of beads found in first row (" +
m_vertPoints.Count.ToString() +
                    ") is too few to filter by expected period. Spot finder
proceeding anyway.");
                return;
            }

// If necessary, generate list of points with bad periods
            // (if there was enough data, this was already generated in
EstimateFirstRowPeriod)
            if (badPeriods == null)
            {
                badPeriods = new List<int>(10);
                for (int i = 0; i < m_vertPoints.Count - 1; ++i)
                {
                    // check if distance between two bead centers is an integer
multiple of the expected period
                    period = m_vertPoints[i + 1].m_xc - m_vertPoints[i].m_xc;
                    int multiple = (int)Math.Round(period /
m_dPredictedPeriod); // note that multiple will usually be 1
                    if (multiple > 1)
                        period = period / multiple;

if (Math.Abs(period - m_dPredictedPeriod) >= 0.7)
                    {
                        badPeriods.Add(i);
                        // If 'i' is 2nd-to-last bead in m_vertPoints and it
has a bad period
                        // (which was measured by the distance from it to the
last bead in m_vertPoints)
                        // then the last bead in m_vertPoints must also have
bad period so add it to the list.
```

```
            if (i == m_vertPoints.Count - 2)
                badPeriods.Add(i + 1);
        }
    }
}

// For every 'bad point', determine if the point itself is bad or
    // if
    // its period looked bad because it was next to a truly bad point.
    int minimumGoodCount; // if a 'bad point' actually has a good
period with respect to this many other points then we will assume that it is
not bad (otherwise delete this truly bad point)
    minimumGoodCount = Math.Max(3, m_vertPoints.Count / 2);
    for (int bad = badPeriods.Count - 1; bad >= 0; --bad)
    {
        BeadCenterData badPoint = m_vertPoints[badPeriods[bad]];
        // determine period of this point in relation to every other
point and count
        // how many of these periods are good
        int goodCount = 0;
        for (int i = 0; i < m_vertPoints.Count; ++i)
        {
            period = Math.Abs(m_vertPoints[i].m_xc - badPoint.m_xc);
            int multiple = (int)Math.Round(period /
m_dPredictedPeriod); // note that multiple will usually be 1
            if (multiple > 1)
                period = period / multiple;

if (Math.Abs(period - m_dPredictedPeriod) < 0.7)
            {
                ++goodCount;
            }
        } if (goodCount < minimumGoodCount)
            m_vertPoints.RemoveAt(badPeriods[bad]); // this really is a
bad point
    }
}

/// <summary>
///  Return subpixel estimate of peak's x location in image.
/// </summary>
/// <param name="xStart"></param>
/// <param name="yStart"></param>
/// <param name="image"></param>
/// <param name="peakIntensity">estimate of image intensity at peak x
location (summed over the smoothing window)</param>
/// <returns>subpixel estimate of peak's x location in image. Return -1
on error</returns>
private double FindBestXFromRunningAverage(int xStart, int yStart,
ImageData image, out double peakIntensity)
{
    peakIntensity = 0; // meaningless value for cases where we cannot
estimate the peak x location so peak intensity is undefined int x, y; // integer pixel coordinate
```

```
        int zx; // zero-based x-coordinate (e.g. the index into sum[])
        int[] sum;
        double xPeak;
        int peakZx; // zx of brightest value of sum that has lower values
on either side
        // (i.e. sum[peakZx-1] and sum[peakZx+1] are both less than
sum[peakZx])
        int peakValue;
        bool bSinglePeak;  // if true, we found a normal 1 pixel peak. If
false, we found a peak that is 2 (or more) pixels wide
        int xSearchLength; // # of pixels in a row to search when looking
for the peak value of a bead // setup search array
        xSearchLength = (int)((1.33 * m_iSpotWidth) + 1.5); // make sure we
get a full peak, but not two peaks in
        sum = new int[xSearchLength];

// make sure that smoothing window does not exceed image boundaries
        yStart -= m_iSmoothWindow;
        if (yStart < 0)
            yStart = 0;
        int yStop = yStart + (2 * m_iSmoothWindow);
        if (yStop >= image.RowCount)
            yStop = image.RowCount - 1;

// make sure that search length does not exceed image width
        int xStop = xStart + xSearchLength;
        if (xStop > image.ColCount)
            xStop = image.ColCount;

// 1) sum over a smoothing window of rows to get well-smoothed
curve = smoothed image of a bead.
        zx = 0;
        for (x = xStart; x < xStop; ++x)
        {
            // Use +/- smoothing_window to minimize the
            // effect of image rotation
            sum[zx] = 0;
            for (y = yStart; y <= yStop; ++y)
            {
                sum[zx] += image.Pixel(y, x);
            }

++zx;
        }

/*
        // Replace the following code  because it sometimes leads to double
peaks-
        // We cannot naively use the the max value in sum, because the max
value can occur
        // at the beginning or ending of the sequence, where we cannot get
a good peak estimate.
        // Go to first valley, so we can find the first peak after the
valley. This guarantees us that,
        // if search length is long enough, then we have a peak value AND
values just before
```

```
                // and just after the peak - which should give us a good sub-pixel
peak estimate.
                zx = 0;
                while ((zx < (xSearchLength-1)) && (sum[zx] >= sum[zx+1]))
                ++zx;

// now go up from the valley to the peak
                while ((zx < (xSearchLength-1)) && (sum[zx] <= sum[zx+1]))
                ++zx;
                */
                peakZx = -1; // no peak is yet found
                peakValue = 0;
                bSinglePeak = false;
                for (zx = 1; zx < (xSearchLength - 1); ++zx)
                {
                    if (peakValue < sum[zx] && sum[zx - 1] < sum[zx] && sum[zx + 1]
< sum[zx])
                    {
                        // single pixel peak found
                        bSinglePeak = true;
                        peakValue = sum[zx];
                        peakZx = zx;
                        // we know that sum[zx+1] is not a peak so we don't have to
check it
                        ++zx;
                    }
                    else if (peakValue < sum[zx] && sum[zx] == sum[zx + 1])
                    {
                        // double pixel peak found
                        bSinglePeak = false;
                        peakValue = sum[zx];
                        peakZx = zx;
                        // we know that sum[zx+1] is not a peak so we don't have to
check it
                        ++zx;
                    }
                }

// peakZx is now the index of the best peak in sum if (peakZx > 0)
                {
                    if (bSinglePeak)
                    {
                        // assume bead center curve is a parabola (near its peak)
and
                        // from that assumption, calculate peak X location
                        xPeak = EstimateSubPixelPeakWithUnitaryXDiff(xStart +
peakZx, sum[peakZx - 1], sum[peakZx], sum[peakZx + 1]);
                        peakIntensity = EstimateSubPixelPeakIntensity(xStart +
peakZx - 1, xPeak, xStart + peakZx + 1,
                            sum[peakZx - 1], sum[peakZx], sum[peakZx + 1]);
                        return xPeak;
                    }
                    else // xSearchLength
                    {
                        // check that we have a simple double pixel peak
                        if (sum[peakZx - 1] < sum[peakZx] &&
```

```
                    (peakZx + 2) < xSearchLength &&
                    sum[peakZx + 2] < sum[peakZx])
                {
                    // peak is in exact middle of two pixels (peakZx and
peakZx+1)
                    xPeak = ((double)(xStart + peakZx)) + 0.5;
                    peakIntensity = EstimateSubPixelPeakIntensity(xStart +
peakZx - 1, xPeak, xStart + peakZx + 1,
                        sum[peakZx - 1], sum[peakZx], sum[peakZx + 1]);
                    return xPeak;
                    // Note that this assumes that sum[peakZx-
1]==sum[peakZx+2], which is not usually
                    // exactly true but close enough for our purposes. We
really want this data point
                    // to avoid gaps in our data so that when we assign
line numbers to points we can
                    // trace a line down from one row to the next without
missing any rows.
                }
                else
                    return -1.0; // peak is 3 pixels wide (or wider).
                // just reject this unexpected result
            }

}
        else
            return -1.0; // no peak found

} // end FindBestXFromRunningAverage()

/// <summary>
    /// Estimate the image intensity at a subpixel image location by
    /// assuming the peak intensities follow a parabolic shape.
    /// Derived from "Numerical Recipes in Fortran", p.395, 2nd Edition.
    /// </summary>
    /// <param name="a">x position before peak</param>
    /// <param name="b">x position exactly at the peak</param>
    /// <param name="c">x position after peak</param>
    /// <param name="fa">intensity before peak</param>
    /// <param name="f_nearestPeak">intensity at pixel nearest the
peak</param>
    /// <param name="fc">intensity after peak</param>
    /// <returns>Estimate of intensity at a parabolic peak</returns>
    private double EstimateSubPixelPeakIntensity(int a, double b, int c,
int fa, int f_nearestPeak, int fc)
    {
        double ba = (double)(b - a);
        double bc = (double)(b - c);

// ba is always positive and bc is always negative. If their
absolute values are
        // identical (or nearly so) then the peak is right in the middle
between them
        // which is an integer pixel position (whose intensity =0.01
f_nearestPeak)
        if (Math.Abs(ba + bc) < 0.01)
```

```
            return f_nearestPeak; // peak is at the integer pixel right
between a and c double k = ba / bc;
            k *= k;

return ((k * fc) - fa) / (k - 1);
    }

/// <summary>
    /// Get raw filter values for each bead,
    /// convert filter values into dye values (i.e. apply crosstalk matrix),
    /// (apply lead/lag correction?),
    /// then finally, write base of each bead out to a file.
    /// </summary>
    /// <param name="tile"></param>
    public bool FindBeadIntensities(TileData tile)
    {
            int minVertIndex, maxVertIndex; // min and max lineIndex of vertical lines
            double xMin, yMin, xMax, yMax; // location in image of min and max lines
            double xBoxMin, yBoxMin, xBoxMax, yBoxMax; // Any bead center within this box will have its entire bead within the image's boundaries.
            double xVertLineBegin, yVertLineBegin; // starting point of current line within the box
            int diagLineIndex; // index of diagonal line that intersects the current vertical line within the box
            double x, y; // intersection of a vertical and diagonal line == a bead center
            double vertIntercept; // x axis intersection of a vertical line
            double diagIntercept; // y axis intersection of a diagonal line
            int xBegin, yBegin; // upper,left pixel of bead
            double xRadius, yRadius; // the distance from the bead center to the edge of the bead
            SpotData spotData = new SpotData(); // data for current spot
            int spotCount;

bool saveAsBinary = Program.resourceIni.ReadBoolValue("DEBUG_FLAGS", "save_bead_data_as_binary", true);
            string resultsFilename = tile.GetResultsFilepath(saveAsBinary);
            FileStream resultsStream = null;
            BinaryWriter resultsWriter = null;
            StreamWriter resultsTextWriter = null;

ushort[] usBeadIntensity = new ushort[4];

if (m_vertLines.Count < 1 || m_diagLines.Count < 1)
            {
                // this should never happen
                Log.IBSEvent("Insufficient line data in FindBeadIntensities");
                return false;
            }
```

```csharp
            //  create file for saving the bead results
            // byte 1 = ascii base (i.e. "A", or "G", etc)
            // bytes 2-3 = unsigned short Guanine intensity corrected for crosstalk
            // bytes 4-5 = same for Adenine
            // bytes 6-7 = Thiamine, bytes 8-9 = Cytosine
            try
            {
                resultsStream = File.OpenWrite(resultsFilename);
                if (saveAsBinary)
                    resultsWriter = new BinaryWriter(resultsStream);
                else
                    resultsTextWriter = new StreamWriter(resultsStream);
            }
            catch (Exception e)
            {
                string strMsg = string.Format("FindBeadIntensities could not open results file {0}. Error={1}",
                                    resultsFilename, e.Message);
                Log.IBSEvent(strMsg);

if (resultsStream != null)
                    resultsStream.Close();
                return false;
            }

// if a region goes to an edge of an image, shrink the region so we only calculate complete beads
            xRadius = Math.Ceiling(((double)m_iSpotWidth) / 2.0);
            xBoxMin = Math.Max(xRadius, m_region.m_xStart);
            xBoxMax = Math.Min(m_region.m_xStop, tile.ColCount - 1 - xRadius);

yRadius = Math.Ceiling(((double)m_iSpotHeight) / 2.0);
            yBoxMin = Math.Max(yRadius, m_region.m_yStart);
            yBoxMax = Math.Min(m_region.m_yStop, tile.RowCount - 1 - yRadius);

if (xBoxMin > xBoxMax || yBoxMin > yBoxMax)
            {
                Log.IBSEvent("Cannot find bead intensities because ROI is ill-defined for region");
            }

// Find leftmost (minimum) and rightmost (maximum) vertical line indices inside the box.
            // We find line index by rearranging global vertical line equation to:
            //    index = (x - slope*y - intercept) / period
            // Assumes all beads are in the same location in each image.
            // pv todo --> There is some evidence that we might have to add a location shift for each filter.
            if (m_region.m_verticalSlope >= 0)
            {
                // vertical lines goes from upper left to lower right of image so:
                // leftmost vertical line will cut through lower left corner of the box
                xMin = xBoxMin;
                yMin = yBoxMax;
```

```
                    // rightmost vertical line will cut through upper right corner
of the box
                    xMax = xBoxMax;
                    yMax = yBoxMin;
                }
                else
                {
                    // vertical lines go from upper right to lower left of image
so:
                    // leftmost vertical line cuts through upper left corner of
image
                    xMin = xBoxMin;
                    yMin = yBoxMin;
                    // rightmost vertical line cuts through lower right corner of
image
                    xMax = xBoxMax;
                    yMax = yBoxMax;
                } minVertIndex = (int)Math.Floor((xMin - m_region.m_verticalSlope *
yMin - m_vertLineIntercept) / m_vertLinePeriod) + 1;
                maxVertIndex = (int)Math.Floor((xMax - m_region.m_verticalSlope *
yMax - m_vertLineIntercept) / m_vertLinePeriod);

// Iterate through all line intersections, in order from left to
right and top to bottom.
                // Save spot data at each intersection (every intersection of a
vertical and diagonal line
                // is a bead center).
                // Pv todo - add check to decide if a bead well is empty or just
low signal
                // Recall image coordinates: (0,0) is upper left corner of image. X
axis is parallel to rows in image.
                // Positive Y axis goes from top of image to bottom of image.
                // global vertical line eq: x = slope*y + xAxisIntercept +
lineIndex*period
                //                          diagonal line eq: y = slope*x +
yAxisIntercept + lineIndex*period
                spotCount = 0;
                for (int curVertLineIndex = minVertIndex; curVertLineIndex <=
maxVertIndex; ++curVertLineIndex)
                {
                    // find starting point of current vertical line within the
image's box.
                    vertIntercept = m_vertLineIntercept + curVertLineIndex *
m_vertLinePeriod; // x axis interception of vert line if (vertIntercept < xBoxMin)
                    {
                        // vertical line intersects the left side of the box
                        xVertLineBegin = xBoxMin;
                        yVertLineBegin = (xBoxMin - vertIntercept) /
m_region.m_verticalSlope; // from x = y*m + b
                    }
                    else if (vertIntercept > xBoxMax)
                    {
                        // vertical line intersects the right side of the box
                        xVertLineBegin = xBoxMax;
```

```
                yVertLineBegin = (xBoxMax - vertIntercept) /
m_region.m_verticalSlope;
                }
                else
                {
                    xVertLineBegin = vertIntercept;
                    yVertLineBegin = yBoxMin; // line starts at top of the box
                }

// for this vertical line , find topmost diagonal line that
intersects it
                diagLineIndex = (int)Math.Floor((yVertLineBegin -
m_diagLineSlope * xVertLineBegin - m_diagLineIntercept) / m_diagLinePeriod) +
1;

while (true)
                {
                    // calc x,y intersection of vertical and diagonal line = a
bead center
                    diagIntercept = m_diagLineIntercept + diagLineIndex *
m_diagLinePeriod;
                    x = (m_region.m_verticalSlope * diagIntercept +
vertIntercept) / (1.0 - m_region.m_verticalSlope * m_diagLineSlope);
                    if (x > xBoxMax)
                        break; // no more bead centers on this vertical line
are inside the box y = m_diagLineSlope * x + diagIntercept;
                    if (y > yBoxMax)
                        break; // no more bead centers on this vertical line
are inside the box if (x >= xBoxMin && y >= yBoxMin)
                    {
                        // vert and horiz line intersection is inside box // Offset bead center by bead radius to find starting
point of bead.
                        // The +0.5 factor is an obscure issue. We did a
subpixel fit of these lines by doing a parabolic
                        // fit of three points. That fit assumed that the pixel
intensity was centered at the integer address
                        // of the pixel. But a pixel's integer address is the
upper left corner of the pixel, not the center of the
                        // pixel in the image. So we add 0.5 to x and y to
correct for this.
                        xBegin = (int)Math.Floor(x + 0.5 - xRadius);
                        yBegin = (int)Math.Floor(y + 0.5 - yRadius);

// initialize bead data for each filter
                        for (int filter = 0; filter < Camera.FilterCnt;
++filter)
                        {
                            spotData.raw[filter] = 0;
                            //spotData.xBegin = xBegin;
                            //spotData.yBegin = yBegin;
                        }
```

```
                    // sum bead intensity in each image
                    for (int row = yBegin; row <= yBegin + m_iSpotHeight;
++row)
                    {
                        for (int col = xBegin; col <= xBegin +
m_iSpotWidth; ++col)
                        {
                            for (int filter = 0; filter < Camera.FilterCnt;
++filter)
                            {
                                spotData.raw[filter] +=
tile.m_image[filter].Pixel[row, col];
                            }
                        }
                    } // end for (each pixel in a bead)

// apply crosstalk matrix and determine base of the
bead
                    ProcessOneBead(spotData);

// write out data on this bead
                    try
                    {
                        if (saveAsBinary)
                        {
                            resultsWriter.Write(spotData.baseId);
                            resultsWriter.Write(spotData.final[0]);
                            resultsWriter.Write(spotData.final[1]);
                            resultsWriter.Write(spotData.final[2]);
                            resultsWriter.Write(spotData.final[3]);
                            // save pixel closest to bead center
                            resultsWriter.Write((ushort)(y + 1)); // row
(the '+ 1' = 0.5 for round-off to nearest int + 0.5 for shift explained above
for xBegin and yBegin
                            resultsWriter.Write((ushort)(x + 1)); // col
                        }
                        else
                        {
                            resultsTextWriter.WriteLine("{0} {1} {2} {3}
{4} {5} {6}",
                                    spotData.baseId.ToString(),
spotData.final[0].ToString(),
                                    spotData.final[1].ToString(),
spotData.final[2].ToString(),
                                    spotData.final[3].ToString(),
                                    ConfigureCameraForm.NumFormat(y, 6, 1),
ConfigureCameraForm.NumFormat(x, 6, 1));
                        }
                    }
                    catch (Exception e)
                    {
                        string strMsg = string.Format("FindBeadIntensities
could not write bead # {0} to results file {1}. Error={2}",
                                    spotCount.ToString(),
resultsFilename, e.Message);
```

```
                    Log.IBSEvent(strMsg);

if (resultsStream != null)
                        resultsStream.Close();
                    return false;
                }

// get ready to process next bead
                ++spotCount;

}

++diagLineIndex; // move down vertical line to next
diagonal line intersection (i.e. move to next bead)

} // end while (find all beads on current vertical line)

} // end for (each vertical line)

resultsStream.Flush();
    resultsStream.Close();
    // pv todo restore this after fixing .bds format
Protocol.FireResultsReadyEvent(tile.Slide, resultsFilename, tile.TileNum);

return true;

} // end FindBeadIntensities()

/// <summary>
/// Determine a spot's base identification. pv todo - add quality check
so if values are too low or too close together then we set id to 4 (unknown).
/// </summary>
/// <param name="spotData"></param>
private void ProcessOneBead(SpotData spotData)
{
    // correct intensities for crosstalk
    for (int to = 0; to < Camera.FilterCnt; ++to)
    {
        double sum = 0;
        for (int from = 0; from < Camera.FilterCnt; ++from)
        {
            sum += (spotData.raw[from] * m_crosstalk[from, to]);
        } if (sum <= 0)
        {
            spotData.final[to] = 0;
        }
        else
        {
            spotData.final[to] = (ushort)sum;
        }
    }

// Determine which base is brightest.
    // hard code sorting of 4 colors
```

```
                if (spotData.final[(int)TileData.FilterIndex.red] >
spotData.final[(int)TileData.FilterIndex.blue])
                {
                    if (spotData.final[(int)TileData.FilterIndex.yellow] >
spotData.final[(int)TileData.FilterIndex.green])
                    {
                        if (spotData.final[(int)TileData.FilterIndex.red] >
spotData.final[(int)TileData.FilterIndex.yellow])
                            spotData.baseId = (byte)TileData.FilterIndex.red;
                        else
                            spotData.baseId = (byte)TileData.FilterIndex.yellow;
                    }
                    else
                    {
                        if (spotData.final[(int)TileData.FilterIndex.red] >
spotData.final[(int)TileData.FilterIndex.green])
                            spotData.baseId = (byte)TileData.FilterIndex.red;
                        else
                            spotData.baseId = (byte)TileData.FilterIndex.green;
                    }
                }
                else // blue > red
                {
                    if (spotData.final[(int)TileData.FilterIndex.yellow] >
spotData.final[(int)TileData.FilterIndex.green])
                    {
                        if (spotData.final[(int)TileData.FilterIndex.blue] >
spotData.final[(int)TileData.FilterIndex.yellow])
                            spotData.baseId = (byte)TileData.FilterIndex.blue;
                        else
                            spotData.baseId = (byte)TileData.FilterIndex.yellow;
                    }
                    else
                    {
                        if (spotData.final[(int)TileData.FilterIndex.blue] >
spotData.final[(int)TileData.FilterIndex.green])
                            spotData.baseId = (byte)TileData.FilterIndex.blue;
                        else
                            spotData.baseId = (byte)TileData.FilterIndex.green;
                    }
                }

}

/// <summary>
        /// For each region in an image, find location of every spot (i.e.
bead) in the region.
        /// Get raw filter values for each spot location,
        /// convert filter values into dye values (i.e. apply crosstalk
matrix),
        /// (apply lead/lag correction?),
        /// then finally, write base of each spot out to a file
        /// </summary>
        /// <param name="tile">contains current tile images that we are
processing</param>
        /// <returns></returns>
        public bool FindBeadLocationsAndIntensities(TileData tile)
```

```csharp
    {
        // if there are no defined regions, process the entire image
        if (m_definedRegionCount == 0)
        {
            // define region based on size of image (i.e. process the entire image)
            if (m_regionData[0].SetDefaultRegionParameters(tile, m_iSmoothWindow, m_defaultLineRoiSize) == false)
                return false;

} for (int i = 0; i < m_regionData.Length; ++i)
        {
            m_region = m_regionData[i];
            if (FindBeadLocationsWithGeometricMask(tile) == false)
                return false;

if (FindBeadIntensities(tile) == false)
                return false;

m_IsFirstRegion = false;

} return true;

}

/// <summary>
    /// Within the line-finding ROI, set dust spot pixels to 0.
    /// The problem is defining what is dust. If there is no image
    /// flattening then just assume saturated pixels are dust.
    /// pv todo - how to find dust after image flattening.
    /// </summary>
    void RemoveDustSpots(TileData tile)
    {
        ushort veryBright = 4095; // dust is saturated
        int x, y; // column and row in the image for (y = m_region.m_yLineRoiStart; y <= m_region.m_yLineRoiStop; ++y)
        {
            // find all bead centers that cross the current row (y)
            for (x = m_region.m_xLineRoiStart; x <= m_region.m_xLineRoiStop; ++x)
            {
                if (tile.m_imageSum.Pixel[y,x] >= veryBright)
                {
                    // we have found a dust particle // go back down the valley to the start of this false dust peak
                    int xBegin = x - 1;
                    while (xBegin > 0 && tile.m_imageSum.Pixel[y,xBegin-1] < tile.m_imageSum.Pixel[y,xBegin])
                    {
                        tile.m_imageSum.Pixel[y, xBegin--] = 0;
```

```csharp
                }

// delete from peak to next valley
                                while (x <= m_region.m_xLineRoiStop &&
                                    tile.m_imageSum.Pixel(y, x + 1) < tile.m_imageSum.Pixel(y, x))
                                {
                                    tile.m_imageSum.Pixel(y, x++) = 0;  // zero-out going forwards down the dusty slope
                                }

// now check rows above and below to get rid of dust speck 2-dimensionally
                                int centerDust = (x + xBegin) / 2;  // center of dust peak on this row // recursively remove dust peak from previous rows (a 0 indicates that we have already removed the dust from above)
                                if (tile.m_imageSum.Pixel(y-1, centerDust) != 0)
                                    RemoveDustHalo(tile, xBegin, x, y-1, -1);

// If next row is below dust brightness level, it is probably still in the dust particle halo
                                // so recurse down just like we had previously recursed upward
                                if (tile.m_imageSum.Pixel(y + 1, centerDust) < veryBright)
                                    RemoveDustHalo(tile, xBegin, x, y+1,  1);
                            }
                        }
                    }

// just for debug, save dust free image to file
            tile.ImageSum.WriteToFile("c:\\Program Files\\IBS\\DNA_Machine\\Images\\dustFreeImage.raw");

}

/// <summary>
        /// Assume dust particle is radially symmetric and approximates a diamond shape
        /// so we recurse until width has been reduced to 0.
        /// </summary>
        /// <param name="xBegin">leftmost column of dust in previous row</param>
        /// <param name="xEnd">rightmost column of dust in previous row</param>
        /// <param name="y">current row</param>
        /// <param name="rowStep">determines if we are recursing up or down in the immage</param>
        private void RemoveDustHalo(TileData tile, int xBegin, int xEnd, int y, int rowStep)
        {
            // shrink dust patch for this round of recursion
            ++xBegin;
            --xEnd;
```

```
        if (xEnd <= xBegin || y < 0 || y >= tile.RowCount)
            return; // we are at the end of the dust particle // remove dust patch on this row
        for (int x = xBegin; x <= xEnd; ++x)
            tile.m_imageSum.Pixel(y, x) = 0;

// go on to next row
        RemoveDustHalo(tile, xBegin, xEnd, y + rowStep,  rowStep);
    }
} // end class
}
``` c.          Appendix C

```csharp
using System;
using System.Collections.Generic;
using System.ComponentModel;
using System.Data;
using System.Drawing;
using System.Text;
using System.Windows.Forms;
using System.IO;
using PolynomialFit2.PolyFit;

namespace GenerateFlatFieldParameters
{
    public partial class Form1 : Form
    {
        public Form1()
        {
            InitializeComponent();
        } private void CreateParametersBtn_Click(object sender, EventArgs e)
        {
            // get ready to ask user to select which image files are to be used
            // for calibration
            InitParameters();
            // get list of image files from user and sequentially process each image file
            if (m_CalImageFileDlg.ShowDialog() == DialogResult.OK &&
                m_CalImageFileDlg.FileNames.GetLength(0) > 0)
            {
                InitParametersFile(); // start putting calibration parameters into parameter file (also size's image arrays)
                ProcessCalImageFile(m_CalImageFileDlg.FileName);

} if (m_paramStream != null)
                m_paramStream.Close();

doneCheckBox.Checked = true;

}
```

```
private void InitParameters()
{
    // set user dialog parameters
    m_CalImageFileDlg = new OpenFileDialog();
    m_CalImageFileDlg.Filter =
        "raw files (*.raw)|*.raw|All files (*.*)|*.*";
    //m_CalImageFileDlg.InitialDirectory =
@"C:\Projects\IBS\Images\AmandaCalibrationData\DomedImages\VWR_01";
    m_CalImageFileDlg.InitialDirectory =
@"\\10.134.213.10\shared\amanda\101507_ColumbiaTrip_Oct07\101107_VWR_EPOXY";
    m_CalImageFileDlg.Title = "Select image calibration file";
    m_CalImageFileDlg.CheckFileExists = true;

m_CalImageFileDlg.Multiselect = false;

// get parameters that user has already set
    m_rowMax = int.Parse(imageRowsTB.Text);
    m_colMax = int.Parse(imageColsTB.Text);
    m_pixelSamplingRate = int.Parse(pixelSamplingRateTB.Text); // used
if CellBasedFlatFieldCheckBox.Checked is true
    m_smoothingWidth = int.Parse(this.SmoothingWindowTB.Text);

// setup arrays
    if (m_image == null ||
        m_image.GetLength(0) < m_rowMax || m_image.GetLength(1) <
m_colMax)
    {
        m_image = new ushort[m_rowMax, m_colMax];
        m_smoothedImage = new ushort[m_rowMax, m_colMax];

//m_gridRowMax = (m_rowMax / m_pixelSamplingRate) + 1;
        //m_gridColMax = (m_colMax / m_pixelSamplingRate) + 1;
        //m_grid = new uint[m_gridRowMax, m_gridColMax];
        //m_gridCount = new uint[m_gridRowMax, m_gridColMax];

}

} private void ProcessCalImageFile(string calImageFilePath)
{
    m_paramStream.WriteLine(calImageFilePath);
    LoadImageFile(calImageFilePath);
    //RemoveSpikesWithSlope(); // this really needs to be done manually
    LocalSmoothing();
    SaveSampledSmoothedImage();
}

// loads file and gets average intensity
private void LoadImageFile(string calImageFilePath)
{

FileStream fs = File.OpenRead(calImageFilePath);
    BinaryReader br = new BinaryReader(fs);
```

```csharp
            for (int row = 0; row < m_rowMax; ++row)
            {
                for (int col = 0; col < m_colMax; ++col)
                {
                    m_image[row, col] = br.ReadUInt16();
                }
            }
            fs.Close();
        } private void RemoveSpikesWithSlope()
        {
            int width = 30; // intensity/width = slope for finding spikes
            int row, col;
            int slopeAvgSectionCount = 20; // # of slopes to calculate to find median slope
            int slopeAvgSectionWidth; // width (in pixels) of a section
            int firstCol, lastCol;
            int[] slopeAvgArray = new int[slopeAvgSectionCount];
            int avgSlope; // median slope in middle of image, use this to compare to all slopes in image
            int slope;
            int firstVal, secondVal;

MessageBox.Show("skipping spike removal");
            return;

// calculate typical slopes in the middle row of the image
            slopeAvgSectionWidth = (m_colMax / slopeAvgSectionCount); // width (in pixels) of a section
            row = m_rowMax / 2;
            for (int section = 0; section < slopeAvgSectionCount; ++section)
            {
                firstCol = section * slopeAvgSectionWidth;
                lastCol = firstCol + slopeAvgSectionWidth - 1; // avoid boundary problems
                slopeAvgArray[section] = Math.Abs(m_image[row, lastCol] - m_image[row, firstCol]);

}

// find median slope in middle of image
            Array.Sort(slopeAvgArray);
            avgSlope = slopeAvgArray[slopeAvgSectionCount / 2];
            // adjust for difference in window width used to find average slope versus
            // window width used to find spikes
            avgSlope = (avgSlope * width) / slopeAvgSectionWidth;

// set spike pixels to 0
            int bigSlope = avgSlope * 3;
            for (row = 0; row < m_rowMax - 1; ++row)
            {
                // replace spike pixels with 0
                for (col = 0; col < m_colMax - width; ++col)
                {
                    if (m_image[row, col] == 0)
                        firstVal = (int)m_image[row + 1, col];
```

```
            else
                firstVal = (int)m_image[row, col];

if (m_image[row, col + width] == 0)
                secondVal = (int)m_image[row + 1, col + width];
            else
                secondVal = (int)m_image[row, col + width];

slope = secondVal - firstVal;
            if (slope > bigSlope)
                m_image[row, col + width] = 0;
        }

// continue search for spikes in first 'width' columns
        for (col = 0; col < width; ++col)
        {
            if (m_image[row, col] == 0)
                firstVal = (int)m_image[row + 1, col];
            else
                firstVal = (int)m_image[row, col];

if (m_image[row, col + width] == 0)
                secondVal = (int)m_image[row + 1, col + width];
            else
                secondVal = (int)m_image[row, col + width];

slope = firstVal - secondVal;
            if (slope > bigSlope)
                m_image[row, col] = 0;
        }

}

// just for debug, write out de-spiked image
    DebugSaveImageFile();

// smooth spike regions
    // replace spike pixel regions with average values
    int firstBadCol, lastBadCol;
    int backoff = 3; // we assume we missed the start and end of the
spike so we want to grow the spike region by this much
    ushort firstAvgPixel, lastAvgPixel; // average pixel values on
either side of a spike
    ushort avgPixel; // average of those first and last avg pixel for (row = 0; row < m_rowMax - 1; ++row)
    {
        for (col = 0; col < m_colMax; ++col)
        {
            if (m_image[row, col] == 0)
            {
                // start of spike found
                firstBadCol = col;
                lastBadCol = firstBadCol;
                while ((lastBadCol < m_colMax) && (m_image[row,
lastBadCol] == 0))
                    ++lastBadCol;
```

```
                // grow spike region
                firstBadCol -= backoff;
                lastBadCol += backoff;

// find average pixel values on either side of the
spike
                firstAvgPixel = AverageRegion(row, firstBadCol, true);
                lastAvgPixel = AverageRegion(row, lastBadCol, false);

// handle special boundary cases
                if (firstAvgPixel == 0 && lastAvgPixel == 0)
                {
                    MessageBox.Show("Bad spike on row=" +
row.ToString() + "  col=" + col.ToString());
                    avgPixel = 0;
                }
                else if (firstAvgPixel == 0)
                    avgPixel = lastAvgPixel;
                else if (lastAvgPixel == 0)
                    avgPixel = firstAvgPixel;
                else
                {
                    // normal case, not at left or right edge of the
image
                    avgPixel = (ushort)(((int)firstAvgPixel +
(int)lastAvgPixel) / 2);
                }

// replace grown spike region with average pixel
                if (firstBadCol < 0)
                    firstBadCol = 0;

if (lastBadCol >= m_colMax)
                    lastBadCol = m_colMax - 1;

for (int x = firstBadCol; x <= lastBadCol; ++x)
                    m_image[row, x] = avgPixel;

}

}

}

// replace last row of image (that we didn't do spike search on
    int row1 = m_rowMax - 2;
    int row2 = m_rowMax - 1;
    for (col = 0; col < m_colMax; ++col)
        m_image[row2, col] = m_image[row1, col];

} private void DebugSaveImageFile()
{
    string filepath;
    FileStream fs = null;
```

```csharp
filepath = m_CalImageFileDlg.FileName + "_DeSpikedImage.raw";
try
{
    fs = File.OpenWrite(filepath);
    BinaryWriter BinOut = new BinaryWriter(fs);

for (int row = 0; row < m_rowMax; ++row)
        for (int col = 0; col < m_colMax; ++col)
            BinOut.Write(m_image[row, col]);
}
catch (Exception e)
{
    MessageBox.Show("DebugSaveImageFile could not write to file <"

filepath + "> Error=" + e.Message);
}
finally
{
    if (fs != null)
        fs.Close();
}
}

/// <summary>
/// return average pixels over a window. Return 0 if window is out of image range
/// </summary>
/// <param name="row"></param>
/// <param name="colBegin">start of smoothing region</param>
/// <param name="colBeginIsReallyColEnd">if true, colBegin was really end of region</param>
/// <returns></returns>
private ushort AverageRegion(int row, int colBegin, bool colBeginIsReallyColEnd)
{
    int colEnd, col;
    int smoothingWindow = 5;

if (colBeginIsReallyColEnd)
    {
        colEnd = colBegin;
        colBegin = colEnd - smoothingWindow;
    }
    else
    {
        colEnd = colBegin + smoothingWindow;
    } if (colBegin < 0 || colEnd > m_colMax)
        return 0;

int sum = 0;
    for (col = colBegin; col < colEnd; ++col)
        sum += (int)m_image[row, col];

return (ushort)((int)sum / (int)smoothingWindow);
} private void SaveSampledSmoothedImage()
```

```
{
    FileStream fs = null;
    ushort backgroundConstant; // camera records this value when shutter is closed
    ushort correctedValue;

backgroundConstant = ushort.Parse(this.backgroundConstantTB.Text);
    // user supplied value try
    {
        fs = File.OpenWrite(m_finalCalibrationImageFilePath);
        BinaryWriter BinOut = new BinaryWriter(fs);

for (int row = 0; row < m_rowMax; row += m_pixelSamplingRate)
            for (int col = 0; col < m_colMax; col += m_pixelSamplingRate)
            {
                correctedValue = (ushort)(m_smoothedImage[row, col] - backgroundConstant);
                BinOut.Write(correctedValue);
            }
    }
    catch (Exception e)
    {
        MessageBox.Show("SaveSampledSmoothedImage could not write to file <" +
            m_finalCalibrationImageFilePath + "> Error=" + e.Message);
    }
    finally
    {
        if (fs != null)
            fs.Close();
    }

} private void InitParametersFile()
{
    string paramFilePath = m_CalImageFileDlg.FileName;
    paramFilePath = paramFilePath.Substring(0, paramFilePath.LastIndexOf("\\") + 1);
    paramFilePath = paramFilePath + parameterFilenamePrefixTB.Text + "_CalibrationParameterFile.txt";
    m_paramStream = File.CreateText(paramFilePath);
    // save size of smoothed and sampled final calibration image
    m_paramStream.WriteLine("rows=" + int.Parse(imageRowsTB.Text) / m_pixelSamplingRate);
    m_paramStream.WriteLine("cols=" + int.Parse(imageColsTB.Text) / m_pixelSamplingRate);
    m_paramStream.WriteLine("backgroundConstant=" + int.Parse(this.backgroundConstantTB.Text));
    m_paramStream.WriteLine("primaryRow=" + int.Parse(this.primaryRowTB.Text));
    m_paramStream.WriteLine("primaryCol=" + int.Parse(this.primaryColTB.Text));
```

```
        m_paramStream.WriteLine("topDeadZone=" + m_topDeadZone.ToString());

// create and save parameter filenames
        m_finalCalibrationImageFilePath = m_CalImageFileDlg.FileName.Substring(0, m_CalImageFileDlg.FileName.LastIndexOf("\\") + 1);
        m_finalCalibrationImageFilePath += parameterFilenamePrefixTB.Text + "_SmoothSampledCalibrationImage.raw";
        m_paramStream.WriteLine(m_finalCalibrationImageFilePath.ToString());
    }

/// <summary>
    /// smooth
    /// </summary>
    private void LocalSmoothing()
    {
        uint sum;
        int smoothCount; // # of pixels in smoothing ROI // replace every pixel by average of its neighbors (including the pixel itself)
        for (int row = m_topDeadZone; row < m_rowMax; ++row)
        {
            for (int col = 0; col < m_colMax; ++col)
            {
                sum = 0;
                smoothCount = 0;
                for (int srow = Math.Max(m_topDeadZone, row - m_smoothingWidth); srow <= Math.Min(m_rowMax - 1, row + m_smoothingWidth); ++srow)
                {
                    for (int scol = Math.Max(0, col - m_smoothingWidth); scol <= Math.Min(m_colMax-1, col + m_smoothingWidth); ++scol)
                    {
                        sum += m_image[srow, scol];
                        ++smoothCount;
                    }
                    m_smoothedImage[row, col] = (ushort)(sum / smoothCount);
                }
            }
        }
    }

// members
    OpenFileDialog m_CalImageFileDlg;
    ushort[,] m_image = null;
    ushort[,] m_smoothedImage = null;
    uint[,] m_grid = null; // maps intensities from spatially diverse regions of the image into a common value
    uint[,] m_gridCount = null; // # of pixels summed to make each grid cell
```

```
        int m_rowMax; // # of rows and columns in the image
        int m_colMax;
        int m_gridRowMax, m_gridColMax; // # of rows and columns in the grid
array
        int m_pixelSamplingRate;
        int m_smoothingWidth;
        StreamWriter m_paramStream = null; // save calibration parameters here
        string m_finalCalibrationImageFilePath; // file path to final
calibration image
        const int m_topDeadZone = 4; // these rows at top of image cannot be
calibrated. Do not use them when smoothing. the camera is returning garbage in
these rows.

} // end class
}

/******** old code ********************************************

/// <summary>
        /// Do 2nd order fit of a row and then go back and replace outliers
        /// </summary>
        /// <param name="samplingRate">sample every 'samplingRate'
pixels</param>
        private void RemoveSpikesWithFit()
        {
            int stepAway = 3; // how far from a bad pixel should we step away
when we start looking for a good pixel
            int row, col;
            int degreeFit = 2;
            RegressionObject Reg = new RegressionObject();
            Reg.Degree = degreeFit;
            int[] error = new int[m_colMax]; // absolute difference between
image and fit of image // just for debug, write out de-spiked image to a binary file
            string imageFilePath = m_CalImageFileDlg.FileName.Substring(0,
m_CalImageFileDlg.FileName.LastIndexOf("\\") + 1);
            imageFilePath += parameterFilenamePrefixTB.Text +
"_PolySmoothed.raw";
            FileStream fs = File.OpenWrite(imageFilePath);
            BinaryWriter BinOut = new BinaryWriter(fs);

for (row = 0; row < m_rowMax; ++row)
            {
                Reg.Init();
                // do 2nd order polynomial fit of row
                for (col = 0; col < m_colMax; ++col)
                {
                    Reg.XYAdd((double)col, (double)m_image[row, col]);
                }

// determine polynomial coefficients
                Reg.Solve();
                double c0, c1, c2;
                c0 = Reg.get_Coeff(0);
                c1 = Reg.get_Coeff(1);
                c2 = Reg.get_Coeff(2);
```

```
            double avgError = 0;
            int fitValue;
            ushort shortFitValue;
            // determine average noise of image with respect to fit
            for (col = 0; col < m_colMax; ++col)
            {
                fitValue = (int)(c0 + col * (c1 + col * c2));
                error[col] = Math.Abs(fitValue - (int)m_image[row, col]);
                avgError += error[col];
                // just for debug, write out smoothed image to a binary file
                shortFitValue = (ushort)fitValue;
                BinOut.Write(shortFitValue);
            }

// go back and smooth image values with large errors
            avgError /= m_colMax;
            int bigError = 3 * (int)avgError; // we might have to tweak this
            for (col = 0; col < m_colMax; ++col)
            {
                int pre, post; // indices to pixels with good values on either side of a pixel with a bad value
                if (error[col] > bigError)
                {
                    // get good image value before bad value
                    pre = col - stepAway;
                    while (pre > 0 && error[pre] > bigError)
                        pre -= stepAway;

// get good image value after bad value
                    post = col + stepAway;
                    while (post < m_colMax && error[post] > bigError)
                        post += stepAway;

if (pre < 0)
                        pre = post;

if (post >= m_colMax)
                    {
                        post = pre;
                        if (post >= m_colMax)
                        {
                            MessageBox.Show("RemoveSpikesWithFit finds bad values on row " + row.ToString());
                            continue;
                        }
                    }

// replace bad value with average of good pixels on either side of it
                    m_image[row, col] = (ushort)(((int)m_image[row, pre] + (int)m_image[row, post]) / 2);
                }
            }

} // end for (each row)

BinOut.Close();
```

```
    }
private void RemoveSpikes()
    {
        ushort lastGoodVal;
        int spikeStep = 10; // look this far back to see a spike in comparison to background for (int row = 0; row < m_rowMax; ++row)
        {
            lastGoodVal = 0; // reset at start of each row
            for (int col = spikeStep; col < m_colMax; ++col)
            {
                if (lastGoodVal == 0)
                {
                    // we are not yet (as far as we can tell) in a spike
                    if ((m_image[row, col] - m_image[row, col - spikeStep]) > (1.3 * m_image[row, col - spikeStep]))
                    {
                        // spike has begun
                        lastGoodVal = m_image[row, col - spikeStep]; // replace spike with last known good value
                        m_image[row, col] = lastGoodVal;
                    }
                }
                else
                {
                    // we are in a spike region so use last known good value for comparison
                    if ((m_image[row, col] - lastGoodVal) > (1.3 * lastGoodVal))
                    {
                        m_image[row, col] = lastGoodVal; // replace spike with last known good value
                    }
                    else
                    {
                        // spike has ended
                        lastGoodVal = 0;
                    }
                }
            }
        }
    } private void CreateAndSaveGrid()
    {
        int gridRow, gridCol;
        int cur, pre;

// zero out all summing arrays
        for (int row = 0; row < m_gridRowMax; ++row)
        {
            for (int col = 0; col < m_gridColMax; ++col)
            {
                m_grid[row, col] = 0;
                m_gridCount[row, col] = 0;
            }
```

```
            }

// sum all pixels within a grid
            for (int row = 0; row < m_rowMax; ++row)
            {
                for (int col = 0; col < m_colMax; ++col)
                {
                    gridRow = row / m_pixelSamplingRate;
                    gridCol = col / m_pixelSamplingRate;
                    m_grid[gridRow, gridCol] += m_image[row, col];
                    ++m_gridCount[gridRow, gridCol];
                }
            }

// smooth grid by replacing sum by its average.
            // Save smoothed values to parameter file
            double diffSum = 0;
            for (gridRow = 0; gridRow < m_gridRowMax; ++gridRow)
            {
                for (gridCol = 0; gridCol < m_gridColMax; ++gridCol)
                {
                    m_grid[gridRow, gridCol] = m_grid[gridRow, gridCol] /
m_gridCount[gridRow, gridCol];
                    //m_paramStream.Write(m_grid[gridRow, gridCol].ToString() +
" ");
                    if (gridCol > 0)
                    {
                        cur = (int)m_grid[gridRow, gridCol];
                        pre = (int)m_grid[gridRow, gridCol-1];
                        diffSum += Math.Abs(cur - pre);
                    }
                }
                //m_paramStream.WriteLine();
            }

// run through grid again looking for anomalies
            int diffAvg = (int)(diffSum / (m_gridRowMax*(m_gridColMax-1)));
            //m_paramStream.WriteLine("Oddballs = 4 x " + diffAvg.ToString());
            diffAvg = 4 * diffAvg;
            for (gridRow = 0; gridRow < m_gridRowMax; ++gridRow)
            {
                m_paramStream.Write(m_grid[gridRow, 0].ToString() + " ");
                for (gridCol = 1; gridCol < m_gridColMax-1; ++gridCol)
                {
                    //cur = (int)m_grid[gridRow, gridCol];
                    //pre = (int)m_grid[gridRow, gridCol - 1];
                    //if (Math.Abs(pre-cur) > diffAvg)

// look for single grid spike
                    if ((m_grid[gridRow, gridCol] > m_grid[gridRow, gridCol -
1]) && // this is a single-cell spike
                        (m_grid[gridRow, gridCol] > m_grid[gridRow, gridCol +
1]) &&
                        (Math.Max((m_grid[gridRow, gridCol] - m_grid[gridRow,
gridCol - 1]), (m_grid[gridRow, gridCol] - m_grid[gridRow, gridCol + 1])) >
diffAvg)
```

EXPERIMENTAL

The following examples serve to illustrate certain exemplary embodiments and aspects of the present invention and are not to be construed as limiting the scope thereof.

Example 1

Materials and Methods

The following is a brief description of the exemplary materials and methods used in the following Examples. All solvents and reagents were reagent grades, purchased commercially and used without further purification. Protected nucleosides 5'-O-(tert-butyldimethylsilyl)-2'-deoxythymidine, $N^4$-benzoyl-5'-O-tert-butyldimethylsilyl-2'-deoxycytidine, $N^6$-Benzoyl-5'-O-tert-butyldimethylsilyl-2'-deoxyadenosine, $N^2$-isobutyryl-5'-O-(tert-butyldimethylsilyl)-2'-deoxyguanosine were purchased from CNH Technologies, Inc. All other chemicals were purchased from Sigma-Aldrich.

Example 2

Synthesis of 3'-O-Azidomethyl Nucleotides

Figure 20:
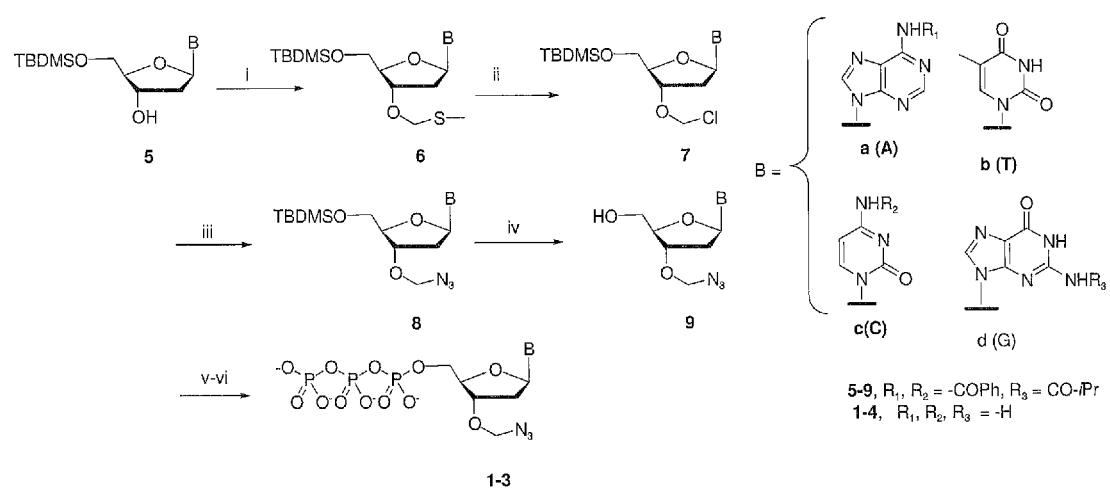
FIG. 20 shows synthesis of 3'-O-azidomethyl-dNTPs where the steps denote treatment with (i) DMSO, AcOH, $Ac_2O$, 48 h; (ii) $SO_2Cl_2$, dry $CH_2Cl_2$, 1-2 h; (iii) $NaN_3$ in DMF, 3 h; (iv) $NH_4F$ in MeOH, 16-20 h; (v) $(MeO)_3PO$, $POCl_3$ then $(t-Bu_3NH)_4P_2O_7$, TEAB, 1 h; vi) $NH_4OH$.

The synthesis of 3'-O-azidomethyl-dNPTs is described in FIG. 20. Briefly, reaction of 5'-O-TBDM-2'-deoxynucleosides (5) with a mixture of DMSO, acetic acid, and acetic anhydride installed the 3'-O-methylthiomethyl group (3'-O-MTM, 6), which upon treatment with $SO_2Cl_2$ converted to activated 3'-O—$CH_2Cl$ (7). The latter can be monitored in TLC as 3'-OH (5) after dissolving in wet organic solvent due to fast hydrolysis of the —$CH_2Cl$ group. The 3'-O—$CH_2Cl$-2'-deoxynucleoside (7) is then treated with $NaN_3$ in dry DMF without purification to convert to 3'-O—$CH_2N_3$ (8). 3'-O-azidomethyl-2'-deoxynucleosides of A, T, and C (9a-9c) were obtained in good yield after deprotection of the 5'-O-TBDMS group as described in the FIG. 20. Similar synthesis route for guanosine (G, 9d), lead only very low yield (>10%) due to formation of a number of side reaction products. To circumvent this, a new method was introduced for the synthesis of guanosine analog (14) which is described in the FIG. 21, which involved protection of the $O^6$— group by diphenycarbamoyl group. After protection of this particular group, the intermediate (12-14) became less polar, making easier to purify, and lead good overall yield in the azidomethyl group installation step.

Example 3

Synthesis of $N^6$-benzoyl-3'-O-(azidomethyl)-dA (9a)

The following describes exemplary synthesis steps for compounds shown in FIG. 20.

A. Synthesis of $N^6$-Benzoyl-3'-O-(methylthiomethyl)-5'-O-(tert-butyldimethylsilyl)-2'-deoxyadenosine (6a)

3.0 g $N^6$-Benzoyl-5'-O-tert-butyldimethylsilyl-2'-deoxyadenosine (5a) (6.38 mmol) was dissolved in a mixture consisting of 11.96 ml, DMSO, 5.46 mL acetic acid, and 17.55 mL acetic anhydride and stirred at room temperature for 48 h. The reaction mixture was then neutralized treating with a sufficient amount of saturated $NaHCO_3$ solution and extracted with $CH_2Cl_2$ (3×100 mL). The combined organic extract was then washed with a saturated $NaHCO_3$ solution (100 mL), dried over $Na_2SO_4$, and concentrated under vacuum. The resultant yellowish oil was then purified on silica gel column (Hex: EtOAc/1:1 to 1:4) to obtain the product $N^6$-benzoyl-3'-O-(methylthiomethyl)-5'-O-(tert-butyldimethylsilyl)-2'-deoxyadenosine (6a) as white powder in 71% yield (2.4 g, $R_f$ 0.6, EtOAc:hex/7:3). HR-MS: obs. m/z 530.2273, calcd. for $C_{25}H_{36}O_4N_5SiS$ 530.2257 $[M+H]^+$. $^1$H-NMR (CDCl$_3$): $\delta_H$ 9.00 (s, 1H), 8.83 (s, 1H), 8.35 (s, 1H), 8.05 (d, J=7.6 Hz, 2H), 7.62 (m, 1H), 7.55 (m, 2H), 6.55 (t, J=7.19 Hz, 1H), 4.73 (m, 2H), 4.68 (m, 1H), 4.24 (m, 1H), 3.88 (dd, J=11.19, 3.19 Hz, 1H), 2.74-2.66 (m, 2H), 2.35 (s, 3H), 0.94 (s, 9H) and 0.13 (s, 6H) ppm.

B. Synthesis of $N^6$-benzoyl-3'-O-(azidomethyl)-2'-deoxyadenosine (9a)

To 0.4 g $N^6$-benzoyl-3'-O-(methylthiomethyl)-5'-O-(tert-butyledimethylsilyl)-2'-deoxyadenosine (0.76 mmol) dissolved in 7 mL dry $CH_2Cl_2$ was treated with 0.4 ml cyclohexene and 155 μL $SO_2Cl_2$ (1.91 mmol) at 0° C. for 2 h. During this time the starting material completely converted to 7a which was shown by disappearance of the starting material and appearance of 3'-OH analog (5a) in TLC (EtOAC:Hex/7:3, $R_f$~0.3; the 3-$CH_2Cl$ (7a) could not detected in TLC due to decomposition in TLC plate to 5a). Then solvent was removed by rotary evaporation and kept about 10 minutes in high vacuum pump. Then dissolved in 5 mL dry DMF and treated with 400 mg $NaN_3$ (6.6 mmol) at room temperature for 3 h. Then the reaction mixture was partitioned in $H_2O/CH_2Cl_2$, the combined organic part was dried over $Na_2SO_4$ and concentrated by rotary evaporation. The crude sample was then dissolved in 5 mL MeOH and treated with 300 mg $NH_4F$ (8.1 mmol) more than 38 h. Then MeOH was removed by rotary evaporation. After pardoning in $H_2O/EtOAc$, the combined organic part was dried over $Na_2SO_4$, concentrated, and purified by silica gel column chromatography (100% EtOAc to 98:2, EtOAc/MeOH) resulting 150 mg of 9a as white powder (48% yield in three steps). HR-MS: Obs. m/z 411.1530, calcd for $C_{18}H_{19}O_4N_8$ 411.1529 $[M+H]^+$. $^1$H-NMR (CDC$_3$): $\delta_H$ 8.84 (brs, 1H), 8.70 (brs, 1H), 8.08 (m, 1H), 7.76-7.54 (m, 5H), 6.47 (t, J=5.6 Hz, 1H), 4.83 (m, 2H), 4.78 (m, 1H), 4.39 (m, 1H), 4.09 (d, J=12.78 Hz, $H_5$', 1H), 3.88 (d, J=12.78 Hz, $H_5$", 1H), 3.09 (m, $H_2$', 1H), and 2.65 (m, $H_2$", 1H) ppm.

Example 4

Synthesis of 3'-O-azidomethyl-dT (9b)

The following describes exemplary synthesis steps for compounds shown in FIGS. 20.

A. Preparation of 3'-O-(methylthiomethyl)-5'-O-(tert-butyldimethylsilyl)-2'-deoxythymidine (6b)

2.0 g 5'-O-(tert-butyldimethylsilyl)-2'-deoxythymidine (5b) (5.6 mmol) was dissolved in a mixture consisting of 10.5 mL DMSO, 4.8 mL acetic acid, and 15.4 mL acetic anhydride and stirred for 48 h at room temperature. The mixture was then quenched by treating with a saturated $NaHCO_3$ solution and extracted with EtOAc (3×100 mL). The combined organic extract was then washed with a saturated solution of $NaHCO_3$ and dried over $Na_2SO_4$, concentrated under vacuum, and finally purified by silica gel column chromatography (Hex: EtOAc/7:3 to 1:1). The 3'-O-

(methylthiomethyl)-5'-O-(tert-butyldimethylsilyl)-2'-deoxythymidine (6b) was obtained as white powder in 75% yield (1.75 g, $R_f$=0.6, hex:EtQAc/1:1). HR-MS: Obs. m/z 417.1890, calcd. for $C_{18}H_{33}N_2O_5SSi$ 417.1879 $[M+H]^+$. $^1$H-NMR (CDCl$_3$): $\delta_H$ 8.16 (s, 1H), 7.48 (s, 1H), 6.28 (m, 1H), 4.62 (m, 2H), 4.46 (m, 1H). 4.10 (m, 1H), 3.78-3.90 (m, 2H), 2.39 (m, 1H), 2.14, 2.14 (s, 3H), 1.97 (m, 1H), 1.92 (s, 3H), 0.93 (s, 9H), and 0.13 (s, 3H) ppm.

B. Preparation of 3'-O-(azidomethyl)-2'-deoxythymidine (9b)

To 1.095 g 3'-O-(methylthiomethyl)-5'-O-(tert-butyldimethylsilyl)-2'-deoxythymidine (6b) (2.6 mmol) dissolved in 10 mL dry CH$_2$Cl$_2$ were added 1.33 mL cyclohexene and 284 µL SO$_2$Cl$_2$ (3.5 mmol) at 0° C. and stirred at the ice-cold temperature for 1.5 h. Then the flask temperature was brought to room temperature and transferred to a round bottom flask. The volatiles were removed by rotary evaporation followed by high vacuum pump. Then the crude sample was dissolved in 5 mL dry DMF and 926 mg NaN$_3$ (15.4 mmol) was added to it and stirred for 3 h at room temperature. The crude sample was dispersed in 50 mL distilled water and extracted with CH$_2$Cl$_2$ (3×50 mL), the organic extracts were combined and dried over Na$_2$SO$_4$ and concentrated by rotary evaporation. The crude sample was then dissolved in MeOH (5 mL) and treated with NH$_4$F (600 mg, 16.2 mmol) for 24 h at room temperature. Then reaction mixture was concentrated and partitioned between H$_2$O/CH$_2$Cl$_2$ and the combined organic extract was dried over Na$_2$SO$_4$, concentrated, and purified the product by silica gel column chromatography using Hex: EtOAc/1:1 to 2:5 resulting the final product (9b) as white powders (~550 mg, 71% yield in three steps, $R_f$=0.3, Hex: EtOAc/1:1.5). HR-MS: Observed m/z 298.1146, calcd for $C_{11}H_{16}O_5N_5$ 151$[M+H]^+$. $^1$H-NMR (CDCl$_3$): $\delta_H$ 8.30 (brs, 1H), 7.40 (s, 1H), 6.14 (t, J=6.8 Hz, 1H), 4.79-4.70 (m, 2H), 4.50 (m, 1H), 4.16 (m, 1H), 4.01-3.84 (m, 2H), 2.45 (m, 2H) and 1.95 (s, 3H) ppm.

Example 5

Synthesis of N$^4$-Benzoyl-3'-O-(azidomethyl)-dC (9c)

The following describes exemplary synthesis steps for compounds shown in FIG. 20.

A. Preparation of N$^4$-Benzoyl-3'-O-(methylthoimethyl)-5'-O-(tert-butyldimethylsilyl)-2'-deoxycytidine (6c)

3.5 g N$^4$-benzoyl-5'-O-tert-butyldimethylsilyl-2'-deoxycytidine (5c) (7.65 mmol) was dissolved in a mixture consisting of 14.7 mL DMSO, 6.7 mL acetic acid, and 21.59 mL acetic anhydride and stirred for 48 h at room temperature. During this period of time, a complete conversion to product was observed by TLC ($R_f$=0.4, EtOAc:hex/10:1). The mixture was then neutralized with a saturated NaHCO$_3$ solution and extracted with CH$_2$Cl$_2$ (3×100 mL). The combined organic extract was then washed with saturated solution of NaHCO$_3$ and dried over Na$_2$SO$_4$, and concentrated under vacuum. The product was then purified by silica gel column chromatography (EtOAc:hex/2:1 to 9:1) to N$^4$-benzoyl-3'-O-(methylthiomethyl)-5'-O-(tert-butyldimethylsilyl)-2'-deoxycytidine (6c) as white powder in 73% yield (2.9 g, $R_f$=6, EtOAe:hex/9:1). HR-MS: obs. m/z 506.2134, cald. for $C_{24}H_{36}O_5N_3SiS$ $[M+H]^+$. 506.2145. $^1$H-NMR (CDCl$_3$): $\delta_H$ 8.43 (d, J=7.1 Hz, 1H), 7.93 (m, 2H), 7.64 (m, 1H), 7.54 (m, 3H), 6.30 (m, 1H), 4.62 & 4.70 (2×d, J=11.59 Hz, 2H), 4.50 (m, 1H), 4.19 (m, 1H), 3.84 & 3.99 (2×dd, J=11.59 & 2.79 Hz, 2H), 2.72 (m, 1H), 2.21 (m, 1H), 2.14 (s, 3H), 0.99 (s, 9H), and 0.16 (s, 6H) ppm.

B. Preparation of N$^4$-Benzoyl-3'-O-(azidomethyl)-2'deoxycytidine (9c)

To 0.5580 g N$^4$-benzoyl-3'-O-(methylthiomethyl)-5'-O-(tert-butyldimethylsilyl)-2'-deoxycytidine (6c) (1.04 mmol) dissolved in 8 mL dry CH$_2$Cl$_2$ were added 0.56 mL cyclohaxene and 220 µL SO$_2$Cl$_2$ (2.7 mmol) at 0° C. and stirred at the ice-cold temperature for 1 h. During this time, the starting material converted to the chlorinated product as shown by the 3'-OH (Se) compound in the TLC. The volatiles were then removed under vacuum and resuspended in dry DMF (5 mL) and treated with NaN$_3$ (400 mg, 6.6 mmol) and stirred for 2 h at room temperature. The sample was then partitioned between water and CH$_2$Cl$_2$ and the organic extracts were combined and dried over Na$_2$SO$_4$ and concentrated under vacuum. The crude sample was then dissolved in MeOH (5 mL) and treated with NH$_4$F (600 mg, 16.2 mmol) for 20 h at room temperature. Then solvent was removed under vacuum and extracted with CH$_2$Cl$_2$ and the organic extract was then dried over Na$_2$SO$_4$ and concentrated under vacuum. The sample was then purified by silica gel column chromatography (Hex:EtOAc 1:4 to 1:10), and the product (9c) was obtained as white powdery substance (~200 mg, 50% yield in three steps, $R_f$=0.5, EtOAc:Hex/5:0.5). HR-MS: Obs. m/z 387.1408, calcd for $C_{17}H_{19}O_5N_6$ 387.1417 $[M+H]^+$. $^1$H-NMR (CDC$_3$): $\delta_H$ 8.30 (d, J=7.2 Hz, 1H), 7.93 (d, J=7.50 Hz, 1H), 7.66-7.51 (m, 5H), 6.18 (t, J=6.4 Hz, 1H), 4.81-4.68 (m, 2H), 4.52 (m, 1H), 4.25 (m, 1H), 4.08-3.88 (m, 2H), 2.69 (m, 1H), and 2.50 (m, 2H) ppm.

Example 6

Synthesis of N$^2$-isobutyryl-O$^6$-diphenylcarbamoyl-3'-O-azidomethyl-dG (14)

Figure 21:
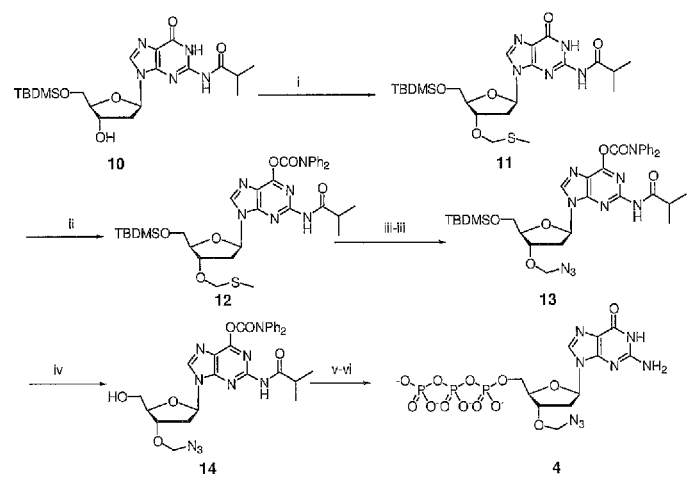
FIG. 21 shows synthesis of 3'-O-azidomethyl-dGTP where the steps denote treatment with (i) DMSO, AcOH, $Ac_2O$, 48 h; (ii) $Ph_2NCOCl$, DIEA, Pyridine 3 h; (iii) $SO_2Cl_2$, dry $CH_2Cl_2$, 1-2 h; (iii) $NaN_3$ in DMF, 3 h; (iv) $NH_4F$ in MeOH, 24 h; (v) $(MeO)_3PO$, $POCl_3$ then $(t-Bu_3NH)_3P_2O_7H$, TEAB, 1 h; (vi) $NH_4OH$.
Figure 22A:
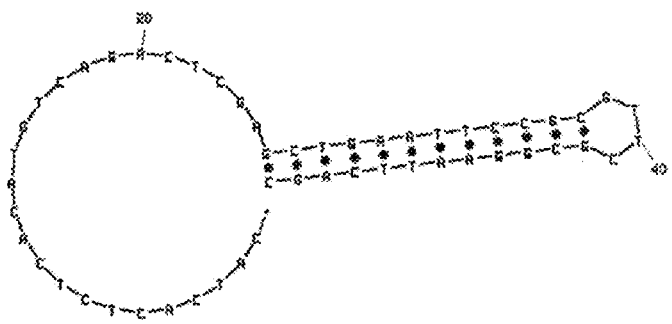
FIG. 22 shows synthetic DNA templates [SEQ ID NOs: 1-4] used in exemplary sequencing experiments.
Figure 22B:
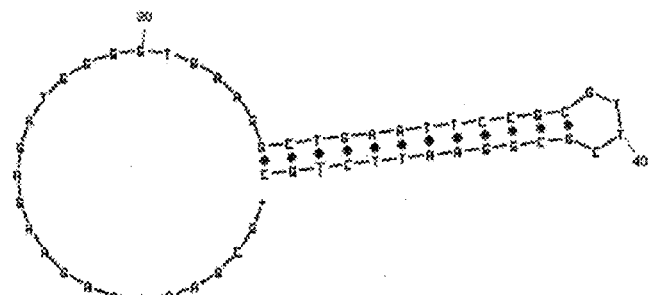
Figure 22C:
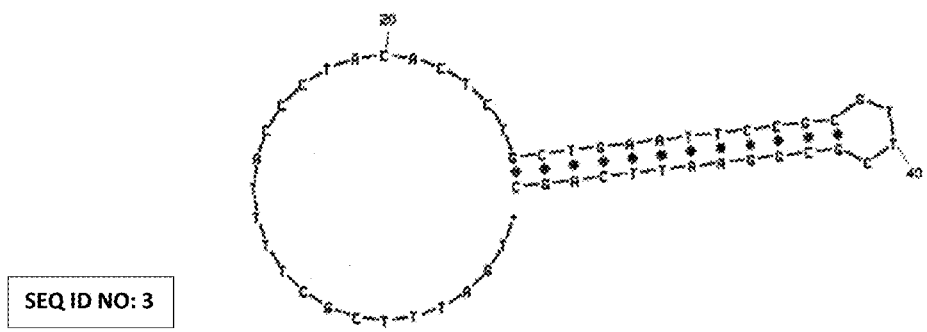
Figure 22D:
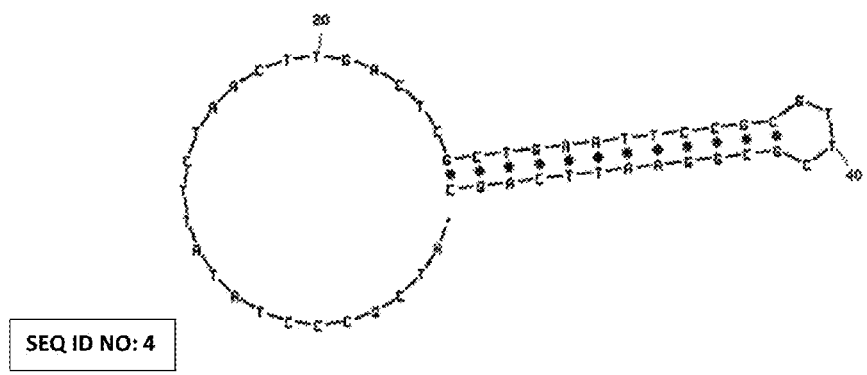
Figure 23:
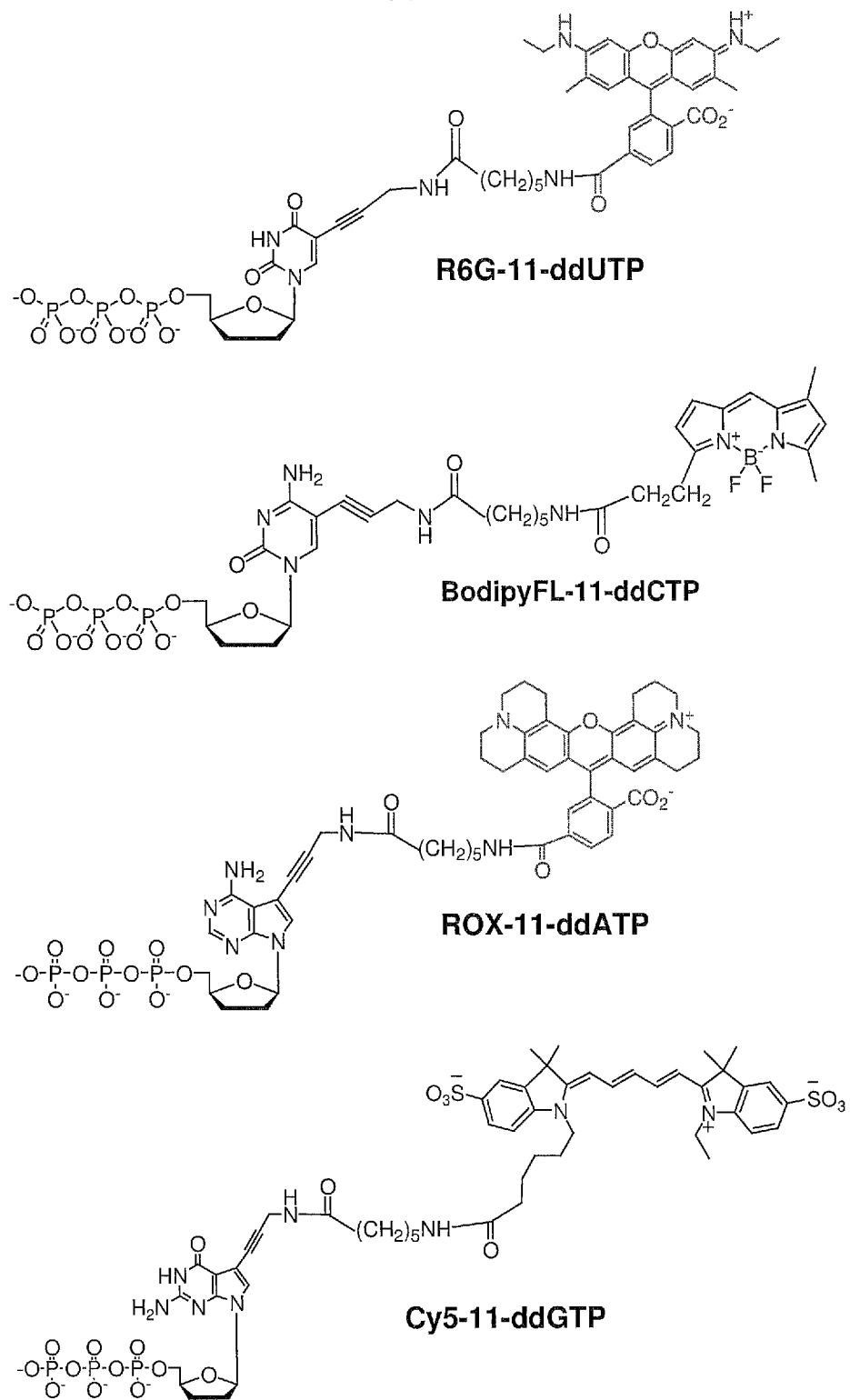
FIG. 23 shows the structures of exemplary labeled 2,3'-dideoxynucleotides used in the sequencing by synthesis.
Figure 24:
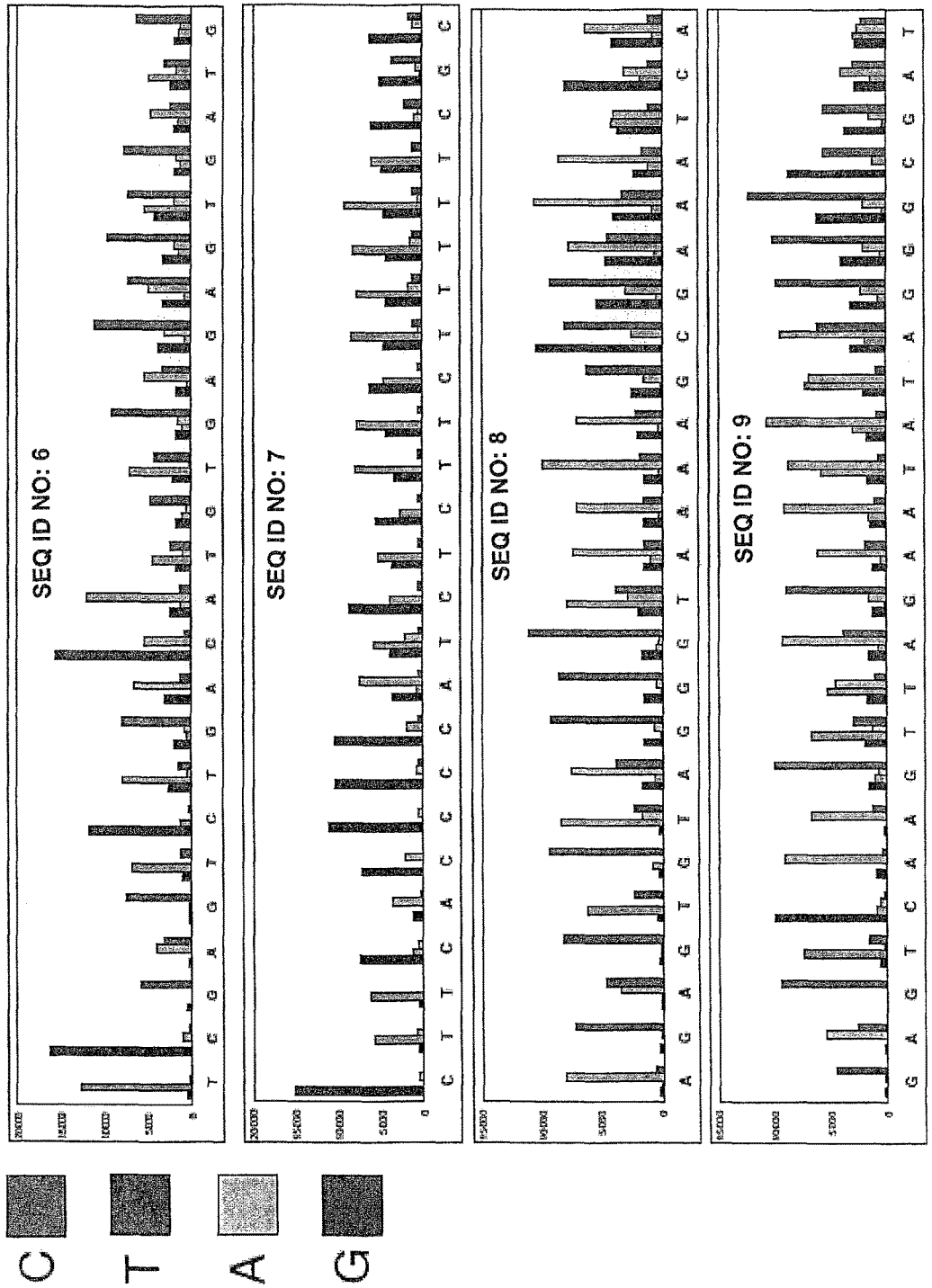
FIG. 24 shows sequencing results using four different 25 nt DNA templates.

The following describes exemplary synthesis steps for compounds shown in FIG. 21.

A. Preparation of N$^2$-isobutyryl-3'-O-(methylthoimethyl)-5'-O-(tert-butyldimethylsilyl)-2'-deoxyguanosine (11)

5 g of N$^2$-isobutyryl-5'-O-(tert-butyldimethylsilyl)-2'-deoxyguanosine (11.0 mmol) dissolved in 21 mL dry DMSO was treated with 10 mL acetic acid and 32 mL acetic anhydride, and stirred for 48 h at room temperature. The crude reaction mixture was then neutralized by adding a K$_2$CO$_3$ solution, and extracted with ethyl acetate (100×3 mL). The combined organic extract was then washed with saturated NaHCO$_3$ solution, dried over Na$_2$SO$_4$ and concentrated under vacuum. Then reaction mixture was purified by a silica gel column chromatography resulting the product 11 as white powder (3.9 g, 69% yield; $R_f$=0.35, CH$_2$Cl$_2$:MeOH/20:1). HR-MS: Obs. m/z 512.2344 cald. for $C_{22}H_{38}O_5SiS$ 512.2363 $[M+H]^+$. $^1$H-NMR (CDCl$_3$): $\delta_H$ 12.0 (s, 1H), 8.95 (brs, 1H), 8.09 (s, 1H), 6.24 (t, J=6.8 Hz, 1H), 4.73 (m, 2H), 4.66 (m, 1H), 4.16 (m, 1H), 3.81 (m, 2H), 2.76 (m, 1H), 2.59 (m, 1H), 2.54 (m, 1H), 2.21 (s, 3H), 1.29 (m, 6H), 0.91 (s, 9H), and 0.10 (s, 6H) ppm.

B. Synthesis of N²-isobutyryl-O⁶-diphenylcarbamoyl-3'-O-(methylthiomethyl)-5'-O-(tert-butyldimethylsilyl)-2'-deoxyguanosine (12)

To 1.0 g N²-isobutyryl-3'-O-(methylthimethyl)-5'-O-(tert-butyldimethylsilyl)-2'-deoxyguanosine (11, 1.95 mmol) dissolved in 22 mL dry pyridine were added diphenylcarbamoyl chloride (0.677 g, 2.92 mmol) and 1.02 mL N,N-diisopropylethylamine, and stirred at room temperature for 3 h under nitrogen atmosphere. The reaction mixture became dark red during this time. The solvent was removed under high vacuum, and product was then purified by silica gel column chromatography using EtOAc:hex/1:1 to 7:3 as mobile phase. The product 12 was isolated as yellowish powder (1.09 g, ~80% yield; $R_f$=0.7, EtOAc:hex (1:1)). HR-MS: Obs. m/z 707.3068 calcd. for $C_{35}H_{47}O_6N_6SiS$ 707.3047 [M+H]⁺. ¹H-NMR (CDCl₃): $\delta_H$ 8.25 (s, 1H), 7.94 (brs, 1H), 7.47-7.37 (m, 10H), 6.42 (m, 1H), 4.75 (m, 2H), 4.71 (m, 1H), 4.18 (m, 1H), 3.88-3.70 (m, 2H), 2.80 (m, 1H), 2.60 (m, 1H), 2.19 (s, 3H), 1.30 (d, J=7.2 Hz, 6H), 0.93 (s, 9H) and 0.14 (s, 6H) ppm.

C. Preparation of N²-isobutyryl-O⁶-diphenylcarbamoyl-3'-O-azidomethyl-2'-deoxyguanosine (14)

To 786 mg 12 (1.1 mmol) dissolved in 8 mL dry CH₂Cl₂ was treated with 0.56 mL cyclohexene and 180 μL SO₂Cl₂ (2.2 mmol) at 0° C. and stirred for 1.5 h at the same temperature. The solvent was then removed by rotary evaporation, and further dried under high vacuum for 10 minutes. The crude product was then dissolved in 5 mL dry DMF and reacted with 600 mg NaN₃ (10 mmol) at 0° C. and stirred at room temperature for 3 h. Reaction mixture was then partitioned H₂O/CH₂Cl₂, the combined organic extract was then dried over Na₂SO₄, and concentrated by rotary evaporation. The crude was then dissolved in 5 mL dry MeOH, treated with 500 mg NH₄F (13.5 mmol) at room temperature for more than 24 h. Then MeOH solvent was removed by rotary evaporation, and partitioned (H₂O/CH₂Cl₂). The combined organic part was dried over Na₂SO₄ and concentrated by rotary evaporation and purified by silica gel column chromatography resulting pure product of 14 as white powder (230 mg, ~36% yield in three steps; hex:EtOAc 1:1 to 1:5, ($R_f$=0.3, Hex:EtOAc/1:4). HR-MS: Obs. m/z 588.2343, calcd for $C_{28}H_{30}O_6N_9$ 588.2319 [M+H]⁺, ¹H-NMR (DFM-d₆): $\delta_H$ 8.64 (brs, 1H), 7.48-7.34 (m, 10H), 6.36 (t, J=7.0 Hz), 4.93 (m, 2H), 4.76 (m, 1H), 4.04 (m, 1H), 3.57 (m, 1H), 3.34 (m, 2H), 2.97 (m, 1H), 2.81 (m, 1H), and 1.10 (m, 6H).

Example 7

General Method for the Preparation of 3'-O-Azidomethyl-Dntps

The protected 3'-O-azidomethyl nucleoside (0.3 mmol) and proton sponge (75.8 mg; 0.35 mmol) were dried in a vacuum desiccator over P₂O₅ overnight before dissolving in trimethyl phosphate (0.60 mL). Then freshly distilled POCl₃ (33 μL, 0.35 mmol) was added drop-wise at 0° C. and the mixture was stirred at 0° C. for 2 h. Subsequently, a well-vortexed mixture of tributylammonium pyrophosphate (552 mg) and tributylamine (0.55 mL; 2.31 mmol) in anhydrous DMF (2.33 mL) was added in one potion at room temperature and stirred for 30 min, Triethyl ammonium bicarbonate solution (TEAB) (0.1 M, 15 mL, pH 8.0) was then added and the mixture was stirred for 1 h at room temperature. Then 15 mL of NH₄OH was added and stirred overnight at room temperature. The resulting mixture was concentrated in vacuo and the residue was diluted with 5 mL of water. The crude mixture was then purified with anion exchange chromatography on DEAE-Sephadex A-25 at 4° C. using a gradient of TEAB (pH 8.0; 0.1-1.0 M). Further purification by RF HPLC to give corresponding target as colorless syrup:

Example 8

3'-O-Azidomethyl Nucleotides Cleavage

The 3'-O-azidomethyl group cleavage can be accomplished with a variety of reducing agents such as phosphines. The cleavage agents that are particularly desirable are those that are soluble in aqueous media and do not cause any damage to the DNA. One particularly desirable agent is tri(carboethoxy)phosphine (TCEP).

The 3'-O-azidomethyl nucleotides can be separated from native nucleotides using RP HPLC. In the next experiment, the kinetics of the 3'-O-azidomethyl TTP cleavage was studied. For this purpose, a 1 mM solution of nucleotide was prepared in water and mixed with 50 mM solution of TCEP/400 mM of Tris at pH 8.0 and incubated at 55 deg C. for various periods of time. After the incubation, the reaction was stopped by mixing with 4 M NaOAc at pH=4.3 and an aliquot of reaction mixture (0.5 nmole of nucleotide) was injected and separated on the RP HPLC column. The integrated peak area was then plotted against time.

Example 9

Sequencing By Synthesis Using 3'-O-Azidomethyl Nucleotides

We established conditions for sequencing by synthesis on the surface using 3'-O-azidomethyl nucleotides. For this purpose we used variants of the 9 deg N polymerase that were developed specifically to incorporate 3'-O-azidomethyl nucleotides. For these sequencing experiments we were using synthetic DNA templates that encompass self priming moieties. Examples of these DNA templates and their secondary structures are shown in FIG. 22A-D.

These oligonucleotides carry a 5'-amino modification through which they are attached to assay surface. The surface constitutes any surface that is bio-compatible, has low fluorescent background and has functional groups on the surface which can be used to covalently attach the DNA. In the described case, pre-activated Codelink (from GE Healthcare) slides were used for this purpose. The solution of the oligonucleotides (50 uM) for spotting was prepared in 150 mM phosphate/bicarbonate spotting buffer (pH=7.5). The arrays were then spotted and incubated in the humid chamber at 25 deg C. overnight. After the incubation, the arrays were blocked by washing in the 1×TBST/2% BSA buffer, rinsed with nuclease free water and dried.

The sequencing was performed in a chambered slide (Grace Biolabs). In the experiment, each well was subjected to different number of cycles using the mixture of 3'-O-azidomethyl nucleotides with each extension cycle followed by a cleavage cycle. Extension cycle consisted of incubating the well with the solution containing: 3'-O-azidomethyl nucleotide mix—75 uM, 9 deg N polymerase mutant—250 ug/ml, 10 mM KCl, 10 mM (NH4)2SO4, 20 mM Tris-HCl, 4 mM MnSO4, 0.1% Triton-X-100, 0.1% acetylated BSA, pH 8.8. The incubation was carried out at 65 deg C. for 20 minutes. After the incubation the wells were washed with Thermopol II buffer 3× and then subjected to cleavage with TCEP (100 mM) in 400 mM Tris-HCl (pH=8.5) at 65 deg C. for 15 minutes. After the cleavage the wells were washed with the extension reaction buffer (3×) and subjected to the next extension reaction. The wells were read out with final readout mixture consisting of: 2,3'-dideoxynucleotide mix (labeled)—2 μM, Therminator II polymerase—250 μg/ml, 10 mM KCl, 10 mM (NH4)2SO$_4$, 20 mM Tris-HCl, 2 mM MnSO$_4$, 0.1% Triton-X-10. The structures of these nucleotides are presented in FIG. 23. After labeling cycle the slide was washed with wash/block buffer (5×SSC, 0.1% Tween, 2% BSA), rinsed with water and dried before imaging. Each well was imaged using a prototype sequencing instrument and bases were then called based on the relative intensity of the observed signal. The result of the experiment is presented in FIG. 24.

Example 10

Synthesis 2'-Fluoro, 3'-O-Azidomethyl Nucleotides

Figure 25:
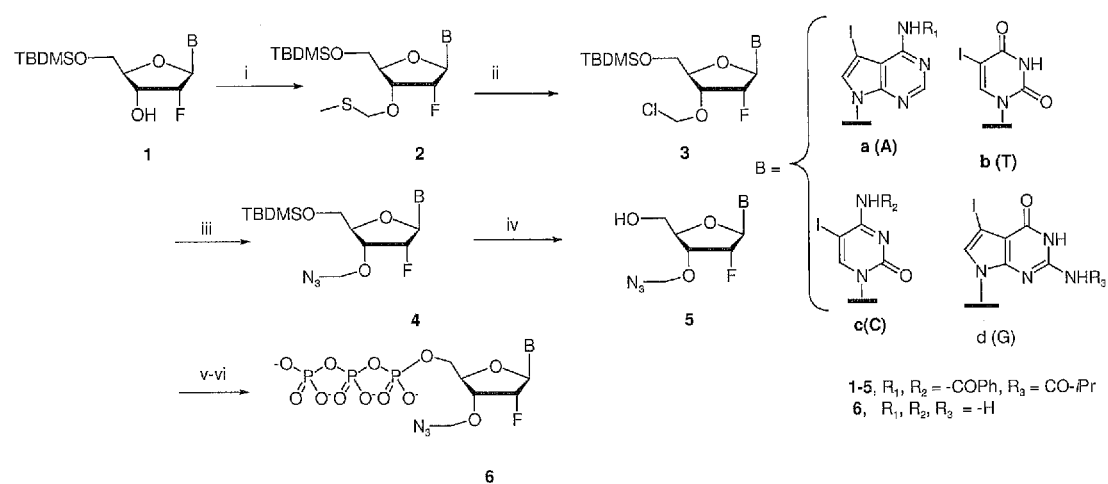
FIG. 25 shows synthesis steps for 2'-fluoro-3'-O-azidomethyl-dNTPs, where the steps comprise the following exemplary conditions (i) DMSO, AcOH, $Ac_2O$, 48 h; (ii) $SO_2Cl_2$, dry $CH_2Cl_2$, 1-2 h; (iii) $NaN_3$ in DMF, 3 h; (iv) $NH_4F$ in MeOH, 16-20 h; (v) $(MeO)_3PO$, $POCl_3$ then $(t-Bu_3NH)_4P_2O_7$, TEAB, 1 h; vi) $NH_4OH$.

The synthesis of 2'-fluoro-3'-O-azidomethyl-dNTPs is described in FIG. 25. Briefly, reaction of 5'-O-TBDMS-2'-fluoro-2-deoxynucleosides (1) with a mixture of DMSO, acetic acid, and acetic anhydride installed the 3'-O-methylthiomethyl group (3'-O-MTMs 2), which upon treatment with SO$_2$Cl$_2$ converted to activated 3'-O—CH$_2$Cl (3). The 2'-fluoro-3'-O—CH$_2$Cl-2'-deoxynucleoside (3) is then treated with NaN$_3$ in dry DMF without purification to convert the 3'-O—CH$_2$Cl to 3'-O—CH$_2$N$_3$ (4). 2'-fluoro-3'-O-azidomethyl-2'-deoxynucleosides of A, T, and C (5a-5c) can be obtained in good yield after deprotection of the 5'-O-TBBMS group as described in FIG. 25. In case of 2'-fluoro-3'-O-azidomethyl-2'-deoxybuanosine (G, 5d), the O$^6$— group is protected by diphenycarbamoyl group to increase yield. Finally, the respective nucleosides are phosphorylated using phosphorous oxychloride followed by tetrabutylammonium pyrophosphate in the presence of proton sponge (1,8-dimethylaminonaphthalene) and converted to their respective triphosphates (6).

Example 11

Synthesis of 2'-Fluoro, 3'-O-Azidomethyl Propargylamino Nucleotides

Figure 26:
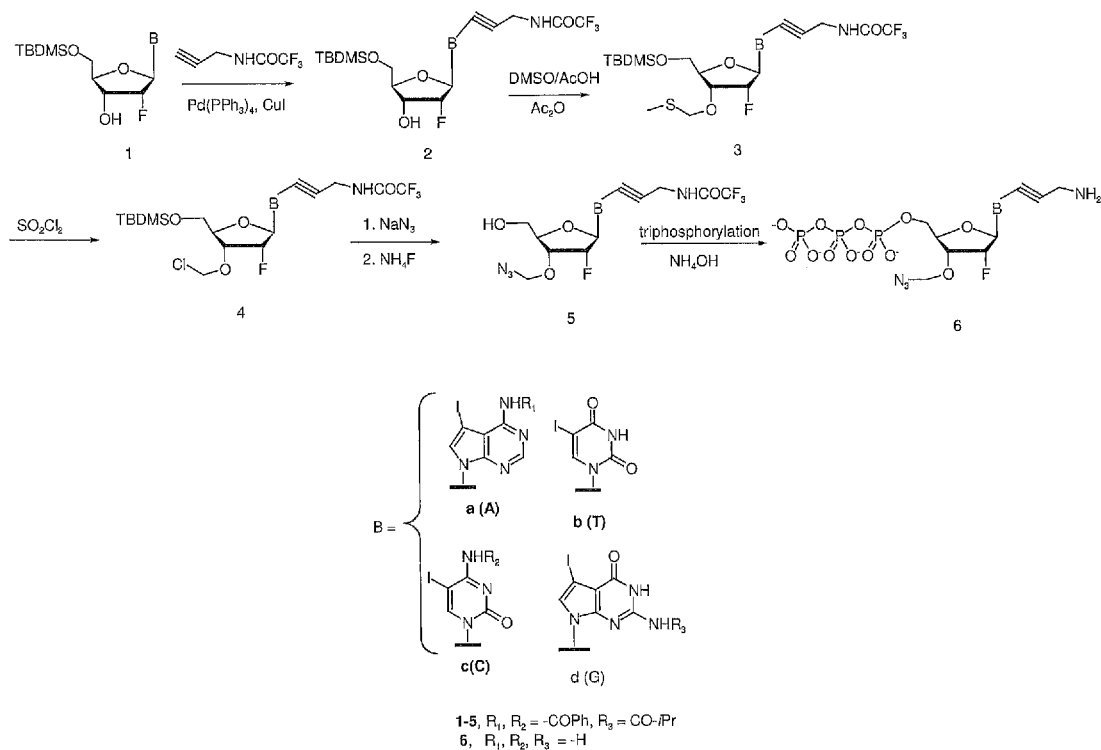
FIG. 26 shows synthesis steps for 2'-fluoro-3'-O-azidomethyl-(propargylamino)-dNTP synthesis.

Synthesis of 2'-fluoro-3'-O-azidomethyl-(propargylamino)-dNTPs is described in FIG. 26. Briefly, reaction of 5'-O-TBDMS-2'-fluoro-(5/7-iodo*)-2'-deoxynucleosides (1) with a mixture of N-trifluoroacetyl-propargylamine, tetrakis (triphenylphosphine) palladium (0) and CuI resulted in the formation of 5/7-propargylamido substituted nucleosides (2). In the next step the mixture of DMSO, acetic acid, and acetic anhydride installed the 3'-O-methylthiomethyl group (3'-O-MTM, 3), which upon treatment with SO$_2$Cl$_2$ converted to activated 3'-O—CH$_2$Cl (4). The 2'-fluoro-3'-O—CH$_2$Cl-5/7-propargylamido-2'-deoxynucleosides (4) were then treated with NaN$_3$ in dry DMF without purification to convert the 3'-O—CH$_2$Cl to 3'-O—CH$_2$N$_3$. (5) 2'-fluoro-3'-O-azidomethyl-(propargylamino)-2'-deoxynucleosides of A, T, and C (5a-5c) can be obtained in good yield after deprotection of the 5'-O-TBDMS group as described in FIG. 26. In case of 2'-fluoro-3'-O-azidomethyl-2'-deoxyguanosine (G, 5d), the O$^6$— group is protected by diphenycarbamoyl group to increase yield. *5-iodo, 2'-fluoro-2'-deoxy purines and 7-iodo-7-deaza-2'-fluoro-2'-deoxy pyrimidines were used as starting material. The synthesis of these compounds is well known to those skilled in the art.

Example 12

Spectral Crosstalk Calibration

Figure 32A:
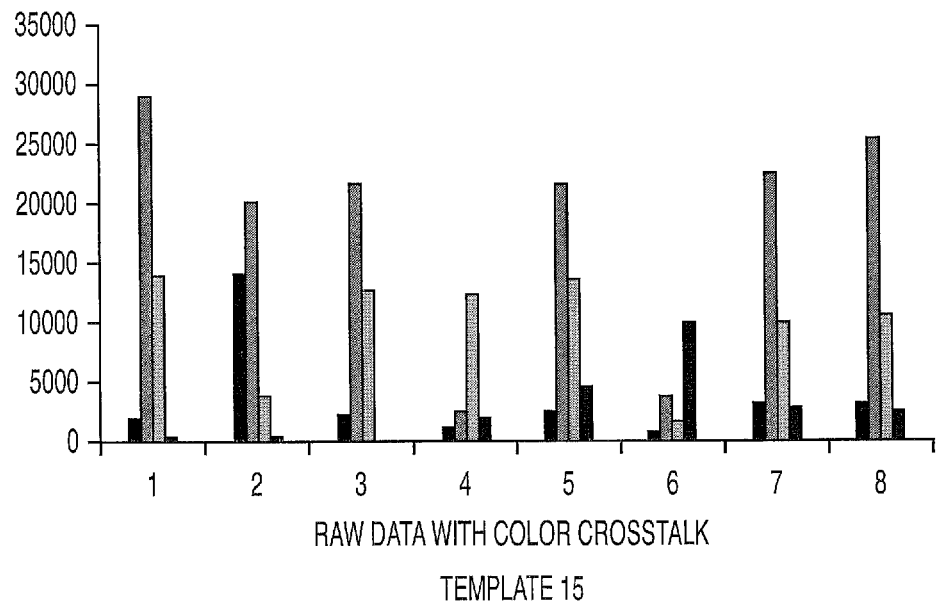
FIG. 32A-B shows sequencing by synthesis probe intensity in four channels (blue, green, yellow, and red) for a spot on a chip.
Figure 32B:
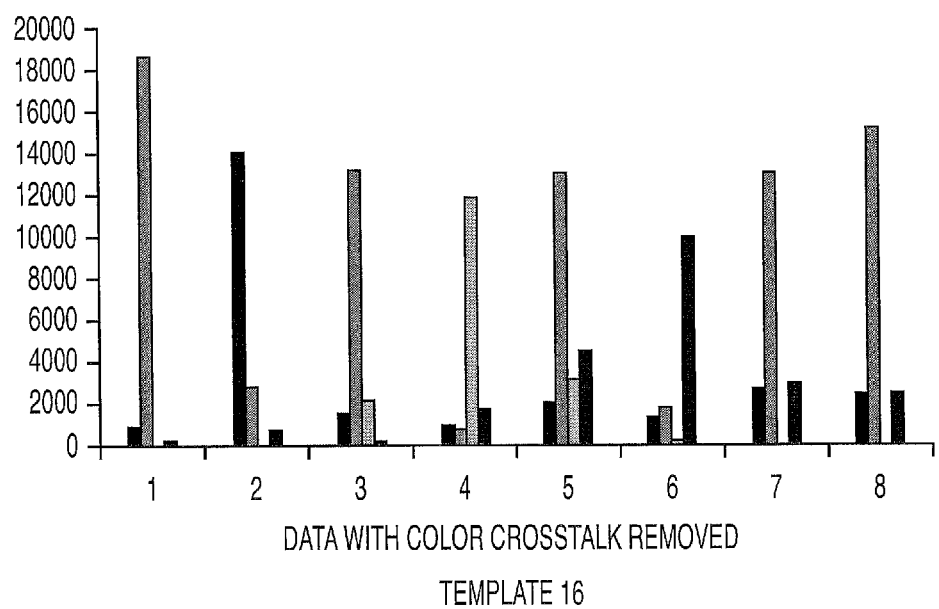

We calibrated the four color detection system of the above described exemplary SBS device using a chip spotted with four separate dyes, one in each of four spots. We then made measurements of the chip in all four channels, calculated the spectral crosstalk factors and constructed the K and K$^{-1}$ matrices. FIG. 32A-B shows the effect of applying the spectral crosstalk calibration matrix K−1 to raw sequencing data. The data demonstrates that the second base in the sequence would be miscalled as green were the spectral crosstalk calibration not performed.

Example 13

Re-Phasing Sequencing by Synthesis Data

As discussed above, dephasing of sequence data is cumulative and can potentially be significant with longer read lengths. We applied the lead/lag compensation described above to both a 16-base and 25-base sequences containing an AGCT repeat. The results are shown in FIGS. 33A-B and 34A-B. FIG. 33A shows the original data captured by the fluorescent detection system and FIG. 33B shows the data after being multiplied by the lead/lag compensation matrix with a lead parameter of 4.5% and a lag parameter of 1%. The relatively high lead parameter was probably due to native nucleotide contamination in the polymerase preparation. FIG. 33A-B illustrates how the compensation helps to correct miscalls. For example, bases at locations 11, 13 and 15 would be a miscall in the original dephased data, but are correctly called (as are all the other bases) in the rephased data. For the 25-base read in FIG. 34A-B, the lead and lag parameters were 1.2% and 1.5% respectively. Although the lead and lag for this sample were not large enough to create miscalls in the original data (FIG. 34A), the lead/lag correction does make the correct base a stronger signal compared to the other colors (FIG. 34B). While in both corrected sequences (FIGS. 33B and 27B), the matrix multiplication produces some negative values, these are probably due to noise, and may be ignored as long as they are small values. FIG. 34A-B shows that we were able to generate data with high fidelity out to 25 bases.

Example 14

Sequencing by Synthesis Data: Extra Washing

In this example, additional washing was done in an attempt to completely remove the cleaving agent prior to the next cycle in sequencing by synthesis. Interestingly, increased washing cycles after cleavage step have only minimal effect on the sequencing performance, as illustrated in the Table below.

Rephased Data

| | 25 nt Templates | | 35 nt Templates | | All Templates | |
| | | | | | % Correct | |
| Washes | Lead | Lag | Lead | Lag | Calls | Qa* |
|---|---|---|---|---|---|---|
| 24 | 2.56% | 1.69% | 1.75% | 1.12% | 92.0% | 0.822 |
| 48 | 1.55% | 2.32% | 1.20% | 1.80% | 96.0% | 0.862 |
| 100 | 1.40% | 2.80% | 095% | 1.65% | 95.5% | 0.826 |

*Qa = Intensity of the correct base signal/intensity of the second highest signal The metric used to measure the dephasing process is the lead percentage derived empirically to compensate for the lead observed in the run. Only at very high wash cycles (i.e. too many washes to be practical) can one improve the base calling accuracy.

Example 15

Sequencing by Synthesis Data: Using a Scavenger

In this example, scavengers were used in an attempt to inhibit any remaining cleaving agent prior to the next cycle in sequencing by synthesis. As noted above, such compounds can be included in the solutions used for sequencing by synthesis (or in a separate additional solution if desired). In this example, the suitable operating concentration for the scavenger in the Extend A/B solutions was explored. Two different scavengers were used.

A. Cystamine Scavenger

3'-O-azidomethyl nucleotides labeled with dyes on a cleavable disulfide linker were used. A range of scavenger concentrations were tested to determine which concentration is acceptable by the polymerase. The table below shows lead and lag values, and percentage of correct calls for the 3'-O-azidomethyl/disulfide chemistry in the absence and in the presence of a first scavenger (cystamine@1 mM).

| | AVG Lead [%] | AVG Lag [%] | Correct calls [%] |
|---|---|---|---|
| NO SCAVENGER | 2.0 | 3.1 | 93.7 |
| CYSTAMINE SCAVENGER | 1.1 | 1.9 | 98.7 |

Figure 38:
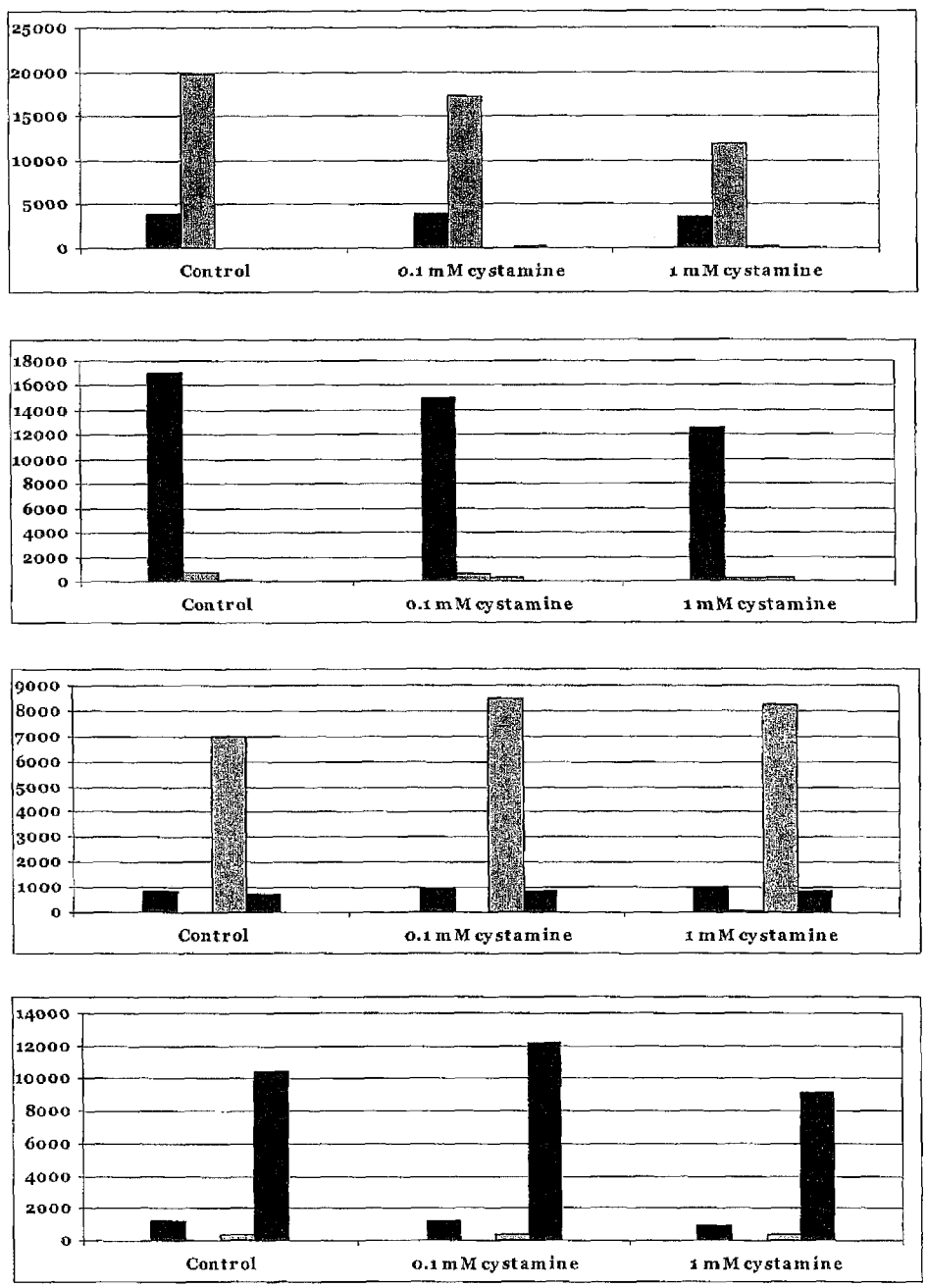
FIG. 38 shows detection of incorporated nucleotides in an extension reaction done in the presence of a first scavenger (cystamine).

It is clear from the data in the table that the use of a scavenger can improve the accuracy of base calling and reduce lead and lag. Importantly, extension reactions performed in the absence and in the presence of this disulfide based scavenger, cystamine, showed the additive does not significantly interfere with the extension reaction (FIG. 38).

B. ATA Scavenger

Figure 39:
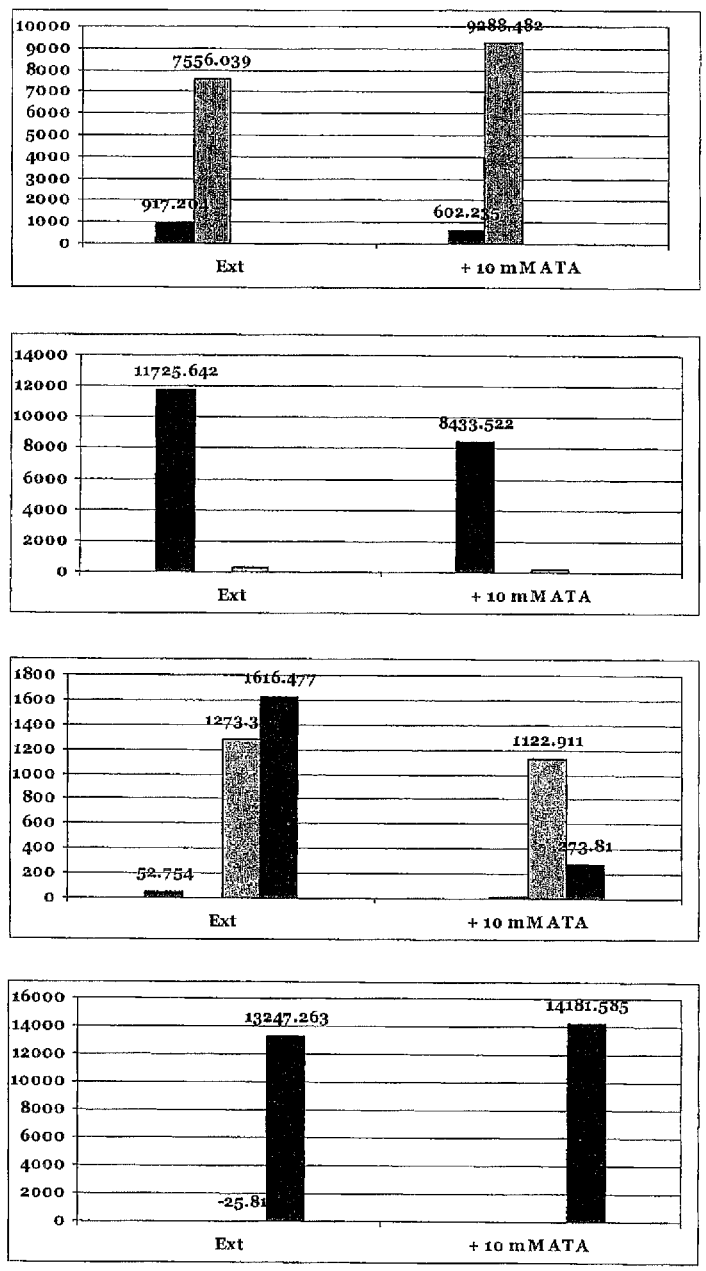
FIG. 39 shows detection of incorporated nucleotides in an extension reaction done in the presence of a second scavenger (ATA).

A second scavenger was also tested, i.e. the azido based scavenger, ATA: (11-Azido-3,6,9-trioxaundecan-1-amine). Extension reactions performed in the absence and in the presence of this azido based scavenger. Nucleotides with 3'-O-azidomethyl groups and with azido based cleavable linkers were used. The results (FIG. 39) show that the additive does not significantly interfere with the extension reaction.

Example 16

Synthesis of Disulfide-Dye Labeled 3'-O-Azidomethyl Nucleotide

Figure 40:
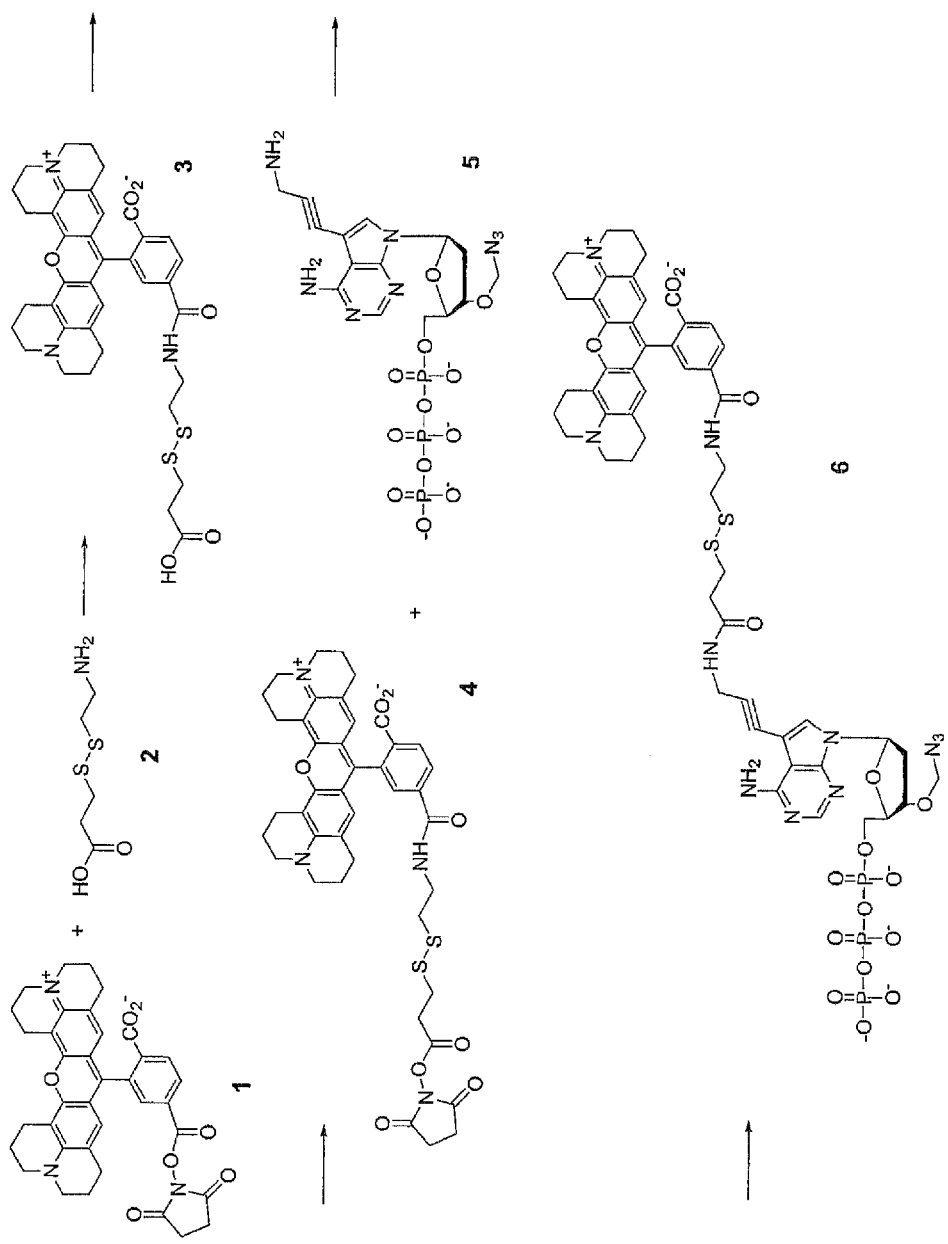
FIG. 40 is a schematic showing one embodiment for the synthesis of 3'-O-azidomethyl, 7-propargylamido-[3-((2-amidoethyl)dithio)propionamido]-6-carboxy-X-rhodamine deoxyadenosine triphosphate.
Figure 41A:
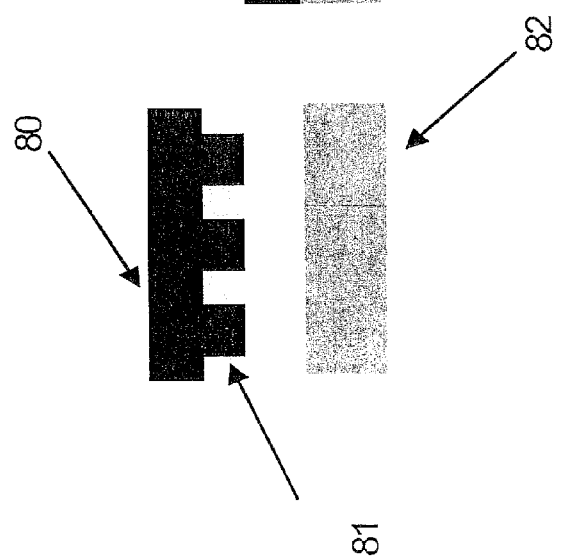
FIG. 41A-D is a schematic showing one embodiment of a hot embossing technique for making slide (or chips) with indentations (which can receive millions to billions of microbeads comprising nucleic acid).
Figure 41B:
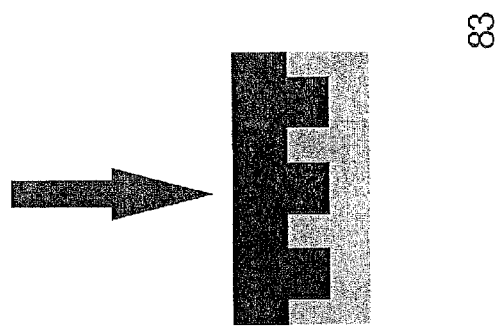
Figure 41C:
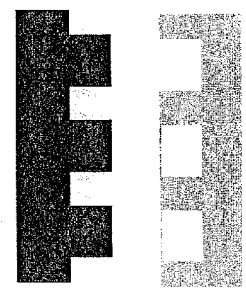
Figure 41D:
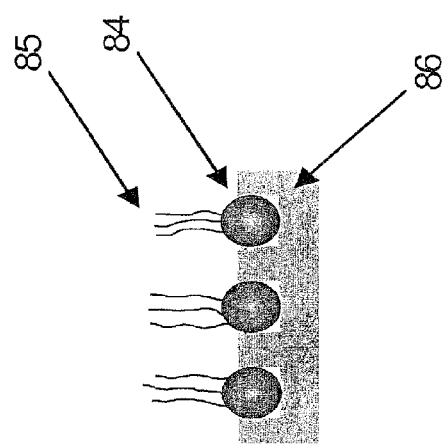

In this example, a method is described for synthesizing a nucleotide analogue containing an azidomethyl group on the 3"-OH and a label attached via a disulfide linker (which is cleavable). The scheme is shown in FIG. 40. Preparation of the linker buffer solution: 11 mg of 3-((2-aminoethyl)dithio) propionic acid hydrochloride (Prod #22101 from Pierce Biotech company, 2) was dissolved in 100 µl of 0.1 M sodium bicarbonate and 900 µl of acetonitrile. 14 µl of triethylamine was added. To a solution of 6-carboxy-X-rhodamine, succinimidyl ester (6-ROX SE, cat. # C6126, Invitrogen, 1) (158 µl L, 25 mM, 3.96 µmol) in DMF was added the above linker solution (500 µl, 50 mM, 25.0 µmol). The reaction mixture was stirred overnight at room temperature and then 800 µl of TEAB buffer (50 mM, pH 8) was added. The mixture was purified by HPLC and concentrated to give 0.51 µmol of product 3, HPLC method: A, 50 mM triethylammonium bicarbonate (TEAB) buffer, pH=8.0; B, acetonitrile and eluted with a linear gradient of 0-70% B over 35 minutes and at a flow rate of 2 ml/min. The column used was NoaPak C18, 8×100 mm. Retention time for product is 20.5 min. Retention time for hydrolysis of starting material is 18.2 min.

To the above linker-dye conjugate product 3 (0.51 µmol) in 300 µl of DMF was added a solution of 2,6-dimethylaminopyridine (DMAP) (25 mM, 31 µl, 0.77 µmol) and a solution of N,N'-disuccinimidyl carbonate (DSC) (25 mM, 31 µl, 0.77 µmol). The reaction mixture was stirred for one hour at room temperature. 7-propargylamino, 3'-O-azidomethyl-dATP 5 (1.5 µmol) was dissolved in 300 µl of water and 40 µl of tri-n-butylamine was added. All solvents were removed under vacuum and the residue dissolved in 300 µl of DMF. This solution was then added to the activated linker-dye conjugate 4 and the mixture was stirred overnight. The reaction mixture was diluted with 800 µl of TEAB buffer (50 mM, pH 8), purified by HPLC and concentrated. 198 nmol of product 6 was obtained (Retention time for product is 18.5 min).

Example 17

Hot Embossing: Millions to Billions of Beads on Slides or Chips

In one embodiment, the present invention contemplates such microspheres or beads disposed at high density into microwells or indentations on a surface. It is not intended that the present invention be limited by the nature of the surface or the method of fabrication. Nonetheless, in one embodiment, the present invention contemplates methods of fabrication to generate beads on slides at high density.

In one preferred embodiment, the method relies on the use of a hot embossing technique as schematically shown in FIG. 41A-D. Briefly, the process employs a stamp (80) having projections (81) that will create desired features (83) of desired dimensions when pressed into the polymer (82). The pressing step (B) is typically done with heat and pressure. Thereafter, the stamp is removed and the polymer is cooled (step C). Finally (step D), microspheres (84) containing biomolecules (85) are loaded into the microwells (86). In another embodiment, the method relies on the use of injection molding technique.

It is not intended that the present invention be limited by the nature of the polymer used in performing the hot embossing or molding process. A variety of polymers can be used including but not limited to: PMMA (polymethyl methacrylate), COP (cycloolefine polymer), and COC (cycloolefine copolymer). In the case of polymers that lack natural functional groups on the surface these groups can be grafted on the surface by performing ozonation, oxidation, corona discharge treatment, surface plasma or UV treatment or combination thereof. These fabrication methods allow one to generate substrates with varying features/wells density. Using standard size microscope slides casted out of PMMA or COP polymers one can create wells with 20 um, 5 um, and 1 um diameters. The slides with approximately 5 um features (e.g. between 4.8 um and 5.3 um) contain about 40 million microwells per slide, while the 1 um feature slide contains about 1 billion features per slide. With the biomolecule-containing microspheres deposited within the microwells, a single slide with such features permits a variety of high throughput, robust assays (e.g. sequencing by synthesis, hybridization, etc.). Nucleic acid fragments representing a large portion of a genome (e.g. human genome) or even an entire genome can be placed on a single slide or handful of slides, and then assayed sequentially or simultaneously.

Example 18

Sequencing: Changing the Spacer Arm Groups or Charge

Figure 42:
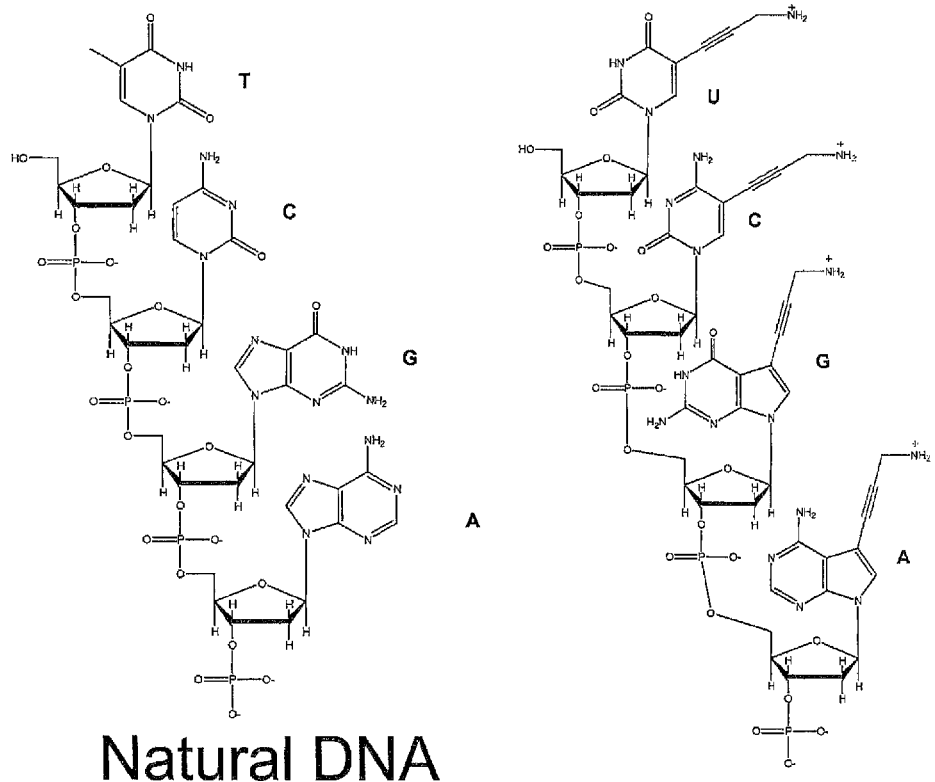
FIG. 42 is a schematic comparing the structure of natural DNA with DNA that was labeled with cleavable terminating nucleotides and then the label was removed. In this particular schematic, the example shows propargylamino derivatives.

When performing sequencing by synthesis process one needs to use labeled nucleotides to be able to read the signal. In most cases these labeled nucleotides after cleavage result in structures that is not of the native nucleotide. For example, if one uses only labeled nucleotides the DNA structure after cleavage of the dye looks like one shown in FIG. 42 (right side). As can be seen, the spacer arm used to attach the dye to the base still remains attached.

Figure 43:
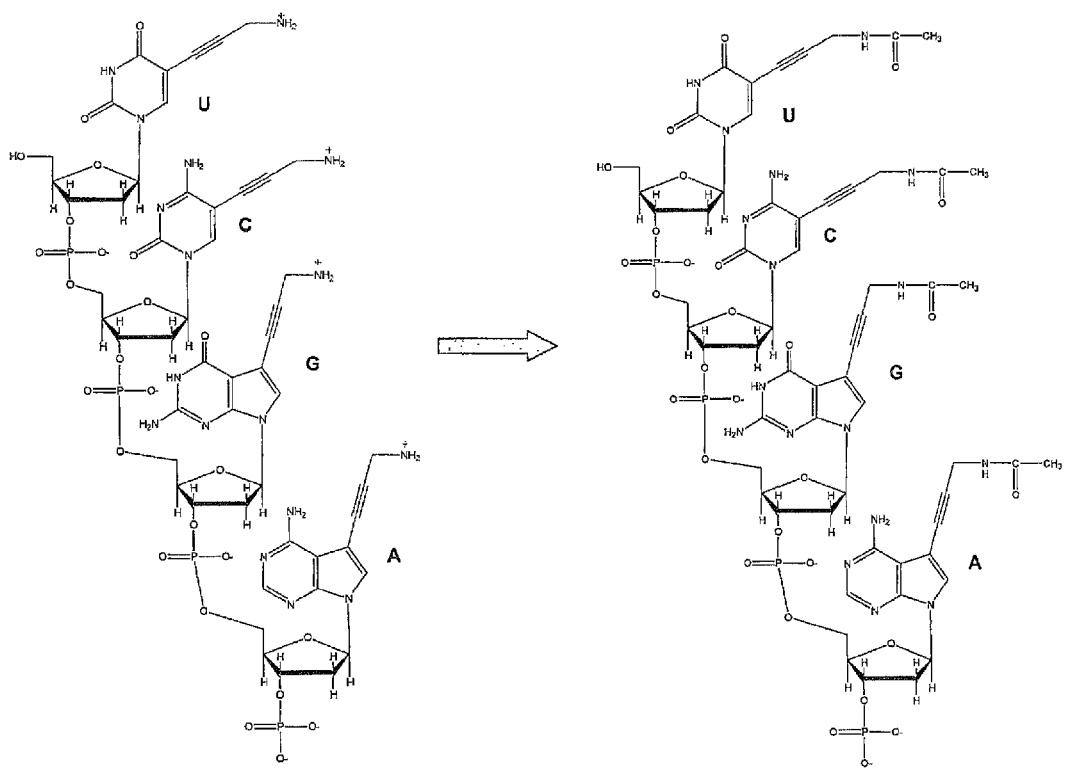
FIG. 43 is a schematic showing a capping step to neutralize the reactive groups after dye cleavage. For amines, one example that could be used is acetylation (such as acetic acid NHS ester); for the thiols (SH) N-methyl-maleimide or iodoacetamide can be used.
Figure 44:
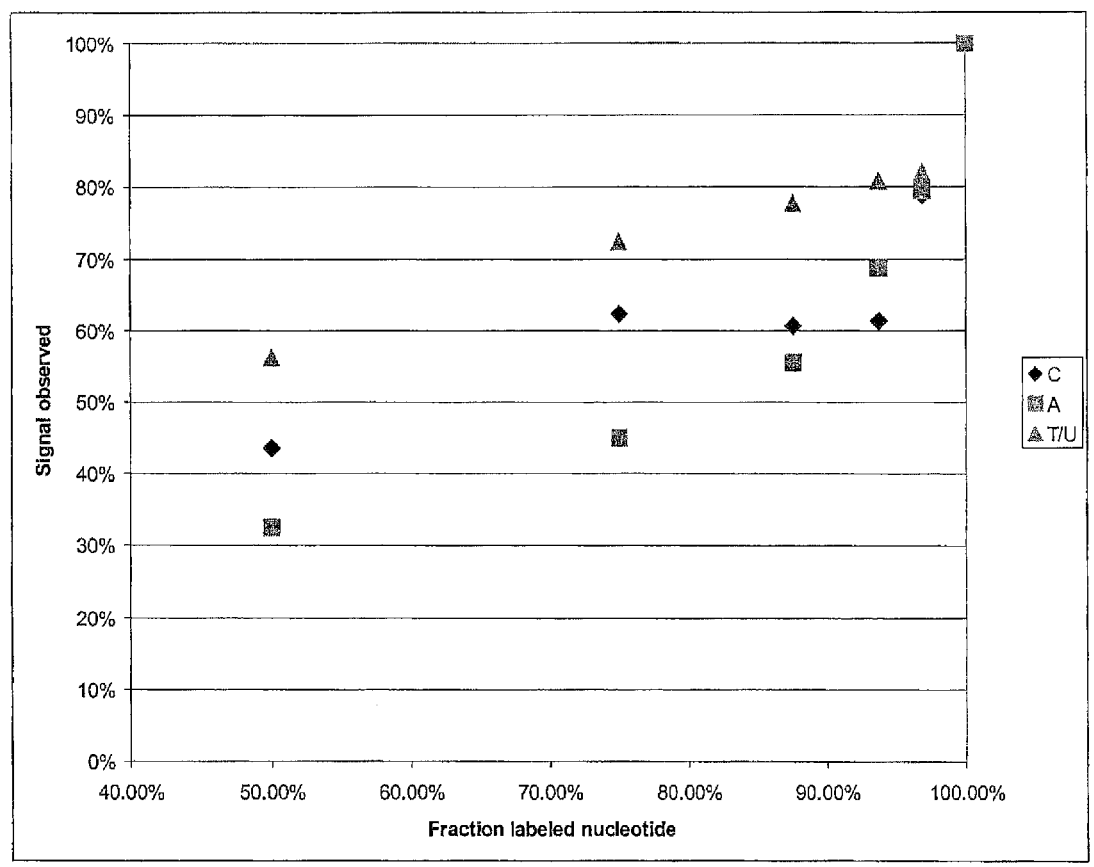
FIG. 44 shows the fluorescence signal from incorporated nucleotide analogues observed as a function of the composition of the extension mixture. In this case labeled nucleotides (3'-O-allyl) were supplemented with up to 1 equivalent of non-labeled terminators (also 3'-O-allyl). The extension was performed and the resulting signal measured. The response is different for different nucleotides tested and is a function of polymerase bias.
Figure 45A:
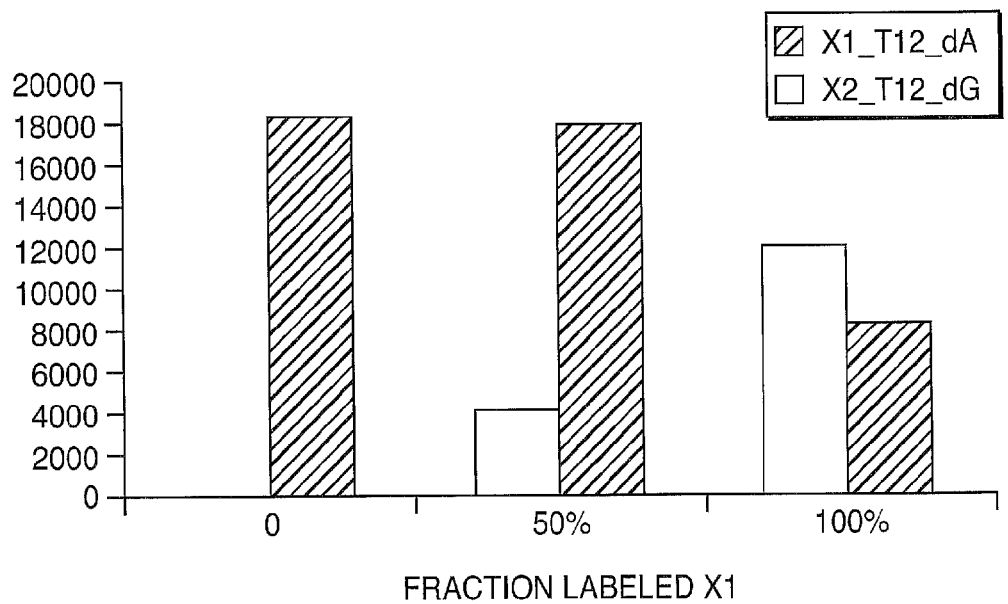
FIG. 45A-D shows the results for two subsequent extensions performed on 4 different DNA templates (FIG. 45A, 45B, 45C, 45D). For extension 1, various amounts of labeled reversible terminating nucleotides were used (0, 50% and 100%). After cleavage, second extension was performed and the resulting signals were measured (bars on the right in each set). As can be seen the use of 100% labeled nucleotides in cycle 1 reduces the signal in subsequent cycle to by 50% compared to non-labeled reversible terminators.
Figure 45B:
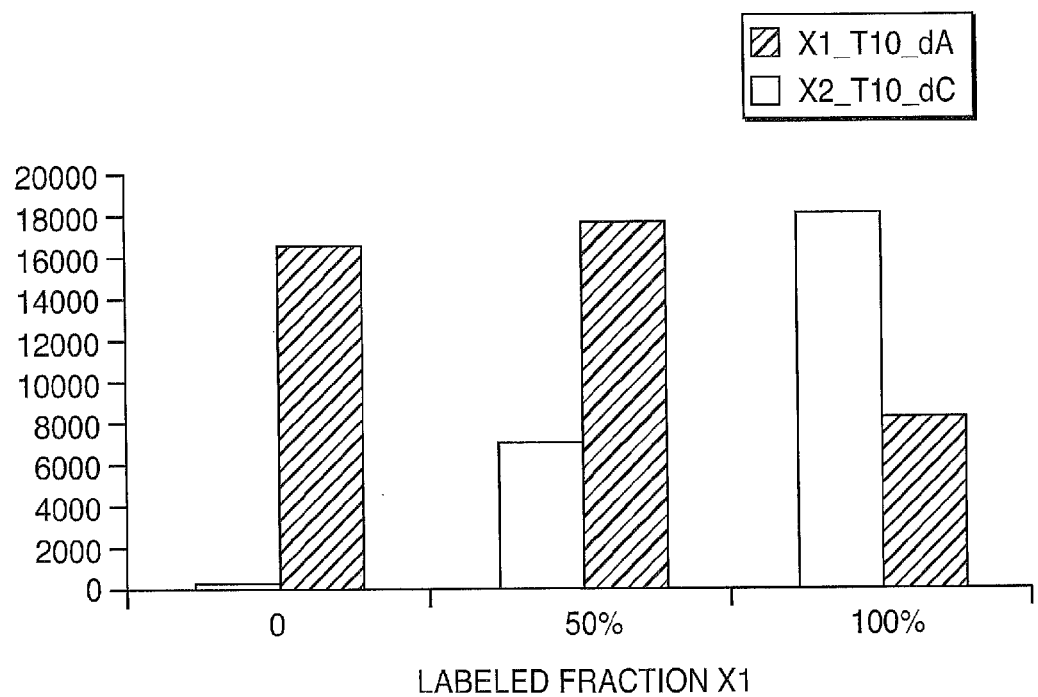
Figure 45C:
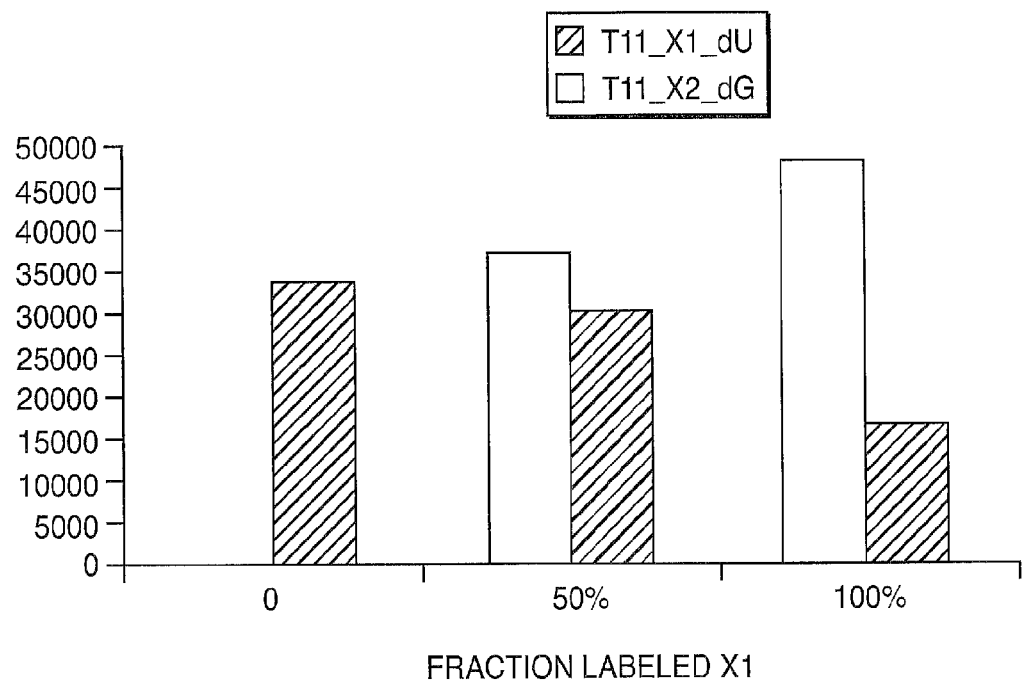
Figure 45D:
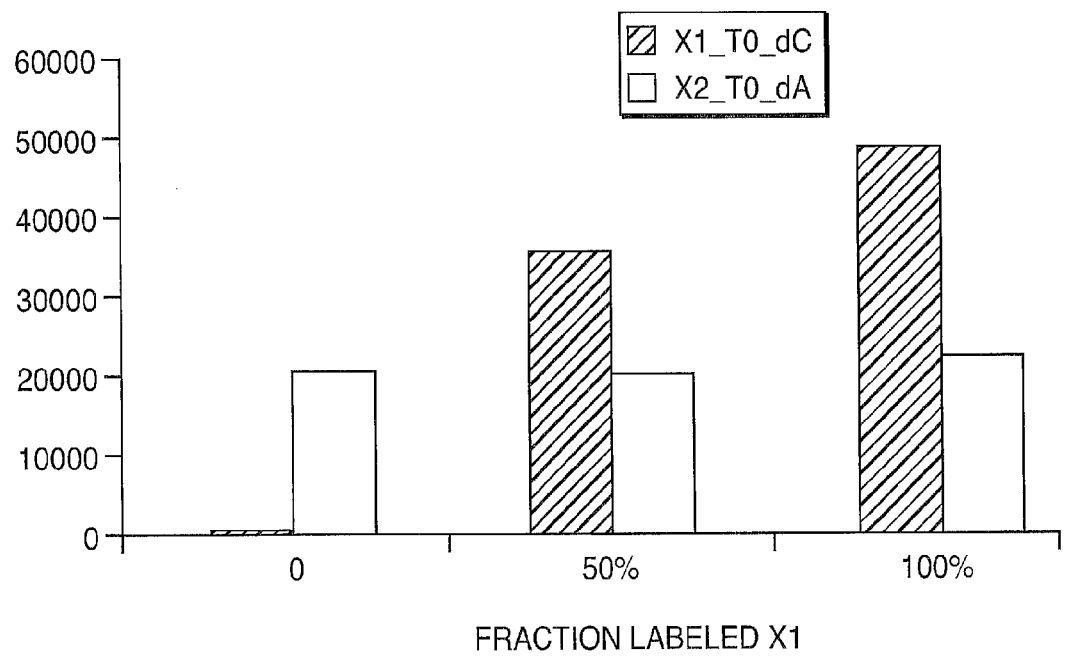
Figure 46:
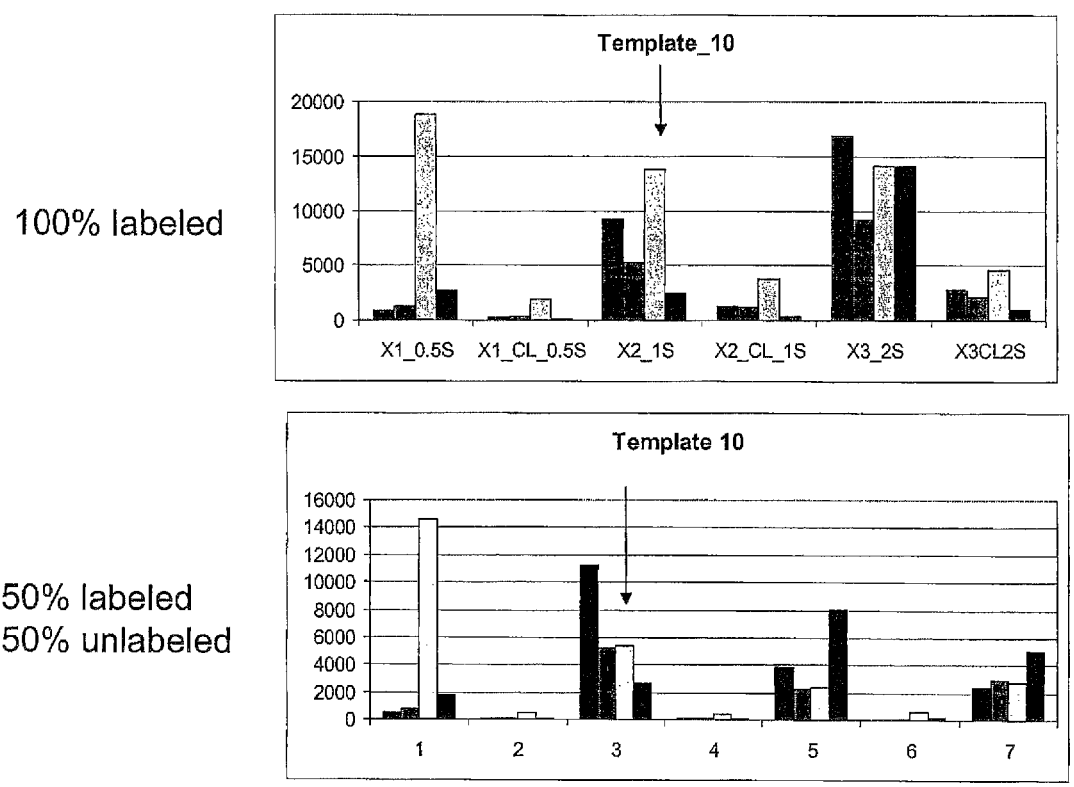
FIG. 46 shows that improvements in sequencing performance can be achieved with a mixture of labeled/unlabeled nucleotides. Using such a nucleotide mixture results in correct base calls.

In some cases the spacer also carries a charge, such as for example when propargylamino nucleotides are used. In the case of disulfide bonds what remains after cleavage is the spacer arm with thiol (SH) group attached. The presence of these spacers and groups may affect the ability of the sequencing polymerases to incorporate the subsequent nucleotide. One approach to minimize or eliminate this undesirable effect is to change the reactivity of the spacer arm groups or their charge by performing a chemical "capping" step, where specific reagent is added to react only with groups on the spacer arm. This is shown schematically in FIG. 43.

Example 19

Sequencing by Synthesis Data: Using Labeled and Unlabeled Nucleotides

As noted previously, the presence of the linkers, spacers and groups on nucleotides may affect the ability of the sequencing polymerases to incorporate the subsequent nucleotide. One approach to minimize or eliminate this undesirable effect is to reduce the amount of labeled nucleotides incorporated in the template. Reducing the amount of labeled nucleotides that are incorporated can be accomplished by reducing the concentration of labeled nucleotides in the extension solution, and/or mixing labeled nucleotides (reversible terminators) with non-labeled reversibly terminating nucleotides. In contrast to labeled nucleotides, non-labeled reversible terminator nucleotides after cleavage convert to native nucleotide.

The effect of reducing the concentration of labeled nucleotides can be best observed by measuring the ability of polymerase to incorporate the subsequent nucleotides efficiently and with high fidelity. This is shown in FIGS. 44,45A-D and 46.

Figure 47:
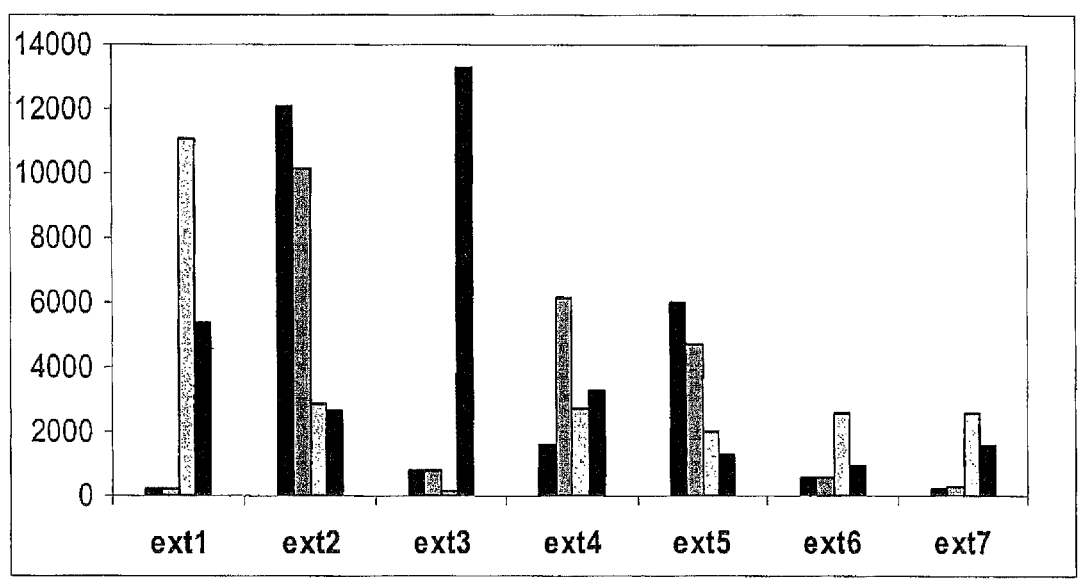
FIG. 47 shows the signal decline observed using labeled nucleotides in sequencing.
Figure 49K:
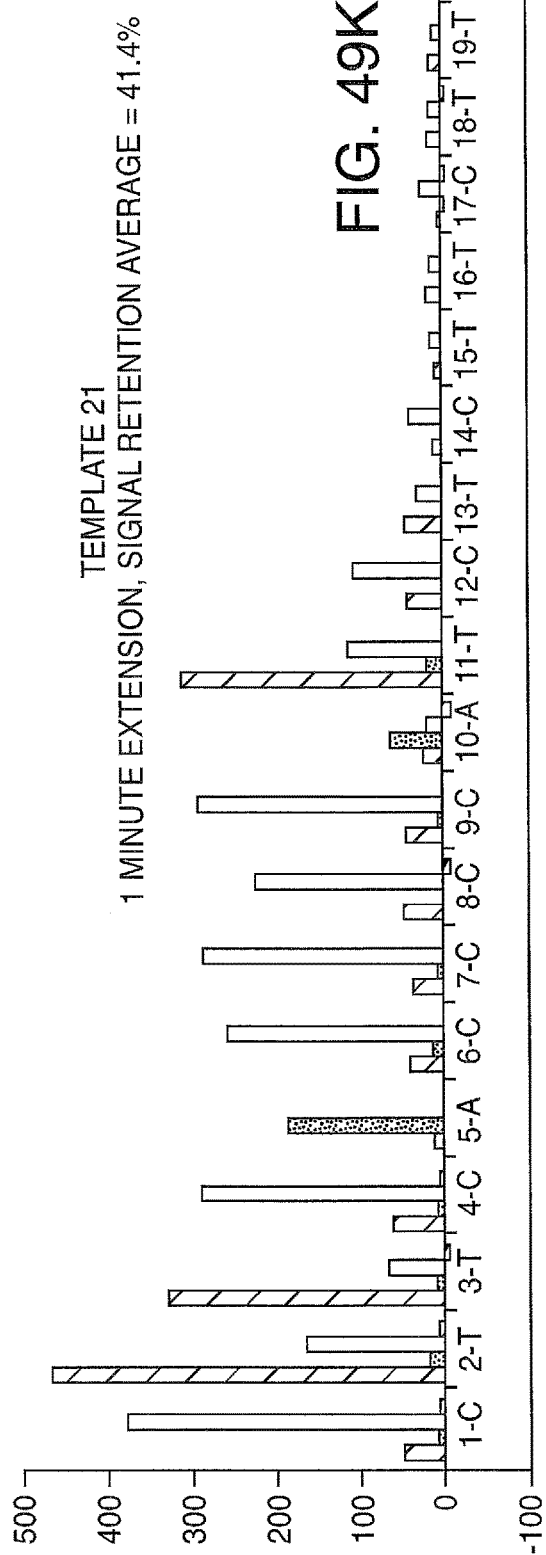
Figure 49L:
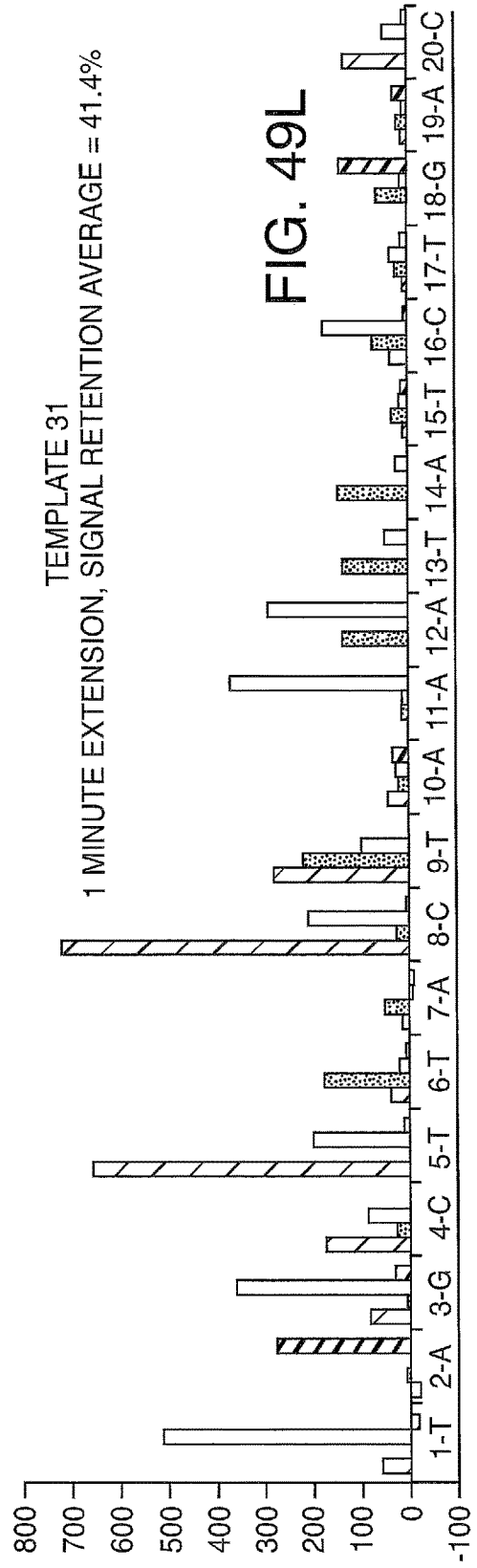
Figure 50:
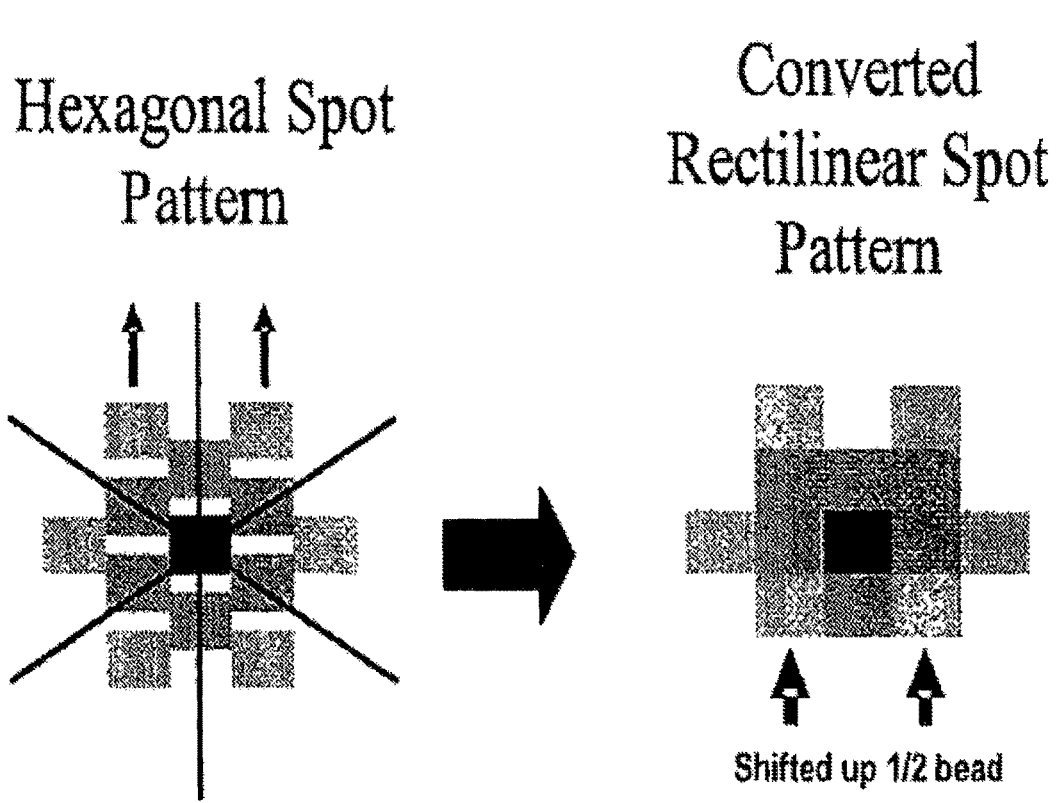
FIG. 50, shows a visual representation of a solution to the neighbor influence problem from spot data that is in hexagonal form. The data is first put into a rectilinear array by shifting the even vertical columns up by ½ of a pixel. A two-dimensional rectilinear matrix, whose elements represent the magnitude of each spot in the original image of the hexagonal array of spots, may be used.

When the amount of labeled nucleotides is reduced, this results in reduction of fluorescent signal as shown in FIG. 47 (where only labeled nucleotides are used in successive extention reactions). In principle only the amount of signal necessary to decode the nucleotide is required. In addition to changing the ratio of labeled and unlabeled nucleotides and optimizing it for particular polymerase, one can also adjust the time of extension (e.g. reduce extension times down to 1-2 minutes) to gain even better control on the signal/incorporation ratio of labeled nucleotides. This is shown in FIGS. 48A-D and 49A-P where additional performance improvement is achieved upon reducing extension time (to 2 minutes and 1 minute, respectively).

All publications and patents mentioned in the above specification are herein incorporated by reference. Various modifications and variations of the described methods and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled in the art and in fields related thereto are intended to be within the scope of the following claims.

The invention claimed is:

1. A method of incorporating labeled nucleotides into nucleic acid, comprising: a) providing a plurality of nucleic acid template molecules, a polymerase, a cleaving agent, a cleaving agent scavenger, and a plurality of nucleotide analogues wherein each nucleotide analogue is labeled with a unique label attached through a cleavable disulfide linker and contains a removable chemical moiety capping the 3'-OH group, wherein said removable chemical moiety comprises a disulfide bond; b) incorporating a first nucleotide analogue with said polymerase; c) detecting the label of the incorporated nucleotide analogue; d) removing the unique label and the chemical moiety of the incorporated nucleotide analogue capping the 3'-OH group with said cleaving agent; and e) introducing said cleaving agent scavenger under conditions such that it reacts with any leftover cleaving agent.

2. The method of claim 1, wherein said cleaving agent is a phosphine.

3. The method of claim 2, wherein said phosphine is Tris(2-carboxy-ethyl)phosphine.

4. The method of claim 1, wherein said cleaving agent scavenger does not contain a nucleic acid base.

5. The method of claim 1, further comprising, prior to step b) hybridizing a primer to said plurality of nucleic acid template molecules, such that said first nucleotide analogue is incorporated into said primer at step b).

6. A method of incorporating labeled nucleotides into nucleic acid, comprising: a) providing a plurality of nucleic acid template molecules, a polymerase, a cleaving agent, a cleaving agent scavenger, and a plurality of nucleotide analogues selected from the group consisting of cytosine, thymine, deaza-adenine and deaza-guanine, wherein each nucleotide analogue comprises a unique label attached through a cleavable disulfide linker to a 5-position of cytosine or thymine or to a 7-position of deaza-adenine or deaza-guanine, and wherein each nucleotide analogue contains a removable chemical moiety capping the 3'-OH group, wherein said removable chemical moiety comprises a disulfide bond; b) incorporating a first nucleotide analogue with said polymerase; c) detecting the label of the incorporated nucleotide analogue; d) removing the chemical moiety of the incorporated nucleotide analogue capping the 3'-OH group and cleaving the cleavable linker with said cleaving agent; and e) introducing said cleaving agent scavenger under conditions such that it reacts with any leftover cleaving agent.

7. The method of claim 6, further comprising, prior to step b) hybridizing a primer to said plurality of nucleic acid template molecules, such that said first nucleotide analogue is incorporated into said primer at step b).

8. The method of claim 6, wherein said cleaving agent is a phosphine.

9. The method of claim 8, wherein said phosphine is Tris(2-carboxy-ethyl)phosphine.

10. The method of claim 6, wherein said cleaving agent scavenger does not contain a nucleic acid base.

* * * * *